United States Patent
Zuo et al.

(10) Patent No.: US 11,242,335 B2
(45) Date of Patent: Feb. 8, 2022

(54) FLUORINE-SUBSTITUTED INDAZOLE COMPOUNDS AND USES THEREOF

(71) Applicant: SUNSHINE LAKE PHARMA CO., LTD., Guangdong (CN)

(72) Inventors: Yinglin Zuo, Dongguan (CN); Xiaojun Wang, Dongguan (CN); Chuanwen Yang, Dongguan (CN); Jiancheng Wang, Dongguan (CN); Shengtian Cao, Dongguan (CN); Fangyuan Wu, Dongguan (CN); Yingjun Zhang, Dongguan (CN); Siegfried Goldmann, Wuppertal (DE)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 109 days.

(21) Appl. No.: 16/500,266

(22) PCT Filed: Apr. 10, 2018

(86) PCT No.: PCT/CN2018/082522
§ 371 (c)(1),
(2) Date: Oct. 2, 2019

(87) PCT Pub. No.: WO2018/188590
PCT Pub. Date: Oct. 18, 2018

(65) Prior Publication Data
US 2021/0101882 A1    Apr. 8, 2021

(30) Foreign Application Priority Data

Apr. 11, 2017    (CN) .......................... 201710232060.X

(51) Int. Cl.
*C07D 401/14*    (2006.01)
*C07D 403/04*    (2006.01)
(Continued)

(52) U.S. Cl.
CPC ......... *C07D 403/04* (2013.01); *C07D 401/14* (2013.01); *C07D 403/14* (2013.01);
(Continued)

(58) Field of Classification Search
CPC .. C07D 403/14; C07D 403/04; C07D 401/14; C07D 405/14; C07D 413/14; C07D 417/14
See application file for complete search history.

(56) References Cited

U.S. PATENT DOCUMENTS 6,162,819 A    12/2000 Schindler et al.
6,180,656 B1    1/2001 Furstner et al.
(Continued)

FOREIGN PATENT DOCUMENTS

CA    2272584 A1    6/1998
CA    2346698 A1    4/2000
(Continued)

OTHER PUBLICATIONS

Burger's Medicinal Chemistry,edited by Manfred E. Wolff, 5th Ed. Part 1, pp. 975-977 (1995). (Year: 1995).*
(Continued)

*Primary Examiner* — Emily A Bernhardt
(74) *Attorney, Agent, or Firm* — Oliff PLC

(57) ABSTRACT

A class of fluorine-substituted indazole compounds and uses thereof having the general formula depicted below

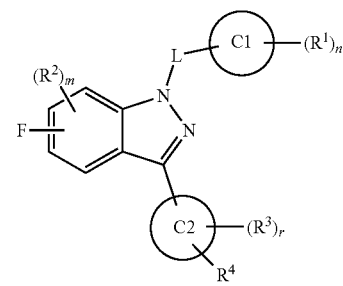

in which C1 is

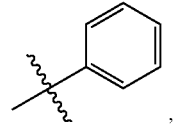

where

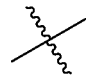

is the bond through which C1 is attached to L, and C2 is

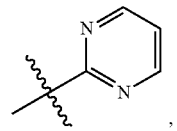

(Continued)

where

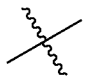

is the bond through which C2 is attached to indazole, and pharmaceutical compositions containing these compounds. The compounds and pharmaceutical compositions of the invention can be used as soluble guanylate cyclase simulators.

14 Claims, No Drawings

(51) Int. Cl.
*C07D 403/14* (2006.01)
*C07D 405/14* (2006.01)
*C07D 413/14* (2006.01)
*C07D 417/14* (2006.01)

(52) U.S. Cl.
CPC ......... *C07D 405/14* (2013.01); *C07D 413/14* (2013.01); *C07D 417/14* (2013.01)

(56) References Cited

U.S. PATENT DOCUMENTS

| | | | |
|---|---|---|---|
| 6,387,940 B1 | 5/2002 | Straub et al. |
| 6,693,102 B2 | 2/2004 | Stasch et al. |
| 6,743,798 B1 | 6/2004 | Straub et al. |
| 6,833,364 B1 | 12/2004 | Straub et al. |
| 6,919,345 B2 | 7/2005 | Stasch et al. |
| 6,982,274 B2 | 1/2006 | Oinuma et al. |
| 7,135,474 B2 | 11/2006 | Weigand et al. |
| 7,173,037 B2 | 2/2007 | Alonso-Alija et al. |
| 7,241,791 B2 | 7/2007 | Steffan et al. |
| 7,427,617 B2 | 9/2008 | Feurer et al. |
| 8,309,551 B2 | 11/2012 | Schirok et al. |
| 8,334,291 B2 | 12/2012 | Schirok et al. |
| 8,420,656 B2 | 4/2013 | Follmann et al. |
| 8,765,769 B2 | 7/2014 | Follmann et al. |
| 8,802,847 B2 | 8/2014 | Fey |
| 8,859,569 B2 | 10/2014 | Follmann et al. |
| 9,023,849 B2 | 5/2015 | Follmann et al. |
| 9,090,609 B2 | 7/2015 | Follmann et al. |
| 9,090,610 B2 | 7/2015 | Follmann et al. |
| 9,095,583 B2 | 8/2015 | Karstens et al. |
| 9,096,592 B2 | 8/2015 | Follmann et al. |
| 9,133,191 B2 | 9/2015 | Follmann et al. |
| 9,150,580 B2 | 10/2015 | Follmann et al. |
| 9,216,978 B2 | 12/2015 | Follmann et al. |
| 9,260,424 B2 | 2/2016 | Rao et al. |
| 9,266,871 B2 | 2/2016 | Follmann et al. |
| 9,284,301 B2 | 3/2016 | Schmidt et al. |
| 9,309,239 B2 | 4/2016 | Follmann et al. |
| 9,365,574 B2 | 6/2016 | Raghavan et al. |
| 9,498,480 B2 | 11/2016 | Follmann et al. |
| 9,505,786 B2 | 11/2016 | Follmann et al. |
| 9,556,168 B2 | 1/2017 | Barr et al. |
| 9,573,946 B2 | 2/2017 | Huang et al. |
| 9,605,008 B2 | 3/2017 | Vakalopoulos et al. |
| 9,682,974 B2 | 6/2017 | Mengel et al. |
| 9,738,610 B2 | 8/2017 | Vincent et al. |
| 9,745,265 B2 | 8/2017 | Barr et al. |
| 9,758,517 B2 | 9/2017 | Chen et al. |
| 10,030,027 B2 | 7/2018 | Berger et al. |
| 10,087,183 B2 | 10/2018 | Keil et al. |
| 10,189,856 B2 | 1/2019 | Hirth-Dietrich et al. |
| 10,350,206 B2 | 7/2019 | Mengel et al. |
| 2004/0235863 A1 | 11/2004 | Feurer et al. |
| 2010/0004235 A1 | 1/2010 | Schirok et al. |
| 2010/0113507 A1 | 5/2010 | Furstner et al. |
| 2012/0029002 A1 | 2/2012 | Straub et al. |
| 2013/0178457 A1 | 7/2013 | Kulkarni et al. |
| 2014/0171434 A1 | 6/2014 | Follmann et al. |
| 2014/0228366 A1 | 8/2014 | Follmann et al. |
| 2016/0002267 A1 | 1/2016 | Follmann et al. |
| 2016/0046604 A1 | 2/2016 | Hitchcock et al. |
| 2016/0052912 A1 | 2/2016 | Hilger et al. |
| 2016/0256460 A1 | 9/2016 | Fluge et al. |
| 2017/0240566 A1 | 8/2017 | Vakalopoulos et al. |

FOREIGN PATENT DOCUMENTS

| | | | |
|---|---|---|---|
| CN | 107964011 A | 4/2018 |
| CN | 107964018 A | 4/2018 |
| WO | 00/06567 A1 | 2/2000 |
| WO | 00/66582 A1 | 11/2000 |
| WO | 01/83490 A1 | 11/2001 |
| WO | 2004/031187 A1 | 4/2004 |
| WO | 2007/065010 A2 | 6/2007 |
| WO | 2012/010576 A1 | 1/2012 |
| WO | 2012/010577 A1 | 1/2012 |
| WO | 2012/010578 A1 | 1/2012 |
| WO | 2012/075678 A1 | 6/2012 |
| WO | 2017/121692 A1 | 7/2017 |
| WO | 2017/121700 A1 | 7/2017 |
| WO | 2017/157991 A1 | 9/2017 |
| WO | 2018/089330 A2 | 5/2018 |

OTHER PUBLICATIONS

Banker et al. "Modern Pharmaceutics", 3rd Ed. p. 596 (1996). (Year: 1996).*
Testa et al. Pure Appl. Chem, vol. 76,pp. 907-914 (2004). (Year: 2004).*
Follman et al. J. Med. Chem. 2017, 60, 5146-5161.*
Jul. 13, 2018 Search Report issued in International Patent Application No. PCT/CN2018/082522.
Jul. 13, 2018 Written Opinion of the International Searching Authority issued in International Patent Application No. PCT/CN2018/082522.

* cited by examiner

FLUORINE-SUBSTITUTED INDAZOLE COMPOUNDS AND USES THEREOF

CROSS-REFERENCE TO RELATED APPLICATIONS

This is a U.S. national stage application of the International Patent Application No. PCT/CN2018/082522, filed Oct. 18, 2018, which claims priority and benefits of Chinese Patent Application No. 201710232060.X, filed on Apr. 11, 2017, both of which are incorporated herein by reference.

FIELD

The invention belongs to the pharmaceutical field, specifically, it relates to fluorine-substituted indazole compounds and uses thereof, further to pharmaceutical compositions containing these compounds. These compounds and pharmaceutical compositions can be used as soluble guanylate cyclase stimulators.

BACKGROUND

Cyclic guanosine monophosphate (cGMP) is a second messenger having action of intracellular signal transduction, and together with nitrogen monoxide (NO), which is released from the endothelium and transmits hormonal and mechanical signals, forms the NO/cGMP system. Guanylate cyclases catalyze the biosynthesis of cGMP from guanosine triphosphate (GTP). The known representatives of this family can be classified both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. NO is able to bind to the iron atom of haem and thus markedly increase the activity of the enzyme. Haem-free enzyme cannot, by contrast, be stimulated by NO. Carbon monoxide (CO) is also able to attach to the central iron atom of haem, but the stimulation by CO is distinctly less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disturbance of the above mentioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

Owing to the expected high efficiency and few side effects, a treatment of such disorders which targets the influence of the cGMP signal path in organisms and is NO-independent is a promising approach. Therapeutic stimulation of soluble guanylate cyclase on NO-based compounds, such as organic nitrates, is formed by bioconversion to give NO and activate soluble guanylate cyclase by NO attacking at the central iron atom of heme. In addition to the side effects, the development of tolerance is one of the disadvantages of this type of treatment.

Soluble guanylate cyclase (sGC) is widely found in mammalian cytosols and has a relatively high content in lung and brain, and is a key signal transduction enzymes in nitric oxide (NO)-sGC-guanosine monophosphate (cGMP) signaling pathway, sGC is activated in the body and will catalyze GTP into cGMP. cGMP is an important second-class messenger molecule that activates several downstream effector molecules such as phosphodiesterase (PDE), cyclic nucleotide gated ion channels (CNG) and protein kinase G (PKG), etc., which in turn triggers a series of cascade reactions downstream to exert important physiological functions in the gastrointestinal system, the blood circulatory system and the nervous system such as promoting relaxation of blood vessels and smooth muscles, inhibiting platelet aggregation, vascular remodeling, apoptosis and inflammation and participation nerve delivery and more.

sGC is a NO sensor and receptor that contains two subunits: alpha and beta, each with three domains, including a heme domain, a central domain and a catalytic domain, wherein heme domains of two subunits share a heme. NO binds to heme of sGC, activates sGC and catalyzes the conversion of its substrate GTP into a secondary signaling molecule cGMP, opens the PKG signaling pathway and leads to vasodilation. As a receptor of NO, sGC plays an important role in the cardiovascular system and nervous system. Disorders of NO signal can lead to the imbalance of physiological functions and lead to various diseases. Therefore, as a new drug that can activate sGC directly, sGC stimulator has aroused increasingly more attention.

sGC stimulators have a dual mechanism of action on sGC in vivo. When the concentration of NO is low, sGC can be directly activated. When NO is at a certain level, sGC stimulators can cooperate with NO and then activates the sGC to catalyze substrate guanosine triphosphate (GTP) transferring into the second-class messenger molecule guanosine monophosphate (cGMP), and then involves in the regulation of many important physiological processes, such as promoting vascular and smooth muscle relaxation; inhibition of platelet aggregation, vascular remodeling, etc. sGC stimulator activates sGC will also mediate other signaling pathways such as TGF-β, which play anti-fibrosis, anti-tumor effect. Therefore, the NO/sGC/cGMP pathway is an effective target for the treatment of a variety of cardiovascular diseases such as pulmonary hypertension, acute heart failure, angina and myocardial infarction-induced vascular remodeling.

Over the years, many researchers have developed NO donors, phosphodiesterase inhibitors and non-NO-dependent sGC stimulators and other drugs, wherein the non-NO-dependent sGC stimulators can avoid the shortcomings of traditional NO donor drugs, such as prone tolerance, lack of specificity and short duration, thus has received widespread attention.

SUMMARY OF THE INVENTION

The present invention provides a novel fluorine-substituted indazole compounds as sGC stimulators and pharmaceutical compositions thereof, and the use of the compounds or the pharmaceutical compositions in the manufacture of a medicament, wherein the medicament is used for the treatment and/or prevention of sGC-mediated diseases such as heart failure, sclerosis, systemic sclerosis, sickle cell anemia, achalasia of cardia, pulmonary fibrosis, idiopathic pulmonary fibrosis, cystic fibrosis, pulmonary hypertension and the like.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

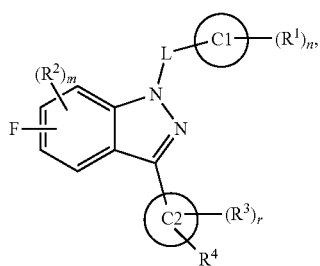

(I)

wherein
L is —(CR$^a$R$^b$)$_t$—, —(CR$^a$R$^b$)$_f$—O—, —(CR$^a$R$^b$)$_f$—S—, —(CR$^a$R$^b$)$_f$—S(=O)—, —(CR$^a$R$^b$)$_f$—S(=O)$_2$—, —(CR$^a$R$^b$)$_f$—N(R$^c$)—, —(CR$^a$R$^b$)$_f$—C(=O)N(R$^c$)—, —C(=O)N(R$^c$)—(CR$^a$R$^b$)$_f$— or —(CR$^a$R$^b$)$_f$—C(=O)—;
t is 1, 2, 3 or 4;
each f is independently 0, 1, 2, 3 or 4;
each R$^a$ and R$^b$ is independently H, D, F, Cl, Br, I, CN, amino, hydroxy, mercapto, C$_{1-6}$ alkyl, C$_{2-6}$ alkenyl, C$_{2-6}$ alkynyl, halo C$_{1-6}$ alkyl, C$_{1-6}$ alkoxy, C$_{1-6}$ alkylamino, halo C$_{1-6}$ alkoxy, acyl, sulfonyl, C$_{3-6}$ cycloalkyl, C$_{2-5}$ heterocyclyl, C$_{6-10}$ aryl or C$_{1-5}$ heteroaryl; or, R$^a$ and R$^b$ together form carbonyl; or, R$^a$ and R$^b$, together with the carbon atom to which they are attached, form a 3- to 8-membered carbocyclic ring or 3- to 8-membered heterocyclic ring;
each R$^c$ is independently H, D, C$_{1-6}$ alkyl, C$_{2-6}$ alkenyl, C$_{2-6}$ alkynyl, halo C$_{1-6}$ alkyl, C$_{3-6}$ cycloalkyl, C$_{2-5}$ heterocyclyl, C$_{6-10}$ aryl or C$_{1-5}$ heteroaryl;
C1 is C$_{6-10}$ aryl, C$_{1-9}$ heteroaryl or C$_{2-9}$ heterocyclyl;
C2 is C$_{6-10}$ aryl, C$_{3-10}$ carbocyclyl, C$_{2-6}$ heterocyclyl or 6- to 10-membered heteroaryl;
each R$^1$ is independently H, D, F, Cl, Br, I, CN, NO$_2$, amino, hydroxy, mercapto, C$_{1-6}$ alkyl, C$_{2-6}$ alkenyl, C$_{2-6}$ alkynyl, halo C$_{1-6}$ alkyl, C$_{1-6}$ alkoxy, halo C$_{1-6}$ alkoxy, C$_{1-6}$ alkylamino, acyl, sulfonyl, —(CR$^{10}$R$^{11}$)$_u$—C$_{3-6}$ cycloalkyl, —(CR$^{10}$R$^{11}$)$_u$—C$_{2-5}$ heterocyclyl, —(CR$^{10}$R$^{11}$)$_u$—C$_{6-10}$ aryl or —(CR$^{10}$R$^{11}$)$_u$—C$_{1-5}$ heteroaryl; wherein each of the amino, hydroxy, mercapto, C$_{1-6}$ alkyl, C$_{2-6}$ alkenyl, C$_{2-6}$ alkynyl, halo C$_{1-6}$ alkyl, C$_{1-6}$ alkoxy, halo C$_{1-6}$ alkoxy, C$_{1-6}$ alkylamino, acyl, sulfonyl, —(CR$^{10}$R$^{11}$)$_u$—C$_{3-6}$ cycloalkyl, —(CR$^{10}$R$^{11}$)$_u$—C$_{2-5}$ heterocyclyl, —(CR$^{10}$R$^{11}$)$_u$—C$_{6-10}$ aryl and —(CR$^{10}$R$^{11}$)$_u$—C$_{1-5}$ heteroaryl is unsubstituted or independently substituted with 1, 2, 3 or 4 substituents selected from D, F, Cl, Br, I, CN, NO$_2$, amino, hydroxy, mercapto, oxo, C$_{1-6}$ alkyl, C$_{2-6}$ alkenyl, C$_{2-6}$ alkynyl, halo C$_{1-6}$ alkyl, C$_{1-6}$ alkoxy, halo C$_{1-6}$ alkoxy, C$_{1-6}$ alkylamino, C$_{3-6}$ cycloalkyl, C$_{2-5}$ heterocyclyl, C$_{6-10}$ aryl and C$_{1-5}$ heteroaryl;
each R$^2$ is independently H, D, F, Cl, Br, I, CN, NO$_2$, amino, hydroxy, mercapto, C$_{1-6}$ alkyl, C$_{2-6}$ alkenyl, C$_{2-6}$ alkynyl, halo C$_{1-6}$ alkyl, halo C$_{1-6}$ alkoxy, C$_{1-6}$ alkylamino, hydroxy C$_{1-6}$ alkyl, cyano C$_{1-6}$ alkyl, amino C$_{1-6}$ alkyl, hydroxy C$_{1-6}$ alkoxy, amino C$_{1-6}$ alkoxy, acyl, sulfonyl or C$_{1-6}$ alkoxy;
each R$^3$ is independently oxo, H, D, F, Cl, Br, I, CN, NO$_2$, mercapto, C$_{1-6}$ alkyl, C$_{2-6}$ alkenyl, C$_{2-6}$ alkynyl, halo C$_{1-6}$ alkyl, —(CR$^{6a}$R$^{6b}$)$_j$—C$_{3-10}$ cycloalkyl, —(CR$^{6a}$R$^{6b}$)$_j$—C$_{2-10}$ heterocyclyl, —(CR$^{6a}$R$^{6b}$)$_j$—C$_{6-10}$ aryl, —(CR$^{6a}$R$^{6b}$)$_j$—C$_{1-9}$ heteroaryl, —(CR$^{6a}$R$^{6b}$)$_j$NR$^{5a}$R$^{5b}$, —(CR$^{6a}$R$^{6b}$)$_j$C(=O)(CR$^{6a}$R$^{6b}$)$_k$NR$^{5a}$R$^{5b}$, —(CR$^{6a}$R$^{6b}$)$_j$C(=O)(CR$^{6a}$R$^{6b}$)$_k$OR$^9$, —(CR$^{6a}$R$^{6b}$)$_j$OR$^9$, —(CR$^{6a}$R$^{6b}$)$_j$S(=O)$_2$(CR$^{6a}$R$^{6b}$)$_k$OR$^9$, —(CR$^{6a}$R$^{6b}$)$_j$S(=O)$_2$(CR$^{6a}$R$^{6b}$)$_k$NR$^{5a}$R$^{5b}$, —(CR$^{6a}$R$^{6b}$)$_j$N(R$^5$)(CR$^{6a}$R$^{6b}$)$_p$C(=O)(CR$^{6a}$R$^{6b}$)$_k$OR$^9$, —(CR$^{6a}$R$^{6b}$)$_j$N(R$^5$)C(=O)(CR$^{6a}$R$^{6b}$)$_k$NR$^{5a}$R$^{5b}$, —(CR$^{6a}$R$^{6b}$)$_j$N(R$^5$)C(=O)R$^8$, —(CR$^{6a}$R$^{6b}$)$_j$N(R$^5$)S(=O)$_2$R$^7$, —(CR$^{6a}$R$^{6b}$)$_j$S(=O)$_2$R$^7$, —(CR$^{6a}$R$^{6b}$)$_j$OS(=O)$_2$R$^7$, —(CR$^{6a}$R$^{6b}$)$_j$OC(=O)(CR$^{6a}$R$^{6b}$)$_k$OR$^9$, —(CR$^{6a}$R$^{6b}$)$_j$OC(=O)R$^8$ or —(CR$^{6a}$R$^{6b}$)$_j$C(=O)R$^8$; each R$^3$ is unsubstituted or independently substituted with 1, 2, 3 or 4 R$^x$; or,
any two adjacent R$^3$, together with the carbon atoms to which they are attached, form a 3- to 6-membered carbocyclic ring, heterocyclic ring, aromatic ring or heteroaromatic ring, and wherein each of 3- to 6-membered carbocyclic ring, heterocyclic ring, aromatic ring and heteroaromatic ring is unsubstituted or independently substituted with 1, 2, 3 or 4 R$^z$;
R$^4$ is D, F, Cl, Br, I, CN, NO$_2$, mercapto, C$_{1-6}$ alkyl, C$_{2-6}$ alkenyl, C$_{2-6}$ alkynyl, halo C$_{1-6}$ alkyl, —(CR$^{6c}$R$^{6d}$)$_g$—C$_{3-6}$ cycloalkyl, —(CR$^{6c}$R$^{6d}$)$_g$—C$_{2-5}$ heterocyclyl, —(CR$^{6c}$R$^{6d}$)$_g$—C$_{6-10}$ aryl, —(CR$^{6c}$R$^{6d}$)$_g$—C$_{1-5}$ heteroaryl, —(CR$^{6c}$R$^{6d}$)$_g$NR$^{5c}$R$^{5d}$, —(CR$^{6c}$R$^{6d}$)$_g$C(=O)(CR$^{6c}$R$^{6d}$)$_h$OR$^{9a}$, —(CR$^{6c}$R$^{6d}$)$_h$NR$^{5c}$R$^{5d}$, —(CR$^{6c}$R$^{6d}$)$_g$C(=O)(CR$^{6c}$R$^{6d}$)$_h$OR$^{9a}$, —(CR$^{6c}$R$^{6d}$)$_g$OR$^{9a}$, —(CR$^{6c}$R$^{6d}$)$_g$S(=O)$_2$(CR$^{6c}$R$^{6d}$)$_h$OR$^{9a}$, —(CR$^{6c}$R$^{6d}$)$_g$S(=O)$_2$(CR$^{6c}$R$^{6d}$)$_h$NR$^{5c}$R$^{5d}$, —(CR$^{6c}$R$^{6d}$)$_g$N(R$^{5e}$)(CR$^{6c}$R$^{6d}$)$_i$C(=O)(CR$^{6c}$R$^{6d}$)$_h$OR$^{9a}$, —(CR$^{6c}$R$^{6d}$)$_g$N(R$^{5e}$)C(=O)R$^{8a}$, —(CR$^{6c}$R$^{6d}$)$_g$N(R$^{5e}$)C(=O)(CR$^{6c}$R$^{6d}$)$_h$NR$^{5c}$R$^{5d}$, —(CR$^{6c}$R$^{6d}$)$_g$N(R$^{5e}$)S(=O)$_2$R$^{7a}$, —(CR$^{6c}$R$^{6d}$)$_g$S(=O)$_2$R$^{7a}$, —(CR$^{6c}$R$^{6d}$)$_g$OS(=O)$_2$R$^{7a}$, —(CR$^{6c}$R$^{6d}$)$_g$OC(=O)(CR$^{6c}$R$^{6d}$)$_h$OR$^{9a}$, —(CR$^{6c}$R$^{6d}$)$_g$OC(=O)R$^{8a}$ or —(CR$^{6c}$R$^{6d}$)$_g$C(=O)R$^{8a}$; R$^4$ is unsubstituted or substituted with 1, 2, 3 or 4 R$^y$;
each R$^5$ and R$^{5e}$ is independently H, D, C$_{1-6}$ alkyl, hydroxy C$_{1-6}$ alkyl, amino C$_{1-6}$ alkyl, cyano C$_{1-6}$ alkyl, halo C$_{1-6}$ alkyl, C$_{1-6}$ alkoxy-C$_{1-6}$-alkyl, C$_{3-6}$ cycloalkyl, C$_{2-5}$ heterocyclyl, C$_{6-10}$ aryl, C$_{1-5}$ heteroaryl, C$_{3-6}$ cycloalkyl-C$_{1-6}$-alkyl, C$_{2-5}$ heterocyclyl-C$_{1-6}$-alkyl, C$_{6-10}$ aryl-C$_{1-6}$-alkyl or C$_{1-5}$ heteroaryl-C$_{1-6}$-alkyl;
each R$^{5a}$, R$^{5b}$, R$^{5c}$ and R$^{5d}$ is independently H, D, C$_{1-6}$ alkyl, C$_{2-6}$ alkenyl, C$_{2-6}$ alkynyl, hydroxy C$_{1-6}$ alkyl, amino C$_{1-6}$ alkyl, cyano C$_{1-6}$ alkyl, halo C$_{1-6}$ alkyl, C$_{1-6}$ alkoxy-C$_{1-6}$-alkyl, C$_{1-6}$ alkoxycarbonyl, C$_{1-6}$ alkylcarbonyl, C$_{1-6}$ alkylaminocarbonyl, C$_{3-6}$ cycloalkyl, C$_{2-5}$ heterocyclyl, C$_{6-10}$ aryl, C$_{1-5}$ heteroaryl, C$_{3-6}$ cycloalkylcarbonyl, C$_{2-5}$ heterocyclylcarbonyl, C$_{6-10}$ arylcarbonyl, C$_{1-5}$ heteroarylcarbonyl, C$_{3-6}$ cycloalkyl-C$_{1-6}$-alkyl, C$_{2-5}$ heterocyclyl-C$_{1-6}$-alkyl, C$_{6-10}$ aryl-C$_{1-6}$-alkyl or C$_{1-5}$ heteroaryl-C$_{1-6}$-alkyl; or, R$^{5a}$ and R$^{5b}$, together with the N atom to which they are attached, form a 3- to 10-membered heterocyclic ring or 3- to 10-membered heteroaromatic ring; or, R$^{5c}$ and R$^{5d}$, together with the N atom to which they are attached, form a 3- to 10-membered heterocyclic ring or 3- to 10-membered heteroaromatic ring;
each R$^{6a}$, R$^{6b}$, R$^{6c}$ and R$^{6d}$ is independently H, D, F, Cl, Br, I, CN, amino, hydroxy, mercapto, C$_{1-6}$ alkyl, C$_{2-6}$ alkenyl, C$_{2-6}$ alkynyl, hydroxy C$_{1-6}$ alkyl, amino C$_{1-6}$ alkyl, cyano C$_{1-6}$ alkyl, halo C$_{1-6}$ alkyl, C$_{1-6}$ alkoxy, halo C$_{1-6}$ alkoxy, C$_{1-6}$ alkylamino, acyl, sulfonyl, C$_{3-6}$ cycloalkyl, C$_{2-5}$ heterocyclyl, C$_{6-10}$ aryl or C$_{1-5}$ heteroaryl;
each R$^7$ and R$^{7a}$ is independently H, D, amino, hydroxy, mercapto, C$_{1-6}$ alkyl, C$_{2-6}$ alkenyl, C$_{2-6}$ alkynyl, halo C$_{1-6}$ alkyl, C$_{1-6}$ alkoxy, halo C$_{1-6}$ alkoxy, C$_{1-6}$ alkylamino, C$_{3-6}$ cycloalkyl, C$_{2-5}$ heterocyclyl, C$_{6-10}$ aryl or C$_{1-5}$ heteroaryl;
each R$^8$ and R$^{8a}$ is independently H, D, amino, hydroxy, mercapto, C$_{1-6}$ alkyl, C$_{2-6}$ alkenyl, C$_{2-6}$ alkynyl, halo C$_{1-6}$ alkyl, $C_{1-6}$ alkoxy, halo $C_{1-6}$ alkoxy, $C_{1-6}$ alkylamino, $C_{3-6}$ cycloalkyl, $C_{2-5}$ heterocyclyl, $C_{6-10}$ aryl or $C_{1-5}$ heteroaryl;

each $R^9$ and $R^{9a}$ is independently H, D, $C_{1-6}$ alkyl, $C_{2-6}$ alkenyl, $C_{2-6}$ alkynyl, halo $C_{1-6}$ alkyl, acyl, sulfonyl, $C_{3-6}$ cycloalkyl, $C_{2-5}$ heterocyclyl, $C_{6-10}$ aryl, $C_{1-5}$ heteroaryl, $C_{3-6}$ cycloalkyl-$C_{1-6}$-alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$ alkyl;

each $R^{10}$ and $R^{11}$ is independently H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{3-6}$ cycloalkyl, $C_{2-5}$ heterocyclyl, $C_{6-10}$ aryl or $C_{1-5}$ heteroaryl; or, $R^{10}$ and $R^{11}$ together form carbonyl; or, $R^{10}$ and $R^{11}$, together with the carbon atom to which they are attached, form a 3- to 8-membered carbocyclic ring or 3- to 8-membered heterocyclic ring;

each $R^x$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkyl sulfonyl, $C_{1-6}$ alkylcarbonylamino, $C_{1-6}$ alkyl sulfonyl amino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl;

each $R^y$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkyl sulfonyl, $C_{1-6}$ alkylcarbonylamino, $C_{1-6}$ alkyl sulfonyl amino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl;

each $R^z$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkyl sulfonyl, $C_{1-6}$ alkylcarbonylamino, $C_{1-6}$ alkyl sulfonyl amino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl;

n is 0, 1, 2, 3 or 4;
m is 0, 1, 2 or 3;
r is 0, 1, 2, 3, 4, 5 or 6;
each u, j and g is independently 0, 1, 2, 3 or 4; and
each h, i, k and p is independently 0, 1, 2, 3 or 4.

In some embodiments, each $R^a$ and $R^b$ is independently H, D, F, Cl, Br, I, CN, amino, hydroxy, mercapto, methyl, ethyl, propyl, butyl, $C_{2-4}$ alkenyl, $C_{2-4}$ alkynyl, halo $C_{1-4}$ alkyl, $C_{1-4}$ alkoxy, $C_{1-4}$ alkylamino, halo $C_{1-4}$ alkoxy, $C_{3-6}$ cycloalkyl, $C_{2-5}$ heterocyclyl, phenyl or $C_{1-5}$ heteroaryl; or, $R^a$ and $R^b$ together form carbonyl; or, $R^a$ and $R^b$, together with the carbon atom to which they are attached, form a 3- to 6-membered carbocyclic ring or 3- to 6-membered heterocyclic ring; and each $R^c$ is independently H, D, methyl, ethyl, propyl, butyl, $C_{2-4}$ alkenyl, $C_{2-4}$ alkynyl, halo $C_{1-4}$ alkyl, $C_{3-6}$ cycloalkyl, $C_{2-5}$ heterocyclyl, phenyl or $C_{1-5}$ heteroaryl.

In some embodiments, C1 is:

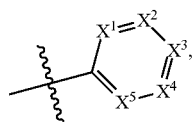
(C1-1)

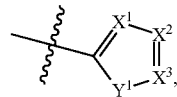
(C1-2)

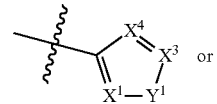
(C1-3)

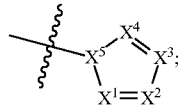
(C1-4)

wherein, each $X^1$, $X^2$, $X^3$, $X^4$ and $X^5$ is independently N or CH;

each $Y^1$ is independently $CH_2$, C(=O), NH, S, S(=O), $S(=O)_2$ or O;

wherein,

is the bond through which C1 is attached to L.

In other embodiments, C1 is

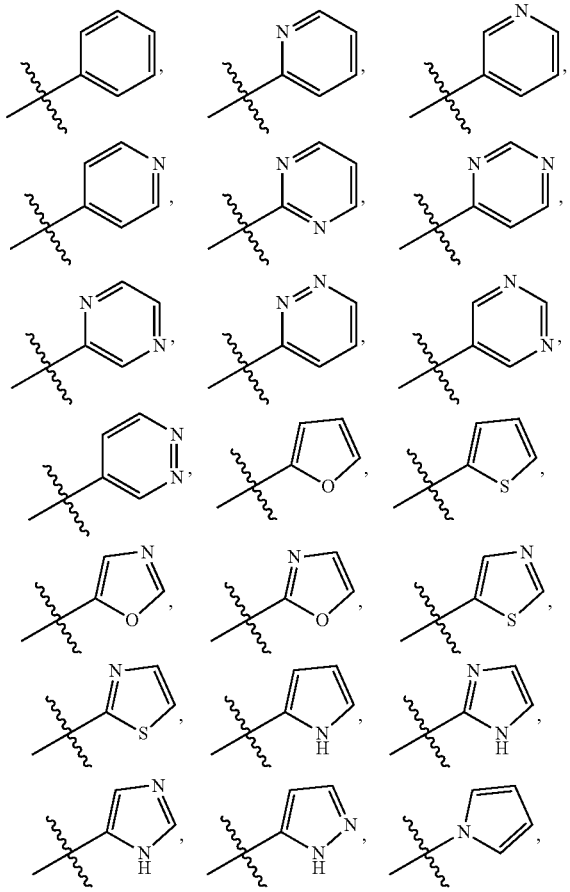

7
-continued

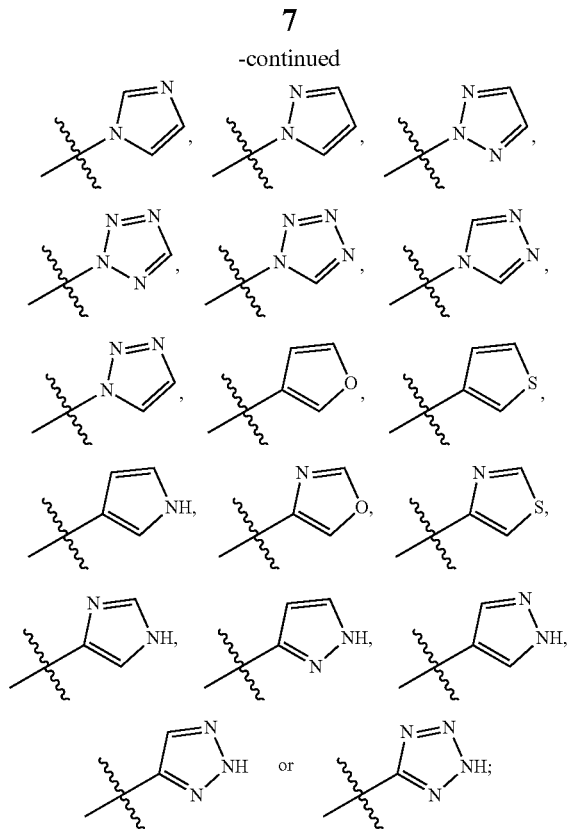

wherein,

is the bond through which C1 is attached to L.

In some embodiments, C2 is:

(C2-1)

(C2-2)

(C2-3)

(C2-4)

8
-continued (C2-5)

(C2-6)

(C2-7)

(C2-8)

(C2-9)

wherein, each $X^6$, $X^7$, $X^8$, $X^9$, $X^{10}$ and $X^{11}$ is independently N or CH;

each $Y^6$, $Y^7$ and $Y^8$ is independently $CH_2$, C(=O), NH, S, S(=O), $S(=O)_2$ or O;

each $Y^5$ is independently $CH_2$, NH, S or O;

e is 0, 1, 2, 3 or 4;

wherein,

is the bond through which C2 is attached to indazole.

In other embodiments, C2 is

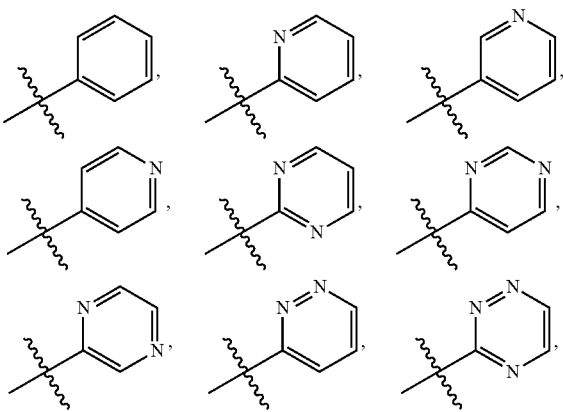

-continued wherein, is the bond through which C2 is attached to indazole.

In some embodiments, the compound having Formula (I) of the invention has Formula (II), Formula (IIa), Formula (IIb) or Formula (IIc), or a stereoisomer, a geometric isomer, a tautomer, an N-oxide, a hydrate, a solvate, a metabolite, an ester, a pharmaceutically acceptable salt or a prodrug thereof,

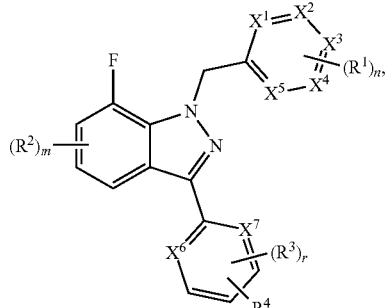

(IIc)

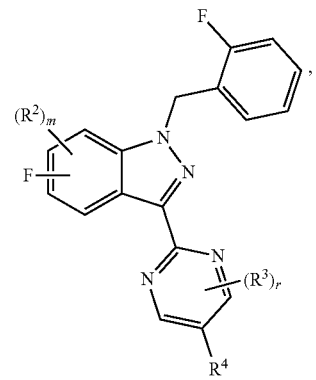

(IV)

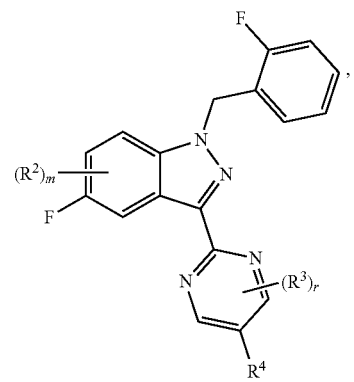

(IVa)

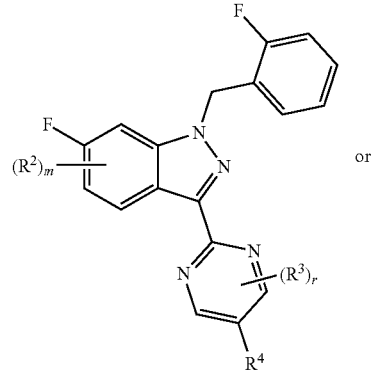

or (IVb)

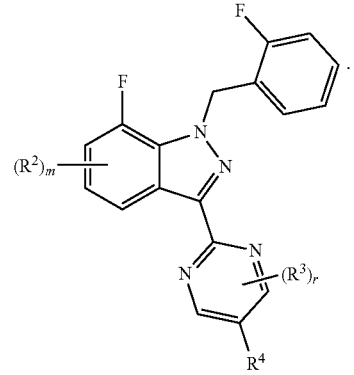

(IVc)

wherein each $X^1$, $X^2$, $X^3$, $X^4$, $X^5$, $X^6$ and $X^7$ is independently N or CH.

In some embodiments, each $R^1$ is independently H, D, F, Cl, Br, I, CN, $NO_2$, amino, hydroxy, mercapto, $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl or $C_{1-5}$ heteroaryl;

wherein each of the $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl and $C_{1-5}$ heteroaryl is unsubstituted or independently substituted with 1, 2, 3 or 4 substituents selected from D, F, Cl, Br, I, CN, $NO_2$, amino, hydroxy, mercapto, oxo, $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl and $C_{1-5}$ heteroaryl.

In other embodiments, each $R^1$ is independently H, D, F, Cl, Br, I, CN, $NO_2$, amino, hydroxy, mercapto, oxo, methyl, ethyl, propyl, butyl, trifluoromethyl, difluoromethyl, methoxy, ethoxy, propoxy, tert-butoxy, trifluoromethoxy, methylamino, dimethylamino, cyclopropyl, cyclobutyl, cyclopentyl, cyclohexyl, piperidinyl, morpholinyl, piperazinyl, epoxypropyl, azetidinyl, phenyl, pyridyl or pyrimidinyl;

wherein each of the methyl, ethyl, propyl, butyl, difluoromethyl, methoxy, ethoxy, propoxy, tert-butoxy, methylamino, dimethylamino, cyclopropyl, cyclobutyl, cyclopentyl, cyclohexyl, piperidinyl, morpholinyl, piperazinyl, epoxypropyl, azetidinyl, phenyl, pyridyl and pyrimidinyl is unsubstituted or independently substituted with 1, 2, 3 or 4 substituents selected from D, F, Cl, Br, I, CN, $NO_2$, amino, hydroxy, mercapto, oxo, methyl, ethyl, propyl, butyl, $C_{2-4}$ alkenyl, $C_{2-4}$ alkynyl, trifluoromethyl, methoxy, ethoxy, propoxy, trifluoromethoxy, $C_{1-3}$ alkylamino, cyclopropyl, cyclobutyl, cyclopentyl, cyclohexyl, $C_{2-5}$ heterocyclyl, phenyl and $C_{1-5}$ heteroaryl.

In some embodiments, the compound having Formula (I) of the invention has Formula (IV), Formula (IVa), Formula (IVb) or Formula (IVc), or a stereoisomer, a geometric isomer, a tautomer, an N-oxide, a hydrate, a solvate, a metabolite, an ester, a pharmaceutically acceptable salt or a prodrug thereof, In some embodiments, $R^4$ is D, F, Cl, Br, I, CN, $NO_2$, mercapto, $C_{1-4}$ alkyl, $C_{2-4}$ alkenyl, $C_{2-4}$ alkynyl, halo $C_{1-4}$ alkyl, $C_{3-6}$ cycloalkyl, $C_{2-5}$ heterocyclyl, $C_{6-10}$ aryl, $C_{1-5}$ heteroaryl, $—NR^{5c}R^{5d}$, $—C(=O)NR^{5c}R^{5d}$, $—OR^{9a}$, $—S(=O)_2OR^{9a}$, $—S(=O)_2NR^{5c}R^{5d}$, $—N(R^{5e})C(=O)$ $(CR^{6c}R^{6d})_nOR^{9a}$, —$N(R^{5e})C(=O)R^{8a}$, —$N(R^{5e})C(=O)NR^{5c}R^{5d}$, —$N(R^{5e})S(=O)_2R^{7a}$, —$S(=O)_2R^{7a}$, —$OS(=O)_2R^{7a}$, —$OC(=O)OR^{9a}$, —$OC(=O)R^{8a}$ or —$C(=O)R^{8a}$; $R^4$ is unsubstituted or substituted with 1, 2, 3 or 4 $R^y$.

In other embodiments, $R^4$ is D, F, Cl, Br, I, CN, NO$_2$, mercapto, methyl, ethyl, propyl, butyl, vinyl, propenyl, allyl, ethynyl, propynyl, trifluoromethyl, difluoromethyl, 2,2-difluoroethyl, chloroethyl, 2,2,2-trifluoroethyl, 2-chloro-1-methylethyl, cyclopropyl, cyclobutyl, cyclopentyl, cyclohexyl, tetrahydrofuranyl, morpholinyl, piperidinyl, piperazinyl, pyrrolidinyl, pyrazolidinyl, oxomorpholinyl, thiomorpholinyl, 4,4-dioxothiomorpholinyl, oxazolidinyl, thiazolidinyl, 1,1-dioxoisothiazolidinyl, oxo-1,3-oxazinylalkyl, phenyl, pyridyl, pyrimidinyl, pyrazolyl, imidazolyl, pyrrolyl, thiazolyl, oxazolyl, triazolyl, tetrazolyl, thienyl, furyl, —$NR^{5c}R^{5d}$, —$C(=O)NR^{5c}R^{5d}$, —$OR^{9a}$, —$S(=O)_2OR^{9a}$, —$S(=O)_2NR^{5c}R^{5d}$, —$N(R^{5e})C(=O)(CR^{6c}R^{6d})_nOR^{9a}$, —$N(R^{5e})C(=O)R^{8a}$, —$N(R^{5e})C(=O)NR^{5c}R^{5d}$, —$N(R^{5e})S(=O)_2R^{7a}$, —$S(=O)_2R^{7a}$, —$OS(=O)_2R^{7a}$, —$OC(=O)OR^{9a}$, —$OC(=O)R^{8a}$ or —$C(=O)R^{8a}$; $R^4$ is unsubstituted or substituted with 1, 2, 3 or 4 $R^y$.

In some embodiments, each $R^2$ is independently H, D, F, Cl, Br, I, CN, NO$_2$, amino, hydroxy, mercapto, C$_{1-4}$ alkyl, C$_{2-4}$ alkenyl, C$_{2-4}$ alkynyl, halo C$_{1-4}$ alkyl, halo C$_{1-4}$ alkoxy, C$_{1-4}$ alkylamino, hydroxy C$_{1-4}$ alkyl, cyano C$_{1-4}$ alkyl, amino C$_{1-4}$ alkyl, hydroxy C$_{1-4}$ alkoxy, amino C$_{1-4}$ alkoxy or C$_{1-4}$ alkoxy.

In other embodiments, each $R^2$ is independently H, D, F, Cl, Br, I, CN, NO$_2$, amino, hydroxy, mercapto, methyl, ethyl, propyl, butyl, trifluoromethyl, trifluoromethoxy, methylamino, dimethylamino, hydroxymethyl, hydroxyethyl, cyanomethyl, cyanoethyl, aminomethyl, aminoethyl, hydroxymethoxy, hydroxyethoxy, amino C$_{1-3}$ alkoxy, methoxy, ethoxy, propoxy or butoxy.

In some embodiments, each $R^3$ is independently oxo, H, D, F, Cl, Br, I, CN, NO$_2$, mercapto, C$_{1-4}$ alkyl, C$_{2-4}$ alkenyl, C$_{2-4}$ alkynyl, halo C$_{1-4}$ alkyl, C$_{3-6}$ cycloalkyl, C$_{2-5}$ heterocyclyl, C$_{6-10}$ aryl, C$_{1-5}$ heteroaryl, —$NR^{5a}R^{5b}$, —$C(=O)NR^{5a}R^{5b}$, —$C(=O)OR^9$, —$OR^9$, —$S(=O)_2OR^9$, —$S(=O)_2NR^{5a}R^{5b}$, —$N(R^5)C(=O)(CR^{6a}R^{6b})_kOR^9$, —$N(R^5)C(=O)NR^{5a}R^{5b}$, —$N(R^5)C(=O)R^8$, —$N(R^5)S(=O)_2R^7$, —$S(=O)_2R^7$, —$OS(=O)_2R^7$, —$OC(=O)OR^9$, —$OC(=O)R^8$ or —$C(=O)R^8$; each $R^3$ is unsubstituted or substituted with 1, 2, 3 or 4 $R^x$; or, any two adjacent $R^3$, together with the carbon atoms to which they are attached, form a 3- to 6-membered heterocyclic ring or heteroaromatic ring, and wherein each of 3- to 6-membered heterocyclic ring and heteroaromatic ring is unsubstituted or and independently substituted with 1, 2, 3 or 4 $R^z$.

In other embodiments, each $R^3$ is independently oxo, H, D, F, Cl, Br, I, CN, NO$_2$, mercapto, methyl, ethyl, propyl, butyl, trifluoromethyl, 2,2-difluoroethyl, cyclopropyl, cyclobutyl, cyclopentyl, cyclohexyl, azetidinyl, pyrrolidinyl, pyrazolidinyl, piperidinyl, piperazinyl, morpholinyl, oxomorpholinyl, thiomorpholinyl, 4,4-dioxothiomorpholinyl, tetrahydrofuranyl, oxazolidinyl, thiazolidinyl, 1,1-dioxoisothiazolidinyl, oxo-1,3-oxazinyl, phenyl, pyridyl, pyrimidinyl, pyrazolyl, imidazolyl, pyrrolyl, thiazolyl, oxazolyl, triazolyl, tetrazolyl, thienyl, furyl, —$NR^{5a}R^{5b}$, —$C(=O)NR^{5a}R^{5b}$, —$C(=O)OR^9$, —$OR^9$, —$S(=O)_2OR^9$, —$S(=O)_2NR^{5a}R^{5b}$, —$N(R^5)C(=O)OR^9$, —$N(R^5)C(=O)NR^{5a}R^{5b}$, —$N(R^5)C(=O)R^8$, —$N(R^5)S(=O)_2R^7$, —$S(=O)_2R^7$, —$OS(=O)_2R^7$, —$OC(=O)OR^9$, —$OC(=O)R^8$ or —$C(=O)R^8$; each $R^3$ is unsubstituted or independently substituted with 1, 2, 3 or 4 $R^x$; or, any two adjacent $R^3$, together with the carbon atoms to which they are attached, form a 3- to 6-membered heterocyclic ring or heteroaromatic ring, and wherein each of 3- to 6-membered heterocyclic ring and heteroaromatic ring is unsubstituted or independently substituted with 1, 2, 3 or 4 $R^z$.

In some embodiments, each $R^{5a}$, $R^{5b}$, $R^{5c}$ and $R^{5d}$ is independently H, D, C$_{1-4}$ alkyl, C$_{2-4}$ alkenyl, C$_{2-4}$ alkynyl, hydroxy C$_{1-4}$ alkyl, amino C$_{1-4}$ alkyl, cyano C$_{1-4}$ alkyl, halo C$_{1-4}$ alkyl, C$_{1-4}$ alkoxy-C$_{1-4}$-alkyl, C$_{1-4}$ alkoxycarbonyl, C$_{1-4}$ alkylcarbonyl, C$_{1-4}$ alkylaminocarbonyl, C$_{3-6}$ cycloalkyl, C$_{2-5}$ heterocyclyl, C$_{6-10}$ aryl, C$_{1-5}$ heteroaryl, C$_{3-6}$ cycloalkylcarbonyl, C$_{2-5}$ heterocyclylcarbonyl, C$_{6-10}$ arylcarbonyl, C$_{1-5}$ heteroarylcarbonyl, C$_{3-6}$ cycloalkyl-C$_{1-3}$-alkyl, C$_{2-5}$ heterocyclyl-C$_{1-3}$-alkyl, C$_{6-10}$ aryl-C$_{1-3}$-alkyl or C$_{1-5}$ heteroaryl-C$_{1-3}$-alkyl; or, $R^{5a}$ and $R^{5b}$, together with the N atom to which they are attached, form a 3- to 6-membered heterocyclic ring or 3- to 6-membered heteroaromatic ring; or, $R^{5c}$ and $R^{5d}$, together with the N atom to which they are attached, form a 3- to 6-membered heterocyclic ring or 3- to 6-membered heteroaromatic ring.

In other embodiments, each $R^{5a}$, $R^{5b}$, $R^{5c}$ and $R^{5d}$ is independently H, D, methyl, ethyl, propyl, butyl, hydroxymethyl, hydroxyethyl, hydroxypropyl, hydroxybutyl, amino C$_{1-4}$ alkyl, cyano C$_{1-4}$ alkyl, trifluoromethoxy, chloroethyl, 2,2,2-trifluoroethyl, 2,2-difluoroethyl, 2-chloro-1-methylethyl, methoxymethyl, methoxyethyl, methoxycarbonyl, ethoxycarbonyl, propoxycarbonyl, methylcarbonyl, ethylcarbonyl, methylaminocarbonyl, ethylaminocarbonyl, cyclopropyl, cyclobutyl, cyclopentyl, cyclohexyl, azetidinyl, pyrrolidyl, tetrahydrofuranyl, tetrahydropyranyl, morpholinyl, piperidinyl, piperazinyl, phenyl, pyridinyl, pyrimidinyl, cyclopropylcarbonyl, cyclopentylcarbonyl, cyclohexylcarbonyl, cyclopropyloxycarbonyl, tetrahydrofurylcarbonyl, tetrahydropyranylcarbonyl, piperidylcarbonyl, piperazinylcarbonyl, morpholinylcarbonyl, tetrahydrothiophenylcarbonyl, pyrrolidinylcarbonyl, phenylcarbonyl, pyridylcarbonyl, pyrimidinylcarbonyl, pyrrolylcarbonyl, imidazolylcarbonyl, pyrazolylcarbonyl, thienylcarbonyl, furylcarbonyl, cyclopropylmethyl, cyclobutylmethyl, tetrahydropyranylmethyl, tetrahydropyranylethyl, tetrahydrofuranylmethyl, tetrahydrofuranylethyl, phenylmethyl, phenylethyl, pyridylmethyl, pyrazolylmethyl, pyrazolylethyl, pyridylethyl or C$_{2-5}$ heterocyclyl-C$_{1-3}$-alkyl; or, $R^{5a}$ and $R^{5b}$, together with the N atom to which they are attached, form an azetidine, pyrrolidine, oxazolidine, thiazolidine, isothiazolidine, piperidine, morpholine, piperazine, thiomorpholine, 1,3-oxazinane, pyrrole, pyrazole, imidazole or triazolyl; or, $R^{5c}$ and $R^{5d}$, together with the N atom to which they are attached, form an azetidine, pyrrolidine, oxazolidine, thiazolidine, isothiazolidine, piperidine, morpholine, piperazine, thiomorpholine, 1,3-oxazinane, pyrrole, pyrazole, imidazole or triazolyl.

In some embodiments, each $R^9$ and $R^{9a}$ is independently H, D, C$_{1-4}$ alkyl, C$_{2-4}$ alkenyl, C$_{2-4}$ alkynyl, halo C$_{1-4}$ alkyl, acyl, sulfonyl, C$_{3-6}$ cycloalkyl, C$_{2-5}$ heterocyclyl, C$_{6-10}$ aryl, C$_{1-5}$ heteroaryl, C$_{3-6}$ cycloalkyl-C$_{1-3}$-alkyl, C$_{2-5}$ heterocyclyl-C$_{1-3}$-alkyl, C$_{6-10}$ aryl-C$_{1-3}$-alkyl or C$_{1-5}$ heteroaryl-C$_{1-3}$-alkyl.

In other embodiments, each $R^9$ and $R^{9a}$ is independently H, D, methyl, ethyl, propyl, butyl, C$_{2-4}$ alkenyl, C$_{2-4}$ alkynyl, trifluoromethyl, chloroethyl, 2,2,2-trifluoroethyl, 2,2-difluoroethyl, 2-chloro-1-methylethyl, cyclopropyl, cyclobutyl, cyclopentyl, cyclohexyl, pyrrolidinyl, tetrahydrofuranyl, morpholinyl, piperidinyl, piperazinyl, phenyl, pyridyl, pyrimidinyl, cyclopropylmethyl, cyclobutylmethyl, phenylmethyl, phenylethyl, pyridylmethyl, pyridylethyl or $C_{2-5}$ heterocyclyl-$C_{1-3}$-alkyl.

In some embodiments, each $R^8$ and $R^{8a}$ is independently H, D, amino, hydroxy, mercapto, methyl, ethyl, propyl, butyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, cyclopropyl, cyclobutyl, cyclopentyl, cyclohexyl, azetidinyl, tetrahydropyranyl, pyrrolidinyl, tetrahydrofuranyl, tetrahydrothienyl, morpholinyl, piperidinyl, piperazinyl, thiomorpholinyl, 1,1-dioxothiomorpholinyl, phenyl, pyrrolyl, thienyl, furyl, pyridyl or pyrimidinyl.

In some embodiments, each $R^x$ is independently oxo, H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkylsulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

In some embodiments, each $R^y$ is independently oxo, H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkylsulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

In some embodiments, each $R^5$ and $R^{5e}$ is independently H, D, methyl, ethyl, propyl, butyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy-$C_{1-4}$ alkyl;

each $R^{6a}$, $R^{6b}$, $R^{6c}$ and $R^{6d}$ is independently H, D, F, Cl, Br, I, CN, amino, hydroxy, mercapto, methyl, ethyl, propyl, butyl, hydroxy $C_{1-4}$ alkyl, amino $C_{1-4}$ alkyl, cyano $C_{1-4}$ alkyl or halo $C_{1-4}$ alkyl.

In another aspect, provided herein is a pharmaceutical composition comprising the compound disclosed herein.

In some embodiments, the pharmaceutical composition disclosed herein further comprises at least one of pharmaceutically acceptable carrier, excipient, diluent, adjuvant and vehicle.

In one aspect, provided herein is use of the compound or the pharmaceutical composition of the invention in the manufacture of a medicament for treating and/or preventing diseases, wherein the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorders and/or arteriosclerosis.

In another aspect, provided herein is use of the compound or the pharmaceutical composition of the invention in the manufacture a medicament as a soluble guanylate cyclase stimulator.

In one aspect, provided herein is the compound or the pharmaceutical composition of the invention for use in treating and/or preventing diseases in a patient, wherein the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorders and/or arteriosclerosis.

In another aspect, provided herein is the compound or the pharmaceutical composition of the invention for use in the manufacture a medicament as a soluble guanylate cyclase stimulator.

In one aspect, provided herein is a method of treating and/or preventing diseases in a patient, comprising administering to the patient a therapeutically effective amount of the compound or the pharmaceutical composition of the invention, wherein the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorders and/or arteriosclerosis.

In another aspect, provided herein is a method of treating and/or preventing diseases mediated by soluble guanylate cyalase in a patient comprising administering to the patient a therapeutically effective amount of the compound or the pharmaceutical composition of the invention.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the *Handbook of Chemistry and Physics*, 75th Ed. 1994. Additionally, general principles of organic chemistry are described in "Organic Chemistry", Thomas Sorrell, University Science Books, Sausalito: 1999, and Smith et al., "*March's Advanced Organic Chemistry*", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e., at least one) of the grammatical objects of the article. By way of example, "a component" means one or more components, and thus, possibly, more than one component are contemplated and may be employed or used in an implementation of the described embodiments.

As used herein, "patient" refers to a human (including adults and children) or other animal. In one embodiment, "patient" refers to a human.

The term "comprise" is an open expression, it means comprising the contents disclosed herein, but don't exclude other contents.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

The term "tautomer" or "tautomeric form" refers to structural isomers of different energies which are interconvertible via a low energy barrier. Where tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

As described herein, compounds disclosed herein may optionally be substituted with one or more substituents, such as are illustrated by Formula above, or as exemplified by particular classes, subclasses, and species of the invention.

It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. The phrase "optionally substituted" refers to that the structure or group is unsubstituted, or the structure or group is substituted with one or more specific substitutents. Unless otherwise indicated, an optionally substituted group may have a substituent at each substitutable position of the group. When more than one position in a given structure can be substituted with more than one substituent selected from specified groups, the substituent may be either the same or different at each position. wherein the substitutents can be, but are not limited to, oxo (=O), H, D, cyano, nitro, halogen, hydroxy, mercapto, amino, alkyl, haloalkyl, hydroxyalkyl, cyanoalkyl, aminoalkyl, alkoxy, haloalkoxy, acyl, acyloxy, sulfonyl, sulfinyl, carboxy, cycloalkyl, cycloalkylalkyl, cycloalkyloxy, heterocyclyl, heterocyclylalkyl, heterocyclyloxy, aryl, arylalkyl, aryloxy, heteroaryl, heteroarylalkyl, heteroaryloxy and the like.

Furthermore, what need to be explained is that the phrase "each . . . is independently", "each . . . and . . . is independently" and "each of . . . and . . . is independently" can be used interchangeably herein, unless otherwise stated, and should be broadly understood. The specific options expressed by the same symbol are independent of each other in different groups; or the specific options expressed by the same symbol are independent of each other in same groups. In the same way, the term "independently" in the description " . . . independently and optionally" should be broadly understood.

The term "optional" or "optionally" refers to that a subsequently described event or circumstance may but need not occur, and that the description includes instances where the event or circumstance occurs and instances where the event or circumstance dese not occur. For example, "optionally substituted with 1, 2, 3 or 4 substituents independently selected from . . . " includes the condition that the group is substituted with 1, or 2, or 3, or 4 substitutents, and the condition that the group is not be substituted with substituent. Furthermore, when the group is substituted with more than one substituent, these substituents are independent of each other, that is, the more than one substituent may be different from each other or may be the same.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" or "$C_{1-6}$ alkyl" is specifically intended to individually disclose methyl, ethyl, $C_3$ alkyl, $C_4$ alkyl, $C_5$ alkyl and $C_6$ alkyl; "$C_{1-4}$ alkyl" is specifically intended to individually disclose $C_1$ alkyl (i.e., methyl), $C_2$ alkyl (i.e., ethyl), $C_3$ alkyl (i.e., propyl, including n-propyl and i-propyl), $C_4$ alkyl (i.e., butyl, including n-butyl, i-butyl, sec-butyl and t-butyl).

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group of 1-20 carbon atoms, wherein the alkyl group is optionally substituted with one or more substituents described herein. In some embodiments, the alkyl group contains 1-12 carbon atoms. In other embodiments, the alkyl group contains 1-6 carbon atoms, i.e., $C_{1-6}$ alkyl. In still other embodiments, the alkyl group contains 1-4 carbon atoms, i.e., $C_{1-4}$ alkyl. In yet other embodiments, the alkyl group contains 1-3 carbon atoms, i.e., $C_{1-3}$ alkyl. In some embodiments, the $C_{1-6}$ alkyl of the invention can be $C_{1-4}$ alkyl; in other embodiments, the $C_{1-6}$ alkyl can be $C_{1-3}$ alkyl.

The examples of the alkyl group include, but are not limited to, methyl, ethyl, propyl (including n-propyl and isopropyl), butyl (including n-butyl, isobutyl, sec-butyl, tert-butyl), n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, and the like.

In some specific structures, when an alkyl group is clearly indicated as a linking group, it should be understood that the alkyl group represents a linking alkylene group. For example, the $C_{1-6}$ alkyl group in group "$C_{3-10}$ cycloalkyl-$C_{1-6}$-alkyl" should be understood as $C_{1-6}$ alkylene.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. Such examples include methylene (—CH$_2$—), ethylene (including —CH$_2$CH$_2$— or —CH(CH$_3$)—), i-propylene (including —CH(CH$_3$)CH$_2$— or —C(CH$_3$)$_2$—), and the like. Wherein, the alkylene group may be optionally substituted with one or more substituents disclosed herein.

The term "alkenyl" refers to linear or branched-chain monovalent hydrocarbon radical of 2 to 12 carbon atoms with at least one site of a carbon-carbon, sp$^2$ double bond, wherein the alkenyl radical may be optionally substituted with one or more substituents described herein, and includes radicals having "cis" and "tans" orientations, or alternatively, "E" and "Z" orientations. In some embodiments, the alkenyl contains 2 to 8 carbon atoms. In other embodiments, the alkenyl contains 2 to 6 carbon atoms. In still other embodiments, the alkenyl contains 2 to 4 carbon atoms. Examples of alkenyl groups include, but are not limited to, ethylenyl (—CH=CH$_2$), allyl (—CH$_2$CH=CH$_2$), and the like.

The term "alkynyl" refers to a linear or branched monovalent hydrocarbon radical of 2 to 12 carbon atoms with at least one site of a carbon-carbon, sp triple bond, wherein the alkynyl radical may be optionally substituted with one or more substituents described herein. In some embodiments, the alkynyl contains 2 to 8 carbon atoms. In other embodiments, the alkynyl contains 2 to 6 carbon atoms. In still other embodiments, the alkynyl contains 2 to 4 carbon atoms. Examples of such groups include, but are not limited to, ethynyl (—C≡CH), propargyl (—CH$_2$C≡CH), 1-propynyl (—C≡C—CH$_3$), and the like.

The term "alkoxy" refers to an alkyl group, as previously defined, attached to the parent molecular moiety via an oxygen atom. Some non-limiting examples of the alkoxy group include methoxy, ethoxy, 1-propoxy, 2-propoxy, 1-butoxy, and the like.

The terms "haloalkyl" or "haloalkoxy" refer to alkyl or alkoxy, as the case may be, substituted with one or more halogen atoms. Some non-limiting examples of such groups include trifluoromethyl, trifluoromethoxy, chloroethyl (such as 2-chloroethyl), 2,2,2-trifluoroethyl, 2,2-difluroethyl, 2-chloro-1-methylethyl, and the like.

The term "amino" refers to group-NH$_2$. The term "carboxy" refers to group —COOH.

The term "hydroxy", "cyano", "nitro", "mercapto" independently refers to group —OH, —CN, —NO$_2$, —SH. The term "oxo" refers to group =O.

The term "alkylamino" refers to an —NH$_2$ group substituted with one or two alkyl groups, wherein the alkyl group is as defined herein. Some non-limiting examples of suitable alkylamino radical include, but are not limited to, methylamino and diethylamino, and the like.

The term "hydroxyalkyl", "cyanoalkyl", "aminoalkyl" respectively refers to an alkyl substituted with one or more hydroxy (—OH), cyano (—CN) or amino (—NH$_2$), wherein the alkyl is as defined herein. In some embodiments, the "hydroxyalkyl", "cyanoalkyl", "aminoalkyl" respectively refers to "hydroxy $C_{1-6}$ alkyl", "cyano $C_{1-6}$ alkyl", "amino $C_{1-6}$ alkyl", i.e., a $C_{1-6}$ alkyl substituted with one or more hydroxy (—OH), cyano (—CN) or amino (—NH$_2$). In some embodiments, the "hydroxy $C_{1-6}$ alkyl", "cyano $C_{1-6}$ alkyl", "amino $C_{1-6}$ alkyl" respectively refers to "hydroxy $C_{1-4}$ alkyl", "cyano $C_{1-4}$ alkyl" or "amino $C_{1-4}$ alkyl". Such examples include, but are not limited to, hydroxymethyl, hydroxyethyl (such as 2-hydroxyethyl), aminomethyl, aminoethyl (such as 2-aminoethyl), cyanomethyl, cyanoethyl (such as 2-cyanoethyl), and the like.

The term "hydroxyalkoxy", "cyanoalkoxy", "aminoalkoxy" respectively refers to an alkoxy substituted with one or more hydroxy (—OH), cyano (—CN) or amino (—NH$_2$), wherein the alkoxy is as defined herein. Such examples include, but are not limited to, hydroxymethoxy, hydroxyethoxy, cyanomethoxy, aminomethoxy, and the like.

The term "alkoxyalkyl", "alkylaminoalkyl" respectively refers to an alkyl substituted with one or more alkoxy or alkylamino, wherein the alkyl, alkoxy and alkylamino are as defined herein. Such examples include, but are not limited to, methoxymethyl, methoxyethyl, methylaminomethyl, methylaminoethyl and the like.

The term "carbocyclyl", "carbocycle" or "carbocyclic ring" refers to a monovalent or multivalent, saturated or partially unsaturated ring having 3 to 12 carbon atoms as a monocyclic, bicyclic or tricyclic ring system, wherein the carbocyclyl group is non-aromatic, and doesn't contain any aromatic ring in the system. In some embodiments, the carbocyclyl group contains 3 to 10 ring carbon atoms, such as $C_{3-10}$ carbocyclyl. In still other embodiments, the carbocyclyl group contains 3 to 8 ring carbon atoms, such as $C_{3-8}$ carbocyclyl. In yet other embodiments, the carbocyclyl contains 3 to 6 ring carbon atoms, such as $C_{3-6}$ carbocyclyl. Some examples of carbocyclyl group include, but are not limited to, cyclopropyl, cyclobutyl, cyclopentyl, cyclohexyl, cycloheptyl, cyclooctyl, etc. wherein the $C_{3-6}$ carbocyclyl includes, but is not limited to cyclopropyl, cyclobutyl, cyclopentyl and cyclohexyl. And wherein the carbocyclyl group is optionally substituted with one or more substituents described herein.

The term "cycloalkyl" refers to a saturated ring having 3 to 12 carbon atoms as a monocyclic, bicyclic, or tricyclic ring system. In some embodiments, the cycloalkyl group contains 3 to 10 ring carbon atoms, such as $C_{3-10}$ cycloalkyl. In other embodiments, the cycloalkyl group contains 3 to 8 ring carbon atoms, such as $C_{3-8}$ cycloalkyl. In still other embodiments, the cycloalkyl group contains 3 to 6 ring carbon atoms, such as $C_{3-6}$ cycloalkyl. Some examples of cycloalkyl group include, but are not limited to, cyclopropyl, cyclobutyl, cyclopentyl, cyclohexyl, cycloheptyl, cyclooctyl, etc., wherein the $C_{3-6}$ cycloalkyl includes, but is not limited to cyclopropyl, cyclobutyl, cyclopentyl and cyclohexyl. Wherein, the cycloalkyl group may be optionally substituted with one or more substituents disclosed herein.

The term "cycloalkylalkyl" refers to a cycloalkyl group attached to the rest of the molecule through an alkyl group, wherein the cycloalkyl and alkyl are as defined herein. In the invention, the description "$C_{3-10}$ cycloalkyl-$C_{1-6}$-alkyl" or "$C_{3-10}$ cycloalkyl-$C_{1-4}$-alkyl", and the like, refers to that $C_{3-10}$ cycloalkyl attaches to the rest of the molecular via $C_{1-6}$ alkyl or $C_{1-4}$ alkyl. The "cycloalkylalkyl" group may be optionally substituted with one or more substituents disclosed herein. Some non-limiting examples include cyclopropylmethyl, cyclopropylethyl, cyclopentylmethyl, cyclohexylmethyl, cyclohexylethyl, and the like.

The term "heterocyclyl" or "heterocyclic ring" refers to a saturated or partially unsaturated, monocyclic, bicyclic or tricyclic ring system in which at least one ring member is selected from nitrogen, sulfur and oxygen, wherein the heterocyclyl group is non-aromatic, and doesn't contain any aromatic ring in the system. Unless otherwise specified, the heterocyclyl group may be carbon or nitrogen linked, and a —CH$_2$— group can be optionally replaced by a —C(=O)— group. In which, the sulfur can be optionally oxygenized to S-oxide and the nitrogen can be optionally oxygenized to N-oxide. And wherein the carbocyclyl group is optionally substituted with one or more substituents described herein.

In some embodiments, the heterocyclyl group may be a $C_{2-9}$ heterocyclyl group, which refers to a heterocyclyl group containing 2 to 9 ring carbon atoms and at least one ring heteroatom selected from O, S and N. In other embodiments, the heterocyclyl group may be a $C_{2-7}$ heterocyclyl group, which refers to a heterocyclyl group containing 2 to 7 ring carbon atoms and at least one heteroatom selected from O, S and N. In still other embodiments, the heterocyclyl group may be a $C_{2-5}$ heterocyclyl group, which refers to a heterocyclyl group containing 2 to 5 ring carbon atoms and at least one heteroatom selected from O, S and N. Some non-limiting examples of the heterocyclyl group include:

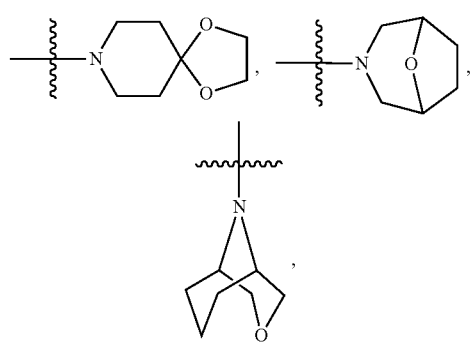

oxiranyl, thietanyl, azetidinyl, pyrrolidinyl, pyrazolinyl, pyrazolidinyl, imidazolinyl, imidazolidinyl, oxazolidinyl, tetrahydrofuranyl, dihydrothienyl, dihydropyranyl, piperidinyl, morpholinyl, tetrahydropyrimidinyl, oxazinanyl, thiomorpholinyl and piperazinyl, etc. A —CH$_2$— group of the heterocyclyl group may be substituted with —C(=O)—, some non-limiting examples of such group include 2-oxopyrrolidinyl, 2-piperidinonyl, 3-morpholinonyl, 3-thiomorpholinonyl and oxotetrahydropyrimidinyl, etc. In some embodiments, examples of $C_{2-5}$ heterocyclyl groups of the invention include, but are not limited to, azetidinyl, pyrrolidinyl (i.e., tetrahydropyrrolyl), pyrazolidinyl, piperidinyl, piperazinyl, morpholinyl, oxomorpholinyl, thiomorpholinyl, 4,4-dioxothiomorpholinyl, tetrahydrofuranyl, oxazolidinyl (i.e., tetrahydrooxazolyl), thiazolidinyl (i.e., tetrahydrothiazolyl), 1,1-dioxoisothiazolidinyl (such as

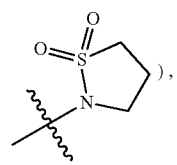 [SMILES: *N1CCCS1(=O)=O]

oxo-1,3-oxazinanyl (such as

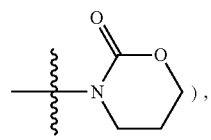 [SMILES: *N1CCCOC1=O]

oxazolidinyl (such as

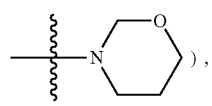 [SMILES: *N1CCCOC1]

dihydropyridine (such as 1,2-dihydropyridine

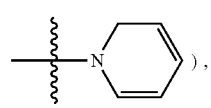

dihydropyrimidine (such as 1,6-dihydropyrimidine

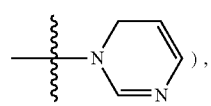

dihydropyrazine (such as 1,2-dihydropyrazine

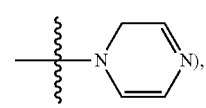

tetrahydropyridine, tetrahydropyrimidine or tetrahydropyrazine and the like.

The term "heterocyclylalkyl" refers to a heterocyclyl group attached to the rest of the molecule through an alkyl group, wherein the heterocyclyl and alkyl are as defined herein. In the invention, the group "$C_{2-9}$ heterocyclyl-$C_{1-6}$-alkyl", and the like, refers to that $C_{2-9}$ cycloalkyl attaches to the rest of the molecular via $C_{1-6}$ alkyl. The heterocyclylalkyl group may be optionally substituted with one or more substituents disclosed herein. Some non-limiting examples of such group included tetrahydropyranylmethyl, tetrahydropyranylethyl, tetrahydrofuranylmethyl, tetrahydrofuranylethyl, pyrrolidinylmethyl, piperidinylmethyl, piperidinylethyl, morpholinylmethyl and morpholinylethyl, etc.

The term "halogen" refers to fluorine (F), chlorine (Cl), bromine (Br) or iodine (I).

The term "aryl" refers to monocyclic, bicyclic and tricyclic carbocyclic ring systems having a total of six to fourteen ring members, or six to twelve ring members, or six to ten ring members, wherein at least one ring in the system is aromatic, and the aryl group has a single point or multipoint of attachment to the rest of the molecule. The term "aryl" and "aromatic ring" can be used interchangeably herein. Some non-limiting examples of the aryl group include phenyl, 2,3-dihydro-1H-indenyl, naphthalenyl and anthracenyl, etc. The aryl group may be optionally substituted with one or more substituents disclosed herein. Unless otherwise specified, the group "$C_{6-14}$ aryl" refers to an aryl group having 6-14 ring carbon atoms.

The term "arylalkyl" or "aralkyl" refers to an aryl group attached to the rest of the molecule through an alkyl group, wherein the aryl and alkyl are as defined herein. For example, the group "$C_{6-14}$ aryl-$C_{1-6}$-alkyl" refers to that $C_{6-14}$ aryl group attaches to the rest of the molecular via $C_{1-6}$ alkyl. The arylalkyl group may be optionally substituted with one or more substituents disclosed herein. Some non-limiting examples of such group include benzyl, phenylethyl and naphthalenylmethyl, etc.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from nitrogen, oxygen and sulfur, and that has a single point or multipoint of attachment to the rest of the molecule. When —$CH_2$— group exsits in heteroaryl group, the —$CH_2$— disclosed herein is optionally replaced with —C(=O)—. Unless specified, the heteroaryl group can be attached to the rest of the molecule (eg., the main structure in the general formula) through any reasonable site (may be C in CH, or N in NH.) The term "heteroaryl" and "heteroaromatic ring" or "heteroaromatic compound" can be used interchangeably herein. In other embodiments, the heteroaryl group may be a $C_{1-9}$ heteroaryl group, which refers to a heteroaryl group containing 1 to 9 ring carbon atoms and at least one ring heteroatom selected from O, S and N. In other embodiments, the heteroaryl group may be a $C_{1-7}$ heteroaryl group, which refers to a heteroaryl group containing 1 to 7 ring carbon atoms and at least one ring heteroatom selected from O, S and N. In still other embodiments, the heteroaryl group may be a $C_{1-6}$ heteroaryl group, which refers to a heteroaryl group containing 1 to 6 ring carbon atoms and at least one ring heteroatom selected from O, S and N. In other embodiments, the heteroaryl group may be a $C_{1-5}$ heteroaryl group, which refers to a heteroaryl group containing 1 to 5 ring carbon atoms and at least one ring heteroatom selected from O, S and N. In still other embodiments, the heteroaryl group may be a $C_{1-4}$ heteroaryl group, which refers to a heteroaryl group containing 1 to 4 ring carbon atoms and at least one ring heteroatom selected from O, S and N. In yet other embodiments, the heteroaryl group may be a $C_{1-3}$ heteroaryl group, which refers to a heteroaryl group containing 1 to 3 ring carbon atoms and at least one ring heteroatom selected from O, S and N. In some embodiments, the term "6- to 10-membered heteroaryl" refers to the heteroaryl consists of 6-10 ring atoms, wherein at least one of the ring atoms is a heteroatom selected from O, N and S. Some non-limiting examples of such group include furyl, imidazolyl, isoxazolyl, oxazolyl, pyrrolyl, pyrazolyl, pyridyl, pyrimidinyl, pyridazinyl, pyrazinyl, thienyl, thiazolyl, etc, and also include the following non-limiting bicyclic ring: benzimidazolyl, benzofuranyl, benzothiophenyl, indolyl, oxoindolyl, indolinyl, imidazopyridyl, pyrazopryridyl, pyrazopyrimidinyl, quinolyl, isoquinolyl and quinazolinyl, etc. The heteroaryl group may be optionally substituted with one or more substituents disclosed herein.

The term "heteroarylalkyl" refers to a heteroaryl group attached to the rest of the molecule through an alkyl group, wherein the heteroaryl and alkyl are as defined herein. The "heteroarylalkyl" group may be optionally substituted with one or more substituents disclosed herein. Some non-limiting examples of such group included pyridylmethyl, pyrrolylethyl and quinolylmethyl, etc.

The term "x- to y-membered" (each x and y is independently any non-zero natural number, and y>x) refers to the cyclic group consists of x to y ring atoms, wherein "x- to y-" includes any natural numbers between x and y. The ring atoms here include carbon atoms and/or heteroatoms such as O, N, S, and P, etc. For example, "3- to 8-membered", "3- to 10-membered", "3- to 6-membered" or "6- to 10-membered" refers to the cyclic group consists of 3 to 8, 3 to 10, 3 to 6 or 6 to 10 ring atoms. The ring atoms include carbon atoms and/or heteroatoms such as O, N, S, and P, etc. For another example, "6- to 10-membered heteroaryl" represents a heteroaryl group consisting of 6, 7, 8, 9 or 10 ring atoms.

The term "acyl" denotes —C(=O)—R, wherein the substituent R is attached to the rest of the molecule through a carbonyl group (—C(=O)—), wherein R is a substituent described herein, including but not limited to alkyl, alkoxy, hydroxy, amino, cycloalkyl, heterocyclyl, aryl, heteroaryl, and the like. Wherein the alkyl, alkoxy, hydroxy, amino, cycloalkyl, heterocyclyl, aryl and heteroaryl are as defined herein, and such examples include, but are not limited to, acetyl (—C(=O)$CH_3$), carboxy (—C(=O)OH), methoxycarbonyl (—C(=O)$OCH_3$), carbamoyl (—C(=O)$NH_2$), benzoyl, and the like. The term "sulfonyl" denotes —S(=O)$_2$—R, wherein the substituent R is attached to the rest of the molecule through a sulfonyl group (—S(=O)$_2$—), wherein R is a substituent described herein, including but not limited to alkyl, alkoxy, hydroxy, amino, cycloalkyl, heterocyclyl, aryl, heteroaryl, and the like. Wherein the alkyl, alkoxy, hydroxy, amino, cycloalkyl, heterocyclyl, aryl and heteroaryl are as defined herein, and such examples include, but are not limited to, sulfonic acid (—S(=O)$_2$OH), methylsulfonyl (—S(=O)$_2$$CH_3$), methoxysulfonyl (—S(=O)$_2$$OCH_3$), aminosulfonyl (—S(=O)$_2$$NH_2$), phenylsulfonyl, and the like.

The term "sulfinyl" denotes —S(=O)—R, wherein the substituent R is attached to the rest of the molecule through a sulfonyl group (—S(=O)—), wherein R is a substituent described herein, including but not limited to alkyl, alkoxy, hydroxy, amino, cycloalkyl, heterocyclyl, aryl, heteroaryl, and the like. Wherein, alkyl, alkoxy, hydroxy, amino, cycloalkyl, heterocyclyl, aryl and heteroaryl are as defined herein, and such examples include, but are not limited to, sulfinyl (—S(=O)OH), methylsulfinyl (—S(=O)CH$_3$), phenylsulfinyl, and the like.

The terms "alkylcarbonyl", "alkylsulfonyl" denote the groups —C(=O)-alkyl and —S(=O)$_2$-alkyl, respectively, wherein the alkyl group is as defined herein. Such examples include, but are not limited to, acetyl (—C(=O)CH$_3$), methylsulfonyl (—S(=O)$_2$CH$_3$), and the like.

The terms "alkylcabonylamino", "alkylsulfonylamino", "alkoxycarbonylamino" denote respectively the group —NH—C(=O)-alkyl, —NH—S(=O)$_2$-alkyl and —NH—C(=O)-alkoxy (i.e., —NH—C(=O)—O-alkyl), wherein the alkyl and alkoxy groups all are as defined in the invention. Such examples include, but are not limited to, methylcarbonylamino (—NH—C(=O)CH$_3$), methylsulfonylamino (—NH—S(=O)$_2$CH$_3$), methoxylcarbonylamino (—NH—C(=O)—O—CH$_3$) and the like.

The term "alkoxycarbonyl", "alkylaminocarbonyl", "cycloalkylcarbonyl", "heterocyclylcarbonyl", "arylcarbonyl", "heteroarylcarbonyl" respectively refers to group —C(=O)-alkoxy, —C(=O)-alkylamino, —C(=O)-cycalkyl, —C(=O)-heterocyclyl, —C(=O)-aryl, —C(=O)-heteroaryl, wherein the alkoxy, alkylamino, cycloalkyl, heterocyclyl, aryl and heteroaryl are all as defined herein. Such examples include, but are not limited to, methoxycarbonyl, ethoxycarbonyl, propoxycarbonyl, methylaminocarbonyl, ethylaminocarbonyl, cyclopropylcarbonyl, cyclopentylcarbonyl, cyclohexylcarbonyl, cyclopropoxycarbonyl, tetrahydrofurylcarbonyl, tetrahydropyranylcarbonyl, piperidylcarbonyl, piperazinylcarbonyl, morpholinylcarbonyl, tetrahydrothienylcarbonyl, pyrrolidinylcarbonyl, phenylcarbonyl, pyridylcarbonyl, pyrimidinylcarbonyl, pyrrolylcarbonyl, imidazolylcarbonyl, pyrazolylcarbonyl, thienylcarbonyl or furylcarbonyl, and the like.

As described herein, a bond drawn from a substituent (R)$_{n1}$ to the center of one ring within a ring system represents substitution of n1 substituents R at any substitutable position on the rings. For example, formula a represents substitution of substituent R$^4$ at any substitutable position on the C2 ring, furthermore, C2 ring can be optionally substituted with r R$^3$. When the C2 ring is a bicyclic system, R$^4$ or R$^3$ may be substituted at any substitutable position on any ring.

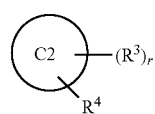

formula a

As described in the present invention, there are two linking sites on the group "—(CR$^a$R$^b$)$_f$—O—" that can be linked to the rest of the molecule, and the connection types of the two linking sites can be interchanged. For example, when L described in the present invention is a group in Formula b, L (ie., —(CR$^a$R$^b$)$_f$—O—) may connect to the rest of the molecule (eg., indazole structure in Formula (I)) via the E-terminus or E' terminus.

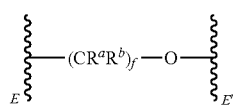

formula b

As described in the present invention, the description "any adjacent two R$^3$, together with the carbon atoms to which they are attached, form a 3- to 6-membered carbocyclic ring, heterocyclic ring, aromatic ring or heteroaromatic ring" means that any adjacent two R$^3$, together with the carbon atoms to which they are attached, may form a 3- to 6-membered carbocyclic ring, a 3- to 6-membered heterocyclic ring, a 3- to 6-membered aromatic ring or a 3- to 6-membered heteroaromatic ring, wherein the carbocyclic ring, heterocyclic ring, aromatic ring and heteroaromatic ring are all as defined in the present invention. Wherein the 3- to 6-membered aromatic ring includes 6-membered aromatic ring, i.e., benzene ring; the 3- to 6-membered heteroaromatic ring includes 5- to 6-membered heteroaromatic ring; the 3- to 6-membered carbocyclic ring and 3- to 6-membered heterocyclic ring include saturated or partially unsaturated carbocyclic ring or heterocyclic ring, and wherein —CH$_2$— may be replaced by —C(=O)—; The sulfur atom in the heterocyclic ring may be optionally oxidized to a S-oxide, and the nitrogen atom may be optionally oxidized to an N-oxide. When ring C2 is aryl or heteroaryl, the 3- to 6-membered carbocyclic ring or 3- to 6-membered heterocyclic ring is an unsaturated carbocyclic or heterocyclic ring, specific examples include but are not limited to,

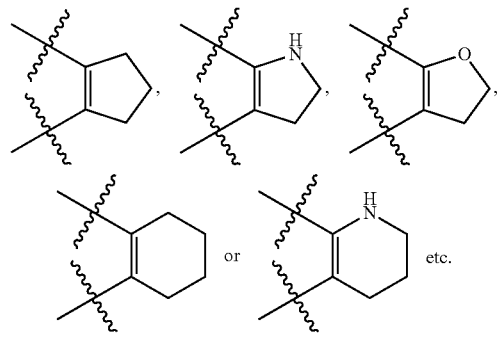

Examples of the 3- to 6-membered aromatic ring and 3- to 6-membered heteroaromatic ring include, but are not limited to,

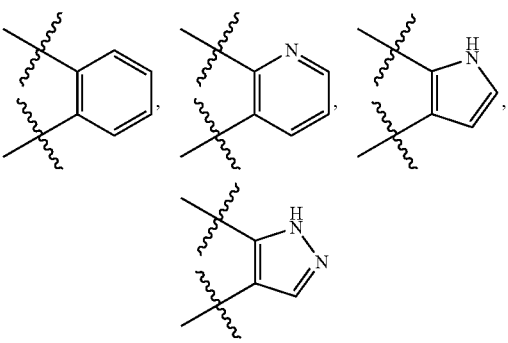

and the like. Further more, the 3- to 6-membered carbocyclic ring, heterocyclic ring, aromatic ring and heteroaryl rings are unsubstituted or optionally substituted with 1, 2, 3 or 4 R$^z$ as described herein.

As described in the present invention, the description "R$^{5a}$ and R$^{5b}$, together with the N atom to which they are attached, form a 3- to 6-membered heterocyclic ring or heteroaromatic ring; or, $R^{5c}$ and $R^{5d}$, together with the N atom to which they are attached, form a 3- to 6-membered heterocyclic ring or heteroaromatic ring" means that $R^{5a}$ and $R^{5b}$, together with the N atom to which they are attached, or, $R^{5c}$ and $R^{5d}$, together with the N atom to which they are attached, may form a 3- to 6-membered heterocyclic ring or 3- to 6-membered heteroaromatic ring, wherein the heterocyclic ring and heteroaromatic ring are all as defined in the present invention. Wherein the 3- to 6-membered heteroaromatic ring includes 5- to 6-membered heteroaromatic ring; the 3- to 6-membered heterocyclic ring or 3- to 6-membered heteroaromatic ring includes but not limited to the following cyclic groups: azetidine, pyrrolidine (i.e., 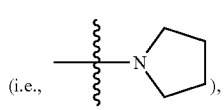), oxazolidine (i.e., 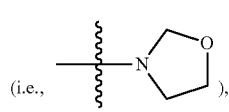), thiazolidine (i.e., 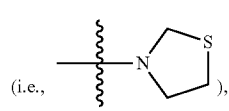), isothiazolidine (i.e., 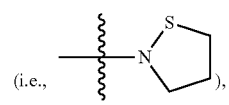), piperidine (i.e., 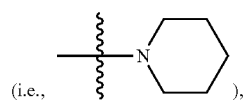), morpholine (i.e., 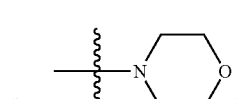), piperazine (i.e., 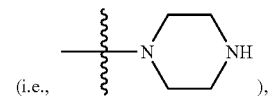), thiomorpholine (i.e, 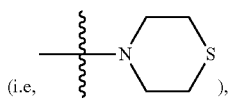), 1,3-oxazinidine (i.e., 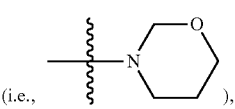), pyrrole (i.e, 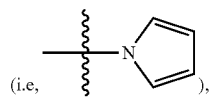), pyrazole (i.e, 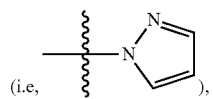), imidazole (i.e, 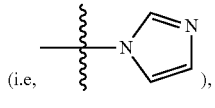), triazole (including but not limited to

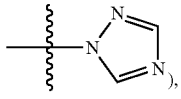 [SMILES: *n1cncn1]), tetrazole (including but not limited to

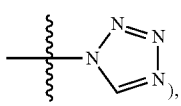), dihydropyridine (i.e, 1,2-dihydropyridine

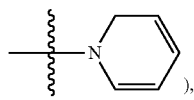

dihydropyrimidine (e.g., 1,6-dihydropyrimidine

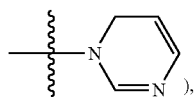

dihydropyrazine (e.g., 1,2-dihydropyrazine

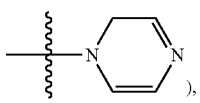

tetrahydropyridine, tetrahydropyrimidine or tetrahydropyrazine, and the like. Furthermore, wherein the —$CH_2$— in "3- to 6-membered heterocyclic ring" may be replaced by —C(=O)—; the sulfur atom in the heterocyclic ring may be optionally oxidized to a S-oxide, and the nitrogen atom may be optionally oxidized to an N-oxide. Such examples include, but are not limited to, dioxoisothiazolidine

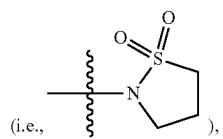

and the like.

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means molecular entities and compositions approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution solutions (such as saline solution, glucose solution, glycerol solution) are preferably employed as carriers, particularly for injectable solutions. Suitable pharmaceutical carriers are described in "Remington's Pharmaceutical Sciences" by E. W. Martin.

The term "sGC stimulator" refers to a compound or agent that has a stimulatory effect on soluble guanylate cyclase (sGC). In some embodiments, "stimulator" and "agonist" may be used interchangeably.

The term "prodrug" refers to a compound that is transformed in vivo into a compound of the invention (i.e., the compound represented by Formula (I), Formula (Ia), Formula (Ib), Formula (Ic), Formula (II), Formula (IIa), Formula (IIb), Formula (IIc), Formula (IId), Formula (III), Formula (IV), Formula (IVa), Formula (IVb), Formula (IVc), Formula (Va), Formula (Vb), Formula (Vc) or Formula (Vd)). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts formed from acid include, but are not limited to, inorganic acid salts such as hydrochloride, hydrobromide, phosphate, sulfate, perchlorate; organic acid salts such as acetate, oxalate, maleate, tartrate, citrate, succinate, malonate; or obtained by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid and ethanolamine. The term "hydrate" refers to the complex where the solvent molecule is water.

An "ester" refers to an in vivo hydrolysable ester of a compound of the invention containing hydroxy or carboxyl group. For example, a pharmaceutically acceptable ester is which is hydrolysed in the human or animal body to produce the parent alcohol or acid. The compounds of the present invention (i.e., the compound represented by Formula (I), Formula (Ia), Formula (Ib), Formula (Ic), Formula (II), Formula (IIa), Formula (IIb), Formula (IIc), Formula (IId), Formula (III), Formula (IV), Formula (IVa), Formula (IVb), Formula (IVc), Formula (Va), Formula (Vb), Formula (Vc) or Formula (Vd)) contain a carboxy group and can form in vivo hydrolysable esters with suitable groups. Such groups include, but are not limited to, alkyl, arylalkyl and the like.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

As used in the present invention, "the compound of the invention", "the compound of the present invention", "the compound described in the present invention", "a compound described in the present invention" or the like are all referred to the compound represented by any one of the general Formula described in the present invention, i.e., the compound represented by Formula (I), Formula (Ia), Formula (Ib), Formula (Ic), Formula (II), Formula (IIa), Formula (IIb), Formula (IIc), Formula (IId), Formula (III), Formula (IV), Formula (IVa), Formula (IVb), Formula (IVc), Formula (Va), Formula (Vb), Formula (Vc) or Formula (Vd).

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Any formula given herein is also intended to represent isotopically unenriched forms as well as isotopically enriched forms of the compounds. Any formula given herein is also intended to represent isotopically unenriched forms as well as isotopically enriched forms of the compounds. Examples of isotopes that can be incorporated into compounds of the invention include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$ respectively.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of the invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is should be understood that deuterium in this context is regarded as a substituent of a compound of the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., $D_2O$, acetone-$d_6$, DMSO-$d_6$.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

As used herein, the abbreviations for any protective groups, amino acids and other compounds are, unless otherwise indicated, in accord with their common usage, recognized abbreviations, or the IUPAC-IUB Commission on Biochemical Nomenclature (See, *Biochem*. 1972, 11: 942-944).

Description of Compounds of the Invention

The present invention provides a novel fluorine-substituted indazole compounds as sGC stimulators and pharmaceutical compositions thereof, and the use of the compounds or the pharmaceutical compositions in the manufacture of a medicament, wherein the medicament is used for the treatment and/or prevention of sGC-mediated diseases such as heart failure, sclerosis, systemic sclerosis, sickle cell anemia, achalasia of cardia, pulmonary fibrosis, idiopathic pulmonary fibrosis, cystic fibrosis, pulmonary hypertension and the like.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

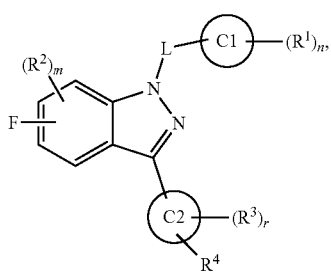
(I)

wherein, C1 is aryl, heteroaryl, carbocyclyl or heterocyclyl; C2 is aryl, heteroaryl, carbocyclyl or heterocyclyl; and each L, $R^1$, $R^2$, $R^3$, $R^4$, m, n and r is as defined herein.

In some embodiments, provided herein is a compound having Formula (Ia), Formula (Ib) or Formula (Ic), or a stereoisomer, a geometric isomer, a tautomer, an N-oxide, a hydrate, a solvate, a metabolite, an ester, a pharmaceutically acceptable salt or a prodrug thereof,

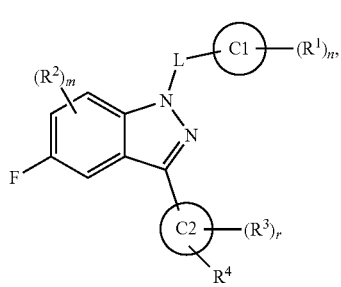
(Ia)

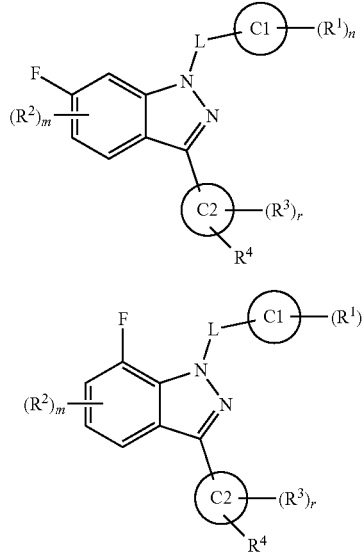
(Ib)

(Ic)

wherein each L, C1, C2, $R^1$, $R^2$, $R^3$, $R^4$, m, n and r is as defined herein.

In some embodiments, L is —$(CR^aR^b)_t$—, —$(CR^aR^b)_f$—O—, —$(CR^aR^b)_f$—S—, —$(CR^aR^b)_f$—S(=O)—, —$(CR^aR^b)_f$—S(=O)$_2$—, —$(CR^aR^b)_f$—N($R^c$)—, —$(CR^aR^b)_f$—C(=O)N($R^c$)—, —C(=O)N($R^c$)—$(CR^aR^b)_f$— or —$(CR^aR^b)_f$—C(=O)—;

t is 1, 2, 3 or 4; and each f is independently 0, 1, 2, 3 or 4.

In some embodiments, each $R^a$ and $R^b$ is independently H, D, F, Cl, Br, I, CN, amino, hydroxy, mercapto, $C_{1-6}$ alkyl, $C_{2-6}$ alkenyl, $C_{2-6}$ alkynyl, halo $C_{1-6}$ alkyl, $C_{1-6}$ alkoxy, $C_{1-6}$ alkylamino, halo $C_{1-6}$ alkoxy, acyl, sulfonyl, $C_{3-6}$ cycloalkyl, $C_{2-5}$ heterocyclyl, $C_{6-10}$ aryl or $C_{1-5}$ heteroaryl; or, $R^a$ and $R^b$ together form carbonyl; or, $R^a$ and $R^b$, together with the carbon atom to which they are attached, form a 3- to 8-membered carbocyclic ring or 3- to 8-membered heterocyclic ring;

each $R^c$ is independently H, D, $C_{1-6}$ alkyl, $C_{2-6}$ alkenyl, $C_{2-6}$ alkynyl, halo $C_{1-6}$ alkyl, acyl, sufonyl, $C_{3-6}$ cycloalkyl, $C_{2-5}$ heterocyclyl, $C_{6-10}$ aryl or $C_{1-5}$ heteroaryl.

In some embodiments, each $R^a$ and $R^b$ is independently H, D, F, Cl, Br, I, CN, amino, hydroxy, mercapto, methyl, ethyl, propyl, butyl, $C_{2-4}$ alkenyl, $C_{2-4}$ alkynyl, halo $C_{1-4}$ alkyl, $C_{1-4}$ alkoxy, $C_{1-4}$ alkylamino, halo $C_{1-4}$ alkoxy, $C_{3-6}$ cycloalkyl, $C_{2-5}$ heterocyclyl, phenyl or $C_{1-5}$ heteroaryl; or, $R^a$ and $R^b$ together form carbonyl; or, $R^a$ and $R^b$, together with the carbon atom to which they are attached, form a 3- to 6-membered carbocyclic ring or 3- to 6-membered heterocyclic ring; and each $R^c$ is independently H, D, methyl, ethyl, propyl, butyl, $C_{2-4}$ alkenyl, $C_{2-4}$ alkynyl, halo $C_{1-4}$ alkyl, $C_{3-6}$ cycloalkyl, $C_{2-5}$ heterocyclyl, phenyl or $C_{1-5}$ heteroaryl.

In some embodiments, each L is independently —CH$_2$—, —CH(CH$_3$)—, —(CH$_2$)$_2$—, —(CH$_2$)$_3$—,

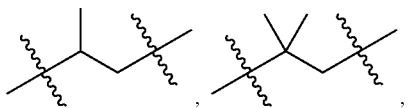

-continued

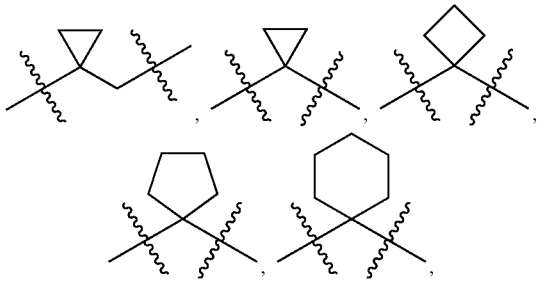

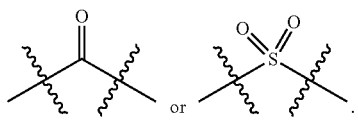

In some embodiments, C1 is $C_{6-10}$ aryl, $C_{1-9}$ heteroaryl, $C_{3-10}$ carbocyclyl or $C_{2-9}$ heterocyclyl.

In some embodiments, C2 is $C_{6-10}$ aryl, $C_{3-10}$ carbocyclyl, $C_{2-9}$ heterocyclyl or 6- to 10-membered heteroaryl.

In some embodiments, C1 is $C_{6-10}$ aryl, $C_{1-9}$ heteroaryl, $C_{3-10}$ carbocyclyl or $C_{2-9}$ heterocyclyl; and C2 is $C_{6-10}$ aryl, $C_{3-10}$ carbocyclyl, $C_{2-9}$ heterocyclyl or 6- to 10-membered heteroaryl.

In some embodiments, C1 is:

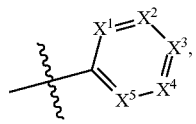 (C1-1)

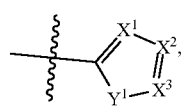 (C1-2)

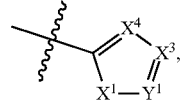 (C1-3)

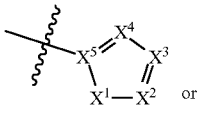 (C1-4)

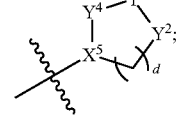 (C1-5)

each $X^1$, $X^2$, $X^3$, $X^4$ and $X^5$ is independently N or CH;
each $Y^1$, $Y^2$, $Y^3$ and $Y^4$ is independently $CH_2$, C(=O), NH, S, S(=O), S(=O)$_2$ or O;
d is 0, 1, 2, 3 or 4;

wherein,

is the bond through which C1 is attached to L.

In some embodiments, C1 is:

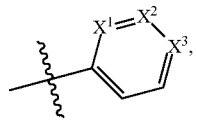 (C1-1a)

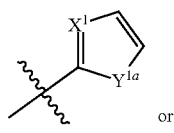 (C1-2a)

or

 (C1-5a)

wherein each $X^1$, $X^2$, $X^3$ and $X^5$ is independently N or CH;
$Y^{1a}$ is $CH_2$, NH, S or O;
$Y^2$ is $CH_2$, C(=O), NH, S, S(=O), S(=O)$_2$ or O;
d is 0, 1, 2, 3 or 4;
wherein,

is the bond through which C1 is attached to L.

In some embodiments, C1 is

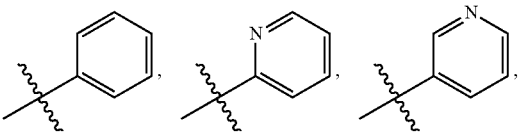

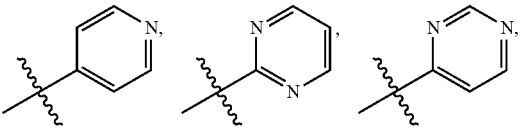

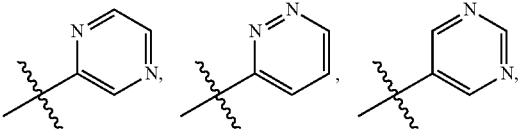

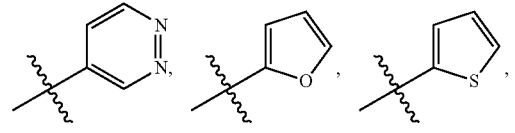

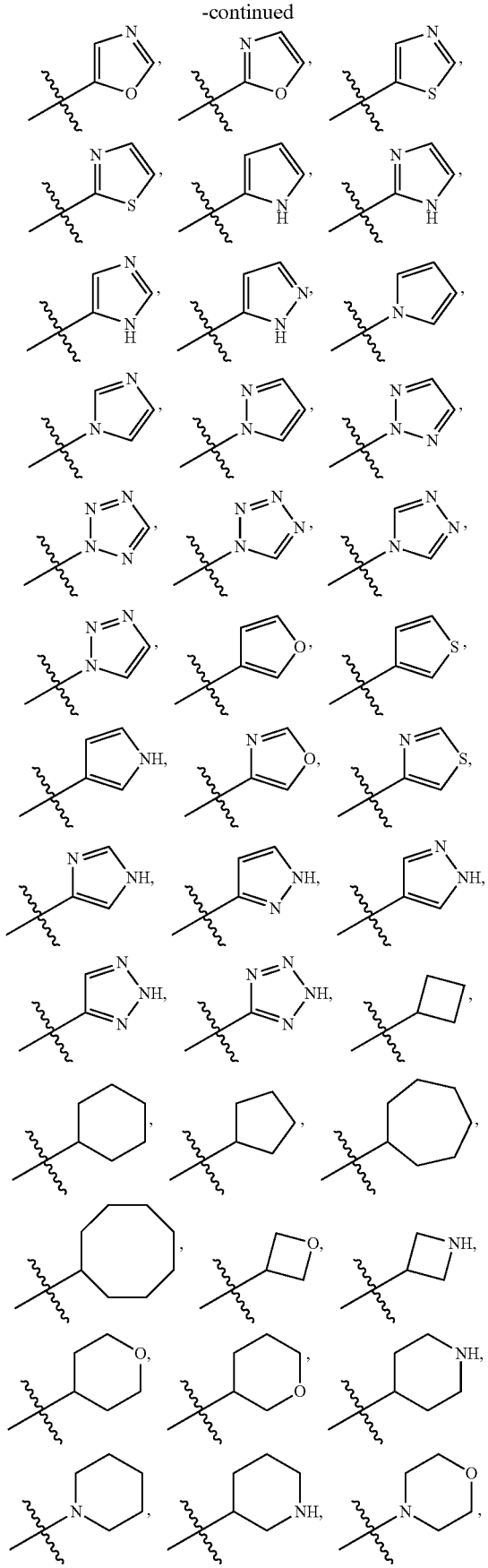
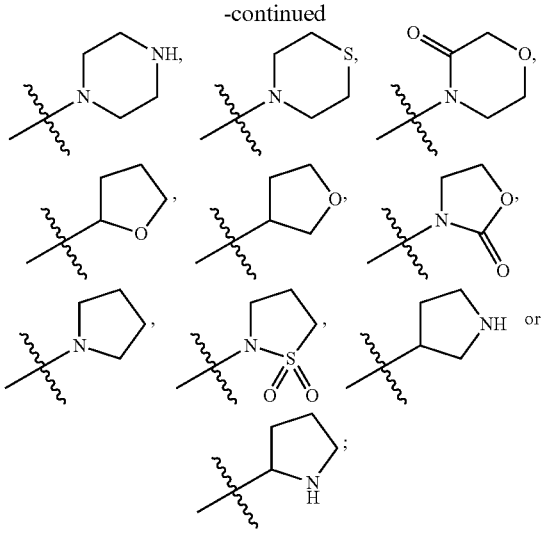
wherein,
is the bond through which C1 is attached to L.
In some embodiments, C2 is:
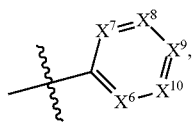 (C2-1)
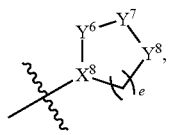 (C2-2)
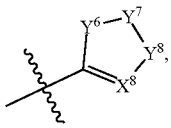 (C2-3)
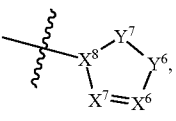 (C2-4)
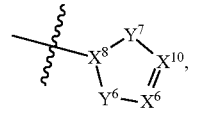 (C2-5)
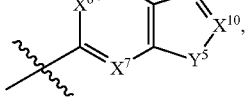 (C2-6)

-continued
(C2-7)
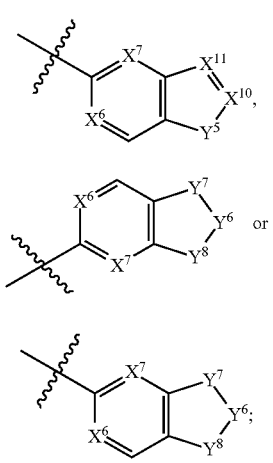
(C2-8)
(C2-9)
each $X^6$, $X^7$, $X^8$, $X^9$, $X^{10}$ and $X^{11}$ is independently N or CH;
each $Y^6$, $Y^7$ and $Y^8$ is independently $CH_2$, C(=O), NH, S, S(=O), S(=O)$_2$ or O;
each $Y^5$ is independently $CH_2$, NH, S or O;
e is 0, 1, 2, 3 or 4;
wherein,
is the bond through which C2 is attached to indazole.
In some embodiments, C2 is
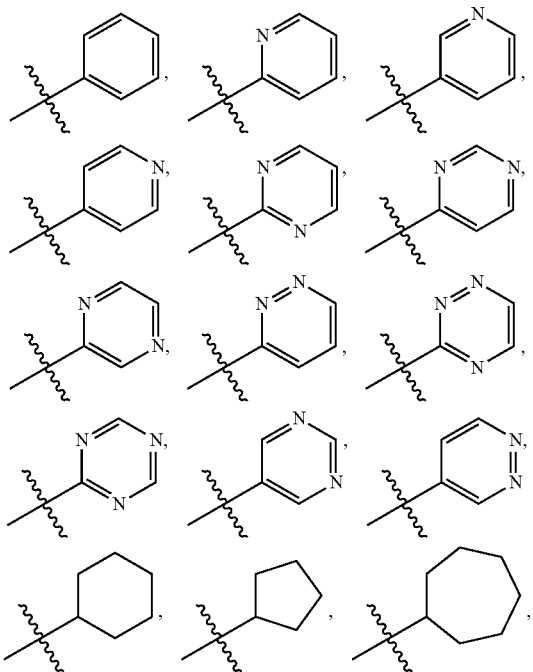
-continued
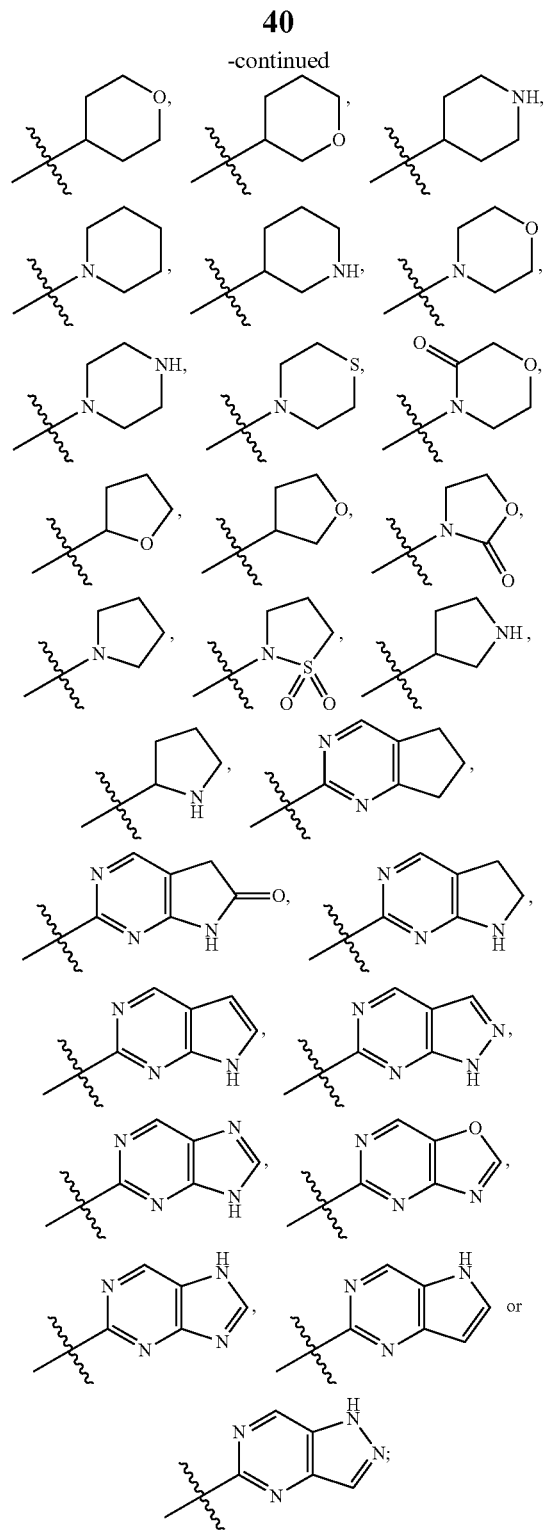
wherein,
is the bond through which C2 is attached to indazole.

In some embodiments, C2 is:

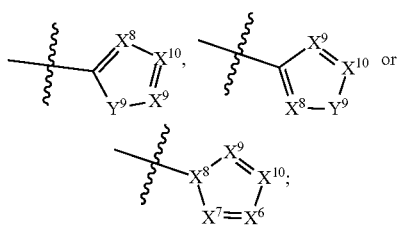

wherein each $X^6$, $X^7$, $X^8$, $X^9$ and $X^{10}$ is independently N or CH;
$Y^9$ is $CH_2$, NH, O or S;
wherein,

is the bond through which C2 is attached to indazole.

In some embodiments, C2 is

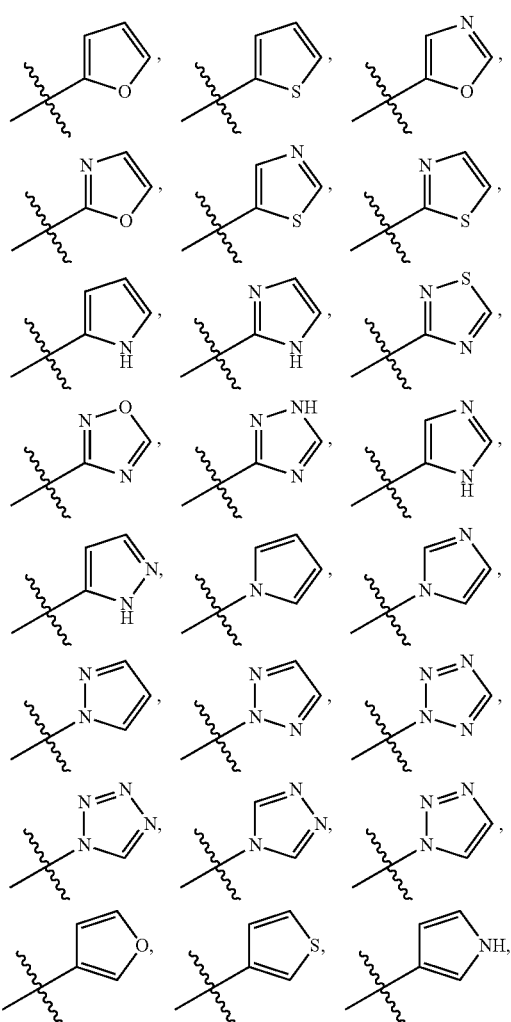

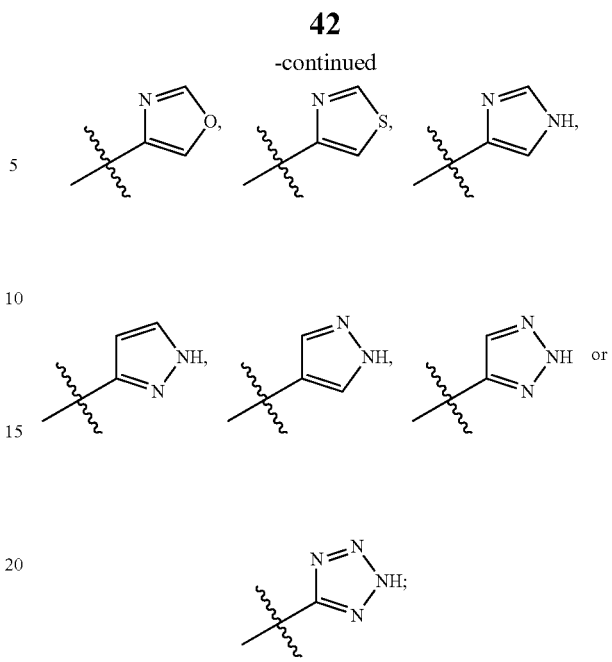

wherein,

is the bond through which C2 is attached to indazole.

In some embodiments, the compound of the invention has Formula (II), or a stereoisomer, a geometric isomer, a tautomer, an N-oxide, a hydrate, a solvate, a metabolite, an ester, a pharmaceutically acceptable salt or a prodrug thereof,

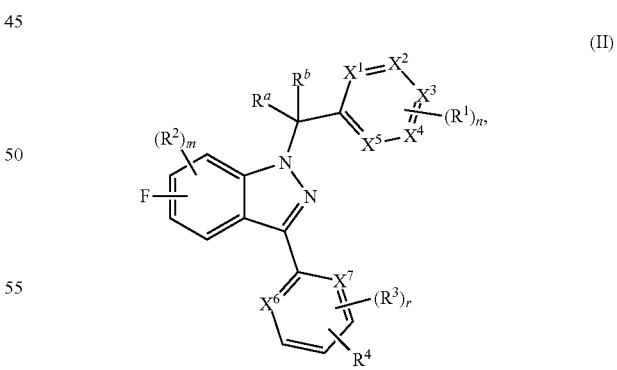

(II)

wherein each $R^1$, $R^2$, $R^3$, $R^4$, $R^a$, $R^b$, m, n, r, $X^1$, $X^2$, $X^3$, $X^4$, $X^5$, $X^6$ and $X^7$ is as defined herein.

In some embodiments, the compound of the invention has Formula (IIa), Formula (IIb) or Formula (IIc), or a stereoisomer, a geometric isomer, a tautomer, an N-oxide, a hydrate, a solvate, a metabolite, an ester, a pharmaceutically acceptable salt or a prodrug thereof,

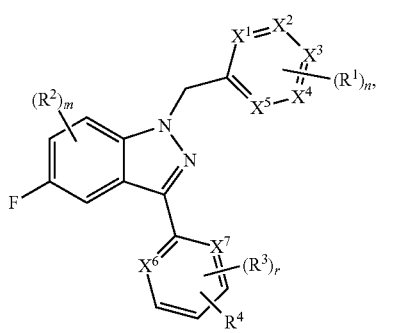

(IIa)

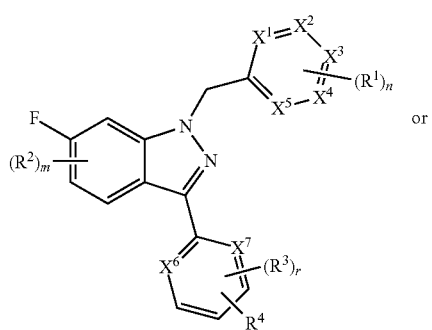

or (IIb)

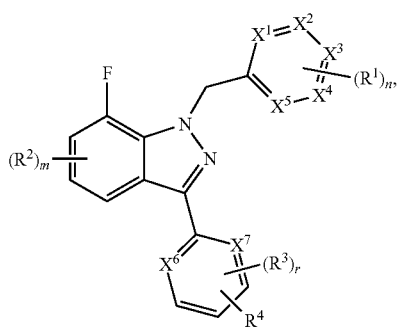

(IIc)

wherein each $R^1$, $R^2$, $R^3$, $R^4$, m, n, r, $X^1$, $X^2$, $X^3$, $X^4$, $X^5$, $X^6$ and $X^7$ is as defined herein.

In some embodiments, the compound of the invention has Formula (IId), or a stereoisomer, a geometric isomer, a tautomer, an N-oxide, a hydrate, a solvate, a metabolite, a ester, a pharmaceutically acceptable salt or a prodrug thereof, (IId)

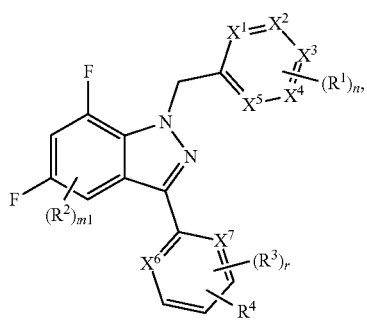

wherein m1 is 0, 1 or 2; and
each $R^1$, $R^2$, $R^3$, $R^4$, n, r, $X^1$, $X^2$, $X^3$, $X^4$, $X^5$, $X^6$ and $X^7$ is as defined herein.

In some embodiments, $R^4$ is D, F, Cl, Br, I, CN, $NO_2$, mercapto, $C_{1-6}$ alkyl, $C_{2-6}$ alkenyl, $C_{2-6}$ alkynyl, halo $C_{1-6}$ alkyl, —$(CR^{6c}R^{6d})_g$—$C_{3-6}$ cycloalkyl, —$(CR^{6c}R^{6d})_g$—$C_{2-5}$ heterocyclyl, —$(CR^{6c}R^{6d})_g$—$C_{6-10}$ aryl, —$(CR^{6c}R^{6d})_g$—$C_{1-5}$ heteroaryl, —$(CR^{6c}R^{6d})_g NR^{5c}R^{5d}$, —$(CR^{6c}R^{6d})_g C(=O)(CR^{6c}R^{6d})_h NR^{5c}R^{5d}$, —$(CR^{6c}R^{6d})_g C(=O)(CR^{6c}R^{6d})_h OR^{9a}$, —$(CR^{6c}R^{6d})_g OR^{9a}$, —$(CR^{6c}R^{6d})_g S(=O)_2(CR^{6c}R^{6d})_h OR^{9a}$, —$(CR^{6c}R^{6d})_g S(=O)_2(CR^{6c}R^{6d})_h NR^{5c}R^{5d}$, —$(CR^{6c}R^{6d})_g N(R^{5e})(CR^{6c}R^{6d})_i C(=O)(CR^{6c}R^{6d})_h OR^{9a}$, —$(CR^{6c}R^{6d})_g N(R^{5e})C(=O)(CR^{6c}R^{6d})_h NR^{5c}R^{5d}$, —$(CR^{6c}R^{6d})_g N(R^{5e})C(=O)R^{8a}$, —$(CR^{6c}R^{6d})_g N(R^{5e})S(=O)_2R^{7a}$, —$(CR^{6c}R^{6d})_g S(=O)_2R^{7a}$, —$(CR^{6c}R^{6d})_g OS(=O)_2R^{7a}$, —$(CR^{6c}R^{6d})_g OC(=O)(CR^{6c}R^{6d})_h OR^{9a}$, —$(CR^{6c}R^{6d})_g OC(=O)R^{8a}$ or —$(CR^{6c}R^{6d})_g C(=O)R^{8a}$; $R^4$ is unsubstituted or substituted with 1, 2, 3 or 4 $R^y$;

wherein each $R^{6c}$, $R^{6d}$, $R^{5c}$, $R^{5d}$, $R^{5e}$, $R^{7a}$, $R^{8a}$, $R^{9a}$, $R^y$, g, h and i is as defined herein.

In some embodiments, $R^4$ is D, F, Cl, Br, I, CN, $NO_2$, mercapto, $C_{1-4}$ alkyl, $C_{2-4}$ alkenyl, $C_{2-4}$ alkynyl, halo $C_{1-4}$ alkyl, $C_{3-6}$ cycloalkyl, $C_{2-5}$ heterocyclyl, $C_{6-10}$ aryl, $C_{1-5}$ heteroaryl, —$NR^{5c}R^{5d}$, —$C(=O)NR^{5c}R^{5d}$, —$OR^{9a}$, —$S(=O)_2OR^{9a}$, —$S(=O)_2NR^{5c}R^{5d}$, —$N(R^{5e})C(=O)(CR^{6c}R^{6d})_h OR^{9a}$, —$N(R^{5e})C(=O)R^{8a}$, —$N(R^{5e})C(=O)NR^{5c}R^{5d}$, —$N(R^{5e})S(=O)_2R^{7a}$, —$S(=O)_2R^{7a}$, —$OS(=O)_2R^{7a}$, —$OC(=O)OR^{9a}$, —$OC(=O)R^{8a}$ or —$C(=O)R^{8a}$; $R^4$ is unsubstituted or substituted with 1, 2, 3 or 4 $R^y$;

wherein each $R^{6c}$, $R^{6d}$, $R^{5c}$, $R^{5d}$, $R^{5e}$, $R^{7a}$, $R^{8a}$, $R^{9a}$, $R^y$ and h is as defined herein.

In other embodiments, $R^4$ is D, F, Cl, Br, I, CN, $NO_2$, mercapto, methyl, ethyl, propyl, butyl, vinyl, propenyl, allyl, ethynyl, propynyl, trifluoromethyl, difluoromethyl, 2,2-difluoroethyl, chloroethyl (including but not limited to: 2-chloroethyl), 2,2,2-trifluoroethyl, 2-chloro-1-methylethyl, cyclopropyl, cyclobutyl, cyclopentyl, cyclohexyl, pyrrolidinyl, tetrahydrofuranyl, morpholinyl, piperidinyl, piperazinyl, pyrrolidinyl, pyrazolidinyl, oxomorpholinyl, thiomorpholinyl, 4,4-dioxothiomorpholinyl, oxazolidinyl, thiazolidinyl, 1,1-dioxoisothiazolidinyl

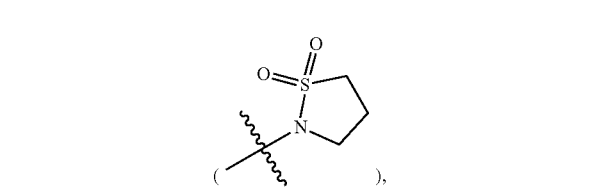 [SMILES: *N1CCCS1(=O)=O]

oxo-1,3-oxazinylalkyl phenyl, pyridyl, pyrimidinyl, pyrazolyl, imidazolyl, pyrrolyl, thiazolyl, oxazolyl, triazolyl, tetrazolyl, thienyl, furyl, —$NR^{5c}R^{5d}$, —$C(=O)NR^{5c}R^{5d}$, —$OR^{9a}$, —$S(=O)_2OR^{9a}$, —$S(=O)_2NR^{5c}R^{5d}$, —$N(R^{5e})C(=O)(CR^{6c}R^{6d})_h OR^{9a}$, —$N(R^{5e})C(=O)R^{8a}$, —$N(R^{5e})C(=O)NR^{5c}R^d$, —$N(R^{5e})S(=O)_2R^{7a}$, —$S(=O)_2R^{7a}$, —$OS(=O)_2R^{7a}$, —$OC(=O)OR^{9a}$, —$OC(=O)R^{8a}$ or —$C(=O)R^{8a}$; $R^4$ is unsubstituted or optionally substituted with 1, 2, 3 or 4 $R^y$;

wherein each $R^{6c}$, $R^{6d}$, $R^{5c}$, $R^{5d}$, $R^{5e}$, $R^{7a}$, $R^{8a}$, $R^{9a}$, $R^y$ and h is as defined herein.

In some embodiments, the compound of the invention has Formula (III), or a stereoisomer, a geometric isomer, a tautomer, an N-oxide, a hydrate, a solvate, a metabolite, an ester, a pharmaceutically acceptable salt or a prodrug thereof,

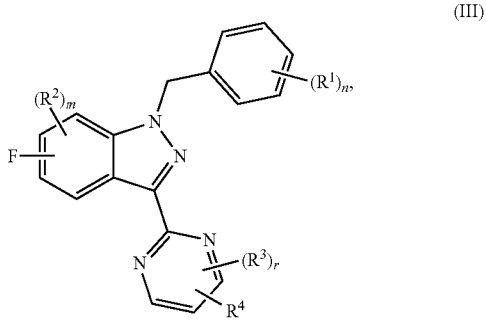

(III)

wherein each $R^1$, $R^2$, $R^3$, $R^4$, m, n and r is as defined herein.

In some embodiments, each $R^1$ is independently H, D, F, Cl, Br, I, CN, $NO_2$, amino, hydroxy, mercapto, oxo, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, acyl, sulfonyl, $-(CR^{10}R^{11})_u-C_{3-6}$ cycloalkyl, $-(CR^{10}R^{11})_u-C_{2-5}$ heterocyclyl, $-(CR^{10}R^{11})_u-C_{6-10}$ aryl or $-(CR^{10}R^{11})_u-C_{1-5}$ heteroaryl; wherein each of the amino, hydroxy, mercapto, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, acyl, sulfonyl, $-(CR^{10}R^{11})_u-C_{3-6}$ cycloalkyl, $-(CR^{10}R^{11})_u-C_{2-5}$ heterocyclyl, $-(CR^{10}R^{11})_u-C_{6-10}$ aryl and $-(CR^{10}R^{11})_u-C_{1-5}$ heteroaryl is unsubstituted or independently substituted with 1, 2, 3 or 4 substituents selected from D, F, Cl, Br, I, CN, $NO_2$, amino, hydroxy, mercapto, oxo, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, $C_{3-6}$ cycloalkyl, $C_{2-5}$ heterocyclyl, $C_{6-10}$ aryl and $C_{1-5}$ heteroaryl; wherein $R^{10}$, $R^{11}$ and u are as defined herein.

In some embodiments, each $R^1$ is independently H, D, F, Cl, Br, I, CN, $NO_2$, amino, hydroxy, mercapto, $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl or $C_{1-5}$ heteroaryl;

wherein each of the $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl and $C_{1-5}$ heteroaryl is unsubstituted or independently substituted with 1, 2, 3 or 4 substituents selected from D, F, Cl, Br, I, CN, $NO_2$, amino, hydroxy, mercapto, oxo (=O), $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl and $C_{1-5}$ heteroaryl.

In some embodiments, each $R^1$ is independently H, D, F, Cl, Br, I, CN, $NO_2$, amino, hydroxy, mercapto, methyl, ethyl, propyl, butyl, trifluoromethyl, difluoromethyl, methoxy, ethoxy, propoxy, tert-butoxy, trifluoromethoxy, methylamino, dimethylamino, cyclopropyl, cyclobutyl, cyclopentyl, cyclohexyl, piperidinyl, morpholinyl, piperazinyl, epoxypropyl, azetidinyl, phenyl, pyridyl or pyrimidinyl;

wherein each of the methyl, ethyl, propyl, butyl, difluoromethyl, methoxy, ethoxy, propoxy, tert-butoxy, methylamino, dimethylamino, cyclopropyl, cyclobutyl, cyclopentyl, cyclohexyl, piperidinyl, morpholinyl, piperazinyl, epoxypropyl, azetidinyl, phenyl, pyridyl and pyrimidinyl is unsubstituted or independently substituted with 1, 2, 3 or 4 substituents selected from D, F, Cl, Br, I, CN, $NO_2$, amino, hydroxy, mercapto, oxo (=O), methyl, ethyl, propyl, butyl, $C_{2-4}$ alkenyl, $C_{2-4}$ alkynyl, trifluoromethyl, methoxy, ethoxy, propoxy, trifluoromethoxy, $C_{1-3}$ alkylamino, cyclopropyl, cyclobutyl, cyclopentyl, cyclohexyl, $C_{2-5}$ heterocyclyl, phenyl and $C_{1-5}$ heteroaryl.

In some embodiments, the compound of the invention has Formula (IV), Formula (IVa), Formula (IVb) or Formula (IVc), or a stereoisomer, a geometric isomer, a tautomer, an N-oxide, a hydrate, a solvate, a metabolite, a ester, a pharmaceutically acceptable salt or a prodrug thereof,

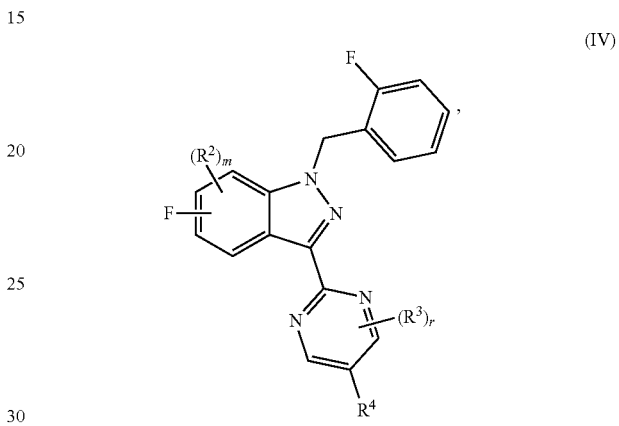

(IV)

(IVa)

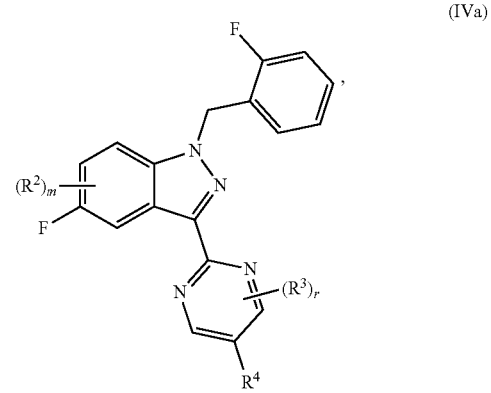

(IVb)

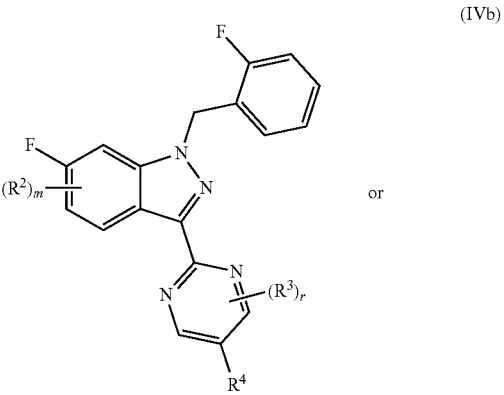

or

-continued (IVc)

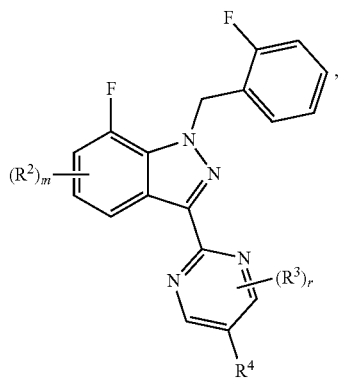

wherein each $R^2$, $R^3$, $R^4$, m and r is as defined herein.

In some embodiments, the compound of the invention has Formula (Va), Formula (Vb) or Formula (Vc), or a stereoisomer, a geometric isomer, a tautomer, an N-oxide, a hydrate, a solvate, a metabolite, an ester, a pharmaceutically acceptable salt or a prodrug thereof, (Va)

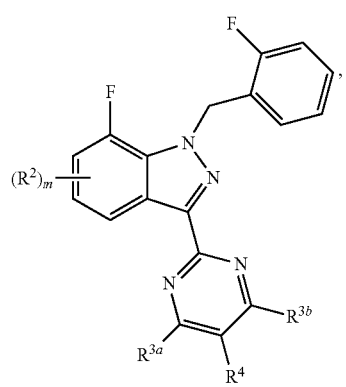

(Vb)

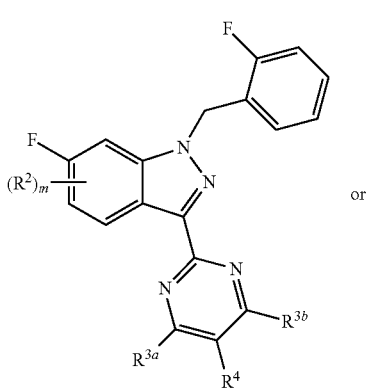

or (Vc)

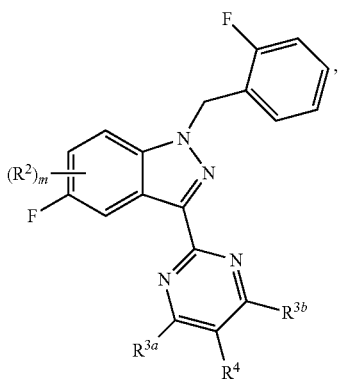

wherein each $R^2$, $R^{3a}$, $R^{3b}$, $R^4$ and m is as defined herein.

In some embodiments, the compound of the invention has Formula (Vd), or a stereoisomer, a geometric isomer, a tautomer, an N-oxide, a hydrate, a solvate, a metabolite, an ester, a pharmaceutically acceptable salt or a prodrug thereof, (Vd)

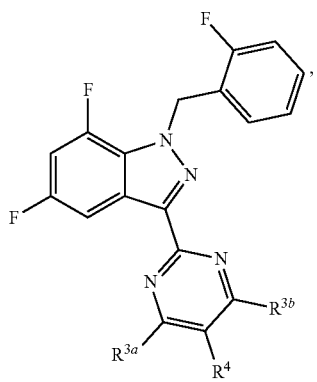

wherein $R^{3a}$, $R^{3b}$ and $R^4$ is as defined herein.

In some embodiments, each $R^2$ is independently H, D, F, Cl, Br, I, CN, $NO_2$, amino, hydroxy, mercapto, $C_{1-6}$ alkyl, $C_{2-6}$ alkenyl, $C_{2-6}$ alkynyl, halo $C_{1-6}$ alkyl, halo $C_{1-6}$ alkoxy, $C_{1-6}$ alkylamino, hydroxy $C_{1-6}$ alkyl, cyano $C_{1-6}$ alkyl, amino $C_{1-6}$ alkyl, hydroxy $C_{1-6}$ alkoxy, amino $C_{1-6}$ alkoxy, acyl, sulfonyl or $C_{1-6}$ alkoxy.

In some embodiments, each $R^2$ is independently H, D, F, Cl, Br, I, CN, $NO_2$, amino, hydroxy, mercapto, $C_{1-4}$ alkyl, $C_{2-4}$ alkenyl, $C_{2-4}$ alkynyl, halo $C_{1-4}$ alkyl, halo $C_{1-4}$ alkoxy, $C_{1-4}$ alkylamino, hydroxy $C_{1-4}$ alkyl, cyano $C_{1-4}$ alkyl, amino $C_{1-4}$ alkyl, hydroxy $C_{1-4}$ alkoxy, amino $C_{1-4}$ alkoxy or $C_{1-4}$ alkoxy.

In other embodiments, each $R^2$ is independently H, D, F, Cl, Br, I, CN, $NO_2$, amino, hydroxy, mercapto, methyl, ethyl, propyl, butyl, trifluoromethyl, trifluoromethoxy, methylamino, dimethylamino, hydroxymethyl, hydroxyethyl, cyanomethyl, cyanoethyl, aminomethyl, aminoethyl, hydroxymethoxy, hydroxyethoxy, amino $C_{1-3}$ alkoxy, methoxy, ethoxy, propoxy or butoxy.

In some embodiments, each $R^3$, $R^{3a}$ and $R^{3b}$ is independently oxo (=O), H, D, F, Cl, Br, I, CN, $NO_2$, mercapto, $C_{1-6}$ alkyl, $C_{2-6}$ alkenyl, $C_{2-6}$ alkynyl, halo $C_{1-6}$ alkyl, —$(CR^{6a}R^{6b})_j$—$C_{3-10}$ cycloalkyl, —$(CR^{6a}R^{6b})_j$—$C_{2-10}$ heterocyclyl, —$(CR^{6a}R^{6b})_j$—$C_{6-10}$ aryl, —$(CR^{6a}R^{6b})_j$—$C_{1-9}$ heteroaryl, —N=NR⁵, —N=CR⁶R⁶ᵉ, —(CR⁶ᵃR⁶ᵇ)ⱼNR⁵ᵃR⁵ᵇ, —(CR⁶ᵃR⁶ᵇ)ⱼC(=O)(CR⁶ᵃR⁶ᵇ)ₖNR⁵ᵃR⁵ᵇ, —(CR⁶ᵃR⁶ᵇ)ⱼC(=O)(CR⁶ᵃR⁶ᵇ)ₖOR⁹, —(CR⁶ᵃR⁶ᵇ)ⱼOR⁹, —(CR⁶ᵃR⁶ᵇ)ⱼS(=O)₂(CR⁶ᵃR⁶ᵇ)ₖOR⁹, —(CR⁶ᵃR⁶ᵇ)ⱼS(=O)₂(CR⁶ᵃR⁶ᵇ)ₖNR⁵ᵃR⁵ᵇ, —(CR⁶ᵃR⁶ᵇ)ⱼN(R⁵)(CR⁶ᵃR⁶ᵇ)ₚC(=O)(CR⁶ᵃR⁶ᵇ)ₖOR⁹, —(CR⁶ᵃR⁶ᵇ)ⱼN(R⁵)C(=O)(CR⁶ᵃR⁶ᵇ)ₖNR⁵ᵃR⁵ᵇ, —(CR⁶ᵃR⁶ᵇ)ⱼN(R⁵)C(=O)R⁸, —(CR⁶ᵃR⁶ᵇ)ⱼN(R⁵)S(=O)₂R⁷, —(CR⁶ᵃR⁶ᵇ)ⱼS(=O)₂R⁷, —(CR⁶ᵃR⁶ᵇ)ⱼOS(=O)₂R⁷, —(CR⁶ᵃR⁶ᵇ)ⱼOC(=O)(CR⁶ᵃR⁶ᵇ)ₖOR⁹, —(CR⁶ᵃR⁶ᵇ)ⱼOC(=O)R⁸ or —(CR⁶ᵃR⁶ᵇ)ⱼC(=O)R⁸; each R³, R³ᵃ and R³ᵇ is unsubstituted or independently substituted with 1, 2, 3 or 4 Rˣ; or, any two adjacent R³, together with the carbon atoms to which they are attached, form a 3- to 6-membered carbocyclic ring, heterocyclic ring, aromatic ring or heteroaromatic ring, and wherein each of 3- to 6-membered carbocyclic ring, heterocyclic ring, aromatic ring and heteroaromatic ring is unsubstituted or independently substituted with 1, 2, 3 or 4 Rᶻ; wherein the "3- to 6-membered carbocyclic ring, heterocyclic ring, aromatic ring or heteroaromatic ring" includes 3- to 6-membered carbocyclic ring, 3- to 6-membered heterocyclic ring, 3- to 6-membered aromatic ring or 3- to 6-membered heteroaromatic ring; further, the "3- to 6-membered aromatic ring" includes 6-membered aromatic ring, and the "3- to 6-membered heteroaromatic ring" includes 5- to 6-membered heteroaromatic ring; that is, any two adjacent R³, together with the carbon atoms to which they are attached, may form a 3- to 6-membered carbocyclic ring, 3- to 6-membered heterocyclic ring, 6-membered aromatic ring or 5- to 6-membered heteroaromatic ring, and wherein each of 3- to 6-membered carbocyclic ring, 3- to 6-membered heterocyclic ring, 6-membered aromatic ring and 5- to 6-membered heteroaromatic ring is unsubstituted or independently substituted with 1, 2, 3 or 4 Rᶻ;

wherein each R⁶ᵃ, R⁶ᵇ, R⁶, R⁶ᵉ, R⁵, R⁵ᵃ, R⁵ᵇ, R⁷, R⁸, R⁹, Rˣ, Rᶻ, j, k and p is as defined herein.

In some embodiments, each R³, R³ᵃ and R³ᵇ is independently oxo (=O), H, D, F, Cl, Br, I, CN, NO₂, mercapto, C₁₋₄ alkyl, C₂₋₄ alkenyl, C₂₋₄ alkynyl, halo C₁₋₄ alkyl, C₃₋₆ cycloalkyl, C₂₋₅ heterocyclyl, C₆₋₁₀ aryl, C₁₋₅ heteroaryl, —NR⁵ᵃR⁵ᵇ, —C(=O)NR⁵ᵃR⁵ᵇ, —C(=O)OR⁹, —OR⁹, —S(=O)₂OR⁹, —S(=O)₂NR⁵ᵃR⁵ᵇ, —N(R⁵)C(=O)(CR⁶ᵃR⁶ᵇ)ₖOR⁹, —N(R⁵)C(=O)NR⁵ᵃR⁵ᵇ, —N(R⁵)C(=O)R⁸, —N(R⁵)S(=O)₂R⁷, —S(=O)₂R⁷, —OS(=O)₂R⁷, —OC(=O)OR⁹, —OC(=O)R⁸ or —C(=O)R⁸; each R³, R³ᵃ and R³ᵇ is unsubstituted or optionally substituted with 1, 2, 3 or 4 Rˣ; or, any two adjacent R³, together with the carbon atoms to which they are attached, form a 3- to 6-membered heterocyclic ring or heteroaromatic ring, and wherein each of 3- to 6-membered heterocyclic ring and heteroaromatic ring is unsubstituted or independently substituted with 1, 2, 3 or 4 Rᶻ; wherein the "3- to 6-membered heterocyclic ring or heteroaromatic ring" includes 3- to 6-membered heterocyclic ring or 3- to 6-membered heteroaromatic ring; further, the "3- to 6-membered heteroaromatic ring" includes 5- to 6-membered heteroaromatic ring; that is, any two adjacent R³, together with the carbon atoms to which they are attached, may form a 3- to 6-membered heterocyclic ring or 5- to 6-membered heteroaromatic ring, and wherein each of 3- to 6-membered heterocyclic ring and 5- to 6-membered heteroaromatic ring is unsubstituted or independently substituted with 1, 2, 3 or 4 Rᶻ;

wherein each R⁶ᵃ, R⁶ᵇ, R⁵, R⁵ᵃ, R⁵ᵇ, R⁷, R⁸, R⁹, Rˣ, Rᶻ and k is as defined herein.

In some embodiments, each R³, R³ᵃ and R³ᵇ is independently oxo (=O), H, D, F, Cl, Br, I, CN, NO₂, mercapto, methyl, ethyl, propyl, butyl, trifluoromethyl, 2,2-difluoroethyl, cyclopropyl, cyclobutyl, cyclopentyl, cyclohexyl, azetidinyl, pyrrolidinyl, pyrazolidinyl, piperidinyl, piperazinyl, morpholinyl, oxomorpholinyl, thiomorpholinyl, 4,4-dioxothiomorpholinyl, tetrahydrofuranyl, oxazolidinyl, thiazolidinyl, 1,1-dioxoisothiazolidinyl

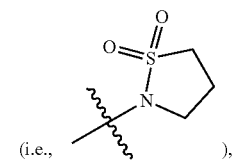

(i.e., ), oxo-1,3-oxazinyl

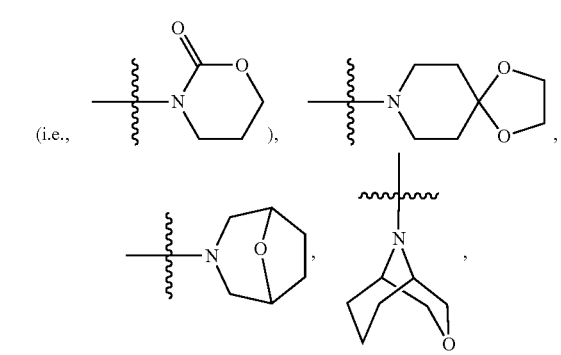

(i.e., ), phenyl, pyridyl, pyrimidinyl, pyrazolyl, imidazolyl, pyrrolyl, thiazolyl, oxazolyl, triazolyl, tetrazolyl, thienyl, furyl, —NR⁵ᵃR⁵ᵇ, —C(=O)NR⁵ᵃR⁵ᵇ, —C(=O)OR⁹, —OR⁹, —S(=O)₂OR⁹, —S(=O)₂NR⁵ᵃR⁵ᵇ, —N(R⁵)C(=O)OR⁹, —N(R⁵)C(=O)NR⁵ᵃR⁵ᵇ, —N(R⁵)C(=O)R⁸, —N(R⁵)S(=O)₂R⁷, —S(=O)₂R⁷, —OS(=O)₂R⁷, —OC(=O)OR⁹, —OC(=O)R⁸ or —C(=O)R⁸; each R³, R³ᵃ and R³ᵇ is unsubstituted or independently substituted with 1, 2, 3 or 4 Rˣ; or, any two adjacent R³, together with the carbon atoms to which they are attached, form a 3- to 6-membered heterocyclic ring or heteroaromatic ring, and wherein each of 3- to 6-membered heterocyclic ring and heteroaromatic ring is unsubstituted or independently substituted with 1, 2, 3 or 4 Rᶻ; wherein the "3- to 6-membered heterocyclic ring or heteroaromatic ring" includes 3- to 6-membered heterocyclic ring or 3- to 6-membered heteroaromatic ring; further, the "3- to 6-membered heteroaromatic ring" includes 5- to 6-membered heteroaromatic ring; that is, any two adjacent R³, together with the carbon atoms to which they are attached, may form a 3- to 6-membered heterocyclic ring or 5- to 6-membered heteroaromatic ring, and wherein each of 3- to 6-membered heterocyclic ring and 5- to 6-membered heteroaromatic ring is unsubstituted or independently substituted with 1, 2, 3 or 4 Rᶻ;

wherein each R⁵, R⁵ᵃ, R⁵ᵇ, R⁷, R⁸, R⁹, Rˣ and Rᶻ is as defined herein.

In some embodiments, each R⁵ and R⁵ᵉ is independently H, D, C₁₋₆ alkyl, hydroxy C₁₋₆ alkyl, amino C₁₋₆ alkyl, cyano C₁₋₆ alkyl, halo C₁₋₆ alkyl, C₁₋₆ alkoxy-C₁₋₆-alkyl, C₃₋₆ cycloalkyl, C₂₋₅ heterocyclyl, C₆₋₁₀ aryl, C₁₋₅ heteroaryl, $C_{3-6}$ cycloalkyl-$C_{1-6}$-alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$-alkyl.

In some embodiments, each $R^5$ and $R^{5e}$ is independently H, D, $C_{1-4}$ alkyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy-$C_{1-4}$-alkyl, $C_{3-4}$ cycloalkyl, $C_{2-5}$ heterocyclyl, $C_{6-10}$ aryl, $C_{1-5}$ heteroaryl, $C_{3-6}$ cycloalkyl-$C_{1-6}$-alkyl, $C_{2-5}$ heterocyclyl-$C_{1-4}$-alkyl, $C_{6-10}$ aryl-$C_{1-4}$-alkyl or $C_{1-5}$ heteroaryl-$C_{1-4}$-alkyl.

In some embodiments, each $R^5$ and $R^{5e}$ is independently H, D, methyl, ethyl, propyl, butyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy-$C_{1-4}$ alkyl.

In some embodiments, each $R^5$ and $R^{5e}$ is independently H, D, methyl, ethyl, propyl, butyl, hydroxymethyl, hydroxyethyl, aminomethyl, cyanomethyl, difluoromethyl, 2,2-difluoroethyl, methoxymethyl, cyclopropyl, cyclopropoxy, phenyl, pyridyl, pyrimidinyl, cyclopropanemethyl, piperidinylmethyl, benzyl, pyridylmethyl or pyrimidinylmethyl.

In some embodiments, each $R^{5a}$, $R^{5b}$, $R^{5c}$ and $R^{5d}$ is independently H, D, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy-$C_{1-6}$-alkyl, $C_{1-6}$ alkoxycarbonyl, $C_{1-6}$ alkylcarbonyl, $C_{1-6}$ alkylaminocarbonyl, $C_{3-6}$ cycloalkyl, $C_{2-5}$ heterocyclyl, $C_{6-10}$ aryl, $C_{1-5}$ heteroaryl, $C_{3-6}$ cycloalkylcarbonyl, $C_{2-5}$ heterocyclylcarbonyl, $C_{6-10}$ arylcarbonyl, $C_{1-5}$ heteroarylcarbonyl, $C_{3-6}$ cycloalkyl-$C_{1-6}$-alkylcarbonyl, $C_{2-5}$ heterocyclyl-$C_{1-6}$-alkylcarbonyl, $C_{6-10}$ aryl-$C_{1-6}$-alkylcarbonyl, $C_{1-5}$ heteroaryl-$C_{1-6}$-alkylcarbonyl, $C_{3-6}$ cycloalkyl-$C_{1-6}$ alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$-alkyl; or, $R^{5a}$ and $R^{5b}$, together with the N atom to which they are attached, form a 3- to 10-membered heterocyclic ring or 3- to 10-membered heteroaromatic ring; or, $R^{5c}$ and $R^{5d}$, together with the N atom to which they are attached, form a 3- to 10-membered heterocyclic ring or 3- to 10-membered heteroaromatic ring; wherein the "3- to 10-membered heteroaromatic ring" includes 5- to 10-membered heteroaromatic ring.

In some embodiments, each $R^{5a}$, $R^{5b}$, $R^{5c}$ and $R^{5d}$ is independently H, D, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy-$C_{1-4}$-alkyl, $C_{1-4}$ alkoxycarbonyl, $C_{1-4}$ alkylcarbonyl, $C_{1-4}$ alkylaminocarbonyl, $C_{3-6}$ cycloalkyl, $C_{2-5}$ heterocyclyl, $C_{6-10}$ aryl, $C_{1-5}$ heteroaryl, $C_{3-6}$ cycloalkylcarbonyl, $C_{2-5}$ heterocyclylcarbonyl, $C_{6-10}$ arylcarbonyl, $C_{1-5}$ heteroarylcarbonyl, $C_{3-6}$ cycloalkyl-$C_{1-3}$-alkyl, $C_{2-5}$ heterocyclyl-$C_{1-3}$-alkyl, $C_{6-10}$ aryl-$C_{1-3}$-alkyl or $C_{1-5}$ heteroaryl-$C_{1-3}$-alkyl; or, $R^{5a}$ and $R^{5b}$, together with the N atom to which they are attached, form a 3- to 6-membered heterocyclic ring or 3- to 6-membered heteroaromatic ring; or, $R^{5c}$ and $R^{5d}$, together with the N atom to which they are attached, form a 3- to 6-membered heterocyclic ring or 3- to 6-membered heteroaromatic ring; wherein the "3- to 6-membered heteroaromatic ring" includes 5- to 6-membered heteroaromatic ring.

In other embodiments, each $R^{5a}$, $R^{5b}$, $R^{5c}$ and $R^{5d}$ is independently H, D, methyl, ethyl, propyl, butyl, hydroxymethyl, hydroxyethyl (including 2-hydroxyethyl and 1-hydroxyethyl), hydroxypropyl, hydroxybutyl, amino $C_{1-4}$ alkyl, cyano $C_{1-4}$ alkyl, trifluoromethoxy, chloroethyl (including 2-chloroethyl and 1-chloroethyl), 2,2,2-trifluoroethyl, 2,2-difluoroethyl, 2-chloro-1-methylethyl, methoxymethyl, methoxyethyl, methoxycarbonyl, ethoxycarbonyl, propoxycarbonyl, methylcarbonyl, ethylcarbonyl, methylaminocarbonyl, ethylaminocarbonyl, cyclopropyl, cyclobutyl, cyclopentyl, cyclohexyl, azetidinyl, pyrrolidyl, tetrahydrofuranyl, tetrahydropyranyl, morpholinyl, piperidinyl, piperazinyl, phenyl, pyridinyl, pyrimidinyl, cyclopropylcarbonyl, cyclopentylcarbonyl, cyclohexylcarbonyl, cyclopropyloxycarbonyl, tetrahydrofurylcarbonyl, tetrahydropyranylcarbonyl, piperidylcarbonyl, piperazinylcarbonyl, morpholinylcarbonyl, tetrahydrothiophenylcarbonyl, pyrrolidinylcarbonyl, phenylcarbonyl, pyridylcarbonyl, pyrimidinylcarbonyl, pyrrolylcarbonyl, imidazolylcarbonyl, pyrazolylcarbonyl, thienylcarbonyl, furylcarbonyl, cyclopropylmethyl, cyclobutylmethyl, tetrahydropyranylmethyl, tetrahydropyranylethyl, tetrahydrofuranylmethyl, tetrahydrofuranylethyl, phenylmethyl, phenylethyl, pyridylmethyl, pyrazolylmethyl, pyrazolylethyl, pyridylethyl or $C_{2-5}$ heterocyclyl-$C_{1-3}$-alkyl; or, $R^{5a}$ and $R^{5b}$, together with the N atom to which they are attached, form an azetidine, pyrrolidine, oxazolidine, thiazolidine, isothiazolidine, oxoisothiazolidine (such as dioxoisothiazolidine), piperidine, morpholine, piperazine, thiomorpholine, 1,3-oxazinane, pyrrole, pyrazole, imidazole or triazolyl; or, $R^{5c}$ and $R^{5d}$, together with the N atom to which they are attached, form azetidine, pyrrolidine, oxazolidine, thiazolidine, isothiazolidine, oxoisothiazolidine (such as dioxoisothiazolidine), piperidine, morpholine, piperazine, thiomorpholine, 1,3-oxazinane, pyrrole, pyrazole, imidazole or triazolyl.

In some embodiments, each $R^6$, $R^{6a}$, $R^{6b}$, $R^{6c}$, $R^{6d}$ and $R^{6e}$ is independently H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{3-6}$ cycloalkyl, $C_{2-5}$ heterocyclyl, $C_{6-10}$ aryl or $C_{1-5}$ heteroaryl.

In some embodiments, each $R^6$, $R^{6a}$, $R^{6b}$, $R^{6c}$, $R^{6d}$ and $R^{6e}$ is independently H, D, F, Cl, Br, I, CN, amino, hydroxy, mercapto, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy, halo $C_{1-4}$ alkoxy, $C_{1-4}$ alkylamino, acyl, sulfonyl, $C_{3-6}$ cycloalkyl, $C_{2-5}$ heterocyclyl, $C_{6-10}$ aryl or $C_{1-5}$ heteroaryl.

In some embodiments, each $R^6$, $R^{6a}$, $R^{6b}$, $R^{6c}$, $R^{6d}$ and $R^{6e}$ is independently H, D, F, Cl, Br, I, CN, amino, hydroxy, mercapto, methyl, ethyl, propyl, butyl, hydroxy $C_{1-4}$ alkyl, amino $C_{1-4}$ alkyl, cyano $C_{1-4}$ alkyl or halo $C_{1-4}$ alkyl.

In some embodiments, each $R^6$, $R^{6a}$, $R^{6b}$, $R^{6c}$, $R^{6d}$ and $R^{6e}$ is independently H, D, F, Cl, Br, I, CN, amino, hydroxy, mercapto, methyl, ethyl, hydroxymethyl, hydroxyethyl, aminomethyl, aminoethyl, cyanomethyl, cyanoethyl, trifluoromethyl, difluoromethyl, monofluromethyl, chloroethyl, methoxy, ethoxy, trifluoromethoxy or difluoromethoxy.

In some embodiments, each $R^7$ and $R^{7a}$ is independently H, D, amino, hydroxy, mercapto, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, $C_{3-6}$ cycloalkyl, $C_{2-5}$ heterocyclyl, $C_{6-10}$ aryl or $C_{1-5}$ heteroaryl.

In some embodiments, each $R^7$ and $R^{7a}$ is independently H, D, amino, hydroxy, mercapto, $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl or $C_{1-5}$ heteroaryl.

In some embodiments, each $R^7$ and $R^{7a}$ is independently H, D, amino, hydroxy, mercapto, methyl, ethyl, propyl, butyl or trifluoromethyl.

In some embodiments, each $R^8$ and $R^{8a}$ is independently H, D, amino, hydroxy, mercapto, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, $C_{3-6}$ cycloalkyl, $C_{2-5}$ heterocyclyl, $C_{6-10}$ aryl or $C_{1-5}$ heteroaryl.

In some embodiments, each $R^8$ and $R^{8a}$ is independently H, D, amino, hydroxy, mercapto, $C_{1-4}$ alkyl, $C_{2-4}$ alkenyl, $C_{2-4}$ alkynyl, halo $C_{1-4}$ alkyl, $C_{1-4}$ alkoxy, halo $C_{1-4}$ alkoxy, $C_{1-4}$ alkylamino, $C_{3-6}$ cycloalkyl, $C_{2-5}$ heterocyclyl, $C_{6-10}$ aryl or $C_{1-5}$ heteroaryl.

In some embodiments, each $R^8$ and $R^{8a}$ is independently H, D, amino, hydroxy, mercapto, methyl, ethyl, propyl, butyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, cyclopropyl, cyclobutyl, cyclopentyl, cyclohexyl, azetidinyl, tetrahydropyranyl, pyrrolidinyl, tetrahydrofuranyl, tetrahydrothienyl, morpholinyl, piperidinyl, piperazinyl, thiomorpholinyl, 1,1-dioxothiomorpholinyl, phenyl, pyrrolyl, thienyl, furyl, pyridyl or pyrimidinyl.

In some embodiments, each $R^9$ and $R^{9a}$ is independently H, D, $C_{1-6}$ alkyl, $C_{2-6}$ alkenyl, $C_{2-6}$ alkynyl, halo $C_{1-6}$ alkyl, acyl, sulfonyl, $C_{3-6}$ cycloalkyl, $C_{2-5}$ heterocyclyl, $C_{6-10}$ aryl, $C_{1-5}$ heteroaryl, $C_{3-6}$ cycloalkyl-$C_{1-6}$-alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$ alkyl.

In some embodiments, each $R^9$ and $R^{9a}$ is independently H, D, $C_{1-4}$ alkyl, $C_{2-4}$ alkenyl, $C_{2-4}$ alkynyl, halo $C_{1-4}$ alkyl, acyl, sulfonyl, $C_{3-6}$ cycloalkyl, $C_{2-5}$ heterocyclyl, $C_{6-10}$ aryl, $C_{1-5}$ heteroaryl, $C_{3-6}$ cycloalkyl-$C_{1-3}$-alkyl, $C_{2-5}$ heterocyclyl-$C_{1-3}$-alkyl, $C_{6-10}$ aryl-$C_{1-3}$-alkyl or $C_{1-5}$ heteroaryl-$C_{1-3}$-alkyl.

In some embodiments, each $R^9$ and $R^{9a}$ is independently H, D, methyl, ethyl, propyl, butyl, $C_{2-4}$ alkenyl, $C_{2-4}$ alkynyl, trifluoromethyl, chloroethyl, 2,2,2-trifluoroethyl, 2,2-difluoroethyl, 2-chloro-1-methyl ethyl, cyclopropyl, cyclobutyl, cyclopentyl, cyclohexyl, pyrrolidinyl, tetrahydrofuranyl, morpholinyl, piperidinyl, piperazinyl, phenyl, pyridyl, pyrimidinyl, cyclopropylmethyl, cyclobutylmethyl, phenylmethyl, phenylethyl, pyridylmethyl, pyridylethyl or $C_{2-5}$ heterocyclyl-$C_{1-3}$-alkyl.

In some embodiments, each $R^{10}$ and $R^{11}$ is independently H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{3-6}$ cycloalkyl, $C_{2-5}$ heterocyclyl, $C_{6-10}$ aryl or $C_{1-5}$ heteroaryl; or, $R^{10}$ and $R^{11}$ together form carbonyl; or, $R^{10}$ and $R^{11}$, together with the carbon atom to which they are attached, form a 3- to 8-membered carbocyclic ring or 3- to 8-membered heterocyclic ring.

In some embodiments, each $R^x$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkylsulfonyl, $C_{1-6}$ alkylcarbonylamino, $C_{1-6}$ alkyl sulfonyl amino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^x$ is independently oxo, H, D, F, Cl, Br, I, CN, amino, hydroxy, mercapto, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy, halo $C_{1-4}$ alkoxy, $C_{1-4}$ alkylamino, acyl, sulfonyl, $C_{1-4}$ alkylcarbonyl, $C_{1-4}$ alkylsulfonyl, $C_{1-4}$ alkylcarbonylamino, $C_{1-4}$ alkyl sulfonyl amino, $C_{1-4}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^x$ is independently oxo (=O), H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkyl sulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

In some embodiments, each $R^y$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkylsulfonyl, $C_{1-6}$ alkylcarbonylamino, $C_{1-6}$ alkylsulfonylamino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^y$ is independently oxo, H, D, F, Cl, Br, I, CN, amino, hydroxy, mercapto, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy, halo $C_{1-4}$ alkoxy, $C_{1-4}$ alkylamino, acyl, sulfonyl, $C_{1-4}$ alkylcarbonyl, $C_{1-4}$ alkylsulfonyl, $C_{1-4}$ alkylcarbonylamino, $C_{1-4}$ alkylsulfonylamino, $C_{1-4}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^y$ is independently oxo, H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkylsulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

In some embodiments, each $R^z$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkylsulfonyl, $C_{1-6}$ alkylcarbonylamino, $C_{1-6}$ alkylsulfonylamino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^z$ is independently oxo, H, D, F, Cl, Br, I, CN, amino, hydroxy, mercapto, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy, halo $C_{1-4}$ alkoxy, $C_{1-4}$ alkylamino, acyl, sulfonyl, $C_{1-4}$ alkylcarbonyl, $C_{1-4}$ alkylsulfonyl, $C_{1-4}$ alkylcarbonylamino, $C_{1-4}$ alkylsulfonylamino, $C_{1-4}$ alkoxycarbonylamino, $C_{3-6}$ cycloalkyl, $C_{2-5}$ heterocyclyl, $C_{6-10}$ aryl or $C_{1-5}$ heteroaryl.

In some embodiments, each $R^z$ is independently oxo, H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkylsulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

In some embodiments, n is 0, 1, 2, 3 or 4.

In some embodiments, m is 0, 1, 2 or 3.

In some embodiments, r is 0, 1, 2, 3, 4, 5 or 6.

In some embodiments, each u, j and g is independently 0, 1, 2, 3 or 4.

In some embodiments, each h, i, k and p is independently 0, 1, 2, 3 or 4.
In some embodiments, the compound of the invention has one of the following structures or a stereoisomer, a geometric isomer, a tautomer, an N-oxide, a hydrate, a solvate, a metabolite, an ester, a pharmaceutically acceptable salt or a prodrug thereof,
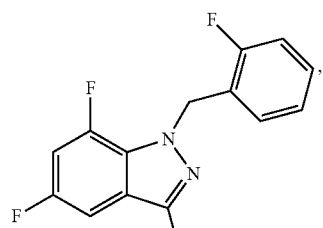
(1)
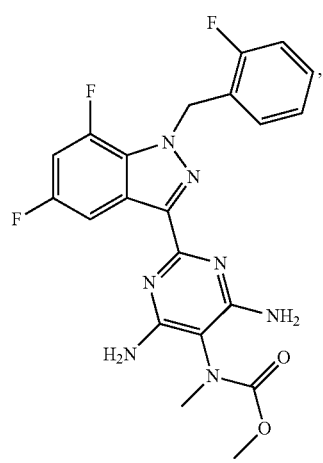
(2)
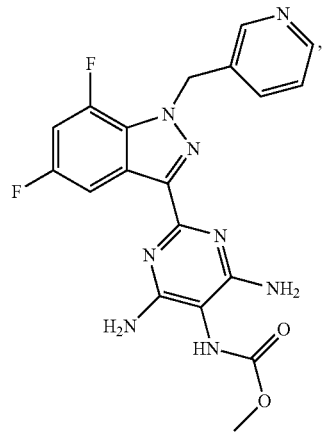
(3)
-continued
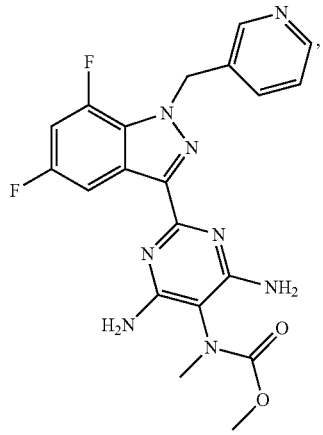
(4)
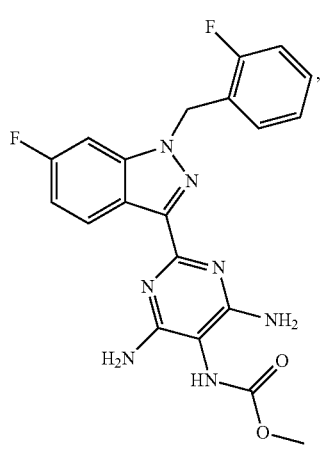
(5)
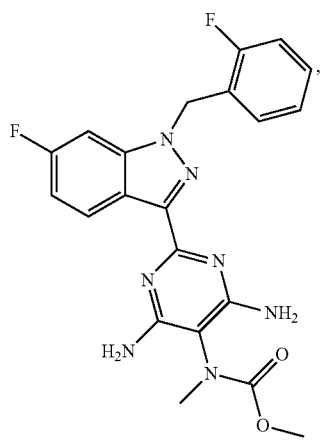
(6)

(7)
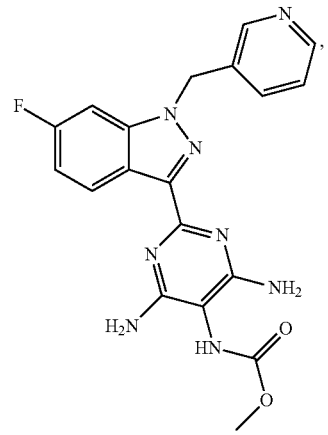
(8)
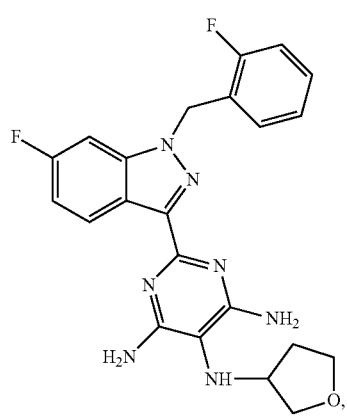
(9)
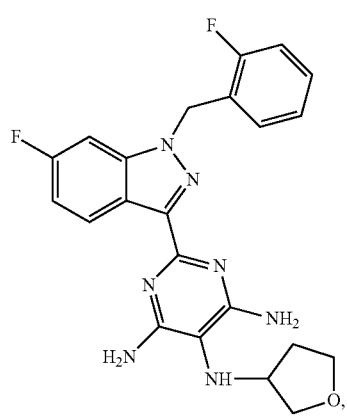
(10)
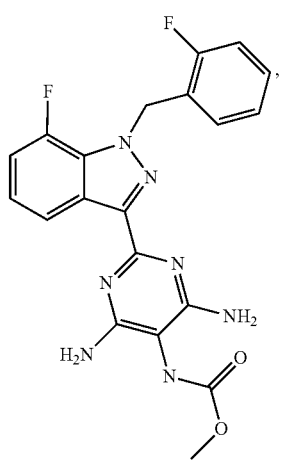
(11)
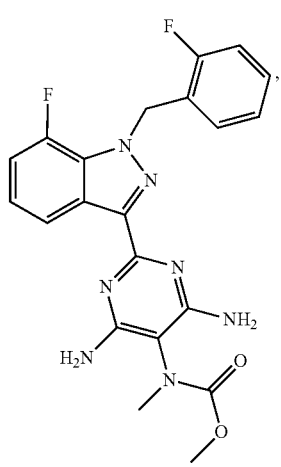
(12)
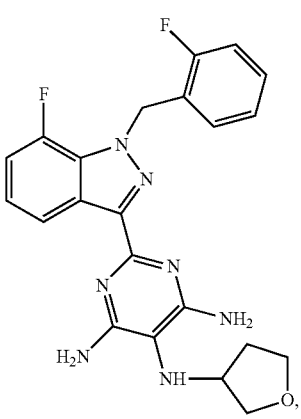

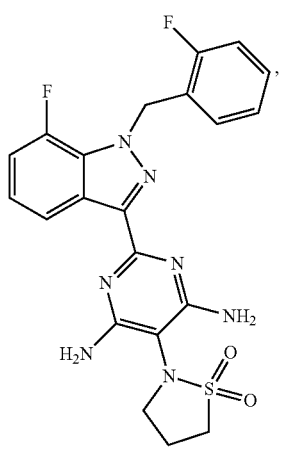
(13)
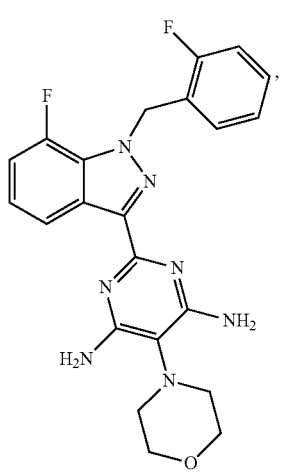
(14)
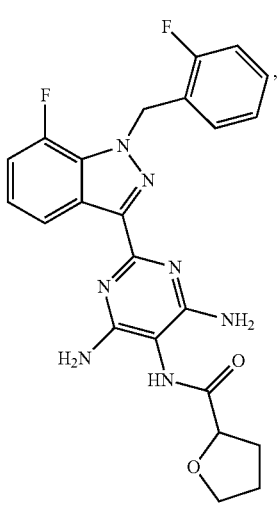
(16)
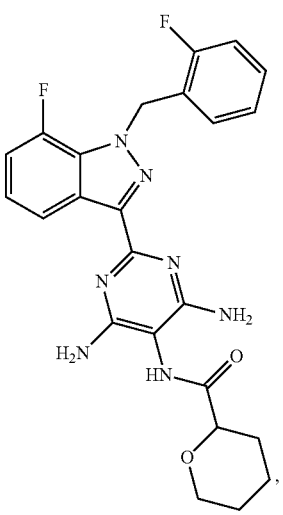
(17)
(15)
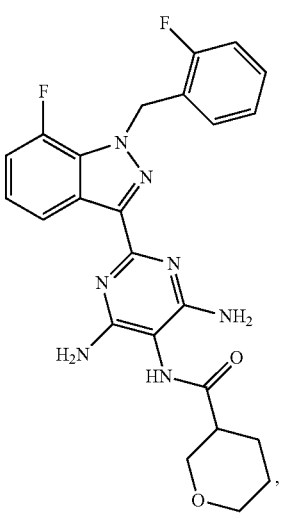
(18)

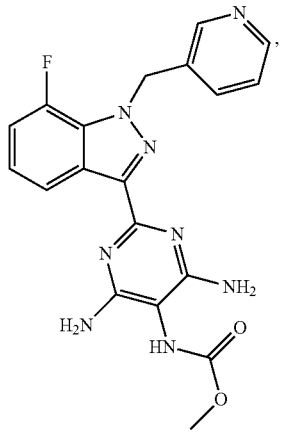
(19)
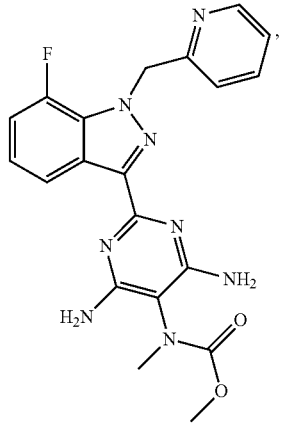
(22)
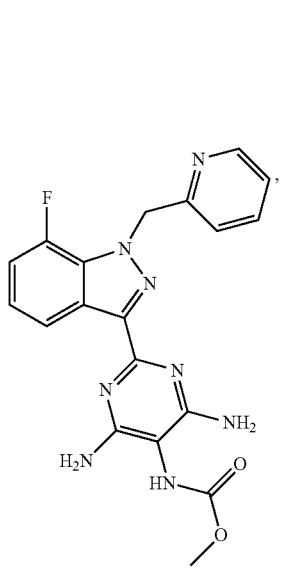
(20)
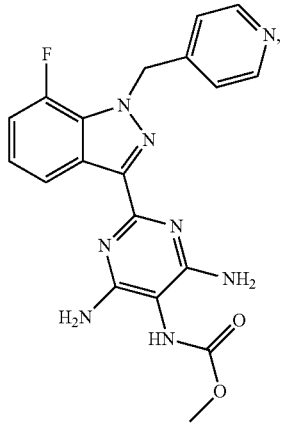
(23)
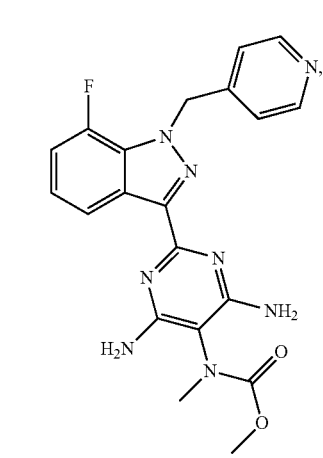
(21)
(24)

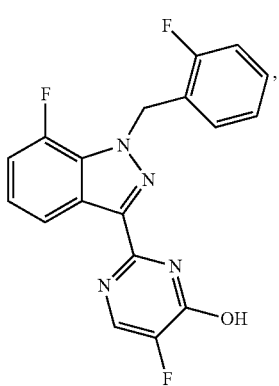
(25)
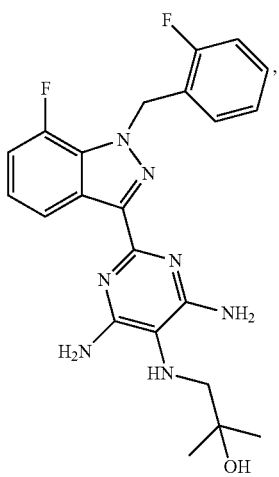
(26)
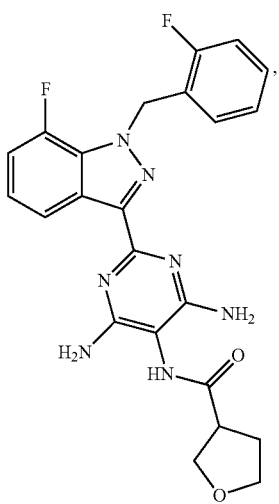
(27)
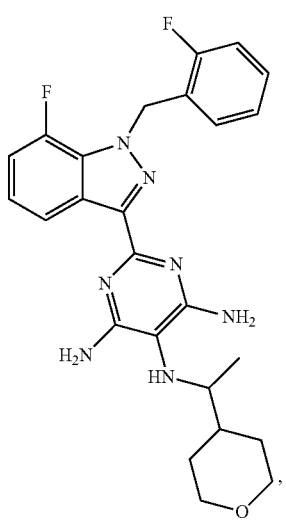
(28)
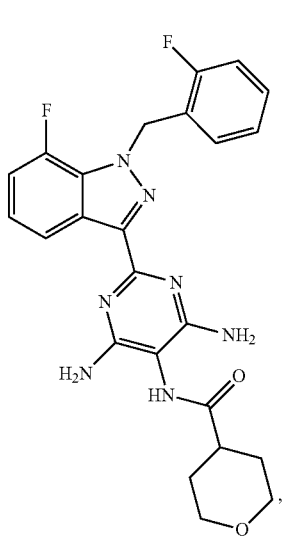
(29)
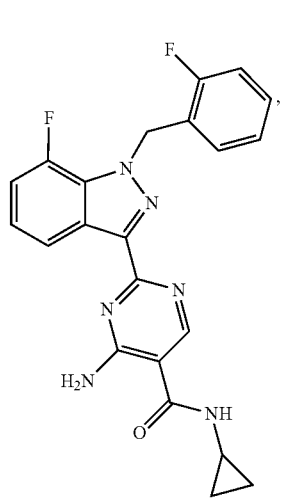
(30)

(31) 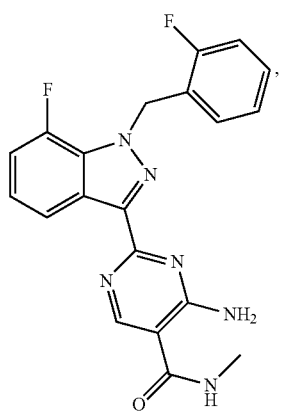
(32) 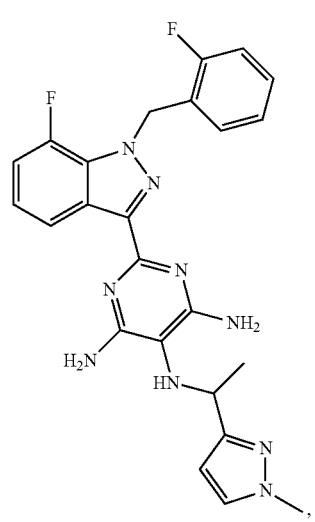
(33) 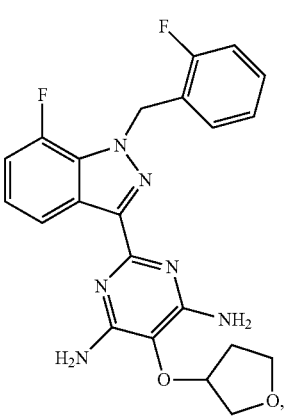
(34) 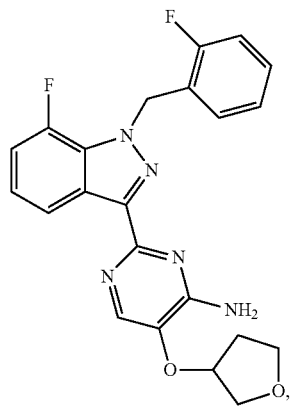
(35) 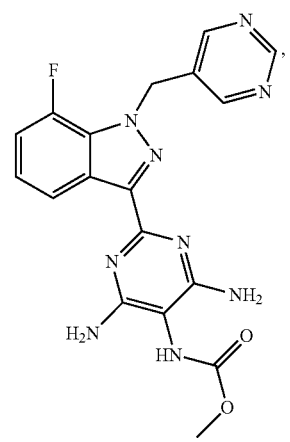
(36) 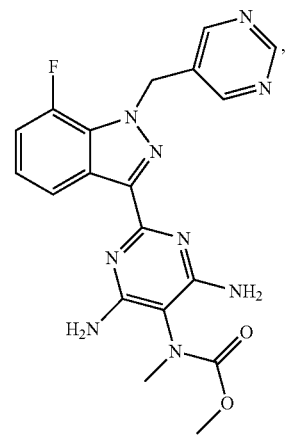
(37) 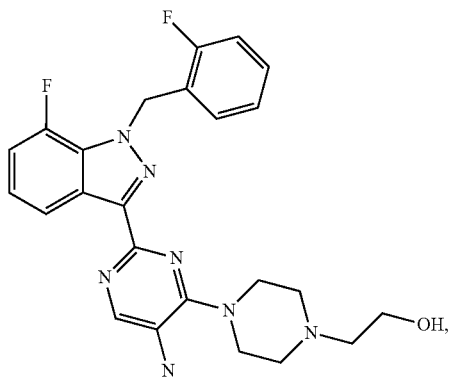

-continued
(38)
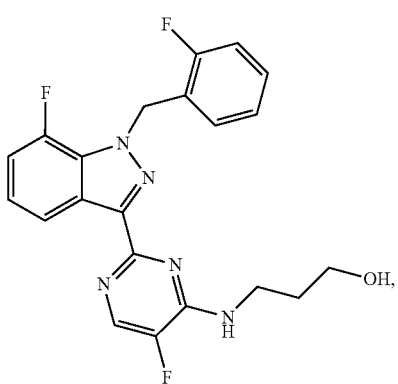
(39)
(40)
-continued
(41)
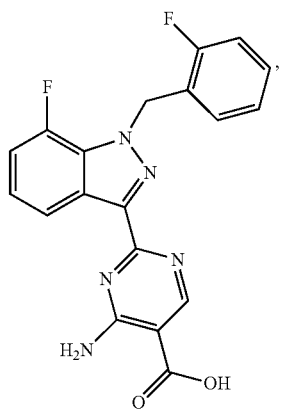
(42)
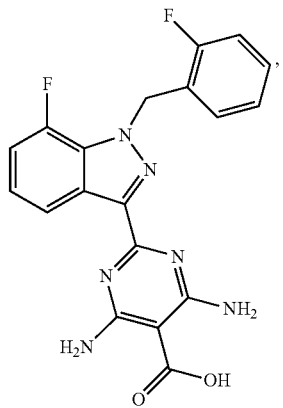
(43)
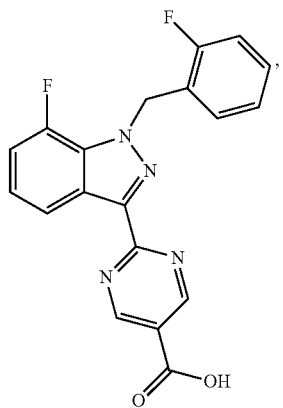
(44)
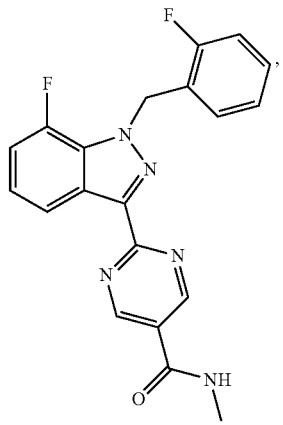

(45)
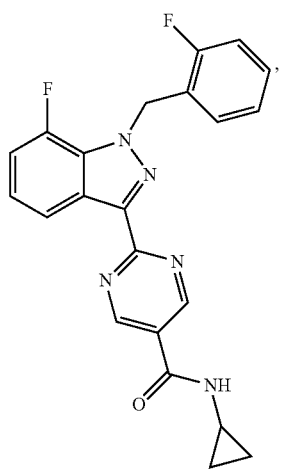
(48)
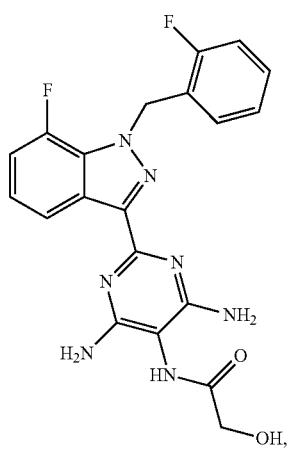
(46)
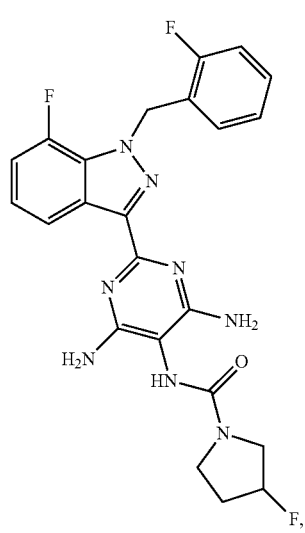
(49)
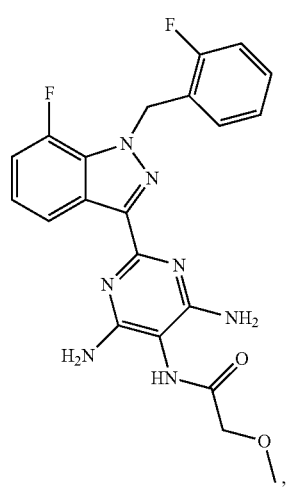
(47)
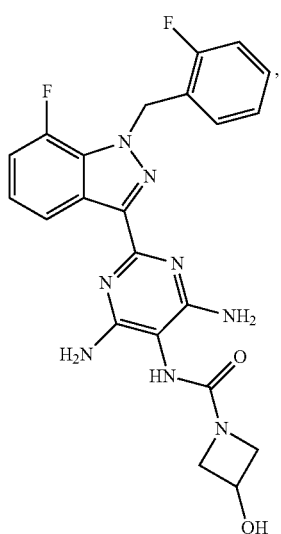
(50)
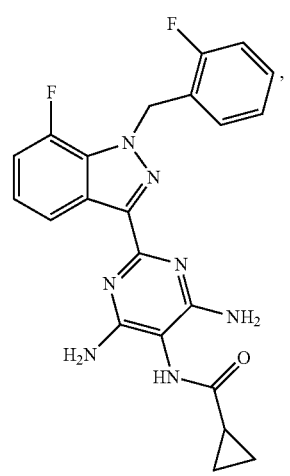

(51) 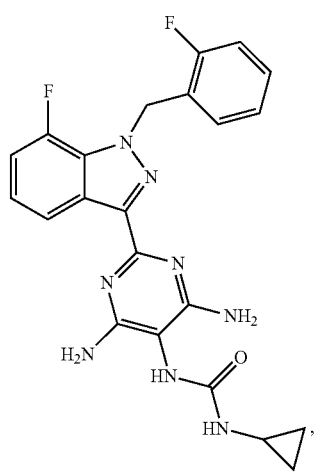
(52) 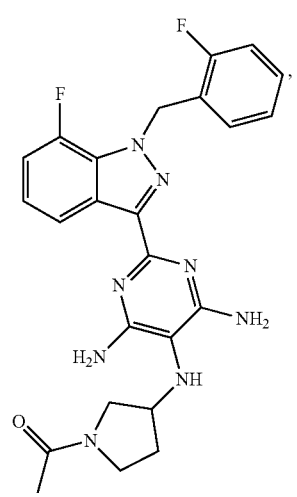
(53) 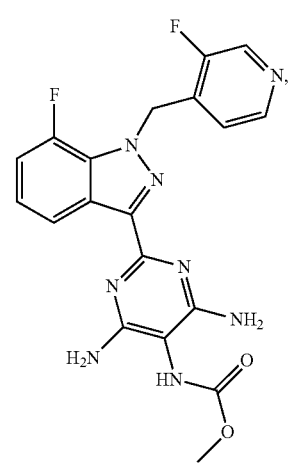
(54) 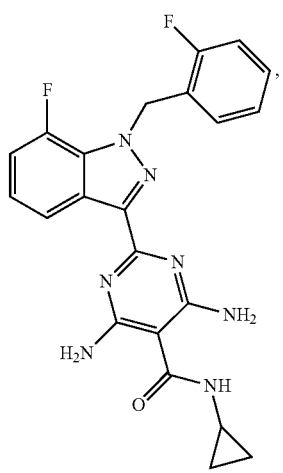
(55) 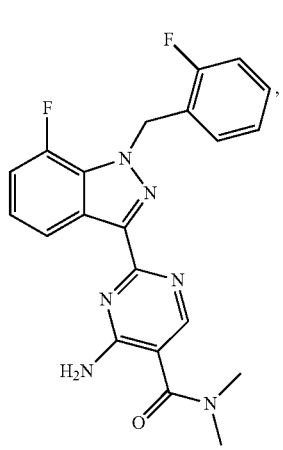
(56) 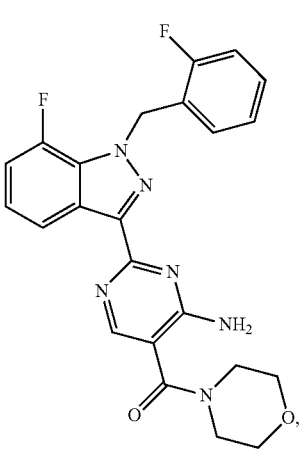

(57)
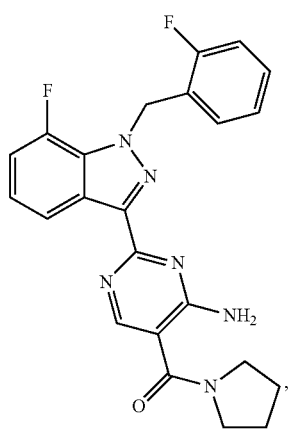
(58)
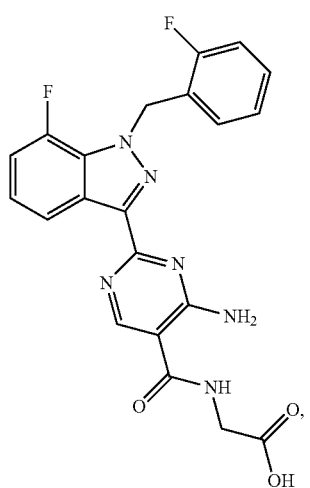
(59)
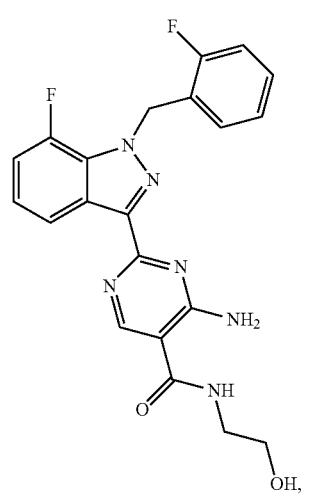
(60)
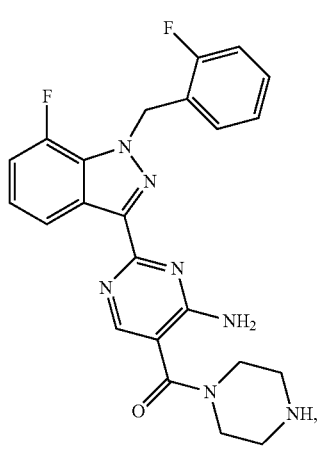
(61)
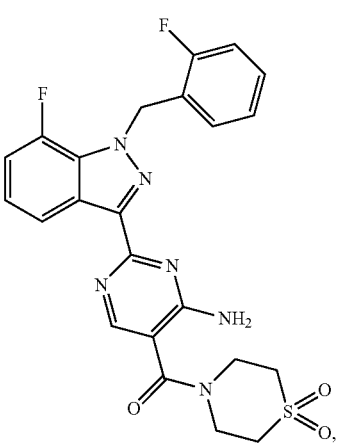
(62)
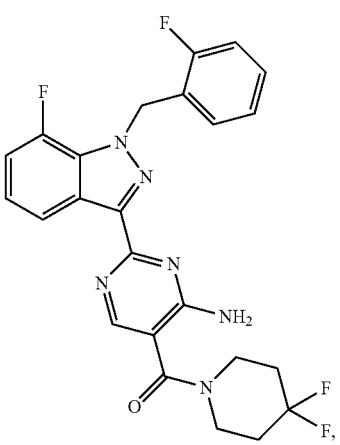

(63) 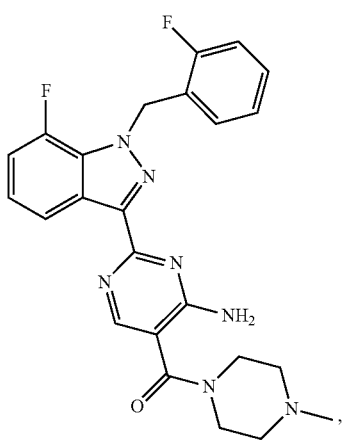

(64) 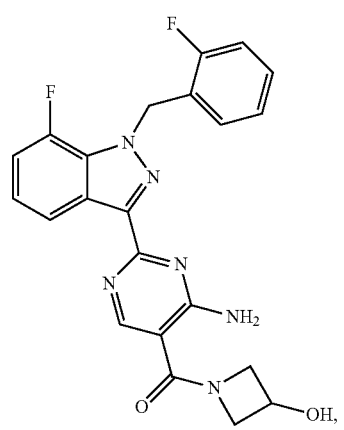

(65) 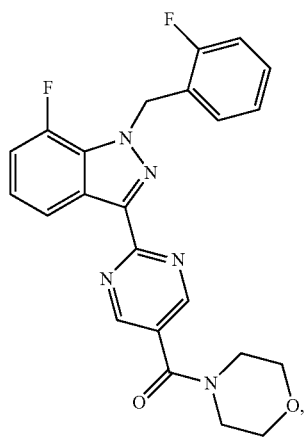

(66) 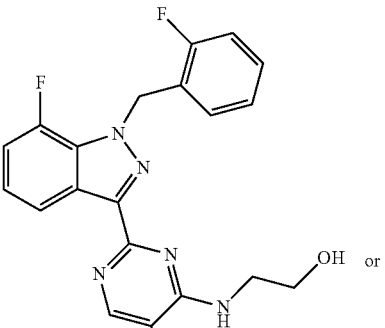

or

(67) 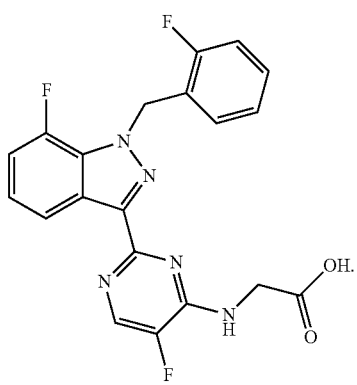

In another aspect, provided herein is a pharmaceutical composition comprising any one of the compounds disclosed herein.

In some embodiments, the pharmaceutical composition disclosed herein further comprises at least one of pharmaceutically acceptable carrier, excipient, diluent, adjuvant and vehicle.

In one aspect, provided herein is use of the compound or the pharmaceutical composition of the invention in the manufacture of a medicament for treating and/or preventing diseases, wherein the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorder and/or arteriosclerosis.

In another aspect, provided herein is use of the compound or the pharmaceutical composition of the invention in the manufacture a medicament as a soluble guanylate cyclase stimulator.

Also provided herein is the use of a compound disclosed herein, or a pharmaceutically acceptable salts thereof, in the manufacture of a medicament for treating sGC-mediated disease, and those diseases described herein. Also provided herein is a pharmaceutical composition comprising a therapeutically effective amount of a compound represented by any Formula of the invention in association with at least one pharmaceutically acceptable carrier, excipient, diluent, adjuvant and vehicle.

In one aspect, provided herein is a method of treating and/or preventing diseases in a patient, comprising administering to the patient a therapeutically effective amount of the compound or the pharmaceutical composition of the invention, wherein the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorders and/or arteriosclerosis.

In another aspect, the present invention relates to a method of stimulating and/or activating soluble guanylate cyclase, comprising contacting the organism (including in vivo or in vitro) with an effective dosage of a compound or a pharmaceutical composition of the present invention.

In one aspect, provided herein is the compound or the pharmaceutical composition of the invention for use in treating and/or preventing the diseases comprise heart failure, angina pectoris, hypertension, pulmonary hypertension, ischaemias, vascular disorder, nephropathy, thromboembolic disorder, male sexual dysfunction, systemic sclerosis, sickle cell anemia, achalasia of the cardia, fibrotic disorder and/or arteriosclerosis.

In another aspect, the invention relates to the compound or pharmaceutical compositions for use in stimulating and/or activating soluble guanylate cyclase.

The present invention also encompasses method of treating or lessening a patient's sGC-mediated disease, or susceptibility to these conditions, comprising administering to a patient a therapeutically effective amount of a compound of the present invention.

Unless otherwise stated, all hydrates, solvates, and pharmaceutically acceptable salts of the compounds of the present invention are within the scope of the present invention.

Specifically, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of the invention, and/or for separating enantiomers of compounds of the invention.

The salt of the compound in the invention may be prepared by any suitable method available in the art, for example, treatment of the free base with an inorganic acid, such as hydrochloric acid, hydrobromic acid, sulfuric acid, nitric acid, phosphoric acid, and the like. or with an organic acid, such as acetic acid, maleic acid, succinic acid, mandelic acid, fumaric acid, malonic acid, pyruvic acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, ethanesulfonic acid, and the like.

The biological activity of the compounds of the invention can be assessed by using any conventionally known method. Suitable assay methods are well known in the art. For example, the sGC activation activity, pharmacokinetic activity, and/or liver microsomal stability, etc., of the compounds of the invention can be assayed by appropriate conventional methods. The detection method provided by the present invention is only presented as an example and does not limit the present invention. The compounds of the invention are active in at least one of the detection methods provided herein. For example, the compounds of the present invention have an activating effect on a recombinant guanylate cyclase reporter cell line. For example, the compound of the present invention can effectively activate the activity of the CHO-K1-Rat sGC monoclonal cell line, that is, the compound of the present invention has godd sGC activation activity. For another example, the compounds of the present invention have better pharmacokinetic properties in vivo, have better absorption and exposure level, and have higher bioavailability.

Pharmaceutical Composition of the Compound of the Invention and Preparations, Administration and Use According to another aspect, the features of the pharmaceutical compositions of the present invention include the fluorine-substituted indazole compounds described in the present invention, the compounds listed in the present invention, or the compounds of Examples 1-63, and pharmaceutically acceptable carriers, adjuvants, or excipients. The amount of compound in the compositions of the present invention is effective to treat or reduce the patient's sGC related disorders.

As described above, the pharmaceutically acceptable composition disclosed herein further comprises a pharmaceutically acceptable carrier, an adjuvant, or an excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the following document: *In Remington: The Science and Practice of Pharmacy,* 21st edition, 2005, ed. D. B. Troy, Lippincott Williams& Wilkins, Philadelphia, and *Encyclopedia of Pharmaceutical Technology*, eds. J. Swarbrick and J. C. Boylan, 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol;

and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The pharmaceutical composition of the present invention can be administered directly or in a pharmaceutical composition or drug form with a suitable carrier or excipient, which is well known in the art. The therapeutic method of the invention may comprise administering an effective compound of the invention to a subject in need thereof. In some embodiments, the subject is a mammalian subject, and in some preferred embodiments, the individual is a human subject.

The effective amount of the compound, pharmaceutical composition or medicament of the present invention can be easily determined by routine experimentation. The most effective and convenient route of administration and the most suitable formulation can also be determined by routine experimentation.

Pharmaceutical dosage forms of the compounds of the invention can be provided in the form of immediate release, controlled release, sustained release or target drug delivery systems. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.).

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e., dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro-)suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

The compounds according to the invention may act systemically and/or locally. They can be administered in a suitable manner, for example by the oral, parenteral, pulmonal, nasal, sublingual, lingual, buccal, rectal, dermal, transdermal, conjunctival, otic route, or as an implant or stent. The compounds of the present invention are preferably administered orally or parenterally.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g., intravenously, intraarterially, intracardially, intraspinally or intralumbally) or include an absorption (e.g., intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g., patches), milch, pastes, foams, sprinkling powders, implants or stents.

The therapeutically effective compound of the invention should be present in the pharmaceutical preparations detailed above in a concentration of about 0.1 to 99.5%, preferably of about 0.5 to 95% by weight of the complete mixture.

The pharmaceutical preparations detailed above may, apart from the compound of the invention also contain other active pharmaceutical ingredients.

The therapeutically effective dose can be estimated first using various methods well known in the art. Initial doses used in animal studies may be based on effective concentrations established in cell culture assays. Dosage ranges appropriate for human subjects can be determined, for example, using data obtained from animal studies and cell culture assays. In certain embodiments, the compounds of the present invention can be prepared as an agent for oral administration. In the case of oral administration, the dosage of the compound of the invention is about 0.01 to 100 mg/kg (wherein the kg represents the body weight of the subject). In some embodiments, the dosage of the medicament is from about 0.01 to 20 mg/kg (wherein the kg represents the body weight of the subject), or optionally from about 0.01 to 10 mg/kg (wherein the kg represents the body weight of the subject), or optionally from about 0.01 to 5.0 mg/kg (wherein the kg represents the body weight of the subject). In certain embodiments, the compounds of the present invention are administered parenterally, with an effective dose of about 0.001 to 1 mg/kg, preferably about 0.01 to 0.5 mg/kg (wherein the kg represents the body weight of the subject).

The dosing regimen for medicament commonly used for oral administration is three times per week, twice per week, once per week, three times daily, twice daily, or once daily. In certain embodiments, the compound of the present invention is administered as an active ingredient in a total amount of about 0.001 to about 50, preferably 0.001 to 10 mg/kg body weight per 24 hours. In order to obtain the desired result, it is optionally possible to administer in multiple single dose forms. A single dose may preferably comprise a compound of the invention in an amount of about 0.001 to about 30, especially 0.001 to 3 mg/kg body weight.

An effective amount, or a therapeutically effective amount, or dose of the medicament (e.g., compound of the invention) refers to the amount of the medicament or compound which ameliorates the disease symptoms in subject or prolongs survival of the subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The compounds according to the invention can be employed by themselves or, if required, in combination with other active compounds. The present invention moreover provides medicaments comprising at least one of the compounds according to the invention and one or more further active compounds, in particular for treatment and/or prevention of the above mentioned diseases.

The compounds according to the invention act as stimulators of soluble guanylate cyclase and have an identical or improved therapeutic profile compared to compounds known from the prior art, such as, for example, with respect to their in vivo properties such as, for example, their pharmacokinetic and pharmacodynamic behaviour and/or their dose-activity relationship and/or their safety profile. They are therefore suitable for the treatment and/or prophylaxis of diseases in man and animals.

The compounds according to the invention lead to vasorelaxation, to an inhibition of platelet aggregation and to a reduction in blood pressure, and also to an increase in coronary blood flow. These effects are mediated via direct stimulation of soluble guanylate cyclase and intracellular cGMP increase. Moreover, the compounds according to the invention enhance the effect of substances increasing the cGMP concentration, such as, for example, EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dsfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemias, sitosterolaemia, xanthomatosis, Tangier disease, adipositas, obesity and/or combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, laesions on glomerulae and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (for example hypercalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarkoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention also represent active compounds for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff s psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of sequelae of cerebral infarct (*Apoplexia cerebri*) such as stroke, cerebral ischaemias and skull-brain trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma (also known as systemic sclerosis), morphea, keloids, hypertrophic scarring (also following surgical procedures), naevi, diabetic retinopathy, proliferative vitreoretinopathy and disorders of the connective tissue (for example sarcoidosis).

The compounds according to the invention are furthermore suitable for controlling postoperative scarring, for example as a result of glaucoma operations. The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The compounds of the present invention are also suitable for the treatment and/or prevention of gastrointestinal diseases, for example, gastrointestinal inflammation, gastrointestinal cancer, gastrointestinal disorders, etc.; and esophageal motility disorders. Gastrointestinal disorders include, for example, irritable bowel syndrome (IBS), non-ulcer dyspepsia, chronic intestinal pseudo-obstruction, functional dyspepsia, colonic pseudo-obstruction, duodenal reflux, gastroesophageal reflux disease (GERD), inflammation of intestinal obstruction (eg., postoperative ileus), gastroparesis, heartburn (high acidity in the gastrointestinal tract), constipation (eg., constipation associated with the use of drugs such as opioids, osteoarthritis drugs, osteoporosis drugs; constipation after surgery; constipation associated with neurological disorders). Esophageal motility disorders include, for example, achalasia of cardia (also known as cardiospasmus), diffuse esophageal spasm, and nutcracker esophagus.

The present invention further provides the use of the compounds according to the invention for the treatment and/or prophylaxis of disorders, in particular the disorders mentioned above.

The present invention further provides the use of the compounds according to the invention for the treatment and/or prophylaxis of heart failure, angina pectoris, hypertension, pulmonary hypertension, ischaemias, vascular disorders, kidney failure, thromboembolic disorders, male sexual dysfunction, systemic sclerosis, sickle cell anemia, fibrotic disorders and/or arteriosclerosis.

The present invention further provides the use of the compounds according to the invention in the manufacture a medicament for the treatment and/or prophylaxis of disorders, in particular the disorders mentioned above.

The present invention further provides the use of the compounds in the manufacture of a medicament according to the invention for the treatment and/or prophylaxis of heart failure, angina pectoris, hypertension, pulmonary hypertension, ischaemias, vascular disorders, kidney failure, thromboembolic disorders, male sexual dysfunction, systemic sclerosis, sickle cell anemia, fibrotic disorders and/or arteriosclerosis.

The present invention further provides a method of treating and/or preventing of disorders, in particular the disorders mentioned above, with effective amount of at least one of the compounds of the invention.

The present invention further provides a method of treating and/or preventing of the following disorders: heart failure, angina pectoris, hypertension, pulmonary hypertension, ischaemias, vascular disorders, kidney failure, thromboembolic disorders, male sexual dysfunction, systemic sclerosis, sickle cell anemia, fibrotic disorders and/or arteriosclerosis.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

(1) organic nitrates and NO donors, for example sodium nitroprusside, nitroglycerin, isosorbide mononitrate, isosorbide dinitrate, molsidomine or SIN-1, and inhaled NO;

(2) compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

(3) agents having an antithrombotic effect, for example and with preference from the group of platelet aggregation inhibitors, of anticoagulants or of profibrinolytic substances;

(4) blood pressure lowering active compounds, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics;

(5) lipid metabolism altering active compounds, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists; and/or (6) agents having an antithrombotic effect, for example and with preference from the group of platelet aggregation inhibitors, of anticoagulants or of profibrinolytic substances.

In a preferred embodiment of the invention, the compounds according to the invention are administered in combination with a platelet aggregation inhibitor such as, by way of example and preferably, aspirin, clopidogrel, ticlopidin, rivaroxaban or dipyridamol.

In a preferred embodiment of the invention, the compounds according to the invention are administered in combination with a thrombin inhibitor such as, by way of example and preferably, ximelagatran, dabigatran, melagatran, bivalirudin or clexane.

In a preferred embodiment of the invention, the compounds according to the invention are administered in combination with a GPIIb/IIIa antagonist such as, by way of example and preferably, tirofiban or abciximab.

In a preferred embodiment of the invention, the compounds according to the invention are administered in combination with a factor Xa inhibitor such as, by way of example and preferably, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as, by way of example and preferably, coumarin.

In a preferred embodiment of the invention, the compounds according to the invention are administered in combination with a calcium antagonist such as, by way of example and preferably, nifedipine, amlodipine, verapamil or diltiazem.

In a preferred embodiment of the invention, the compounds according to the invention are administered in combination with an alpha-1 receptor blocker (e.g., prazosin).

In a preferred embodiment of the invention, the compounds according to the invention are administered in combination with a beta receptor blocker such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin II antagonist such as, by way of example and preferably, losartan, candesartan, valsartan, telmisartan or embusartan.

In a preferred embodiment of the invention, the compounds according to the invention are administered in combination with an ACE inhibitor such as, by way of example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, by way of example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a loop diuretic such as, for example, furosemide, torasemide, bumetanide and piretanide, with potassium-sparing diuretics such as, for example, amiloride and triamterene, with aldosterone antagonists such as, for example, spironolactone, potassium canrenoate and eplerenone and also thiazide diuretics such as, for example, hydrochlorothiazide, chlorthalidone, xipamide and indapamide.

In a preferred embodiment of the invention, the compounds according to the invention are administered in combination with a CETP inhibitor such as, by way of example and preferably, dalcetrapib, BAY 60-5521, anacetrapib or CETP vaccine (CETi-1).

In a preferred embodiment of the invention, the compounds according to the invention are administered in combination with a thyroid receptor agonist such as, by way of example and preferably, D-thyroxin, 3,5,3'-triiodothyronin (T3), CGS 23425 or axitirome (CGS 26214).

In a preferred embodiment of the invention, the compounds according to the invention are administered in combination with a HMG-CoA reductase inhibitor from the class of the statins such as, by way of example and preferably, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as, by way of example and preferably, BMS-188494 or TAK-475.

In a preferred embodiment of the invention, the compounds according to the invention are administered in combination with an ACAT inhibitor such as, by way of example and preferably, avasimibe, melinamide, pactimibe, eflucimibe or SMP-797.

In a preferred embodiment of the invention, the compounds according to the invention are administered in combination with an MTP inhibitor such as, by way of example and preferably, implitapide, BMS-201038, R-103757 or JTT-130.

In a preferred embodiment of the invention, the compounds according to the invention are administered in combination with a PPAR-gamma agonist such as, by way of example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, by way of example and preferably, ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent such as, by way of example and preferably, cholestyramine, colestipol, colesolvam, cholestagel or colestimide.

In a preferred embodiment of the invention, the compounds according to the invention are administered in combination with a bile acid reabsorption inhibitor such as, by way of example and preferably, ASBT (=IBAT) inhibitors, for example AZD-7806, S-8921, AK-105, BARI-1741, SC-435 or SC-635.

In a preferred embodiment of the invention, the compounds according to the invention are administered in combination with an lipoprotein (a) antagonist such as, by way of example and preferably, gemcabene calcium (CI-1027) or nicotinic acid.

General Synthetic Procedures

In the present invention, if the chemical name of the compound doesn't match the corresponding structure, the compound is characterized by the corresponding structure.

Generally, the compounds disclosed herein may be prepared by methods described herein, wherein the substituents are as defined for Formula (I), Formula (Ia), Formula (Ib), Formula (Ic), Formula (II), Formula (IIa), Formula (IIb), Formula (IIc), Formula (IId), Formula (III), Formula (IV), Formula (IVa), Formula (IVb), Formula (IVc), Formula (Va), Formula (Vb), Formula (Vc) or Formula (Vd) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ethyl ether were obtained by refluxing the solvent with sodium. Anhydrous $CH_2Cl_2$ and $CHCl_3$ were obtained by refluxing the solvent with $CaH_2$. EtOAc, PE, hexane, N,N-dimethylacetamide and N,N-dimethylformamide were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded by a Bruker Avance 400 MHz spectrometer or Bruker Avance III HD 600 spectrometer, using $CDCl_3$, DMSO-$d_6$, $CD_3OD$ or acetone-$d_6$ (reported in ppm) as solvent, and using TMS (0 ppm) or chloroform (7.25 ppm) as the reference standard. When peak multiplicities are reported, the following abbreviations are used: s (singlet), d (doublet), t (triplet), m (multiplet), q (quartet), br (broadened), dd (doublet of doublets), dt (doublet of triplets), dq (doublet of quartets), ddd (doublet of doublet of doublets), ddt (doublet of doublet of triplets), dddd (doublet of doublet of doublet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315B DAD detector were applied in the analysis, and an ESI source was used in the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1:

TABLE 1

| The gradient condition of the mobile phase in Low-resolution mass spectrum analysis | | |
|---|---|---|
| Time (min) | A ($CH_3CN$, 0.1% HCOOH) | B ($H_2O$, 0.1% HCOOH) |
| 0-3 | 5-100 | 95-0 |
| 3-6 | 100 | 0 |
| 6-6.1 | 100-5 | 0-95 |
| 6.1-8 | 5 | 95 |

The following abbreviations are used throughout the specification:

$CDCl_3$ chloroform-d

DMSO-$d_6$ dimethyl sulfoxide-$d_6$

DMSO dimethylsulfoxide g gram mg milligram mol mole mmol millimole h hour, hours min minute, minutes mL milliliter μL microliter rt room temperature The following reaction schemes describe the steps for preparing the compounds disclosed herein. Wherein, unless otherwise specified, $L^1$ is F, Cl, Br, I or other suitable leaving group; $L^2$ is H or a leaving group such as Cl, Br, and the like; $L^3$ is a leaving group such as Cl, Br, and the like; each L, C1, $R^1$, $R^2$, $R^{5c}$, $R^{5d}$, $R^{5e}$, $R^{8a}$, m and n is as defined herein.

Schemes

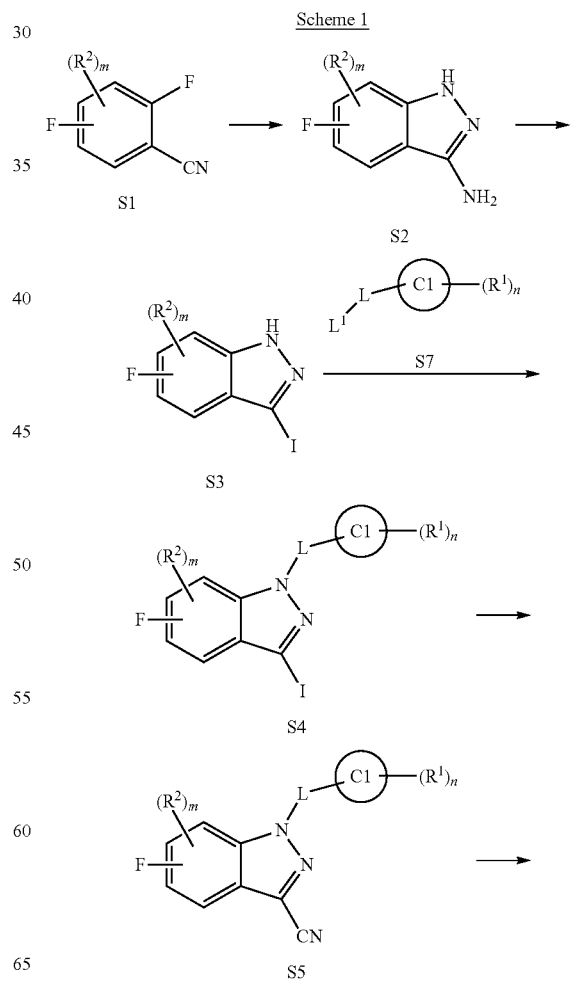

Scheme 1

-continued

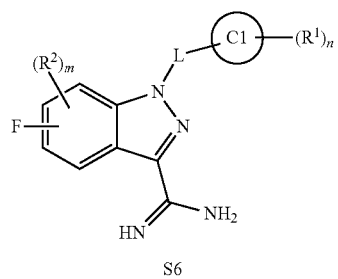

S6

Compound S6 can be prepared by the process illustrated in scheme 1, and the reaction process is as follows: compound S1 can react with hydrazine hydrate to give compound S2; compound S2 with a suitable reagent (such as boron trifluoride diethyl etherate and isoamyl nitrite) can undergo diazo-reaction and then the product can react with iodine-containing reagent (such as sodium iodide, etc.) to give compound S3; compound S3 with compound S7 can undergo substitution reaction to give compound S4, then compound S4 can undergo cyanation reaction to give a cyano-substituted indazole derivative S5; at last, the compound S5 can undergo addition reaction in the presence of a suitable reagent to give a formamidine derivative S6.

Scheme 2

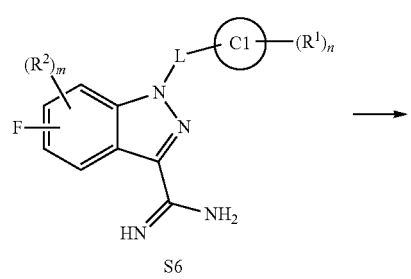

-continued

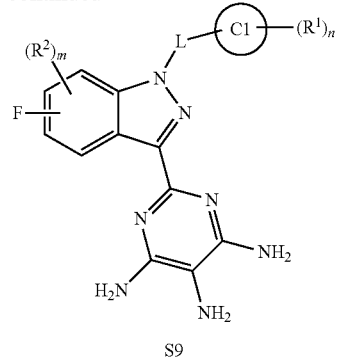

S9

Compound S9 can be prepared by the process illustrated in scheme 2, and the reaction process is as follows: compound S6 can react with benzeneazomalononitrile to give compound S8, then the compound S8 can undergo hydrogenation reduction in the presence of metal palladium catalyst to give compound S9.

Scheme 3

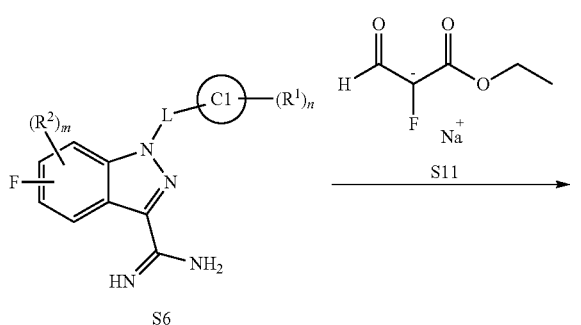

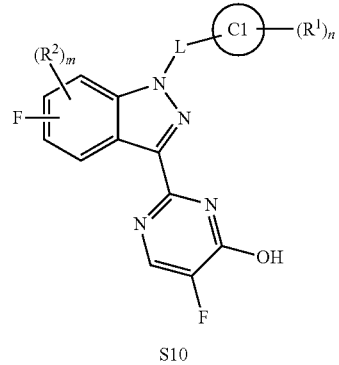

S10

Compound S10 can be prepared by the process illustrated in scheme 3, and the reaction process is as follows: compound S6 can react with compound S11 to give compound S10.

Scheme 4

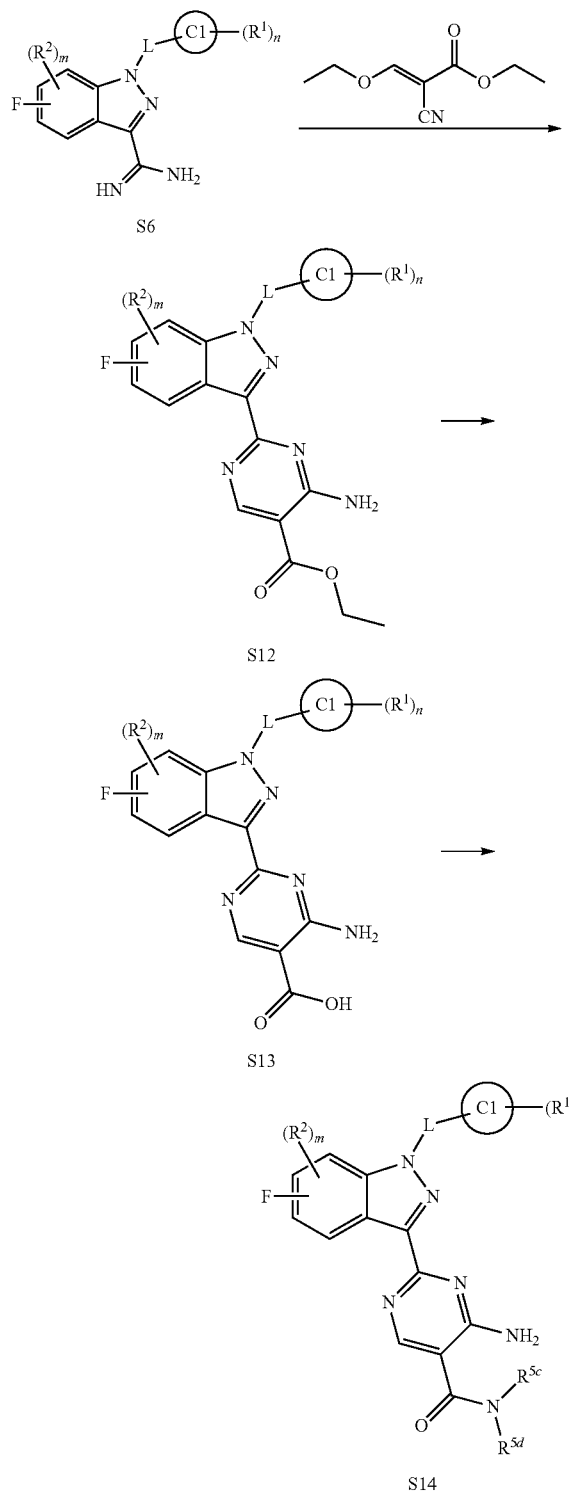

Scheme 5

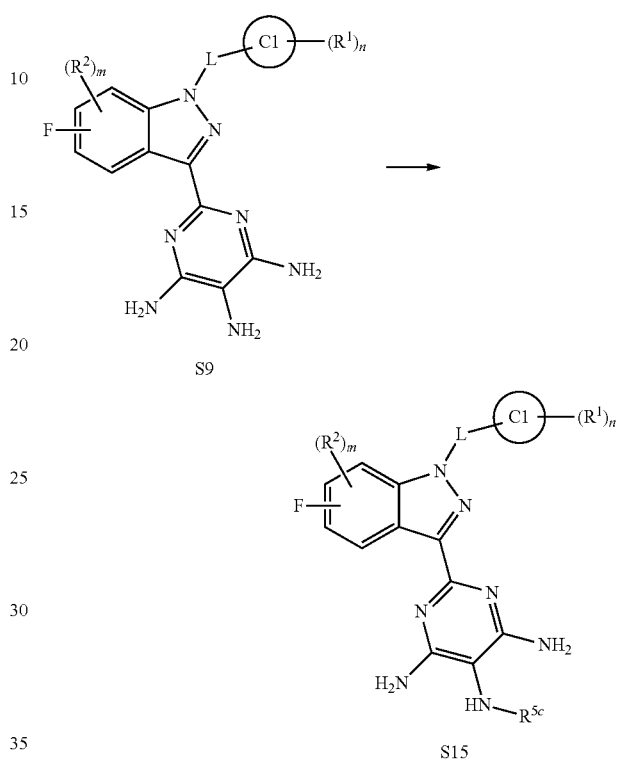

S13 with compound $NHR^{5c}R^{5d}$ can undergo condensation reaction in the presence of a condensation agent to give compound S14.

Compound S14 can be prepared by the process illustrated in scheme 4, and the reaction process is as follows: compound S6 can react directly with ethyl (ethoxymethylene) cyanoacetate to give compound S12, then compound S12 can be hydrolyzed in the presence of a base (such as sodium hydroxide, etc.) to give compound S13, then the compound Compound S15 can be prepared by the process illustrated in scheme 5, and the reaction process is as follows: compound S9 can react with a suitable reagent to give compound S15. For example, when $R^{5c}$ is tetrahydropyranylethyl

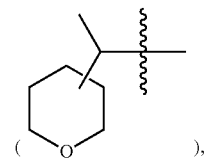

the compound S15 can be given by reacting compound S9 with tetrahydropyranylethanone

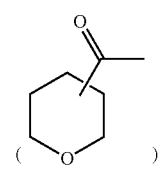

in the presence of acetic acid and sodium cyanoborohydride.

Scheme 6

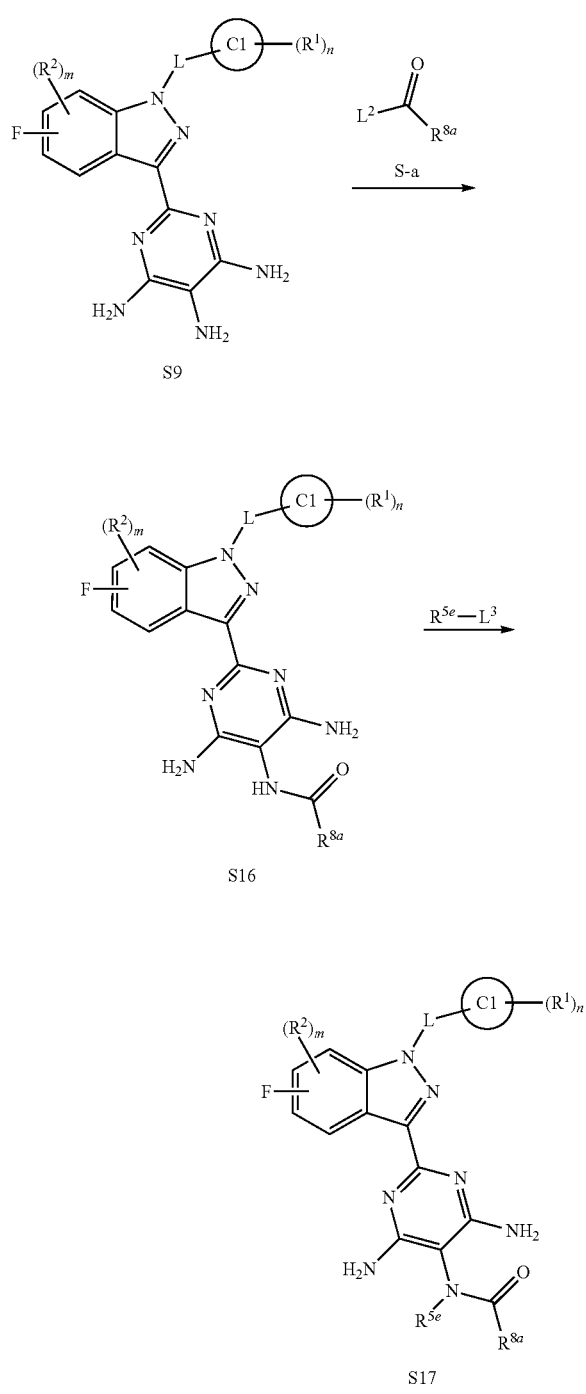

Compound S16 and S17 can be prepared by the process illustrated in scheme 6, and the reaction process is as follows: compound S9 with compound S-a can undergo condensation reaction in the presence of a suitable reagent (condensation reagent or base) to give compound S16, then compound S16 can react with compound $R^{5e}$-$L^3$ to give compound S17.

The following examples disclosed herein are presented to further describe the invention. However, these examples should not be used to limit the scope of the invention.

EXAMPLES

Example 1 methyl (4,6-diamino-2-(5,7-difluoro-1-(2-fluorobenzyl)-1H-indazol-3-yl) pyrimidin-5-yl)carbamate

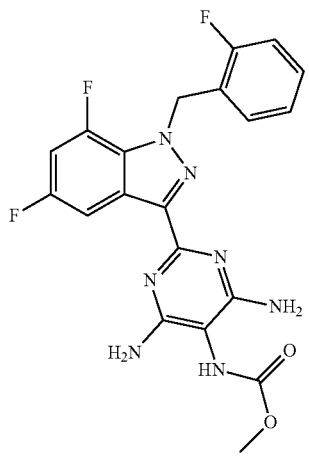 [SMILES: COC(=O)Nc1c(N)nc(-c2nn(Cc3ccccc3F)c3c(F)cc(F)cc23)nc1N]

Step 1: 5,7-difluoro-1H-indazol-3-amine 2,3,5-Trifluorobenzonitrile (14.0 g, 89.1 mmol) was dissolved in n-butanol (200 mL), then hydrazine hydrate (75 mL, 1540 mmol) was added under nitrogen protection. After the addition, the mixture was heated to 150° C. and refluxed overnight. After the reaction was completed, the reaction mixture was cooled to rt, and extracted with EtOAc (100 mL×3). The combined organic layers were washed with water (100 mL×3) and saturated brine (50 mL×2), dried over anhydrous sodium sulfate, filtered, and the filtrate was concentrated in vacuo. The residue was purified by silica gel chromatograph (petroleum ether/ethyl acetate (v/v)=2/1) to give the title compound as a yellow solid (9.8 g, 65%).

MS (ESI, pos. ion) m/z: 170.1 (M+1).

Step 2: 5,7-difluoro-3-iodo-1H-indazole 5,7-Difluoro-1H-indazol-3-amine (10.0 g, 59.1 mmol) was dissolved in anhydrous tetrahydrofuran (100 mL), then boron trifluoride diethyl etherate (15.0 mL, 118 mmol) was added dropwise slowly under an ice-bath condition. After the addition, then the reaction flask was placed in a circumstance of −10° C., and a solution of isoamyl nitrite (10.3 mL, 76.7 mmol) in tetrahydrofuran (35 mL) was added dropwise slowly. After the addition, the reaction mixture was stirred for 30 min. Ethyl ether (200 mL) was added to precipitate out the product, and the mixture was filtered by suction to give a black brown solid. The solid then dissolved in acetone (250 mL), and sodium iodide (11.5 g, 76.7 mmol) was added under an ice-bath condition, and the resulting mixture was stirred at rt for 30 minutes. The reaction mixture was extracted with EtOAc (250 mL×3). The combined organic layers were washed with water (250 mL×2) and saturated brine (150 mL×2), dried over anhydrous sodium sulfate, filtered, and the filtrate was concentrated in vacuo to give the title compound as black oil (16.5 g, 99.7%).

Step 3: 5,7-difluoro-1-(2-fluorobenzyl)-3-iodo-1H-indazole 5,7-Difluoro-3-iodo-1H-indazole (16.5 g, 58.9 mmol) was dissolved in N,N-dimethylformamide (100 mL), then 1-(bromomethyl)-2-fluorobenzene (12.3 g, 64.8 mmol) and cesium carbonate (21.1 g, 64.8 mmol) were added. The mixture was stirred for 2 h at rt. The reaction mixture was extracted with EtOAc (200 mL×3). The combined organic layers were washed with water (150 mL×3) and saturated brine (100 mL×2), dried over anhydrous sodium sulfate, filtered, and the filtrate was concentrated in vacuo to give the title compound as brownness oil (22.9 g, 99.9%).

MS (ESI, pos. ion) m/z: 389.25 (M+1).

Step 4: 5,7-difluoro-1-(2-fluorobenzyl)-1H-indazole-3-carbonitrile 5,7-Difluoro-1-(2-fluorobenzyl)-3-iodo-1H-indazole (22.9 g, 59.0 mmol) was dissolved in dimethylsulfoxide (300 mL), then cuprous cyanide (5.81 g, 64.9 mmol) was added. The mixture was heated to 150° C. and stirred for 3 hours. The mixture was cooled to rt, and the reaction mixture was poured into a mixture of strong aqua ammonia (100 mL) and water (500 mL), then the resulting mixture was extracted with a mixed solvent of petroleum ether and ethyl acetate (v/v=10/1, 200 mL×3). The organic layers were combined, and washed with water (100 mL×3) and saturated brine (100 mL×2) in turn. The organic layer was dried over anhydrous sodium sulfate and concentrated in vacuo to remove the solvent. The residue was purified by silica-gel column chromatography (ethyl acetate/petroleum ether (v/v)=1/100) to give a yellow solid (3.2 g, 19.0%).

MS (ESI, pos. ion) m/z: 288.3 (M+1).

Step 5: 5,7-difluoro-1-(2-fluorobenzyl)-1H-indazole-3-carboximidamide

To a solution of sodium methoxide (0.60 g, 10.0 mmol) in methanol (150 mL) was added 5,7-difluoro-1-(2-fluorobenzyl)-1H-indazole-3-carbonitrile (3.20 g, 11.0 mmol). The mixture was stirred at rt for 2 hours. Then to the mixture were added ammonium chloride (0.72 g, 13.0 mmol) and glacial acetic acid (2.5 mL, 130 mmol). The reaction mixture was heated to 75° C. and refluxed for 4 hours. After the addition, the mixture was cooled to rt and concentrated in vacuo to remove the solvent. To the residue were added water (150 mL) and ethyl acetate (150 mL), then to the mixture was added aqueous sodium hydroxide solution (2 mol/L) to adjust pH 10. The reaction mixture was stirred at rt for 1 h. The mixture was partitioned to give the organic layer, and the aqueous layer was extracted with ethyl acetate (200 mL×2). The combined organic layers were washed with water (100 mL×2) and saturated brine (100 mL×2). The organic layers were dried over anhydrous sodium sulfate and concentrated in vacuo to give a yellow solid (2.7 g, 80.0%).

MS (ESI, pos. ion) m/z: 305.3 (M+1).

Step 6: 2-(5,7-difluoro-t-(2-fluorobenzyl)-1H-indazol-3-yl)-5-(phenyldiazenyl)pyrimidine-4,6-diamine 5,7-Difluoro-1-(2-fluorobenzyl)-1H-indazole-3-carboximidamide (2.6 g, 8.5 mmol) was dissolved in N,N-dimethylformamide (50 mL), then triethylamine (1.5 mL, 11 mmol) was added into the mixture. The resulting mixture was heated to 85° C., and to the mixture was added a solution of benzeneazomalononitrile (1.8 g, 11 mmol) in N,N-dimethylformamide (50 mL). After the addition, the mixture was heated to 100° C. and stirred for 4 h. Then the reaction mixture was stirred at room temperature overnight. To the reaction mixture was added water (300 mL), and the resulting mixture was stirred for 1 hour at room temperature to precipitate out the solid. Then the mixture was filtered by suction through a Buchner funnel. The filter cake was washed with water (50 mL×2) and methanol (50 mL×2) to give a yellow solid (4.0 g, 98.0%).

MS (ESI, pos. ion) m/z: 475.4 (M+1).

Step 7: 2-(5,7-difluoro-1-(2-fluorobenzyl)-1H-indazol-3-yl)pyrimidine-4,5,6-triamine 2-(5,7-Difluoro-1-(2-fluorobenzyl)-1H-indazol-3-yl)-5-(phenyldiazenyl)pyrimidine-4,6-diamine (4.0 g, 8.4 mmol) was dissolved in N,N-dimethylformamide (100 mL), then 10% Pd/C (1.0 g) was added. The resulting mixture was stirred at rt overnight in hydrogen atmosphere. The reaction mixture was filtered through a celite pad, and the filter cake was washed with ethyl acetate (30 mL×3). The filtrate was concentrated in vacuo to remove the solvent, and the residue was purified by silica-gel column chromatography (ethyl acetate) to give a yellow solid (1.2 g, 37.0%).

MS (ESI, pos. ion) m/z: 386.05 (M+1).

Step 8: methyl (4,6-diamino-2-(5,7-difluoro-1-(2-fluorobenzyl)-1H-indazol-3-yl)pyrimidin-5-yl)carbamate 2-(5,7-Difluoro-1-(2-fluorobenzyl)-1H-indazol-3-yl)pyrimidine-4,5,6-triamine (200 mg, 0.52 mmol) was dissolved in dichloromethane (30 mL), then pyridine (0.1 mL, 1 mmol) and methylchloroformate (0.1 mL, 1.0 mmol) were added dropwise under an ice-bath condition. After the addition, the reaction mixture was continued to stir for 2 hour. The reaction mixture was concentrated in vacuo to remove the solvent, and the residue was purified by silica-gel column chromatography (ethyl acetate) to give a light yellow solid (46 mg, 19.1%).

MS (ESI, pos. ion) m/z: 444.0 (M+1);
$^1$H NMR (400 MHz, DMSO-$d_6$) δ (ppm) 8.38 (d, J=9.1 Hz, 1H), 8.00 and 7.70 (2 br s, 1H), 7.44-7.31 (m, 2H), 7.30-7.18 (m, 1H), 7.14 (t, J=7.5 Hz, 1H), 6.99 (t, J=7.4 Hz, 1H), 6.20 (s, 4H), 5.82 (s, 2H), 3.63 (s, 3H).

Example 2 methyl (4,6-diamino-2-(5,7-difluoro-1-(2-fluorobenzyl)-1H-indazol-3-yl) pyrimidin-5-yl)(methyl)carbamate

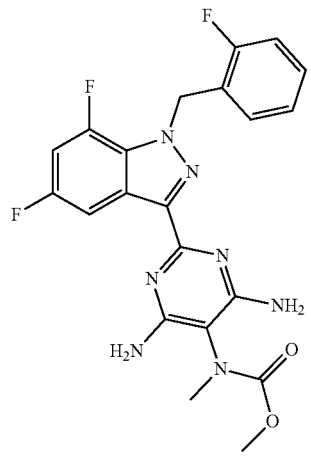 [SMILES: COC(=O)N(C)c1c(N)nc(-c2nn(Cc3ccccc3F)c3c(F)cc(F)cc23)nc1N]

Methyl (4,6-diamino-2-(5,7-difluoro-1-(2-fluorobenzyl)-1H-indazol-3-yl)pyrimidin-5-yl)carbamate (550 mg, 1.24 mmol) was dissolved in N,N-dimethylformamide (30 mL). Then 60% sodium hydride (75 mg, 1.88 mmol) was added at 0° C., and the mixture was stirred maintaining at this temperature for 20 minutes, and then iodomethane (85 µL, 1.37 mmol) was added into the mixture. The resulting mixture was continued to stir for 30 minutes and then stirred for 1 hour at rt. The reaction mixture was quenched with saturated aqueous ammonium chloride (20 mL), and the resulting mixture was extracted with ethyl acetate (50 mL×2). The combined organic layers were washed with water (40 mL) and saturated brine (40 mL), dried over anhydrous sodium sulfate, and filtered. The filtrate with concentrated in vacuo to remove the solvent, and the residue was purified by silica-gel column chromatography (petroleum ether/ethyl acetate (v/v)=1/2) to give a white solid (260 mg, 45.8%).

MS (ESI, pos. ion) m/z: 458.2 (M+1);

$^1$H NMR (400 MHz, DMSO-d$_6$) δ (ppm) 8.37 (dd, J=9.2, 1.7 Hz, 1H), 7.46-7.30 (m, 2H), 7.29-7.18 (m, 1H), 7.13 (t, J=7.5 Hz, 1H), 6.96 (t, J=7.0 Hz, 1H), 6.42 (s, 4H), 5.82 (s, 2H), 3.66 and 3.54 (2 s, 3H), 3.01 (s, 3H).

Example 3

Methyl (4,6-diamino-2-(5,7-difluoro-1-(pyridin-3-ylmethyl)-1H-indazol-3-yl) pyrimidin-5-yl)carbamate

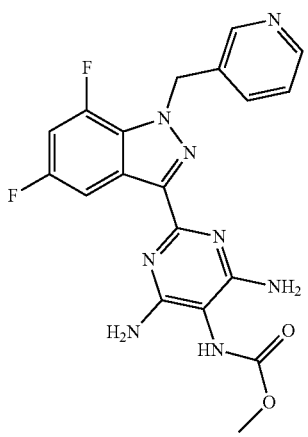 [SMILES: COC(=O)Nc1c(N)nc(-c2nn(Cc3cccnc3)c3c(F)cc(F)cc23)nc1N]

Step 1: 5,7-difluoro-3-iodo-1-(pyridin-3-ylmethyl)-1H-indazole 5,7-Difluoro-3-iodo-1H-indazole (3.0 g, 10.7 mmol) was dissolved in N,N-dimethylformamide (150 mL), then 3-(bromomethyl)pyridine hydrobromide (3.0 g, 12.0 mmol) and cesium carbonate (7.3 g, 22.0 mmol) were added. The mixture was stirred for 2 h at rt. The reaction mixture was extracted with ethyl ether (100 mL×2). The combined organic layers were washed with water (50 mL) and saturated brine (50 mL), dried over anhydrous sodium sulfate, and filtered. The filtrate was concentrated in vacuo to give a yellow solid (3.50 g, 88.0%).

MS (ESI, pos. ion) m/z: 372.1 (M+1).

Step 2: 5,7-difluoro-1-(pyridin-3-ylmethyl)-1H-indazole-3-carbonitrile

Cuprous cyanide (845 mg, 9.44 mmol) was dissolved in dimethylsulfoxide (20 mL) under nitrogen protection. The mixture was heated to 150° C., and a solution of 5,7-difluoro-3-iodo-1-(pyridin-3-ylmethyl)-1H-indazole (3.50 g, 9.43 mmol) in dimethylsulfoxide (25 mL) was added dropwise. After addition, the mixture was continued to stir for 2.5 hours at 150° C. The reaction mixture was cooled to rt, and quenched with ammonium hydroxide (15 mL) and water (30 mL). The mixture was stirred for 10 minutes, and then extracted with ethyl acetate (100 mL×2). The combined organic layers were washed with water (50 mL) and saturated brine (50 mL), dried over anhydrous sodium sulfate. and filtered. The filtrate with concentrated in vacuo to remove the solvent, and the residue was purified by silica-gel column chromatography (petroleum ether/ethyl acetate (v/v)=2/1) to give a white solid (1.23 g, 48.3%).

MS (ESI, pos. ion) m/z: 271.2 (M+1).

Step 3: 5,7-difluoro-1-(pyridin-3-ylmethyl)-1H-indazole-3-carboximidamide

To a 100 mL two-neck flask was added sodium methoxide (250 mg, 4.63 mmol), then to the mixture were added methanol (25 mL) and 5,7-difluoro-1-(pyridin-3-ylmethyl)-1H-indazole-3-carbonitrile (1.03 g, 3.81 mmol). The mixture was stirred at rt for 2 hours, then ammonium chloride (265 mg, 4.95 mmol) and glacial acetic acid (0.90 mL, 16 mmol) were added. The resulting mixture was refluxed overnight. The mixture was cooled to rt, and concentrated by rotary evaporation to remove the solvent. To the reaction mixture were added water (100 mL) and ethyl acetate (20 mL), the to the mixture was added aqueous sodium hydroxide solution (2 mol/L) to adjust pH 10. The reaction mixture was stirred at rt for 10 minutes. The reaction mixture was extracted with ethyl ether (50 mL×2). The combined organic layers were washed with water (20 mL×2) and saturated brine (40 mL), dried over anhydrous sodium sulfate, and filtered. The filtrate was concentrated in vacuo to give a yellow solid (1.0 g, 91.0%).

MS (ESI, pos. ion) m/z: 288.2 (M+1).

Step 4: 2-(5,7-difluoro-1-(pyridin-3-ylmethyl)-1H-indazol-3-yl)-5-(phenyldiazenyl) pyrimidine-4,6-diamine 5,7-Difluoro-1-(pyridin-3-ylmethyl)-1H-indazole-3-carboximidamide (1.0 g, 3.5 mmol) was dissolved in N,N-dimethylformamide (50 mL), then triethylamine (0.80 mL, 5.8 mmol) was added into the mixture. The resulting mixture was heated to 85° C. under nitrogen protection, and to the mixture was added benzeneazomalononitrile (900 mg, 5.30 mmol). After the addition, the mixture was heated to 100° C. and stirred for 5 hours. The mixture was cooled to room temperature and used directly in the next group without further purification.

MS (ESI, pos. ion) m/z: 458.1 (M+1).

Step 5: 2-(5,7-difluoro-1-(pyridin-3-ylmethyl)-1H-indazol-3-yl)pyrimidine-4,5,6-triamine To the reaction mixture of the previous step was added 10% Pd/C (100 mg). The resulting mixture was stirred at room temperature overnight in hydrogen atmosphere. The reaction mixture was filtered through a celite pad, and the filter cake was washed with methanol (20 mL×2), then the filtrates were collected. The combined filtrates were concentrated in vacuo to remove the solvent. The residue was purified by silica gel chromatography eluted with dichloromethane/methanol (v/v)=15/1 to give a brown solid (902 mg, 97.4%).

MS (ESI, pos. ion) m/z: 369.1 (M+1).

Step 6: methyl (4,6-diamino-2-(5,7-difluoro-1-(pyridin-3-ylmethyl)-1H-indazol-3-yl) pyrimidin-5-yl) carbamate 2-(5,7-Difluoro-1-(pyridin-3-ylmethyl)-1H-indazol-3-yl) pyrimidine-4,5,6-triamine (900 mg, 2.44 mmol) was dissolved in dichloromethane (15 mL), then pyridine (10 mL, 124 mmol) and methylchloroformate (0.60 mL, 7.8 mmol) were added dropwise at 0° C. After the addition, the reaction mixture was continued to stir for 2 hour at 0° C., and then stirred at room temperature overnight. The reaction mixture was concentrated in vacuo to remove the solvent. The residue was purified by silica gel chromatography eluted with dichloromethane/methanol ((v/v)=8/1) to give a light yellow solid (620 mg, 59.5%).

MS (ESI, pos. ion) m/z: 427.3 (M+1);
$^1$H NMR (400 MHz, DMSO-$d_6$) δ (ppm) 8.50 (d, J=2.4 Hz, 2H), 8.39 (d, J=9.1 Hz, 1H), 8.05 and 7.72 (2br s, 1H), 7.54 (d, J=7.8 Hz, 1H), 7.47-7.27 (m, 2H), 6.25 (s, 4H), 5.82 (s, 2H), 3.63 (s, 3H).

Example 4 methyl (4,6-diamino-2-(5,7-difluoro-1-(pyridin-3-ylmethyl)-1H-indazol-3-yl) pyrimidin-5-yl)(methyl) carbamate

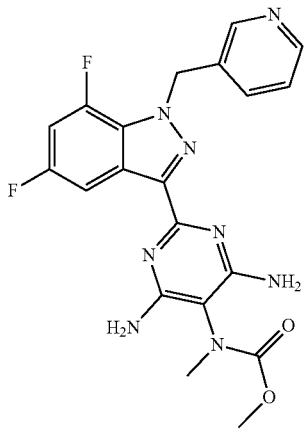 [SMILES: COC(=O)N(C)c1c(N)nc(-c2nn(Cc3cccnc3)c3c(F)cc(F)cc23)nc1N]

Methyl (4,6-diamino-2-(5,7-difluoro-1-(pyridin-3-ylmethyl)-1H-indazol-3-yl) pyrimidin-5-yl)carbamate (180 mg, 0.422 mmol) was dissolved in N,N-dimethylformamide (20 mL). Then 60% sodium hydride (30 mg, 0.75 mmol) was added at 0° C., and the mixture was stirred at this temperature for 20 minutes, and then iodomethane (55 μL, 0.88 mmol) was added into the mixture. The resulting mixture was continued to stir for 30 minutes at 0° C. and then stirred for 1 hour at room temperature. The reaction mixture was quenched with saturated aqueous ammonium chloride (20 mL), and the resulting mixture was extracted with ethyl acetate (50 mL×2). The combined organic layers were washed with water (40 mL) and saturated brine (40 mL), dried over anhydrous sodium sulfate. The reaction mixture was filtered and the filtrate was concentrated in vacuo to remove the solvent. The residue was purified by silica gel chromatography eluted with dichloromethane/methanol (v/v=10/1) to give a yellow solid (50 mg, 26.9%).

MS (ESI, pos. ion) m/z: 441.1 (M+1);
$^1$H NMR (400 MHz, DMSO-$d_6$) δ (ppm) 8.50 (dd, J=4.7, 1.5 Hz, 2H), 8.37 (dd, J=9.2, 2.2 Hz, 1H), 7.51 (dd, J=6.1, 1.9 Hz, 1H), 7.43-7.30 (m, 2H), 6.41 (d, J=7.6 Hz, 4H), 5.80 (s, 2H), 3.66 and 3.54 (2s, 3H), 3.01 (s, 3H).

Example 5 methyl (4,6-diamino-2-(6-fluoro-1-(2-fluorobenzyl)-1H-indazol-3-yl)pyrimidin-5-yl)carbamate

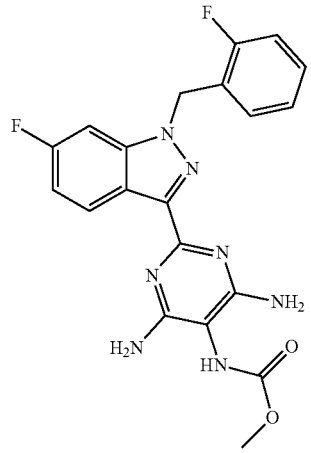 [SMILES: COC(=O)Nc1c(N)nc(-c2nn(Cc3ccccc3F)c3cc(F)ccc23)nc1N]

Step 1: 6-fluoro-1H-indazol-3-amine 2,4-Difluorobenzonitrile (10.00 g, 71.89 mmol) was added into a 500 mL two-neck flask, then n-butanol (200 mL) was added. Then to the mixture was added hydrazine hydrate (70.0 mL, 1443 mmol) under nitrogen protection. After addition, the mixture was heated to 150° C. and stirred for 17 hours. After the reaction was completed, the reaction mixture was cooled to rt, and extracted with EtOAc (200 mL×3). The combined organic layers were washed with water (200 mL×2) and saturated brine (200 mL), dried over anhydrous sodium sulfate, filtered, and the filtrate was concentrated in vacuo. The residue was purified by silica gel chromatograph (petroleum ether/ethyl acetate (v/v)=1/2) to give the title compound as yellow liquid (4.85 g, 44.7%).

MS (ESI, pos. ion) m/z: 152.2 (M+1).

Step 2: 6-fluoro-3-iodo-1H-indazole

6-Fluoro-1H-indazol-3-amine (4.85 g, 32.1 mmol) was dissolved in tetrahydrofuran (50 mL), then boron trifluoride diethyl etherate (8.0 mL, 64.8 mmol) was added dropwise slowly under an ice-bath condition. After the addition, then the reaction flask was placed in a circumstance of −10° C., then a solution of isoamyl nitrite (5.6 mL, 42.0 mmol) in tetrahydrofuran (20 mL) was added dropwise slowly. After the addition, the reaction mixture was stirred for 30 min. Ethyl ether (100 mL) was added to precipitate the solid product, and the mixture was filtered by suction to give a black brown solid. The solid then was dissolved in acetone (120 mL), and sodium iodide (6.25 g, 41.7 mmol) was added under an ice-bath condition, and the resulting mixture was stirred at rt for 30 minutes. The reaction mixture was extracted with ethyl acetate (100 mL×3), and the combined organic layers were washed with water (200 mL×2) and saturated brine (150 mL), dried over anhydrous sodium sulfate and concentrated in vacuo to remove the solvent to give a brownish black solid, which was used in the next step without further purification.

MS (ESI, pos. ion) m/z: 263.0 (M+1).

Step 3:
6-fluoro-1-(2-fluorobenzyl)-3-iodo-1H-indazole

6-Fluoro-3-iodo-1H-indazole (500 mg, 1.91 mmol) was added into a 50 mL flask, then N,N-dimethylformamide (10 mL), 1-(bromomethyl)-2-fluorobenzene (399 mg, 2.11 mmol) and cesium carbonate (688 mg, 2.11 mmol) were added. The mixture was stirred for 2 h at room temperature. The reaction mixture was extracted with ethyl acetate (60 mL×3). The combined organic layers were washed with water (100 mL×3) and saturated brine (100 mL×2), dried over anhydrous sodium sulfate, filtered, and the filtrate was concentrated in vacuo to give the title compound as brownish black oil (0.706 g, 99.9%).

MS (ESI, pos. ion) m/z: 371.0 (M+1).

Step 4: 6-fluoro-1-(2-fluorobenzyl)-1H-indazole-3-carbonitrile

6-Fluoro-1-(2-fluorobenzyl)-3-iodo-1H-indazole (1.5 g, 4.1 mmol) was added into a 50 mL flask, then dimethylsulfoxide (20 mL) and cuprous cyanide (0.44 g, 4.9 mmol) was added into the flask. The mixture was heated to 150° C. and stirred for 3 hours. The mixture was cooled to room temperature, and the reaction mixture was quenched with strong aqua ammonia (20 mL) and water (100 mL), then the resulting mixture was extracted with a mixed solvent of petroleum ether and ethyl acetate (v/v=10/1, 50 mL×3). The organic layers were combined, washed with water (100 mL×3) and saturated brine (100 mL×2) in turn, dried over anhydrous sodium sulfate, and the filtrate was concentrated on a rotary evaporator. The residue was purified by silica gel column chromatography eluted with petroleum ether/ethyl acetate (v/v=10/1) to give a light yellow solid (589 mg, 54.0%).

MS (ESI, pos. ion) m/z: 270.2 (M+1).

Step 5: 6-fluoro-1-(2-fluorobenzyl)-1H-indazole-3-carboximidamide

To a solution of sodium methoxide (122 mg, 2.26 mmol) in methanol (15 mL) was added 6-fluoro-1-(2-fluorobenzyl)-1H-indazole-3-carbonitrile (589 mg, 2.19 mmol). The mixture was stirred at room temperature for 2 hours. Then to the mixture were added ammonium chloride (144 mg, 2.70 mmol) and glacial acetic acid (0.25 mL, 4.4 mmol). The reaction mixture was heated to 75° C. and refluxed for 4 hours. The mixture was concentrated in vacuo to remove the solvent. To the residue were added water (50 mL) and ethyl acetate (50 mL), then to the mixture was added aqueous sodium hydroxide solution (2 mol/L) to adjust pH 10. The reaction mixture was stirred at rt for 20 min, then partitioned to give the organic layer. The aqueous layer was extracted with ethyl acetate (50 mL×2). The combined organic layers were washed with water (100 mL×2) and saturated brine (100 mL×2), dried over anhydrous sodium sulfate, filtered, and the filtrate was concentrated in vacuo to give the title compound as orange oil (602 mg, 96.2%).

MS (ESI, pos. ion) m/z: 287.2 (M+1).

Step 6: 2-(6-fluoro-1-(2-fluorobenzyl)-1H-indazol-3-yl)-5-(phenyldiazenyl)pyrimidine-4,6-diamine 6-Fluoro-1-(2-fluorobenzyl)-1H-indazole-3-carboximidamide (602 mg, 2.10 mmol) was dissolved in N,N-dimethylformamide (2.5 mL), then triethylamine (0.35 mL, 2.5 mmol) was added into the mixture. The resulting mixture was heated to 85° C., and to the flask was added dropwise slowly a solution of benzeneazomalononitrile (447.7 mg, 2.63 mmol) in N,N-dimethylformamide (2.5 mL). After the addition, the mixture was heated to 100° C. and stirred for 4 h. The mixture was cooled to room temperature and stirred overnight. The mixture was used directly in the next group without further purification.

MS (ESI, pos. ion) m/z: 457.3 (M+1).

Step 7: 2-(6-fluoro-1-(2-fluorobenzyl)-1H-indazol-3-yl)pyrimidine-4,5,6-triamine To the reaction mixture of the previous step was added 10% Pd/C (227 mg). The resulting mixture was stirred at room temperature overnight in hydrogen atmosphere. The reaction mixture was filtered through a celite pad, and the filter cake was washed with ethyl acetate (60 mL×3). The filtrate was concentrated in vacuo to remove the solvent, and the residue was purified by silica-gel column chromatography (ethyl acetate) to give a brown-black foamy solid (0.717 g, 93.0%).

MS (ESI, pos. ion) m/z: 368.2 (M+1).

Step 8: methyl (4,6-diamino-2-(6-fluoro-1-(2-fluorobenzyl)-1H-indazol-3-yl)pyrimidin-5-yl)carbamate 2-(6-Fluoro-1-(2-fluorobenzyl)-1H-indazol-3-yl)pyrimidine-4,5,6-triamine (700 mg, 1.91 mmol) was added into a 50 mL flask, then pyridine (10 mL, 1 mmol) and methylchloroformate (0.44 mL, 5.6 mmol) were added dropwise under an ice-bath condition. After the addition, the reaction mixture was stirred for 10 hour under the ice-bath condition. To the reaction mixture was added ethyl acetate (100 mL). The organic layer was washed with water (100 mL×2) and saturated brine (100 mL), dried over anhydrous sodium sulfate, filtered, and the filtrate was concentrated in vacuo. The residue was purified by silica gel chromatograph (dichloromethane/methanol (v/v)=5/1) to give the title compound as a light yellow solid (0.758 g, 93.5%).

MS (ESI, pos. ion) m/z: 426.2 (M+1);

$^1$H NMR (400 MHz, DMSO-$d_6$) δ (ppm) 8.61 (dd, J=8.8, 5.3 Hz, 1H), 8.38 (s, 1H), 8.07 (s, 1H), 7.82 (d, J=8.9 Hz, 1H), 7.74 (s, 2H), 7.38 (d, J=5.6 Hz, 1H), 7.32 (t, J=9.0 Hz, 1H), 7.28-7.21 (m, 1H), 7.21-7.10 (m, 2H), 5.88 (s, 2H), 3.65 (s, 3H).

Example 6 methyl (4,6-diamino-2-(6-fluoro-1-(2-fluorobenzyl)-1H-indazol-3-yl) pyrimidin-5-yl)(methyl)carbamate

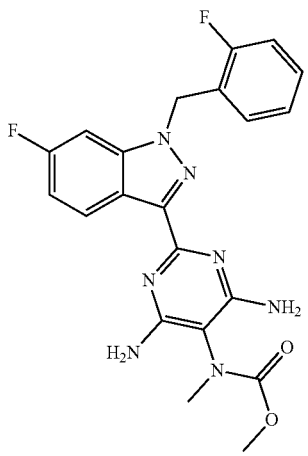 [SMILES: COC(=O)N(C)c1c(N)nc(-c2nn(Cc3ccccc3F)c3cc(F)ccc23)nc1N]

Methyl (4,6-diamino-2-(6-fluoro-1-(2-fluorobenzyl)-1H-indazol-3-yl)pyrimidin-5-yl)carbamate (0.95 g, 2.2 mmol) was dissolved in N,N-dimethylformamide (15 mL). Then 60% sodium hydride (119 mg, 4.94 mmol) and iodomethane (0.15 mL, 2.4 mmol) were added under an ice-bath condition, and the mixture was stirred for 3 hours at room temperature. The reaction mixture was concentrated on a rotary evaporator directly, and the residue was purified by silica gel chromatograph (ethyl acetate) to give the title compound as a light yellow solid (0.385 g, 39.0%).

MS (ESI, pos. ion) m/z: 440.2 (M+1);
$^1$H NMR (400 MHz, DMSO-$d_6$) δ (ppm) 8.72 (t, J=4.0 Hz, 1H), 7.60 (d, J=9.3 Hz, 1H), 7.34 (s, 1H), 7.22 (t, J=9.0 Hz, 1H), 7.09 (dd, J=19.9, 7.5 Hz, 3H), 6.32 (br s, 4H), 5.73 (s, 2H), 3.65 and 3.53 (2s, 3H), 3.00 (s, 3H).

Example 7 methyl (4,6-diamino-2-(6-fluoro-1-(pyridin-3-ylmethyl)-1H-indazol-3-yl) pyrimidin-5-yl)carbamate

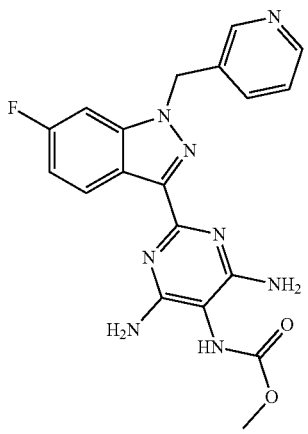 [SMILES: COC(=O)Nc1c(N)nc(-c2nn(Cc3cccnc3)c3cc(F)ccc23)nc1N]

Step 1: 6-fluoro-3-iodo-1-(pyridin-3-ylmethyl)-1H-indazole

To a 250 mL two-neck flask were added 6-fluoro-3-iodo-1H-indazole (7.51 g, 28.7 mmol), N,N-dimethylformamide (113 mL), cesium carbonate (19.7 g, 60.5 mmol) and 3-(bromomethyl)pyridine hydrobromide (7.94 g, 31.4 mmol). The mixture was stirred for 2 h at room temperature. The reaction mixture was poured into ice-water (500 mL), and the resulting mixture was extracted with ethyl acetate (100 mL×3). The combined organic layers were washed with water (200 mL×2) and saturated brine (100 mL), dried over anhydrous sodium sulfate and filtered. The filtrate was concentrated on a rotary evaporator to give a yellow solid (7.07 g, 69.9%).

MS (ESI, pos. ion) m/z: 354.05 (M+1).

Step 2: 6-Fluoro-1-(pyridin-3-ylmethyl)-1H-indazole-3-carbonitrile

To a 500 mL two-neck flask were added 6-fluoro-3-iodo-1-(pyridin-3-ylmethyl)-1H-indazole (7.07 g, 20.0 mmol), dimethyl sulfoxide (100 mL) and cuprous cyanide (2.21 g, 24.7 mmol). The mixture was heated to 150° C. and stirred for 2 hours. The reaction mixture was cooled to rt, and quenched with ammonium hydroxide (70 mL) and water (300 mL). The mixture was stirred for 10 minutes, and then extracted with ethyl acetate (300 mL×5). The organic layers were combined, and concentrated in vacuo to remove the solvent. The residue was purified by silica gel chromatograph (petroleum ether/ethyl acetate (v/v)=10/1) to give the title compound as a yellow solid (1.41 g, 27.9%).

MS (ESI, pos. ion) m/z: 253.20 (M+1).

Step 3: 6-fluoro-1-(pyridin-3-ylmethyl)-1H-indazole-3-carboximidamide

Sodium methoxide (1.21 g, 22.4 mmol) was added into methanol (50 mL), then 6-fluoro-1-(pyridin-3-ylmethyl)-1H-indazole-3-carbonitrile (1.41 g, 5.59 mmol) was added. The mixture was stirred at rt for 3 hours, then ammonium chloride (360 mg, 6.73 mmol) and glacial acetic acid (1.3 mL, 23 mmol) were added. The resulting mixture was refluxed overnight. The mixture was cooled to rt, and concentrated by rotary evaporation to remove the solvent. To the reaction mixture were added water (30 mL) and ethyl acetate (30 mL), then to the mixture was added aqueous sodium hydroxide solution (2 mol/L) to adjust pH 10. The reaction mixture was extracted with EtOAc (50 mL×3), dried over anhydrous sodium sulfate and filtered. The filtrate was concentrated on a rotary evaporator to give a brown solid (1.45 g, 96.3%).

MS (ESI, pos. ion) m/z: 270.0 (M+1).

Step 4: 2-(6-fluoro-1-(pyridin-3-ylmethyl)-1H-indazol-3-yl)-5-(phenyldiazenyl) pyrimidine-4,6-diamine 6-Fluoro-1-(pyridin-3-ylmethyl)-1H-indazole-3-carboximidamide (1.40 g, 5.20 mmol) was dissolved in N,N-dimethylformamide (20 mL), then triethylamine (1.1 mL, 7.9 mmol) was added into the mixture. The resulting mixture was heated to 85° C. under nitrogen protection, and to the mixture was added benzeneazomalononitrile (1.2 g, 7.1 mmol). After the addition, the mixture was heated to 100° C. and stirred for 5 h. The mixture was warmed to room temperature, and water (20 mL) was added into the mixture. The resulting mixture was stirred at rt for 1 hour. Then there was a white solid precipitate out, and the mixture was filtered by suction. The filter cake was washed with water (50 mL×2) and ethanol (50 mL×2), and then dried in oven to give a claybank solid (1.10 g, 48.0%).

MS (ESI, pos. ion) m/z: 440.1 (M+1).

Step 5: 2-(6-fluoro-1-(pyridin-3-ylmethyl)-1H-indazol-3-yl)pyrimidine-4,5,6-triamine 2-(6-Fluoro-1-(pyridin-3-ylmethyl)-1H-indazol-3-yl)-5-(phenyldiazenyl)pyrimidine-4,6-diamine (1.1 g, 2.5 mmol) was dissolved in N,N-dimethylformamide (30 mL), then 10% Pd/C (110 mg) was added. The resulting mixture was stirred at room temperature overnight in hydrogen atmosphere. The reaction mixture was filtered through a celite pad, and the filter cake was washed with methanol (30 mL×3), then the filtrate was collected and concentrated in vacuo to give a brown solid (800 mg, 91.0%).

MS (ESI, pos. ion) m/z: 351.2 (M+1).

Step 6: methyl (4,6-diamino-2-(6-fluoro-1-(pyridin-3-ylmethyl)-1H-indazol-3-yl) pyrimidin-5-yl)carbamate 2-(6-Fluoro-1-(pyridin-3-ylmethyl)-1H-indazol-3-yl)pyrimidine-4,5,6-triamine (500 mg, 1.43 mmol) was dissolved in dichloromethane (5 mL), then pyridine (8 mL, 99.4 mmol) and methylchloroformate (0.25 mL, 3.2 mmol) were added dropwise at 0° C. After the addition, the reaction mixture was continued to stir for 2 hours at 0° C. There was many solid precipitated out in the reaction mixture. The mixture was filtered, and the afforded solid was purified by preparative chromatography to give a white solid (165 mg, 28.3%).

MS (ESI, pos. ion) m/z: 409.3 (M+1);
$^1$H NMR (400 MHz, DMSO-$d_6$) δ (ppm) 8.88-8.58 (m, 3H), 8.34 and 8.05 (2 br s, 1H), 8.03-7.45 (m, 7H), 7.34 (t, J=9.0 Hz, 1H), 5.95 (s, 2H), 3.66 (s, 3H).

Example 8 methyl (4,6-diamino-2-(6-fluoro-1-(pyridin-3-ylmethyl)-1H-indazol-3-yl) pyrimidin-5-yl)(methyl)carbamate

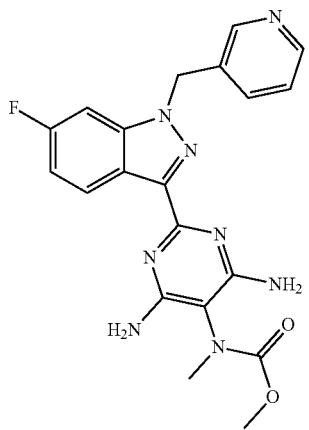 [SMILES: COC(=O)N(C)c1c(N)nc(-c2nn(Cc3cccnc3)c3cc(F)ccc23)nc1N]

Methyl (4,6-diamino-2-(6-fluoro-1-(pyridin-3-ylmethyl)-1H-indazol-3-yl)pyrimidin-5-yl)carbamate (35 mg, 0.086 mmol) was dissolved in N,N-dimethylformamide (20 mL). Then 60% sodium hydride (6.0 mg, 0.15 mmol) was added at 0° C., and the mixture was stirred maintaining at this temperature for 20 minutes, and then iodomethane (8.0 μL, 0.13 mmol) was added into the mixture. The resulting mixture was continued to stir for 30 minutes at 0° C. and then stirred for 1 hour at room temperature. To the reaction mixture was added saturated aqueous ammonium chloride (10 mL) to quench the reaction. The resulting mixture was concentrated in vacuo to remove the solvent, and the residue was purified by silica gel chromatograph (petroleum ether/ethyl acetate (v/v)=1/10) to give the title compound as a white solid (30.0 mg, 82.9%).

MS (ESI, pos. ion) m/z: 423.3 (M+1);
$^1$H NMR (400 MHz, DMSO-$d_6$) δ (ppm) 8.73 (dd, J=8.8, 5.6 Hz, 1H), 8.60 (s, 1H), 8.48 (d, J=4.4 Hz, 1H), 7.68 (dd, J=24.6, 8.7 Hz, 2H), 7.34 (dd, J=7.7, 4.9 Hz, 1H), 7.09 (t, J=9.0 Hz, 1H), 6.43 (d, J=10.8 Hz, 4H), 5.80 (s, 2H), 3.66 and 3.53 (2s, 3H), 3.01 (s, 3H).

Example 9

2-(6-fluoro-1-(2-fluorobenzyl)-1H-indazol-3-yl)-$N^5$-(tetrahydrofuran-3-yl) pyrimidine-4,5,6-triamine

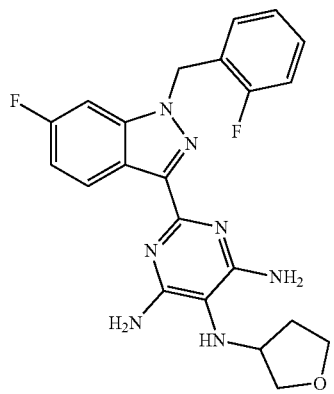 [SMILES: Nc1nc(-c2nn(Cc3ccccc3F)c3cc(F)ccc23)nc(N)c1NC1CCOC1]

To a 50 mL two-neck flask were added 2-(6-fluoro-1-(2-fluorobenzyl)-1H-indazol-3-yl)pyrimidine-4,5,6-triamine (0.12 g, 0.33 mmol), dihydrofuran-3(2H)-one (0.042 g, 0.49 mmol) and methanol (10 mL). Then acetic acid (0.16 mL, 2.8 mmol) was added under an ice-bath condition. The mixture was stirred at rt for 1 hour, then to the mixture was added sodium cyanoborohydride (0.10 g, 1.6 mmol). Then the resulting mixture was stirred at rt overnight. The reaction mixture was concentrated in vacuo to remove the solvent, and to the residue was added saturated aqueous sodium bicarbonate (50 mL). The resulting mixture was extracted with ethyl acetate (30 mL×2). The combined organic layers were washed with water (30 mL) and saturated brine (30 mL), dried over anhydrous sodium sulfate and filtered. The filtrate was concentrated on a rotary evaporator and the residue was purified by silica gel chromatograph (dichloromethane/methanol (v/v)=100/1) to give a light yellow solid (0.091 g, 64.0%).

MS (ESI, pos. ion) m/z: 438.2 (M+1);
$^1$H NMR (400 MHz, DMSO-$d_6$) δ (ppm) 8.72 (dd, J=8.9, 5.7 Hz, 1H), 7.61 (dd, J=9.8, 1.8 Hz, 1H), 7.41-7.32 (m, 1H), 7.29-7.20 (m, 1H), 7.14 (t, J=7.5 Hz, 1H), 7.14-7.06 (m, 2H), 6.07 (s, 4H), 5.72 (s, 2H), 3.93 (q, J=7.5 Hz, 1H), 3.79-3.72 (m, 1H), 3.70-3.66 (m, 1H), 3.63 (dd, J=8.8, 5.4

Hz, 1H), 3.53 (dd, J=8.8, 3.4 Hz, 1H), 3.45 (d, J=6.8 Hz, 1H), 1.95-1.86 (m, 1H), 1.81-1.75 (m, 1H);
$^{19}$F NMR (376 MHz, DMSO-d$_6$) δ (ppm) −115.21 (s), −117.65 (s).

Example 10 methyl (4,6-diamino-2-(7-fluoro-1-(2-fluorobenzyl)-1H-indazol-3-yl)pyrimidin-5-yl)carbamate

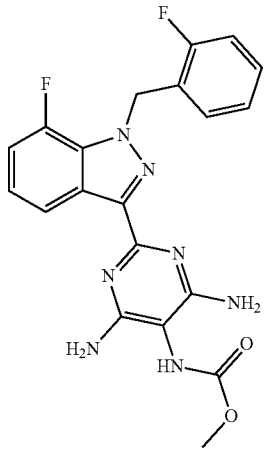 [SMILES: COC(=O)Nc1c(N)nc(-c2nn(Cc3ccccc3F)c3c(F)cccc23)nc1N]

Step 1: 7-fluoro-1H-indazol-3-amine 2,3-difluorobenzonitrile (10.0 g, 71.9 mmol) was dissolved in n-butanol (200 mL), then hydrazine hydrate (70.0 mL, 1440 mmol) was added dropwise under nitrogen protection. After the addition, the mixture was heated to 150° C. and refluxed for 10 hours. The reaction mixture was cooled to room temperature, and extracted with ethyl acetate (200 mL×3). The combined organic layers were washed with water (200 mL×3) and saturated brine (100 mL×2), dried over anhydrous sodium sulfate, filtered, and the filtrate was concentrated in vacuo to give the title compound as a yellow solid (10.8 g, 99.4%).
MS (ESI, pos. ion) m/z: 152.1 (M+1).

Step 2: 7-fluoro-3-iodo-1H-indazole

7-Fluoro-1H-indazol-3-amine (10.0 g, 66.2 mmol) was dissolved in anhydrous tetrahydrofuran (100 mL) which was placed in a 500 mL reaction flask, then boron trifluoride diethyl etherate (16.8 mL, 133 mmol) was added dropwise slowly at 0° C. under nitrogen protection. After the addition, then the reaction flask was placed in a circumstance of −10° C., then a solution of isoamyl nitrite (11.6 mL, 86.3 mmol) in tetrahydrofuran (35 mL) was added dropwise slowly. After the addition, the reaction mixture was stirred for 30 min. Ethyl ether (200 mL) was added to precipitate the product, and the mixture was filtered by suction to give a black brown solid. The filter cake was then dissolved in acetone (250 mL), and sodium iodide (13.0 g, 86.7 mmol) was added under an ice-bath condition, and the resulting mixture was stirred at rt for 30 minutes. The reaction mixture was extracted with ethyl acetate (250 mL×3), and the combined organic layers were washed with water (250 mL×2) and saturated brine (150 mL×2), dried over anhydrous sodium sulfate and concentrated in vacuo to remove the solvent and give a brownish black solid, which was used in the next step without further purification.
MS (ESI, pos. ion) m/z: 262.9 (M+1).

Step 3: 7-fluoro-1-(2-fluorobenzyl)-3-iodo-1H-indazole 7-fluoro-3-iodo-1H-indazole (17.4 g, 66.4 mmol) was dissolved in N,N-dimethylformamide (120 mL) which was placed in a 250 mL single neck flask, then 1-(bromomethyl)-2-fluorobenzene (8.81 mL, 73.0 mmol) and cesium carbonate (23.8 g, 73.0 mmol) were added. The mixture was stirred for 2 h at room temperature. The reaction mixture was extracted with EtOAc (200 mL×3). The combined organic layers were washed with water (150 mL×3) and saturated brine (100 mL×2), dried over anhydrous sodium sulfate, filtered, and the filtrate was concentrated in vacuo to give light yellow transparent oil (11.0 g, 44.8%).
MS (ESI, pos. ion) m/z: 370.9 (M+1).

Step 4: 7-fluoro-1-(2-fluorobenzyl)-1H-indazole-3-carbonitrile

7-Fluoro-1-(2-fluorobenzyl)-3-iodo-1H-indazole (11.0 g, 29.7 mmol) was dissolved in dimethylsulfoxide (200 mL) which were placed in a 500 mL single flask, then cuprous cyanide (3.00 g, 33.5 mmol) was added. The mixture was heated to 150° C. and stirred for 3 hours under nitrogen protection. The mixture was cooled to rt, and the reaction mixture was poured into a mixture of strong aqua ammonia (100 mL) and water (500 mL) to quench the reaction, then the resulting mixture was extracted with a mixed solvent of petroleum ether and ethyl acetate (v/v=1/10). The organic layers were combined, and washed with water (100 mL×3) and saturated brine (100 mL×2) in turn, dried over anhydrous sodium sulfate, and concentrated in vacuo to give a brown solid (8.0 g, 99.9%).
MS (ESI, pos. ion) m/z: 270.4 (M+1).

Step 5: 7-fluoro-1-(2-fluorobenzyl)-1H-indazole-3-carboximidamide

To a solution of sodium methoxide (1.4 g, 26 mmol) in methanol (150 mL) was added 7-fluoro-1-(2-fluorobenzyl)-1H-indazole-3-carbonitrile (7.0 g, 26 mmol). The mixture was stirred at room temperature for 2 hours. Then to the mixture were added ammonium chloride (1.7 g, 32 mmol) and acetic acid (3 mL). The reaction mixture was heated to 75° C. and refluxed for 5 hours. The mixture was cooled to rt and concentrated in vacuo to remove the solvent. To the residue were added water (150 mL) and ethyl acetate (150 mL), then to the mixture was added aqueous sodium hydroxide solution (2 mol/L) to adjust pH 10. The reaction mixture was stirred at rt for 1 h. The mixture was filtered through a celite pad, and the filtrate was extracted with ethyl acetate (200 mL×2). The combined organic layers were washed with water (100 mL×2) and saturated brine (100 mL×2). The organic layers were dried over anhydrous sodium sulfate and concentrated in vacuo to give yellowish-brown oil (7.5 g, 100%).
MS (ESI, pos. ion) m/z: 287.1 (M+1).

Step 6: 2-(7-fluoro-1-(2-fluorobenzyl)-1H-indazol-3-yl)-5-(phenyldiazenyl)pyrimidine-4,6-diamine 7-Fluoro-1-(2-fluorobenzyl)-1H-indazole-3-carboximidamide (6.8 g, 24 mmol) was dissolved in N,N-dimethylformamide (15 mL), then triethylamine (4.1 mL, 29 mmol) was added into the mixture. The resulting mixture was heated to 85° C., and to the mixture was added a solution of benzeneazomalononitrile (5.1 g, 30 mmol) in N,N-dimethylformamide (15 mL). After the addition, the mixture was heated to 100° C. and stirred for 4 h, then the mixture was stirred at rt overnight. To the reaction mixture was added water (1.0 L), and the resulting mixture was stirred for 1 hour at room temperature. Then the mixture was filtered by suction through a Buchner funnel. The filter cake were washed with water (100 mL×2) and methanol (50 mL×2) and dried to give a yellow solid (10.5 g, 96.0%).

MS (ESI, pos. ion) m/z: 457 (M+1).

Step 7: 2-(7-fluoro-1-(2-fluorobenzyl)-1H-indazol-3-yl)pyrimidine-4,5,6-triamine 2-(7-Fluoro-1-(2-fluorobenzyl)-1H-indazol-3-yl)-5-(phenyldiazenyl)pyrimidine-4,6-diamine (10.0 g, 21.9 mmol) was dissolved in N,N-dimethylformamide (200 mL), then 10% Pd/C (2.76 g) was added. The resulting mixture was stirred at rt overnight in hydrogen atmosphere. The reaction mixture was filtered through a celite pad, and the filtrate was concentrated in vacuo to remove the solvent. The residue was purified by silica-gel column chromatography (ethyl acetate) to give a yellow solid (2.2 g, 27.0%).

MS (ESI, pos. ion) m/z: 368.1 (M+1).

Step 8: methyl (4,6-diamino-2-(7-fluoro-1-(2-fluorobenzyl)-1H-indazol-3-yl)pyrimidin-5-yl)carbamate 2-(7-Fluoro-1-(2-fluorobenzyl)-1H-indazol-3-yl)pyrimidine-4,5,6-triamine (500 mg, 1.36 mmol) was dissolved in dichloromethane (30.0 mL), then pyridine (0.16 mL, 2.0 mmol) and methylchloroformate (0.125 mL, 1.62 mmol) were added dropwise at 0° C. After the addition, the reaction mixture was continued to stir for 1 hour. The resulting mixture was concentrated in vacuo to remove the solvent, and the residue was purified by silica gel chromatograph (ethyl acetate/methanol (v/v)=1/1) to give the title compound as a light yellow solid (208 mg, 35.2%).

MS (ESI, pos. ion) m/z: 426.1 (M+1);
$^1$H NMR (400 MHz, DMSO-$d_6$) δ (ppm) 8.56 (d, J=8.0 Hz, 1H), 8.01 and 7.69 (2 br s, 1H), 7.35 (dd, J=13.5, 6.4 Hz, 1H), 7.30-7.07 (m, 4H), 6.96 (t, J=7.6 Hz, 1H), 6.17 (s, 4H), 5.84 (s, 2H), 3.63 (s, 3H).

Example 11 methyl (4,6-diamino-2-(7-fluoro-1-(2-fluorobenzyl)-1H-indazol-3-yl)pyrimidin-5-yl)(methyl)carbamate

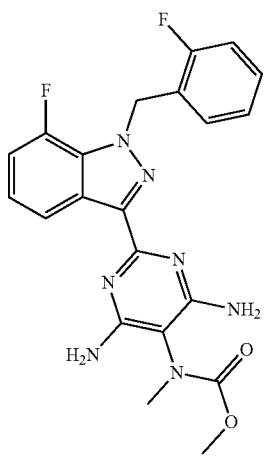 [SMILES: COC(=O)N(C)c1c(N)nc(-c2nn(Cc3ccccc3F)c3c(F)cccc23)nc1N]

Methyl (4,6-diamino-2-(7-fluoro-1-(2-fluorobenzyl)-1H-indazol-3-yl)pyrimidin-5-yl) carbamate (0.10 g, 0.24 mmol) and N,N-dimethylformamide (10 mL) were added into a 50 mL two-neck flask. Then 60% sodium hydride (0.014 g, 0.35 mmol) was added at 0° C. The mixture was then stirred for 30 minutes at 0° C. Iodomethane (0.018 mL, 0.29 mmol) was added under an ice-bath condition, and the mixture was stirred for 4 hours at rt. The reaction mixture was quenched with water, and the resulting mixture was extracted with ethyl acetate (30 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=80/1, 0.5% triethylamine) to give a white solid (58 mg, 56.0%).

MS (ESI, pos. ion) m/z: 440.0 (M+1);
$^1$H NMR (400 MHz, DMSO-$d_6$) δ (ppm) 8.55 (d, J=8.0 Hz, 1H), 7.35 (dd, J=13.2, 6.2 Hz, 1H), 7.27-7.20 (m, 2H), 7.20-7.15 (m, 1H), 7.12 (t, J=7.6 Hz, 1H), 6.93 (t, J=6.9 Hz, 1H), 6.35 (s, 4H), 5.83 and 3.66 (2s, 3H), 3.66 (s, 0.85H), 3.54 (s, 2.15H), 3.01 (s, 3H);
$^{19}$F NMR (376 MHz, DMSO-$d_6$) δ (ppm) −118.77 (d, J=6.9 Hz), −134.38 (d, J=6.9 Hz).

Example 12

2-(7-fluoro-1-(2-fluorobenzyl)-1H-indazol-3-yl)-N$^5$-(tetrahydrofuran-3-yl)pyrimidine-4,5,6-triamine

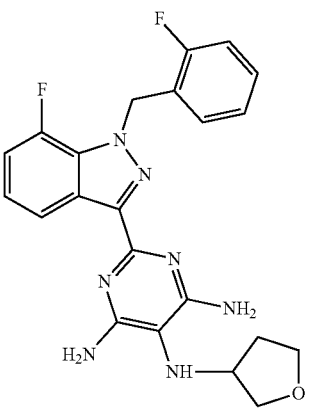 [SMILES: Nc1nc(-c2nn(Cc3ccccc3F)c3c(F)cccc23)nc(N)c1NC1CCOC1]

To a 50 mL two-neck flask were added 2-(7-fluoro-1-(2-fluorobenzyl)-1H-indazol-3-yl)pyrimidine-4,5,6-triamine (0.12 g, 0.33 mmol), dihydrofuran-3(2H)-one (0.042 g, 0.49 mmol) and methanol (10.0 mL). Then acetic acid (0.19 mL, 3.3 mmol) was added under an ice-bath condition. The mixture was stirred at rt for 1 hour, then to the mixture was added sodium cyanoborohydride (0.10 g, 1.6 mmol). Then the resulting mixture was stirred at rt overnight. The reaction mixture was concentrated in vacuo to remove the solvent, and to the residue was added saturated aqueous sodium bicarbonate (40 mL). The resulting mixture was extracted with ethyl acetate (30 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=100/1) to give a light yellow solid (0.055 g, 38.0%).

MS (ESI, pos. ion) m/z: 438.2 (M+1);

¹H NMR (400 MHz, DMSO-d₆) δ (ppm) 8.55 (d, J=8.0 Hz, 1H), 7.35 (dd, J=13.5, 6.3 Hz, 1H), 7.28-7.20 (m, 2H), 7.20-7.09 (m, 2H), 6.96 (t, J=7.5 Hz, 1H), 6.09 (s, 4H), 5.82 (s, 2H), 3.94 (q, J=7.6 Hz, 1H), 3.75 (s, 1H), 3.73-3.60 (m, 2H), 3.54 (dd, J=8.7, 3.3 Hz, 1H), 3.47 (d, J=6.9 Hz, 1H), 1.92 (td, J=14.6, 7.5 Hz, 1H), 1.78 (ddd, J=16.1, 7.5, 4.5 Hz, 1H);

¹⁹F NMR (376 MHz, DMSO-d₆) δ (ppm) −118.76 (d, J=7.1 Hz), −134.44 (d, J=7.1 Hz).

Example 13

2-(4,6-diamino-2-(7-fluoro-1-(2-fluorobenzyl)-1H-indazol-3-yl)pyrimidin-5-yl)isothiazolidine 1,1-dioxide

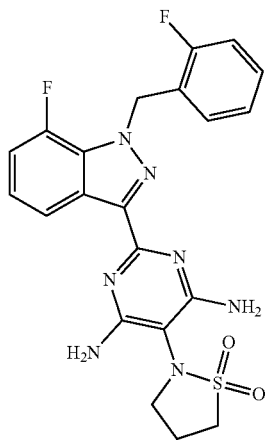 [SMILES: Nc1nc(-c2nn(Cc3ccccc3F)c3c(F)cccc23)nc(N)c1N1CCCS1(=O)=O]

Step 1: 3-chloro-N-(4,6-diamino-2-(7-fluoro-1-(2-fluorobenzyl)-1H-indazol-3-yl)pyrimidin-5-yl)propane-1-sulfonamide To a 50 mL two-neck flask were added 2-(7-fluoro-1-(2-fluorobenzyl)-1H-indazol-3-yl)pyrimidine-4,5,6-triamine (0.050 g, 0.14 mmol) and dichloromethane (5 mL). Then pyridine (0.22 mL, 2.7 mmol) and 3-chloropropane-1-sulfonyl chloride (0.020 mL, 0.16 mmol) were added at 0° C. The mixture was stirred at room temperature overnight. To the reaction mixture was added dichloromethane (30 mL), and the resulting mixture was washed with water (30 mL) and saturated brine (30 mL), dried over anhydrous sodium sulfate and filtered. The filtrate was concentrated on a rotary evaporator and the residue was purified by silica gel chromatograph (dichloromethane/methanol (v/v)=60/1, 0.5% triethylamine) to give a light yellow solid (0.046 g, 67.0%).

MS (ESI, pos. ion) m/z: 508.1 (M+1).

Step 2: 2-(4,6-diamino-2-(7-fluoro-1-(2-fluorobenzyl)-1H-indazol-3-yl)pyrimidin-5-yl) isothiazolidine 1,1-dioxide To a 50 mL single neck flask were added 3-chloro-N-(4,6-diamino-2-(7-fluoro-1-(2-fluorobenzyl)-1H-indazol-3-yl) pyrimidin-5-yl) propane-1-sulfonamide (0.11 g, 0.22 mmol), potassium carbonate (0.060 g, 0.43 mmol) and N,N-dimethylformamide (5.0 mL). The mixture was stirred at 80° C. overnight. The reaction mixture was cooled to rt, and to the mixture was added water (30 mL), and the resulting mixture was extracted with ethyl acetate (30 mL×2). The combined organic layers were washed with water (30 mL) and saturated brine (10 mL), dried over anhydrous sodium sulfate and filtered. The filtrate was concentrated on a rotary evaporator and the residue was purified by silica gel chromatograph (dichloromethane/methanol (v/v)=80/1, 0.5% triethylamine) to give a light yellow solid (0.081 g, 79.0%).

MS (ESI, pos. ion) m/z: 472.2 (M+1);

¹H NMR (400 MHz, DMSO-d₆) δ (ppm) 8.55 (d, J=8.0 Hz, 1H), 7.35 (dd, J=13.5, 5.9 Hz, 1H), 7.22 (ddt, J=12.4, 7.8, 6.0 Hz, 3H), 7.13 (t, J=7.5 Hz, 1H), 6.97 (t, J=7.6 Hz, 1H), 6.49 (s, 4H), 5.84 (s, 2H), 3.49 (q, J=7.1 Hz, 4H), 2.50-2.41 (m, 2H);

¹⁹F NMR (376 MHz, DMSO-d₆) δ (ppm) −118.72 (d, J=7.2 Hz), −134.13 (d, J=7.2 Hz).

Example 14

2-(7-fluoro-1-(2-fluorobenzyl)-1H-indazol-3-yl)-5-morpholinopyrimidine-4,6-diamine

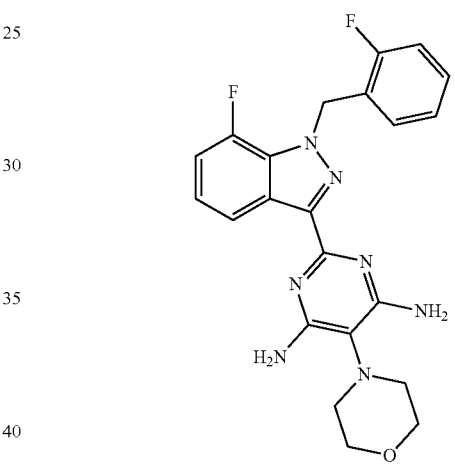

Step 1: 2-morpholinomalononitrile

Morpholine-4-carbaldehyde (3.00 g, 26.1 mmol) and n-heptane (30.0 mL) were added into a 100 mL single flask, then copper(II) trifluoromethanesulfonate (0.94 g, 2.6 mmol) and trimethylsilyl cyanide (4.89 mL, 39.1 mmol) were added. The mixture was heated to 80° C. for 8 hours under nitrogen protection. The reaction mixture was cooled to rt, and concentrated to remove the solvent. To the residue was added ethyl acetate (80 mL). The mixture was washed with water (80 mL) and saturated brine (80 mL), dried over anhydrous sodium sulfate and filtered. The filtrate was concentrated on a rotary evaporator and the residue was purified by silica gel chromatograph (petroleum ether/ethyl acetate (v/v)=7/1) to give a white solid (1.82 g, 46.2%).

MS (ESI, neg. ion) m/z: 150.1 (M−1);

¹H NMR (400 MHz, CDCl₃) δ (ppm) 4.66 (s, 1H), 3.85-3.79 (m, 4H), 2.78-2.72 (m, 4H).

Step 2: 2-(7-fluoro-1-(2-fluorobenzyl)-1H-indazol-3-yl)-5-morpholinopyrimidine-4,6-diamine To a 50 mL single neck flask were added 2-(7-fluoro-1-(2-fluorobenzyl)-1H-indazol-3-yl)pyrimidine-4,5,6-triamine (0.20 g, 0.54 mmol), N,N-dimethylformamide (10 mL) and triethylamine (0.11 mL, 0.79 mmol). The mixture was heated to 80° C., and then 2-morpholinomalononitrile (0.12 g, 0.79 mmol) was added. The resulting mixture was heated to 100° C. and stirred overnight. The reaction mixture was cooled to rt, and extracted with ethyl acetate (80 mL). The combined organic layers were washed with water (80 mL) and saturated brine (80 mL), dried over anhydrous sodium sulfate and filtered. The filtrate was concentrated on a rotary evaporator and the residue was purified by silica gel chromatograph (dichloromethane/methanol (v/v)=200/1, 0.5% triethylamine) to give a white solid (16 mg, 7.0%).

MS (ESI, pos. ion) m/z: 438.1 (M+1);

$^1$H NMR (400 MHz, DMSO-d$_6$) δ (ppm) 8.56 (d, J=8.0 Hz, 1H), 7.35 (dd, J=13.5, 6.3 Hz, 1H), 7.28-7.20 (m, 2H), 7.20-7.09 (m, 2H), 6.94 (t, J=7.3 Hz, 1H), 6.13 (s, 4H), 5.82 (s, 2H), 3.74 (s, 4H), 2.94 (s, 4H);

$^{19}$F NMR (376 MHz, DMSO-d$_6$) δ (ppm) −118.76 (d, J=7.0 Hz), −134.45 (d, J=7.0 Hz).

Example 15

3-(4,6-diamino-2-(7-fluoro-1-(2-fluorobenzyl)-1H-indazol-3-yl)pyrimidin-5-yl)oxazolidin-2-one

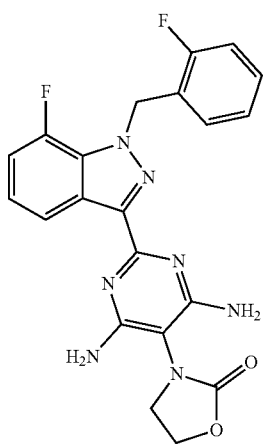 [SMILES: Nc1nc(-c2nn(Cc3ccccc3F)c3c(F)cccc23)nc(N)c1N1CCOC1=O]

Step 1: 2-chloroethyl (4,6-diamino-2-(7-fluoro-1-(2-fluorobenzyl)-1H-indazol-3-yl) pyrimidin-5-yl)carbamate 2-(7-Fluoro-1-(2-fluorobenzyl)-1H-indazol-3-yl)pyrimidine-4,5,6-triamine (150 mg, 0.408 mmol) was dissolved in dichloromethane (20 mL), then pyridine (0.10 mL, 1.2 mmol) and 2-chloroethyl chloroformate (0.050 mL, 0.48 mmol) were added dropwise. The reaction mixture was continued to stir for 1 hour. The reaction mixture was extracted with dichloromethane (70 mL×2). The combined organic layers were washed with water (30 mL) and saturated brine (40 mL), dried over anhydrous sodium sulfate, and filtered. The filtrate was concentrated in vacuo to give a yellow solid (175 mg, 90.5%).

MS (ESI, pos. ion) m/z: 474.1 (M+1).

Step 2: 3-(4,6-diamino-2-(7-fluoro-1-(2-fluorobenzyl)-1H-indazol-3-yl)pyrimidin-5-yl) oxazolidin-2-one 2-chloroethyl (4,6-diamino-2-(7-fluoro-1-(2-fluorobenzyl)-1H-indazol-3-yl)pyrimidin-5-yl) carbamate (175 mg, 0.369 mmol) was dissolved in anhydrous tetrahydrofuran (10 mL) at 0° C. Then 60% sodium hydride (23 mg, 0.58 mmol) was added at 0° C., and the mixture was stirred at 0° C. for 2 hours. The reaction mixture was quenched with aqueous ammonium chloride solution (20 mL), and extracted with ethyl acetate (50 mL×2). The combined organic layers were washed with water (20 mL) and saturated brine (20 mL), dried over anhydrous sodium sulfate, filtered and concentrated to remove the solvent. The residue was purified by silica-gel column chromatography (ethyl acetate) to give a white solid (21 mg, 13.0%).

MS (ESI, pos. ion) m/z: 438.1 (M+1);

$^1$H NMR (400 MHz, DMSO-d$_6$) δ (ppm) 8.55 (d, J=8.0 Hz, 1H), 7.35 (dd, J=13.2, 6.3 Hz, 1H), 7.29-7.09 (m, 4H), 6.96 (t, J=7.4 Hz, 1H), 6.61 (s, 4H), 5.84 (s, 2H), 4.43 (t, J=8.0 Hz, 2H), 3.71-3.63 (m, 2H).

Example 16

N-(4,6-diamino-2-(7-fluoro-1-(2-fluorobenzyl)-1H-indazol-3-yl)pyrimidin-5-yl)tetrahydrofuran-2-carboxamide

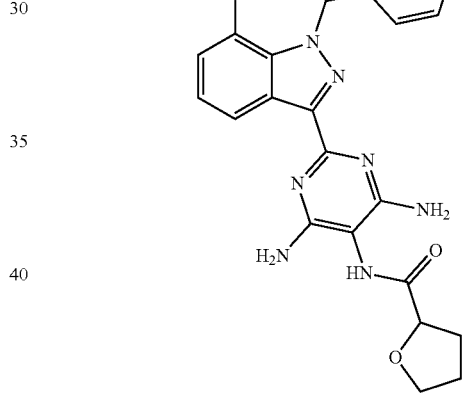

To a 50 mL two-neck flask were added 2-(7-fluoro-1-(2-fluorobenzyl)-1H-indazol-3-yl)pyrimidine-4,5,6-triamine (0.10 g, 0.27 mmol), tetrahydrofuran-2-carboxylic acid (0.035 g, 0.30 mmol) and N,N-dimethylformamide (10 mL). Then O-(7-azabenzotriazol-1-yl)-N,N,N',N'-te-tramethyluronium hexafluorophosphate (0.12 g, 0.32 mmol) and N,N-diisopropylethylamine (0.13 mL, 0.79 mmol) were added at 0° C. The mixture was stirred for 6 hours under an ice-bath condition. The reaction mixture was poured into water (30 mL), and the resulting mixture was extracted with ethyl acetate (30 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=80/1, 0.5% triethylamine) to give a white solid (0.081 g, 64.0%).

MS (ESI, pos. ion) m/z: 466.1 (M+1);

$^1$H NMR (400 MHz, DMSO-d$_6$) δ (ppm) 8.70 (s, 1H), 8.57 (d, J=8.0 Hz, 1H), 7.35 (dd, J=14.0, 6.8 Hz, 1H), 7.29-7.10 (m, 4H), 6.98 (t, J=7.5 Hz, 1H), 6.00 (s, 4H), 5.84

(s, 2H), 4.46 (dd, J=7.9, 6.1 Hz, 1H), 3.99 (dd, J=14.5, 7.0 Hz, 1H), 3.82 (dd, J=13.7, 7.2 Hz, 1H), 2.22-2.03 (m, 2H), 1.98-1.79 (m, 2H);

$^{19}$F NMR (376 MHz, DMSO-d$_6$) δ (ppm) −118.75 (d, J=7.1 Hz), −134.30 (d, J=7.2 Hz).

Example 17

N-(4,6-diamino-2-(7-fluoro-1-(2-fluorobenzyl)-1H-indazol-3-yl)pyrimidin-5-yl)tetrahydro-2H-pyran-2-carboxamide

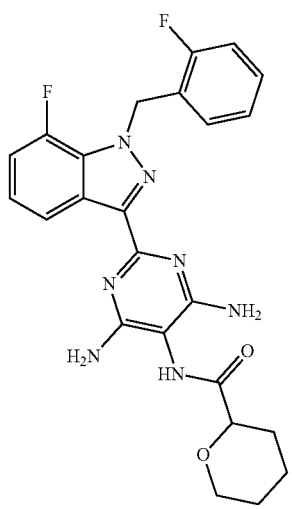 [SMILES: Nc1nc(-c2nn(Cc3ccccc3F)c3c(F)cccc23)nc(N)c1NC(=O)C1CCCCO1]

To N,N-dimethylformamide (20 mL) were added 2-(7-fluoro-1-(2-fluorobenzyl)-1H-indazol-3-yl)pyrimidine-4,5,6-triamine (100 mg, 0.272 mmol) and tetrahydro-2H-pyran-2-carboxylic acid (53 mg, 0.41 mmol). Then O-(7-azabenzotriazol-1-yl)-N,N,N',N'-te-tramethyluronium hexafluorophosphate (155 mg, 0.408 mmol) and N,N-diisopropylethylamine (0.20 mL, 1.2 mmol) were added. The mixture was stirred at room temperature overnight. The reaction mixture was extracted with ethyl ether (50 mL×2). The combined organic layers were washed with water (40 mL) and saturated brine (40 mL), dried over anhydrous sodium sulfate, and filtered. The filtrate with concentrated in vacuo to remove the solvent, and the residue was purified by silica-gel column chromatography (petroleum ether/ethyl acetate (v/v)=1/5) to give a yellow solid (40 mg, 30.7%).

MS (ESI, pos. ion) m/z: 480.1 (M+1);

$^1$H NMR (400 MHz, DMSO-d$_6$) δ (ppm) 8.57 (d, J=9.0 Hz, 2H), 7.35 (dd, J=13.6, 5.9 Hz, 1H), 7.30-7.08 (m, 4H), 6.97 (t, J=7.1 Hz, 1H), 6.00 (s, 4H), 5.84 (s, 2H), 4.05-3.95 (m, 2H), 3.53-3.45 (m, 1H), 1.96-1.81 (m, 2H), 1.69-1.48 (m, 4H).

Example 18

N-(4,6-diamino-2-(7-fluoro-1-(2-fluorobenzyl)-1H-indazol-3-yl)pyrimidin-5-yl)tetrahydro-2H-pyran-3-carboxamide

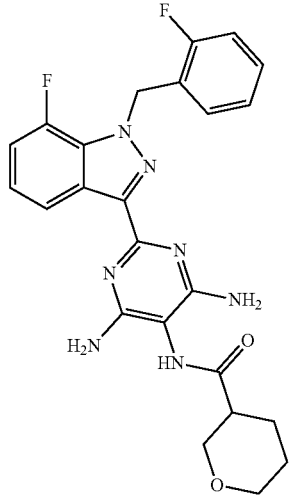 [SMILES: Nc1nc(-c2nn(Cc3ccccc3F)c3c(F)cccc23)nc(N)c1NC(=O)C1CCCOC1]

To N,N-dimethylformamide (20 mL) were added 2-(7-fluoro-1-(2-fluorobenzyl)-1H-indazol-3-yl)pyrimidine-4,5,6-triamine (120 mg, 0.327 mmol) and tetrahydro-2H-pyran-3-carboxylic acid (64 mg, 0.492 mmol). Then O-(7-azabenzotriazol-1-yl)-N,N,N',N'-te-tramethyluronium hexafluorophosphate (187 mg, 0.492 mmol) and N,N-diisopropylethylamine (0.22 mL, 1.3 mmol) were added. The mixture was stirred at rt overnight. The reaction mixture was extracted with ethyl ether (50 mL×2). The combined organic layers were washed with water (40 mL) and saturated brine (40 mL), dried over anhydrous sodium sulfate, and filtered. The filtrate with concentrated in vacuo to remove the solvent, and the residue was purified by silica-gel column chromatography (petroleum ether/ethyl acetate (v/v)=1/5) to give a yellow solid (49 mg, 31.3%).

MS (ESI, pos. ion) m/z: 480.2 (M+1);

$^1$H NMR (400 MHz, DMSO-d$_6$) δ (ppm) 8.72 (s, 1H), 8.56 (d, J=7.6 Hz, 1H), 7.42-7.09 (m, 5H), 6.98 (s, 1H), 6.03 (s, 4H), 5.84 (s, 2H), 4.10 (d, J=9.7 Hz, 1H), 3.80 (d, J=9.4 Hz, 1H), 2.67 (s, 1H), 2.07 (s, 1H), 1.64 (dd, J=51.2, 20.9 Hz, 4H), 1.40 (d, J=6.3 Hz, 1H).

Example 19 methyl (4,6-diamino-2-(7-fluoro-1-(pyridin-3-ylmethyl)-1H-indazol-3-yl)pyrimidin-5-yl)carbamate

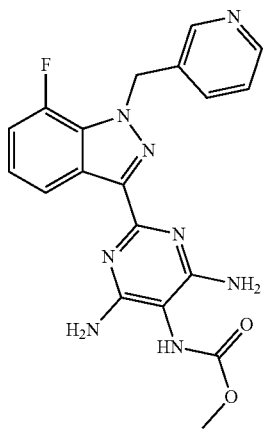 [SMILES: COC(=O)Nc1c(N)nc(-c2nn(Cc3cccnc3)c3c(F)cccc23)nc1N]

Step 1: 7-fluoro-3-iodo-1-(pyridin-3-ylmethyl)-1H-indazole

7-Fluoro-3-iodo-1H-indazole (0.993 g, 3.79 mmol) was added into a 100 mL flask, then N,N-dimethylformamide (20 mL), 3-(bromomethyl)pyridine hydrobromide (1.491 g, 5.72 mmol) and cesium carbonate (2.71 g, 8.32 mmol) were added. The mixture was stirred for 3 h at room temperature. The reaction mixture was extracted with EtOAc (100 mL×3). The combined organic layers were washed with water (200 mL×3) and saturated brine (200 mL×2), dried over anhydrous sodium sulfate and filtrate. The filtrate was concentrated on a rotary evaporator to give brownish black oil (781 mg, 58.4%).

MS (ESI, pos. ion) m/z: 354.0 (M+1).

Step 2: 7-fluoro-1-(pyridin-3-ylmethyl)-1H-indazole-3-carbonitrile

To a flask were added 7-fluoro-3-iodo-1-(pyridin-3-ylmethyl)-1H-indazole (5.76 g, 16.3 mmol), then dimethyl sulfoxide (80 mL) and cuprous cyanide (1.613 g, 18.01 mmol) were added. The mixture was heated to 150° C. under an oil bath condition and stirred for 4 hours. The mixture was cooled to room temperature, and the reaction mixture was poured into a mixture of strong aqua ammonia (100 mL) and water (500 mL), then the resulting mixture was extracted with a mixed solvent of petroleum ether and ethyl acetate (v/v=10/1). The organic layers were combined, and washed with water (100 mL×3) and saturated brine (100 mL×2) in turn, dried over anhydrous sodium sulfate, and filtered. The filtrate was concentrated on a rotary evaporator. The residue was purified by silica gel column chromatography eluted with petroleum ether/ethyl acetate (v/v=5/1) to give a yellow solid (1.36 g, 33.1%).

MS (ESI, pos. ion) m/z: 253.2 (M+1).

Step 3: 7-fluoro-1-(pyridin-3-ylmethyl)-1H-indazole-3-carboximidamide

To a solution of sodium methoxide (70 mg, 1.30 mmol) in methanol (20 mL) was added 7-fluoro-1-(pyridin-3-ylmethyl)-1H-indazole-3-carbonitrile (303 mg, 1.20 mmol). The mixture was stirred at rt for 2 hours. Then to the mixture were added ammonium chloride (84 mg, 1.56 mmol) and acetic acid (0.14 mL, 2.4 mmol). The reaction mixture was placed in a 75° C. oil-bath and refluxed for 4 hours. The mixture was evaporated in vacuo to remove the solvent. To the residue were added water (100 mL) and ethyl acetate (50 mL), then to the mixture was added aqueous sodium hydroxide solution (2 mol/L) to adjust pH 10. The reaction mixture was stirred at room temperature for 30 minutes. The reaction mixture was partitioned, and the aqueous layer were extracted with EtOAc (30 mL×3). The combined organic layers were washed with water (100 mL×2) and saturated brine (100 mL), dried over anhydrous sodium sulfate and filtrate. The filtrate was concentrated on a rotary evaporator to remove the solvent and give deep brown oil (248 mg, 76.8%).

MS (ESI, pos. ion) m/z: 270.1 (M+1).

Step 4: 2-(7-fluoro-1-(pyridin-3-ylmethyl)-1H-indazol-3-yl)-5-(phenyldiazenyl) pyrimidine-4,6-diamine 7-Fluoro-1-(pyridin-3-ylmethyl)-1H-indazole-3-carboximidamide (2.99 g, 11.1 mmol) was placed in a 250 mL flask, then N,N-dimethylformamide (40 mL) and triethylamine (1.9 mL, 14.0 mmol) were added into the mixture. The resulting mixture was heated to 85° C., and to the flask was added dropwise slowly a solution of benzeneazomalononitrile (2.54 g, 14.9 mmol) in N,N-dimethylformamide (40 mL). After the addition, the mixture was heated to 100° C. and stirred for 4 h. The mixture was cooled to rt and stirred overnight, which was used in the next step without further purification.

MS (ESI, pos. ion) m/z: 440.1 (M+1).

Step 5: 2-(7-fluoro-1-(pyridin-3-ylmethyl)-1H-indazol-3-yl)pyrimidine-4,5,6-triamine To the reaction mixture of the previous step was added 10% Pd/C (0.438 g). The resulting mixture was stirred at room temperature overnight in hydrogen atmosphere (4.5 MPa). The reaction mixture was filtered through a celite pad, and the filter cake was washed with ethyl acetate (60 mL×3). The filtrate was concentrated in vacuo to remove the solvent, and the residue was purified by silica-gel column chromatography (dichloromethane/methanol (v/v)=10/1) to give a brown-black foamy solid (687 mg, 51.0%).

MS (ESI, pos. ion) m/z: 351.2 (M+1).

Step 6: methyl (4,6-diamino-2-(7-fluoro-1-(pyridin-3-ylmethyl)-1H-indazol-3-yl) pyrimidin-5-yl)carbamate 2-(7-Fluoro-1-(pyridin-3-ylmethyl)-1H-indazol-3-yl)pyrimidine-4,5,6-triamine (491 mg, 1.40 mmol) was added into a 50 mL flask, then dichloromethane (20 mL), pyridine (0.17 mL, 2.1 mmol) and methylchloroformate (0.13 mL, 1.7 mmol) were added dropwise under an ice-bath condition. Then the reaction mixture was stirred for 2 hours under the ice-bath condition. The reaction mixture was extracted with dichloromethane (80 mL×3), and the resulting mixture was washed with water (100 mL×2) and saturated brine (100 mL) in turn, dried over anhydrous sodium sulfate and filtered. The filtrate was concentrated on a rotary evaporator and the residue was purified by silica gel chromatograph (dichloromethane/methanol (v/v)=5/1) to give a yellow solid (500 mg, 87.4%).

MS (ESI, pos. ion) m/z: 409.2 (M+1);
$^1$H NMR (400 MHz, DMSO-$d_6$) δ (ppm) 8.58 (s, 2H), 8.44 (d, J=7.8 Hz, 1H), 8.34 and 8.05 (2 br s, 1H), 7.79 (s, 2H), 7.67 (d, J=7.9 Hz, 2H), 7.53-7.32 (m, 4H), 5.96 (s, 2H), 3.66 (s, 3H).

Example 20 methyl (4,6-diamino-2-(7-fluoro-1-(pyridin-3-ylmethyl)-1H-indazol-3-yl) pyrimidin-5-yl)(methyl)carbamate

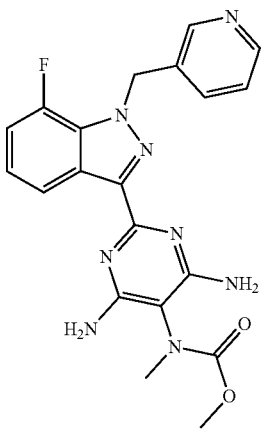 [SMILES: COC(=O)N(C)c1c(N)nc(-c2nn(Cc3cccnc3)c3c(F)cccc23)nc1N]

Methyl (4,6-diamino-2-(7-fluoro-1-(pyridin-3-ylmethyl)-1H-indazol-3-yl)pyrimidin-5-yl)carbamate (302.6 mg, 0.7409 mmol) was placed in a 50 mL flask, then N,N-dimethylformamide (10 mL) was added. Then 60% sodium hydride (45 mg, 1.1 mmol) and iodomethane (50 μL, 0.80 mmol) was added under an ice-bath condition, and the mixture was stirred for 2 hours at room temperature. The reaction mixture was concentrated on a rotary evaporator directly, and the residue was purified by silica gel chromatograph (dichloromethane/methanol (v/v)=10/1) to give the title compound as a light yellow solid (210 mg, 67.1%).

MS (ESI, pos. ion) m/z: 423.2 (M+1);
$^1$H NMR (400 MHz, DMSO-d$_6$) δ (ppm) 8.56 (d, J=8.1 Hz, 1H), 8.48 (s, 2H), 7.54 (d, J=7.7 Hz, 1H), 7.34 (dd, J=7.7, 4.8 Hz, 1H), 7.25 (dd, J=12.0, 7.7 Hz, 1H), 7.18 (dd, J=7.7, 4.6 Hz, 1H), 6.44 (d, J=10.3 Hz, 4H), 5.85 (s, 2H), 3.66 and 3.53 (2 s, 3H), 3.01 (s, 3H).

Example 21 methyl (4,6-diamino-2-(7-fluoro-1-(pyridin-2-ylmethyl)-1H-indazol-3-yl) pyrimidin-5-yl)carbamate

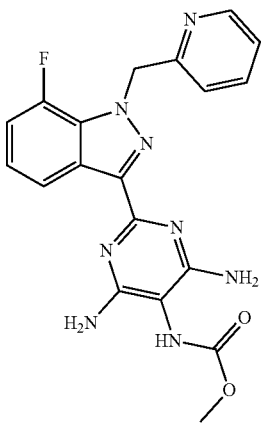 [SMILES: COC(=O)Nc1c(N)nc(-c2nn(Cc3ccccn3)c3c(F)cccc23)nc1N]

Step 1: 7-fluoro-3-iodo-1-(pyridin-2-ylmethyl)-1H-indazole

The title compound was prepared according to the process of step 1 in example 19 by using 7-fluoro-3-iodo-1H-indazole (10.1 g, 38.5 mmol), 2-(bromomethyl)pyridine hydrobromide (10.0 g, 39.5 mmol) and cesium carbonate (26.5 g, 81.3 mmol) which were dissolved in N,N-dimethylformamide (150 mL) to give brown oil (11.5 g, 84.5%).

MS (ESI, pos. ion) m/z: 354.1 (M+1).

Step 2: 7-fluoro-1-(pyridin-2-ylmethyl)-1H-indazole-3-carbonitrile

The title compound was prepared according to the process of step 2 in example 19 by using 7-fluoro-3-iodo-1-(pyridin-2-ylmethyl)-1H-indazole (9.0 g, 25 mmol) and cuprous cyanide (2.3 g, 26 mmol) which were dissolved in dimethyl sulfoxide (45 mL) to give the crude product, which was purified by silica gel chromatograph (petroleum ether/ethyl acetate (v/v)=4/1) to give the title compound as a yellow solid (500 mg, 7.8%).

MS (ESI, pos. ion) m/z: 253.2 (M+1).

Step 3: 7-fluoro-1-(pyridin-2-ylmethyl)-1H-indazole-3-carboximidamide

The title compound was prepared according to the process of step 3 in example 19 by using 7-fluoro-1-(pyridin-2-ylmethyl)-1H-indazole-3-carbonitrile (700 mg, 2.78 mmol), sodium methoxide (225 mg, 4.16 mmol), ammonium chloride (225 mg, 4.21 mmol) and glacial acetic acid (0.65 mL, 11 mmol) which were dissolved in methanol (60 mL) to give a yellow solid (650 mg, 87.0%).

MS (ESI, pos. ion) m/z: 270.2 (M+1).

Step 4: 2-(7-fluoro-1-(pyridin-2-ylmethyl)-1H-indazol-3-yl)-5-(phenyldiazenyl) pyrimidine-4,6-diamine 7-Fluoro-1-(pyridin-2-ylmethyl)-1H-indazole-3-carboximidamide (650 mg, 2.41 mmol) was dissolved in N,N-dimethylformamide (50 mL), then triethylamine (0.50 mL, 3.6 mmol) was added into the mixture. The resulting mixture was heated to 85° C. under nitrogen protection, and to the mixture was added benzeneazomalononitrile (620 mg, 3.64 mmol). After the addition, the mixture was heated to 100° C. and stirred for 5 h. The mixture was used directly in the next group without further purification.

MS (ESI, pos. ion) m/z: 440.1 [M+1]$^+$.

Step 5: 2-(7-fluoro-1-(pyridin-2-ylmethyl)-1H-indazol-3-yl)pyrimidine-4,5,6-triamine To the reaction mixture of the previous step was added 10% Pd/C (300 mg). The resulting mixture was stirred at rt for 2 days under hydrogen atmosphere. The mixture was filtered through a celite pad, and the filter cake was washed with methanol. The filtrates were collected and concentrated in vacuo to remove the solvent. The crude product was purified by silica gel chromatograph (dichloromethane/methanol (v/v)=10/1) to give the title compound as a brown solid (410 mg, 51.0%).

MS (ESI, pos. ion) m/z: 351.1 (M+1).

Step 6: methyl (4,6-diamino-2-(7-fluoro-1-(pyridin-2-ylmethyl)-1H-indazol-3-yl) pyrimidin-5-yl)carbamate 2-(7-Fluoro-1-(pyridin-2-ylmethyl)-1H-indazol-3-yl)pyrimidine-4,5,6-triamine (600 mg, 1.71 mmol) was dissolved in pyridine (10 mL), then methylchloroformate (0.6 mL, 8.0 mmol) were added dropwise at 0° C. The reaction mixture was continued to stir for 0.5 hour at 0° C., then heated to rt and stirred overnight. The resulting mixture was concentrated in vacuo to remove the solvent, and the residue was purified by silica gel chromatograph (methanol/dichloromethane (v/v)=1/15) to give the title compound as a light yellow solid (310 mg, 44.3%).

MS (ESI, pos. ion) m/z: 409.2 (M+1);

$^1$H NMR (400 MHz, DMSO-d$_6$) δ (ppm) 8.56 (d, J=7.9 Hz, 1H), 8.48 (d, J=4.4 Hz, 1H), 8.01 (s, 1H), 7.75 (dd, J=10.9, 4.4 Hz, 1H), 7.33-7.27 (m, 1H), 7.19 (dq, J=12.4, 7.6 Hz, 2H), 7.02 (d, J=7.8 Hz, 1H), 6.16 (s, 4H), 5.86 (s, 2H), 3.62 (s, 3H).

Example 22 methyl (4,6-diamino-2-(7-fluoro-1-(pyridin-2-ylmethyl)-1H-indazol-3-yl) pyrimidin-5-yl)(methyl)carbamate

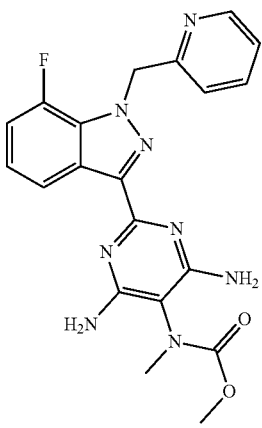 [SMILES: COC(=O)N(C)c1c(N)nc(-c2nn(Cc3ccccn3)c3c(F)cccc23)nc1N]

Methyl (4,6-diamino-2-(7-difluoro-1-(pyridin-2-ylmethyl)-1H-indazol-3-yl)pyrimidin-5-yl)carbamate (350 mg, 0.857 mmol) was dissolved in N,N-dimethylformamide (20 mL). Then 60% sodium hydride (100 mg, 2.50 mmol) was added at 0° C., and the mixture was stirred at this temperature for 20 minutes, and then iodomethane (0.15 mL, 2.41 mmol) was added into the mixture. The resulting mixture was continued to stir for 30 minutes and then stirred for 1.5 hours at room temperature. The reaction mixture was extracted with ethyl ether (50 mL×2). The combined organic layers were washed with water (40 mL) and saturated brine (40 mL), dried over anhydrous sodium sulfate and concentrated in vacuo to remove the solvent. The crude product was purified by silica-gel column chromatography (ethyl acetate/methanol (v/v)=15/1) to give a light yellow solid (120 mg, 33.2%).

MS (ESI, pos. ion) m/z: 423.1 (M+1);

$^1$H NMR (400 MHz, DMSO-d$_6$) δ (ppm) 8.56 (d, J=7.9 Hz, 1H), 8.48 (d, J=4.3 Hz, 1H), 7.74 (t, J=7.7 Hz, 1H), 7.37-7.27 (m, 1H), 7.25-7.11 (m, 2H), 6.99 (d, J=7.8 Hz, 1H), 6.35 (s, 4H), 5.86 (s, 2H), 3.66 and 3.54 (2 s, 3H), 3.02 (s, 3H).

Example 23 methyl (4,6-diamino-2-(7-fluoro-1-(pyridin-4-ylmethyl)-1H-indazol-3-yl) pyrimidin-5-yl)carbamate

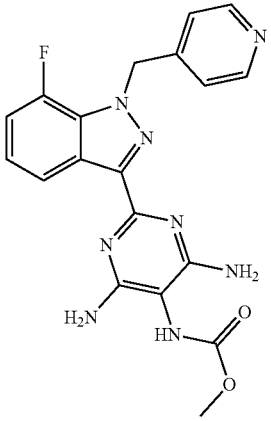 [SMILES: COC(=O)Nc1c(N)nc(-c2nn(Cc3ccncc3)c3c(F)cccc23)nc1N]

Step 1: 7-fluoro-3-iodo-1-(pyridin-4-ylmethyl)-1H-indazole

The title compound was prepared according to the process of step 1 in example 19 by using 7-fluoro-3-iodo-1H-indazole (5.2 g, 20 mmol), 4-(bromomethyl)pyridine hydrobromide (5.0 g, 20 mmol) and cesium carbonate (14 g, 42.97 mmol) which were dissolved in N,N-dimethylformamide (150 mL) to give a yellow solid (6.0 g, 86.0%).

MS (ESI, pos. ion) m/z: 354.1 (M+1).

Step 2: 7-fluoro-1-(pyridin-4-ylmethyl)-1H-indazole-3-carbonitrile

Cuprous cyanide (1.50 g, 16.7 mmol) was dissolved in dimethylsulfoxide (20 mL) under nitrogen protection. The mixture was heated to 150° C., and a solution of 7-fluoro-3-iodo-1-(pyridin-4-ylmethyl)-1H-indazole (6.0 g, 17 mmol) in dimethylsulfoxide (25 mL) was added dropwise. After addition, the mixture was continued to stir for 2.5 hours at 150° C. The reaction mixture was cooled to rt, and quenched with ammonium hydroxide (25 mL) and water (30 mL). The mixture was stirred for 10 minutes, and then extracted with ethyl acetate (100 mL×2). The combined organic layers were washed with water (50 mL) and saturated brine (50 mL) dried over anhydrous sodium sulfate and concentrated in vacuo to remove the solvent. The crude product was purified by silica-gel column chromatography (petroleum ether/ethyl acetate (v/v)=2/1) to give a light yellow solid (1.71 g, 40.0%).

MS (ESI, pos. ion) m/z: 253.2 (M+1).

Step 3: 7-fluoro-1-(pyridin-4-ylmethyl)-1H-indazole-3-carboximidamide

The title compound was prepared according to the process of step 3 in example 19 by using 7-fluoro-1-(pyridin-4-ylmethyl)-1H-indazole-3-carbonitrile (1.70 g, 6.70 mmol), sodium methoxide (550 mg, 10.2 mmol), ammonium chloride (540 mg, 10.1 mmol) and glacial acetic acid (1.50 mL, 26.0 mmol) which were dissolved in methanol (100 mL) to give a yellow solid (1.71 g, 94.0%).

MS (ESI, pos. ion) m/z: 270.1 (M+1).

Step 4: 2-(7-fluoro-1-(pyridin-4-ylmethyl)-1H-indazol-3-yl)-5-(phenyldiazenyl) pyrimidine-4,6-diamine 7-Fluoro-1-(pyridin-4-ylmethyl)-1H-indazole-3-carboximidamide (1.71 g, 6.35 mmol) was dissolved in N,N- dimethylformamide (50 mL), then triethylamine (1.32 mL, 9.50 mmol) was added into the mixture. The resulting mixture was heated to 85° C. under nitrogen protection, and to the mixture was added benzeneazomalononitrile (1.62 g, 9.52 mmol). After the addition, the mixture was heated to 100° C. and stirred for 4 h. The reaction was stopped, and the reaction mixture was used directly in the next step without further purification.

MS (ESI, pos. ion) m/z: 440.3 (M+1).

Step 5: 2-(7-fluoro-1-(pyridin-4-ylmethyl)-1H-indazol-3-yl)pyrimidine-4,5,6-triamine To the reaction mixture of the previous step was added 10% Pd/C (300 mg). The resulting mixture was stirred at room temperature overnight in hydrogen atmosphere. The reaction mixture was filtered through a celite pad, and the filter cake was washed with methanol (20 mL). The filtrate was collected and concentrated in vacuo to remove the solvent, and the residue was purified by silica-gel column chromatography (dichloromethane/methanol (v/v)=10/1) to give a brown solid (1.01 g, 45.4%).

MS (ESI, pos. ion) m/z: 351.1 (M+1).

Step 6: methyl (4,6-diamino-2-(7-fluoro-1-(pyridin-4-ylmethyl)-1H-indazol-3-yl) pyrimidin-5-yl)carbamate 2-(7-Fluoro-1-(pyridin-4-ylmethyl)-1H-indazol-3-yl)pyrimidine-4,5,6-triamine (1.0 g, 2.9 mmol) was dissolved in pyridine (10 mL), then methylchloroformate (1.0 mL, 13 mmol) was added dropwise at 0° C. The reaction mixture was continued to stir for 0.5 hour at 0° C., then warmed to room temperature and stirred overnight. The reaction mixture was concentrated in vacuo to remove the solvent. The crude product was purified by silica gel chromatography eluted with dichloromethane/methanol ((v/v)=10/1) to give a creamy solid (220 mg, 19.0%).

MS (ESI, pos. ion) m/z: 409.1 (M+1);
$^1$H NMR (400 MHz, DMSO-$d_6$) δ (ppm) 8.58 (d, J=7.9 Hz, 1H), 8.51 (d, J=5.9 Hz, 2H), 8.02 and 7.70 (2 br s, 1H), 7.32-7.14 (m, 2H), 7.07 (d, J=5.6 Hz, 2H), 6.18 (s, 4H), 5.83 (s, 2H), 3.63 (s, 3H).

Example 24 methyl (4,6-diamino-2-(7-fluoro-1-(pyridin-4-ylmethyl)-1H-indazol-3-yl) pyrimidin-5-yl)(methyl) carbamate

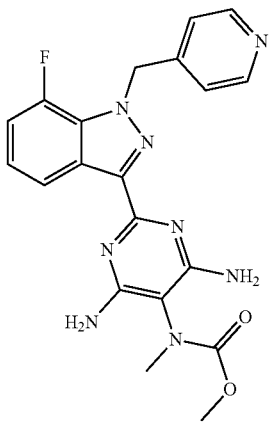 [SMILES: COC(=O)N(C)c1c(N)nc(-c2nn(Cc3ccncc3)c3c(F)cccc23)nc1N]

The title compound was prepared according to the process of example 22 by using methyl (4,6-diamino-2-(7-fluoro-1-(pyridin-4-ylmethyl)-1H-indazol-3-yl)pyrimidin-5-yl) carbamate (650 mg, 1.59 mmol), 60% sodium hydride (160 mg, 4.00 mmol) and iodomethane (0.250 mL, 4.02 mmol) which were dissolved in N,N-dimethylformamide (20.0 mL) to give a white solid (120 mg, 17.9%).

MS (ESI, pos. ion) m/z: 423.1 (M+1);
$^1$H NMR (400 MHz, DMSO-$d_6$) δ (ppm) 8.58 (d, J=7.9 Hz, 1H), 8.50 (d, J=5.1 Hz, 2H), 7.28-7.15 (m, 2H), 7.05 (d, J=4.4 Hz, 2H), 6.37 (s, 4H), 5.82 (s, 2H), 3.67 and 3.55 (2 s, 3H), 3.02 (s, 3H).

Example 25

5-fluoro-2-(7-fluoro-1-(2-fluorobenzyl)-1H-indazol-3-yl)pyrimidin-4-ol

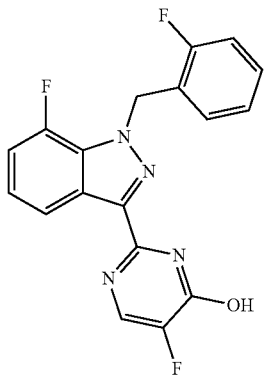 [SMILES: Oc1nc(-c2nn(Cc3ccccc3F)c3c(F)cccc23)ncc1F]

Step 1:
1-ethoxy-2-fluoro-1,3-dioxopropane-2-sodium salt

60% Sodium hydride (1.08 g, 27.0 mmol) was placed in a 100 mL flask, then tetrahydrofuran (20 mL) and ethanol (0.13 mL) were added into the flask at 0° C. Then a solution of ethyl formate (2 g, 27.0 mmol) and ethyl 2-fluoroacetate (2.62 mL, 27.0 mmol) in tetrahydrofuran (15 mL) were added dropwise. After the addition, the mixture was warmed to room temperature and stirred for 20 hours. The reaction mixture was concentrated on a rotary evaporator to give a yellow solid (4.21 g, 100.0%).

Step 2: 5-fluoro-2-(7-fluoro-1-(2-fluorobenzyl)-1H-indazol-3-yl)pyrimidin-4-ol

7-Fluoro-1-(2-fluorobenzyl)-1H-indazole-3-carboximidamide (0.905 g, 3.16 mmol), 1-ethoxy-2-fluoro-1,3-dioxopropane-2-sodium salt (1.225 g, 7.85 mmol) were placed in a 100 mL flask, then ethanol (30 mL) was added into the mixture. The mixture was heated to reflux and stirred overnight. The reaction mixture was cooled to rt, concentrated on a rotary evaporator directly, and the residue was purified by silica gel chromatograph (petroleum ether/ethyl acetate (v/v)=3/1) to give the title compound as a white flocculent solid (126 mg, 11.2%).

MS (ESI, pos. ion) m/z: 357.2 (M+1);

$^1$H NMR (400 MHz, DMSO-d$_6$) δ (ppm) 8.22 (s, 1H), 8.16 (d, J=7.6 Hz, 1H), 7.33 (dd, J=21.4, 9.5 Hz, 3H), 7.22 (dd, J=19.3, 10.2 Hz, 2H), 7.14 (t, J=7.2 Hz, 1H), 5.88 (s, 2H).

Example 26

1-((4,6-diamino-2-(7-fluoro-1-(2-fluorobenzyl)-1H-indazol-3-yl) pyrimidin-5-yl)amino)-2-methylpropan-2-ol

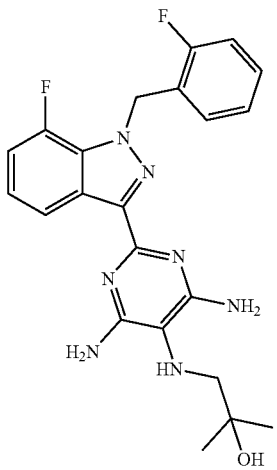 [SMILES: CC(C)(O)CNc1c(N)nc(-c2nn(Cc3ccccc3F)c3c(F)cccc23)nc1N]

Step 1: 2-benzyloxy-2-methylpropanal

2-Methyl-2-benzyloxypropan-1-ol (1.00 g, 5.55 mmol) was added into dichloromethane (30 mL), then Dess-Martin periodinane (3.53 g, 8.32 mmol) was added, and the mixture was stirred at room temperature for 1.5 hours. The reaction mixture was poured into saturated aqueous sodium bicarbonate solution (60 mL). The mixture was partitioned, and the aqueous layer was extracted with dichloromethane (40 mL). The combined organic layers were washed with water (60 mL) and saturated brine (60 mL), dried over anhydrous sodium sulfate and filtered. The filtrate was concentrated on a rotary evaporator and the residue was purified by silica gel chromatograph (petroleum ether/ethyl acetate (v/v)=15/1) to give colorless oil (0.87 g, 88.0%).

Step 2: N$^5$-(2-benzyloxy-2-methylpropyl)-2-(7-fluoro-1-(2-fluorobenzyl)-1H-indazol-3-yl)-pyrimidine-4,5,6-triamine To 20 mL methanol were added 2-(7-fluoro-1-(2-fluorobenzyl)-1H-indazol-3-yl)pyrimidine-4,5,6-triamine (0.26 g, 0.71 mmol) and 2-benzyloxy-2-methylpropanal (0.15 g, 0.84 mmol). Then acetic acid (0.20 mL, 3.5 mmol) was added at 0° C. The mixture was stirred at 0° C. for 1 hour, then to the mixture was added sodium cyanoborohydride (0.22 g, 3.5 mmol). Then the resulting mixture was stirred at room temperature overnight. The reaction mixture was concentrated in vacuo to remove the solvent, and to the residue was added saturated aqueous sodium bicarbonate solution (50 mL). The resulting mixture was extracted with ethyl acetate (50 mL×2). The combined organic layers were washed with water (60 mL) and saturated brine (60 mL), dried over anhydrous sodium sulfate and filtered. The filtrate was concentrated on a rotary evaporator and the residue was purified by silica gel chromatograph (dichloromethane/methanol (v/v)=200/1, 0.5% triethylamine) to give a brown solid (0.26 g, 69.0%).

MS (ESI, pos. ion) m/z: 530.1 (M+1).

Step 3: 1-((4,6-diamino-2-(7-fluoro-1-(2-fluorobenzyl)-1H-indazol-3-yl)pyrimidin-5-yl) amino)-2-methylpropan-2-ol N$^5$-(2-Benzyloxy-2-methylpropyl)-2-(7-fluoro-1-(2-fluorobenzyl)-1H-indazol-3-yl)-pyrimidine-4,5,6-triamine (0.15 g, 0.28 mmol) was added in methanol (20 mL), then 10% Pd/C (0.20 g) was added. The mixture was heated to 50° C. and stirred overnight under nitrogen protection. The mixture was cooled to room temperature and filtered by suction. The filtrate was concentrated on a rotary evaporator and the residue was purified by silica gel chromatography eluted with dichloromethane/methanol (v/v=100/1, 0.5% triethylamine) to give a light yellow solid product (0.016 g, 13.0%).

MS (ESI, pos. ion) m/z: 440.1 (M+1);
$^1$H NMR (400 MHz, DMSO-d$_6$) δ (ppm) 8.54 (d, J=8.0 Hz, 1H), 7.35 (dd, J=13.6, 5.8 Hz, 1H), 7.23 (t, J=10.1 Hz, 2H), 7.19-7.10 (m, 2H), 6.97 (t, J=7.1 Hz, 1H), 6.16 (s, 4H), 5.81 (s, 2H), 4.69 (s, 1H), 3.20 (t, J=7.4 Hz, 1H), 2.67 (d, J=7.0 Hz, 2H), 1.16 (s, 6H);
$^{19}$F NMR (376 MHz, DMSO-d$_6$) δ (ppm) −118.76 (d, J=7.1 Hz), −134.46 (d, J=6.8 Hz).

Example 27

N-(4,6-diamino-2-(7-fluoro-1-(2-fluorobenzyl)-1H-indazol-3-yl)pyrimidin-5-yl)tetrahydrofuran-3-carboxamide

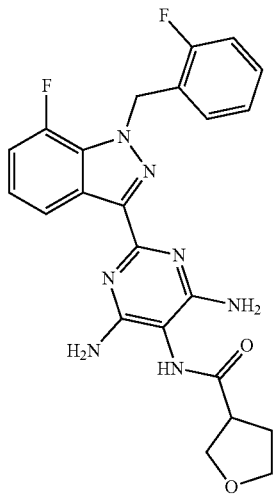 [SMILES: Nc1nc(-c2nn(Cc3ccccc3F)c3c(F)cccc23)nc(N)c1NC(=O)C1CCOC1]

To N,N-dimethylformamide (10 mL) were added 2-(7-fluoro-1-(2-fluorobenzyl)-1H-indazol-3-yl)pyrimidine-4,5,6-triamine (0.10 g, 0.27 mmol) and tetrahydrofuran-3-carboxylic acid (0.035 g, 0.30 mmol). Then O-(7-azabenzotriazol-1-yl)-N,N,N',N'-te-tramethyluronium hexafluorophosphate (0.12 g, 0.32 mmol) and N,N-diisopropylethylamine (0.13 mL, 0.79 mmol) were added at 0° C. The mixture was stirred at 0° C. for 6 hours. The reaction mixture was quenched with water (50 mL), and the resulting mixture was extracted with ethyl acetate (30 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=100/1, 0.5% triethylamine) to give a white solid (0.046 g, 36.0%).

MS (ESI, pos. ion) m/z: 466.6 (M+1);

$^1$H NMR (400 MHz, DMSO-d$_6$) δ (ppm) 8.81 (s, 1H), 8.56 (d, J=8.0 Hz, 1H), 7.35 (dd, J=13.5, 6.3 Hz, 1H), 7.30-7.08 (m, 4H), 6.98 (t, J=7.5 Hz, 1H), 6.16 (d, J=59.0 Hz, 4H), 5.84 (s, 2H), 3.95 (t, J=8.3 Hz, 1H), 3.85-3.73 (m, 2H), 3.69 (q, J=7.4 Hz, 1H), 3.28-3.15 (m, 1H), 2.21-2.05 (m, 2H);

$^{19}$F NMR (376 MHz, DMSO-d$_6$) δ (ppm) −118.72 (d, J=7.1 Hz), −134.24 (d, J=7.1 Hz).

Example 28

2-(7-fluoro-1-(2-fluorobenzyl)-1H-indazol-3-yl)-N$^5$-(1-(tetrahydro-2H-pyran-4-yl)ethyl)pyrimidine-4,5,6-triamine

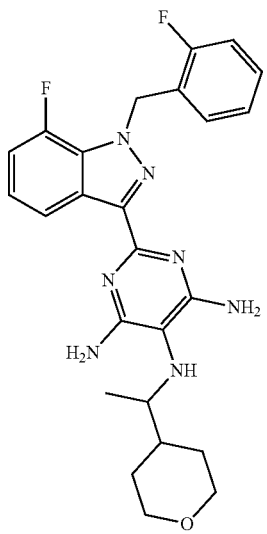 [SMILES: CC(Nc1c(N)nc(-c2nn(Cc3ccccc3F)c3c(F)cccc23)nc1N)C1CCOCC1]

To 15 mL methanol were added 2-(7-fluoro-1-(2-fluorobenzyl)-1H-indazol-3-yl)pyrimidine-4,5,6-triamine (0.20 g, 0.54 mmol) and 1-(tetrahydro-2H-pyran-4-yl)ethanone (0.10 g, 0.78 mmol). Then acetic acid (0.16 mL, 2.8 mmol) was added at 0° C. The mixture was heated to room temperature and stirred for 1 hour, then cooled to 0° C., and to the mixture was added sodium cyanoborohydride (0.17 g, 2.7 mmol). Then the resulting mixture was stirred at room temperature overnight. The reaction mixture was concentrated in vacuo to remove the solvent, and to the residue was added saturated aqueous sodium bicarbonate (40 mL). The resulting mixture was extracted with ethyl acetate (30 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=200/1, 0.5% triethylamine) to give a light yellow solid (0.11 g, 42.0%).

MS (ESI, pos. ion) m/z: 480.7 (M+1);

$^1$H NMR (400 MHz, DMSO-d$_6$) δ (ppm) 8.56 (d, J=8.0 Hz, 1H), 7.38-7.30 (m, 1H), 7.27-7.19 (m, 2H), 7.19-7.09 (m, 2H), 6.97 (t, J=7.0 Hz, 1H), 5.90 (s, 4H), 5.81 (s, 2H), 3.96-3.85 (m, 2H), 3.31-3.21 (m, 3H), 2.89-2.76 (m, 1H), 1.82-1.74 (m, 1H), 1.72-1.64 (m, 1H), 1.64-1.51 (m, 1H), 1.40-1.26 (m, 2H), 0.95 (d, J=6.4 Hz, 3H);

$^{19}$F NMR (376 MHz, DMSO-d$_6$) δ (ppm) −118.77 (d, J=7.1 Hz), −134.46 (d, J=7.1 Hz).

Example 29

N-(4,6-diamino-2-(7-fluoro-1-(2-fluorobenzyl)-1H-indazol-3-yl)pyrimidin-5-yl)tetrahydro-2H-pyran-4-carboxamide

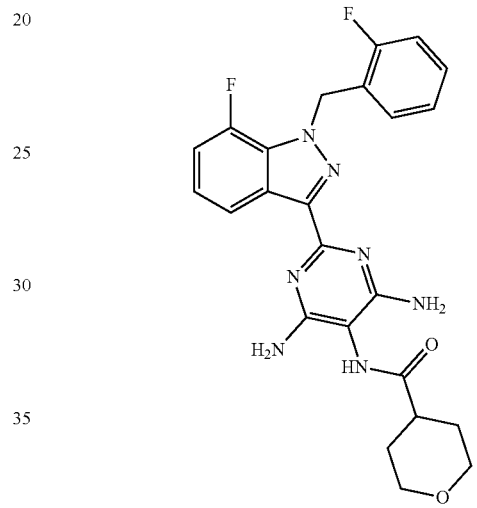

To N,N-dimethylformamide (20 mL) were added 2-(7-fluoro-1-(2-fluorobenzyl)-1H-indazol-3-yl)pyrimidine-4,5,6-triamine (140 mg, 0.3811 mmol) and tetrahydro-2H-pyran-4-carboxylic acid (60 mg, 0.461 mmol). Then O-(7-azabenzotriazol-1-yl)-N,N,N',N'-te-tramethyluronium hexafluorophosphate (217 mg, 0.571 mmol) and N,N-diisopropylethylamine (0.25 mL, 1.5 mmol) were added. The mixture was stirred at room temperature overnight. The reaction mixture was extracted with ethyl ether (50 mL×2). The combined organic layers were washed with water (40 mL) and saturated brine (40 mL), dried over anhydrous sodium sulfate, and filtered. The filtrate with concentrated in vacuo to remove the solvent, and the crude product was purified by silica-gel column chromatography (petroleum ether/ethyl acetate (v/v)=1/5) to give a yellow solid (101 mg, 55.28%).

MS (ESI, pos. ion) m/z: 480.1 (M+1);

$^1$H NMR (400 MHz, DMSO-d$_6$) δ (ppm) 8.67 (s, 1H), 8.57 (d, J=8.0 Hz, 1H), 7.35 (dd, J=13.2, 6.3 Hz, 1H), 7.31-7.10 (m, 4H), 6.98 (t, J=7.5 Hz, 1H), 6.02 (s, 4H), 5.84 (s, 2H), 3.91 (d, J=8.5 Hz, 2H), 3.31 (s, 4H), 2.63 (t, J=11.5 Hz, 1H), 1.85 (d, J=12.9 Hz, 2H), 1.77-1.59 (m, 2H).

Example 30

4-amino-2-(7-fluoro-1-(2-fluorobenzyl)-1H-indazol-3-yl)pyrimidine-5-carboxylic acid

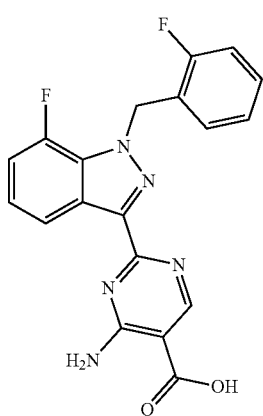 [SMILES: Nc1nc(-c2nn(Cc3ccccc3F)c3c(F)cccc23)ncc1C(=O)O]

Step 1: ethyl 4-amino-2-(7-fluoro-1-(2-fluorobenzyl)-1H-indazol-3-yl)pyrimidine-5-carboxylate 7-Fluoro-1-(2-fluorobenzyl)-1H-indazole-3-carboximidamide (1.80 g, 6.29 mmol) and ethyl (ethoxymethylene)cyanoacetate (1.06 g, 6.27 mmol) were added into ethanol (50 mL). The mixture was heated to reflux and stirred overnight. The mixture was cooled to rt and concentrated to remove the solvent. The residue was purified by silica gel chromatography (dichloromethane, 0.5% triethylamine) to give a white solid product (0.72 g, 28.0%).

MS (ESI, pos. ion) m/z: 410.0 (M+1).

Step 2: 4-amino-2-(7-fluoro-1-(2-fluorobenzyl)-1H-indazol-3-yl)pyrimidine-5-carboxylic acid To a 100 mL single flask were added ethyl 4-amino-2-(7-fluoro-1-(2-fluorobenzyl)-1H-indazol-3-yl)pyrimidine-5-carboxylate (0.75 g, 1.8 mmol), water (10 mL), methanol (10 mL) and tetrahydrofuran (10 mL), then to the mixture was added sodium hydroxide (0.11 g, 2.8 mmol). The resulting mixture was stirred overnight. The mixture was evaporated to remove the solvent, and the residue was added into water (150 mL). The mixture was adjusted with hydrochloric acid (2 mol/L) to pH 4, then filtered by suction. The filter cake was washed with water, and the filter cake was concentrated in vacuo to give a light yellow solid (0.62 g, 89.0%).

MS (ESI, pos. ion) m/z: 382.4 (M+1);

$^1$H NMR (400 MHz, DMSO-$d_6$) δ (ppm) 8.87 (s, 1H), 8.53 (d, J=7.8 Hz, 1H), 8.18 (s, 1H), 7.91 (s, 1H), 7.40-7.20 (m, 4H), 7.15 (t, J=7.4 Hz, 1H), 7.06 (t, J=7.2 Hz, 1H), 5.89 (s, 2H).

Example 31

4-amino-N-cyclopropyl-2-(7-fluoro-1-(2-fluorobenzyl)-1H-indazol-3-yl) pyrimidine-5-carboxamide

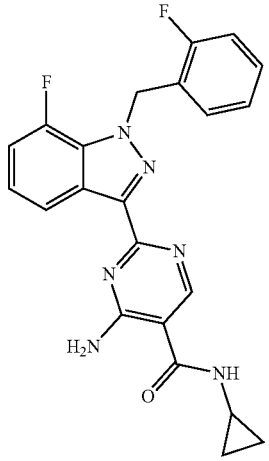 [SMILES: Nc1nc(-c2nn(Cc3ccccc3F)c3c(F)cccc23)ncc1C(=O)NC1CC1]

To a 50 mL single neck flask were added 4-amino-2-(7-fluoro-1-(2-fluorobenzyl)-1H-indazol-3-yl)pyrimidine-5-carboxylic acid (0.10 g, 0.26 mmol), N,N-dimethylformamide (10 mL) and cyclopropylamine (0.022 mL, 0.32 mmol). Then O-(7-azabenzotriazol-1-yl)-N,N,N',N'-tetramethyluronium hexafluorophosphate (0.12 g, 0.32 mmol) and N,N-diisopropylethylamine (0.13 mL, 0.79 mmol) were added at 0° C. The mixture was warmed to room temperature and stirred overnight. The reaction mixture was poured into water (50 mL), and the resulting mixture was extracted with ethyl acetate (40 mL×2). The combined organic layers were washed with water (50 mL) and saturated brine (50 mL) in turn, dried over anhydrous sodium sulfate and filtered. The filtrate was concentrated on a rotary evaporator and the residue was purified by silica gel chromatograph (dichloromethane/ethyl acetate (v/v)=10/1) to give a white solid (0.046 g, 42.0%).

MS (ESI, pos. ion) m/z: 421.6 (M+1);

$^1$H NMR (400 MHz, DMSO-$d_6$) δ (ppm) 8.73 (s, 1H), 8.60 (d, J=3.7 Hz, 1H), 8.49 (d, J=7.8 Hz, 1H), 8.02 (s, 2H), 7.40-7.20 (m, 4H), 7.15 (t, J=7.5 Hz, 1H), 7.04 (t, J=7.1 Hz, 1H), 5.88 (s, 2H), 2.79-2.87 (m, 1H), 0.77-0.67 (m, 2H), 0.65-0.52 (m, 2H).

Example 32

4-amino-2-(7-fluoro-1-(2-fluorobenzyl)-1H-indazol-3-yl)-N-methyl pyrimidine-5-carboxamide

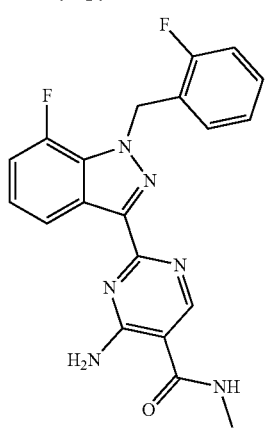

To a 50 mL single flask were added 4-amino-2-(7-fluoro-1-(2-fluorobenzyl)-1H-indazol-3-yl)pyrimidine-5-carboxylic acid (0.15 g, 0.39 mmol), N,N-dimethylformamide (10 mL) and a solution of aminomethane in tetrahydrofuran (0.24 mL, 0.48 mmol, 2 mol/L). Then O-(7-azabenzotriazol-1-yl)-N,N,N',N'-te-tramethyluronium hexafluorophosphate (0.18 g, 0.47 mmol) and N,N-diisopropylethylamine (0.19 mL, 1.2 mmol) were added at 0° C. The mixture was warmed to room temperature and stirred overnight. The reaction mixture was poured into water (50 mL), and the resulting mixture was extracted with ethyl acetate (40 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/ethyl acetate (v/v)=10/1) to give a white solid (0.031 g, 20%).

MS (ESI, pos. ion) m/z: 395.5 (M+1);
$^1$H NMR (400 MHz, DMSO-d$_6$) δ (ppm) 8.76 (s, 1H), 8.61 (d, J=4.5 Hz, 1H), 8.50 (d, J=7.8 Hz, 1H), 8.04 (s, 2H), 7.40-7.20 (m, 4H), 7.15 (t, J=7.4 Hz, 1H), 7.04 (t, J=7.5 Hz, 1H), 5.88 (s, 2H), 2.79 (d, J=4.4 Hz, 3H).

Example 33 methyl (4,6-diamino-2-(7-fluoro-1-(pyrimidin-5-ylmethyl)-1H-indazol-3-yl)pyrimidin-5-yl)carbamate

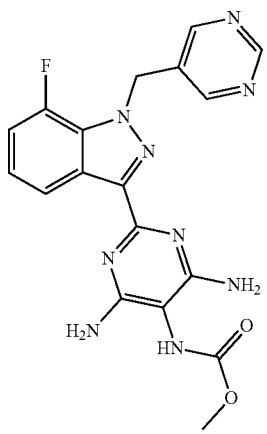 [SMILES: COC(=O)Nc1c(N)nc(-c2nn(Cc3cncnc3)c3c(F)cccc23)nc1N]

Step 1: 7-fluoro-3-iodo-1-(pyrimidin-5-ylmethyl)-1H-indazole

7-Fluoro-3-iodo-1H-indazole (500 mg, 1.91 mmol) was dissolved in N,N-dimethylformamide (30 mL), then 5-(bromomethyl)pyrimidine hydrobromide (490 mg, 1.93 mmol) and cesium carbonate (1.55 g, 4.76 mmol) were added. The mixture was stirred for 3 hours at room temperature. The reaction mixture was extracted with ethyl acetate (90 mL×3). The combined organic layers were washed with water (40 mL) and saturated brine (40 mL), dried over anhydrous sodium sulfate, and filtered. The filtrate was concentrated in vacuo to give yellow oil (610 mg, 90.27%).

MS (ESI, pos. ion) m/z: 355.4 (M+1).

Step 2: 7-fluoro-1-(pyrimidin-5-ylmethyl)-1H-indazole-3-carbonitrile

Cuprous cyanide (1.8 g, 20 mmol) and 7-fluoro-3-iodo-1-(pyrimidin-5-ylmethyl)-1H-indazole (5.8 g, 16 mmol) was dissolved in dimethylsulfoxide (120 mL) under nitrogen protection. The mixture was stirred at 150° C. for 3 hours. The reaction mixture was cooled to room temperature, and quenched with ammonium hydroxide. The mixture was extracted with ethyl acetate (200 mL×3). The combined organic layers were washed with water (100 mL) and saturated brine (100 mL), dried over anhydrous sodium sulfate, and filtered. The filtrate with concentrated in vacuo to remove the solvent, and crude product was purified by silica-gel column chromatography (petroleum ether/ethyl acetate (v/v)=2/1) to give a white solid (3.61 g, 87.0%).

MS (ESI, pos. ion) m/z: 254.4 (M+1).

Step 3: 7-fluoro-1-(pyrimidin-5-ylmethyl)-1H-indazole-3-carboximidamide

To a 50 mL two-neck flask was added sodium methoxide (1.5 g, 28 mmol), then to the mixture were added methanol (30 mL) and 7-fluoro-1-(pyrimidin-5-ylmethyl)-1H-indazole-3-carbonitrile (1.8 g, 7.1 mmol). Then to the mixture were added ammonium chloride (460 mg, 8.600 mmol) and glacial acetic acid (1.6 mL, 28 mmol). The reaction mixture was refluxed for 4 hours. The mixture was evaporated by rotary evaporation to remove the solvent, and to the residue was added water (120 mL). The resulting mixture was adjusted with aqeous sodium hydroxide solution (2 mol/L) to pH 10. The reaction mixture was extracted with ethyl acetate (150 mL×2). The combined organic layers were washed with water (50 mL) and saturated brine (50 mL), dried over anhydrous sodium sulfate, and filtered. The filtrate was concentrated in vacuo to give a light yellow solid (1.72 g, 90.0%).

MS (ESI, pos. ion) m/z: 271.4 (M+1).

Step 4: 2-(7-fluoro-1-(pyrimidin-5-ylmethyl)-1H-indazol-3-yl)-5-(phenyldiazenyl) pyrimidine-4,6-diamine 7-Fluoro-1-(pyrimidin-5-ylmethyl)-1H-indazole-3-carboximidamide (1.72 g, 6.36 mmol) was dissolved in N,N-dimethylformamide (80 mL), then triethylamine (3.1 mL, 22 mmol) was added into the mixture. The resulting mixture was heated to 85° C. under nitrogen protection, and to the mixture was added benzeneazomalononitrile (2.17 g, 12.8 mmol). The mixture was heated to 100° C. and stirred for 5 h. The reaction mixture was cooled to room temperature and used directly in the next step without further purification.

MS (ESI, pos. ion) m/z: 441.1 (M+1).

Step 5: 2-(7-fluoro-1-(pyrimidin-5-ylmethyl)-1H-indazol-3-yl)pyrimidine-4,5,6-triamine To the reaction mixture of the previous step was added 10% Pd/C (250 mg). The mixture was stirred at rt overnight in hydrogen atmosphere. The mixture was filtered through a celite pad, and the filter cake was washed with methanol, then the filtrates were collected. The filtrates were concentrated in vacuo to remove the solvent. The crude product was purified by silica gel chromatography eluted with dichloromethane/methanol ((v/v)=10/1) to give a brown solid (1.35 g, 63%).

MS (ESI, pos. ion) m/z: 352.5 (M+1).

Step 6: methyl (4,6-diamino-2-(7-fluoro-1-(pyrimidin-5-ylmethyl)-1H-indazol-3-yl) pyrimidin-5-yl) carbamate 2-(7-Fluoro-1-(pyrimidin-5-ylmethyl)-1H-indazol-3-yl) pyrimidine-4,5,6-triamine (400 mg, 1.139 mmol) was dissolved in pyridine (3 mL), then methylchloroformate (200 μL, 2.588 mmol) was added dropwise at 0° C. The reaction mixture was continued to stir for 0.5 hour at 0° C., then heated to room temperature and stirred for 4 hours. To the reaction mixture was added ethyl acetate (5 mL), and the mixture was stirred for 5 minutes, then there was a large amount of the solid precipitated out. The mixture was filtered, then the filter cake was collected and dried in vacuo to give a light yellow solid (340 mg, 72.94%).

MS (ESI, pos. ion) m/z: 410.1 (M+1);

$^1$H NMR (400 MHz, DMSO-d$_6$) δ (ppm) 9.15 (s, 1H), 8.85 (s, 2H), 8.50-8.34 (m, 2H), 7.85 (s, 4H), 7.46-7.34 (m, 2H), 5.95 (s, 2H), 3.66 (s, 3H).

Example 34 methyl (4,6-diamino-2-(7-fluoro-1-(pyrimidin-5-ylmethyl)-1H-indazol-3-yl) pyrimidin-5-yl)(methyl)carbamate

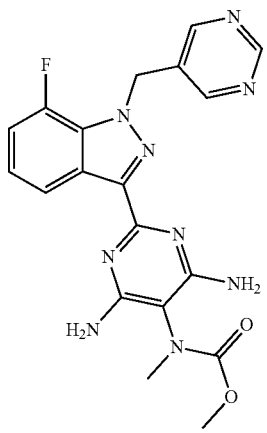 [SMILES: COC(=O)N(C)c1c(N)nc(-c2nn(Cc3cncnc3)c3c(F)cccc23)nc1N]

Methyl (4,6-diamino-2-(7-fluoro-1-(pyrimidin-5-ylmethyl)-1H-indazol-3-yl) pyrimidin-5-yl)carbamate (280 mg, 0.684 mmol) was dissolved in N,N-dimethylformamide (10 mL). Then 60% sodium hydride (55 mg, 1.375 mmol) was added at 0° C., and the mixture was stirred for maintaining at this temperature for 20 minutes, and then iodomethane (65 μL, 1.04 mmol) was added into the mixture. The resulting mixture was continued to stir for 30 minutes and then stirred for 1 hour at room temperature. The reaction mixture was extracted with ethyl acetate (50 mL×2). The combined organic layers were washed with water (40 mL) and saturated brine (40 mL), dried over anhydrous sodium sulfate, and filtered. The filtrate was concentrated in vacuo to remove the solvent. The crude product was purified by silica gel chromatography eluted with dichloromethane/methanol ((v/v)=15/1) to give a white solid (103 mg, 35.57%).

MS (ESI, pos. ion) m/z: 424.5 (M+1);

$^1$H NMR (400 MHz, DMSO-d$_6$) δ (ppm) 9.13 (s, 1H), 8.67 (d, J=3.5 Hz, 2H), 8.55 (d, J=8.1 Hz, 1H), 7.26 (dd, J=12.1, 7.7 Hz, 1H), 7.18 (td, J=7.8, 4.5 Hz, 1H), 6.36 (s, 4H), 5.85 (s, 2H), 3.66 and 3.54 (2 s, 3H), 3.01 (s, 3H).

Example 35

N-(4,6-diamino-2-(7-fluoro-1-(2-fluorobenzyl)-1H-indazol-3-yl)pyrimidin-5-yl)-3-fluoropyrrolidine-1-carboxamide

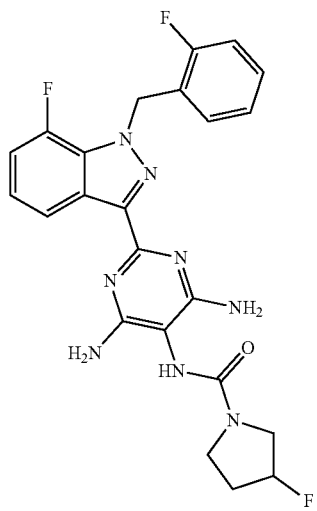 [SMILES: Nc1nc(-c2nn(Cc3ccccc3F)c3c(F)cccc23)nc(N)c1NC(=O)N1CCC(F)C1]

Step 1: phenyl (4,6-diamino-2-(7-fluoro-1-(2-fluorobenzyl)-1H-indazol-3-yl)pyrimidin-5-yl)carbamate 2-(7-Fluoro-1-(2-fluorobenzyl)-1H-indazol-3-yl)pyrimidine-4,5,6-triamine (1.52 g, 4.14 mmol) and pyridine (3.3 mL, 41 mmol) was dissolved in dichloromethane (30.00 mL), then phenyl carbonochloridate (0.78 mL, 6.2 mmol) was added dropwise at 0° C. After the addition, the reaction mixture was stirred at room temperature overnight. To the mixture was added dichloromethane (80 mL), and the resulting mixture was washed with saturated aqueous sodium bicarbonate solution (100 mL), water (100 mL) and saturated brine (100 mL). The aqueous layer was dried over anhydrous sodium sulfate, and filtered. The filtrate was evaporated to remove the solvent and give a yellow solid (1.43 g, 70.9%).

Step 2: N-(4,6-diamino-2-(7-fluoro-1-(2-fluorobenzyl)-1H-indazol-3-yl)pyrimidin-5-yl)-3-fluoropyrrolidine-1-carboxamide Phenyl (4,6-diamino-2-(7-fluoro-1-(2-fluorobenzyl)-1H-indazol-3-yl)pyrimidin-5-yl) carbamate (0.30 g, 0.62 mmol), 3-fluoropyrrolidine hydrochloride (0.15 g, 1.2 mmol) and triethylamine (0.86 mL, 6.2 mmol) were added into N,N-dimethylformamide (15 mL). The mixture was stirred at 50° C. overnight. The reaction mixture cooled to rt and poured into water (50 mL). The resulting mixture was extracted with ethyl acetate (50 mL×2). The combined organic layers were washed with water (50 mL) and saturated brine (50 mL), dried over anhydrous sodium sulfate, and filtered. The filtrate was evaporated to remove the solvent, and the residue was purified by silica gel chromatography eluted with dichloromethane/methanol (v/v=30/1, 0.5% triethylamine) to give a light yellow solid product (0.053 g, 18%).

MS (ESI, pos. ion) m/z: 483.2 (M+1);

$^1$H NMR (400 MHz, DMSO-d$_6$) δ (ppm) 8.57 (d, J=8.0 Hz, 1H), 7.35 (dd, J=13.5, 6.1 Hz, 1H), 7.28-7.08 (m, 5H), 6.98 (t, J=7.3 Hz, 1H), 6.07 (s, 4H), 5.83 (s, 2H), 5.37 (d, J=53.6 Hz, 1H), 3.78-3.46 (m, 4H), 2.22-1.94 (m, 2H);

$^{19}$F NMR (376 MHz, DMSO-d$_6$) δ (ppm) −118.74 (d, J=7.2 Hz), −134.32 (d, J=7.2 Hz), −175.08 (s).

Example 36

N-(4,6-diamino-2-(7-fluoro-1-(2-fluorobenzyl)-1H-indazol-3-yl)pyrimidin-5-yl)-3-hydroxyazetidine-1-carboxamide

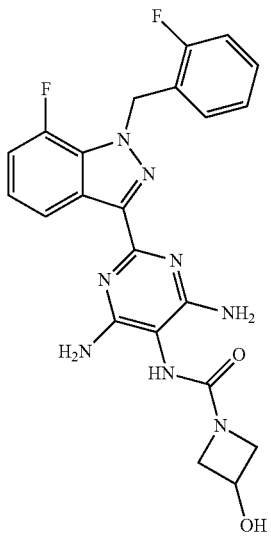 [SMILES: Nc1nc(-c2nn(Cc3ccccc3F)c3c(F)cccc23)nc(N)c1NC(=O)N1CC(O)C1]

Phenyl (4,6-diamino-2-(7-fluoro-1-(2-fluorobenzyl)-1H-indazol-3-yl)pyrimidin-5-yl) carbamate (0.30 g, 0.62 mmol), azetidin-3-ol hydrochloride (0.20 g, 1.8 mmol) and triethylamine (0.86 mL, 6.2 mmol) were added into N,N-dimethylformamide (20 mL). The mixture was stirred at 50° C. overnight. The reaction mixture cooled to rt and poured into water (60 mL). The resulting mixture was extracted with ethyl acetate (50 mL×2). The combined organic layers were washed with water (60 mL) and saturated brine (60 mL), dried over anhydrous sodium sulfate, and filtered. The filtrate was evaporated to remove the solvent, and the residue was purified by silica gel chromatography eluted with dichloromethane/methanol ((v/v)=10/1, 0.5% triethylamine) to give a light yellow solid product (0.052 g, 18%).

MS (ESI, pos. ion) m/z: 467.1 (M+1);

$^1$H NMR (400 MHz, DMSO-d$_6$) δ (ppm) 8.56 (d, J=8.0 Hz, 1H), 7.39-7.31 (m, 1H), 7.30-7.08 (m, 4H), 6.97 (t, J=7.5 Hz, 1H), 6.04 (s, 4H), 5.83 (s, 2H), 5.55 (d, J=6.0 Hz, 1H), 4.46-4.38 (m, 1H), 4.12 (t, J=7.6 Hz, 2H), 3.77-3.70 (m, 2H).

Example 37

N-(4,6-diamino-2-(7-fluoro-1-(2-fluorobenzyl)-1H-indazol-3-yl)pyrimidin-5-yl)-2-hydroxyacetamide

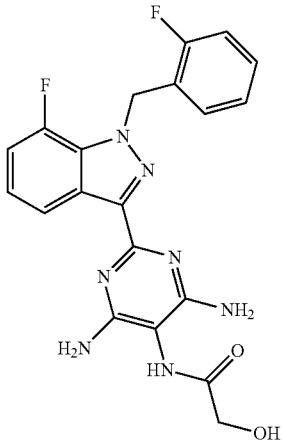 [SMILES: Nc1nc(-c2nn(Cc3ccccc3F)c3c(F)cccc23)nc(N)c1NC(=O)CO]

To N,N-dimethylformamide (10.00 mL) were added 2-(7-fluoro-1-(2-fluorobenzyl)-1H-indazol-3-yl)pyrimidine-4,5,6-triamine (0.20 g, 0.54 mmol) and 2-hydroxyacetic acid (0.05 g, 0.7 mmol). Then triethylamine (0.23 mL, 1.7 mmol) and O-(7-azabenzotriazol-1-yl)-N,N,N',N'-te-tramethyluronium hexafluorophosphate (0.27 g, 0.71 mmol) were added. The mixture was heated to 80° C. and stirred overnight. The reaction mixture cooled to rt and poured into water (60 mL). The resulting mixture was extracted with ethyl acetate (50 mL×2). The combined organic layers were washed with water (60 mL) and saturated brine (60 mL), dried over anhydrous sodium sulfate, and filtered. The filtrate was evaporated to remove the solvent, and the residue was purified by silica gel chromatography eluted with dichloromethane/methanol (v/v=40/1, 0.5% triethylamine) to give a yellow solid product (0.06 g, 30%).

MS (ESI, pos. ion) m/z: 426.3 (M+1).

Example 38

N-(4,6-diamino-2-(7-fluoro-1-(2-fluorobenzyl)-1H-indazol-3-yl)pyrimidin-5-yl)-2-methoxyacetamide

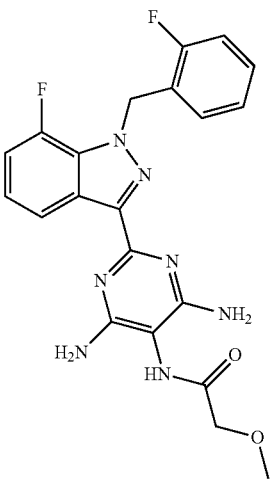 [SMILES: COCC(=O)Nc1c(N)nc(-c2nn(Cc3ccccc3F)c3c(F)cccc23)nc1N]

2-(7-Fluoro-1-(2-fluorobenzyl)-1H-indazol-3-yl)pyrimidine-4,5,6-triamine (0.20 g, 0.54 mmol) and pyridine (0.44 mL, 5.5 mmol) were dissolved in dichloromethane (30.00 mL), then 2-methoxyacetyl chloride (0.055 mL, 0.60 mmol) were added dropwise at 0° C. After the addition, the reaction mixture was stirred at room temperature overnight. The reaction mixture was poured into saturated aqueous sodium bicarbonate solution, and the resulting mixture was extracted with dichloromethane (40 mL×2). The combined organic layers were washed with water (50 mL) and saturated brine (50 mL), dried over anhydrous sodium sulfate, and filtered. The filtrate was evaporated to remove the solvent, and the residue was purified by silica gel chromatography eluted with dichloromethane/methanol ((v/v)=60/1, 0.5% triethylamine) to give a yellow solid product (0.15 g, 63%).

MS (ESI, pos. ion) m/z: 440.1 (M+1);
$^1$H NMR (400 MHz, DMSO-d$_6$) δ (ppm) 8.63 (s, 1H), 8.56 (d, J=8.0 Hz, 1H), 7.35 (dd, J=13.3, 6.6 Hz, 1H), 7.31-7.08 (m, 4H), 6.98 (t, J=7.5 Hz, 1H), 6.14 (s, 4H), 5.83 (s, 2H), 4.04 (s, 2H), 3.39 (s, 3H).

Example 39

N-(4,6-diamino-2-(7-fluoro-1-(2-fluorobenzyl)-1H-indazol-3-yl)pyrimidin-5-yl)cyclopropanecarboxamide

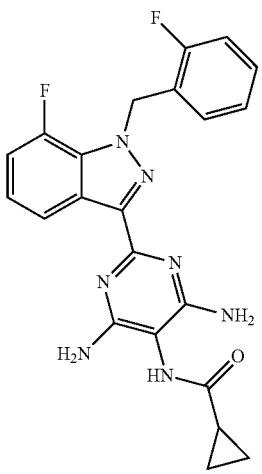 [SMILES: Nc1nc(-c2nn(Cc3ccccc3F)c3c(F)cccc23)nc(N)c1NC(=O)C1CC1]

2-(7-Fluoro-1-(2-fluorobenzyl)-1H-indazol-3-yl)pyrimidine-4,5,6-triamine (0.35 g, 0.95 mmol) and pyridine (1.5 mL, 19 mmol) were dissolved in dichloromethane (25 mL), then cyclopropanecarbonyl chloride (0.26 mL, 2.9 mmol) were added dropwise at 0° C. After the addition, the reaction mixture was stirred at room temperature for 5 hours. To the mixture was added dichloromethane (30 mL), and the resulting mixture was washed with saturated aqueous sodium bicarbonate solution (50 mL), water (50 mL) and saturated brine (50 mL). The organic layer was dried over anhydrous sodium sulfate and filtered. The filtrate was evaporated to remove the solvent, and the residue was purified by silica gel chromatography eluted with dichloromethane/methanol (v/v=30/1, 0.5% triethylamine) to give a light yellow solid product (0.15 g, 36%).

MS (ESI, pos. ion) m/z: 436.1 (M+1);
$^1$H NMR (400 MHz, DMSO-d$_6$) δ (ppm) 9.02 (s, 1H), 8.56 (d, J=8.0 Hz, 1H), 7.40-7.30 (m, 1H), 7.29-7.09 (m, 4H), 6.98 (t, J=7.5 Hz, 1H), 6.01 (s, 4H), 5.83 (s, 2H), 1.88-1.77 (m, 1H), 0.86-0.72 (m, 4H).

Example 40

1-cyclopropyl-3-(4,6-diamino-2-(7-fluoro-1-(2-fluorobenzyl)-1H-indazol-3-yl)pyrimidin-5-yl)urea

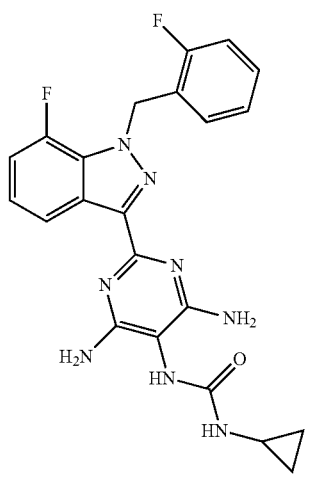 [SMILES: Nc1nc(-c2nn(Cc3ccccc3F)c3c(F)cccc23)nc(N)c1NC(=O)NC1CC1]

Phenyl (4,6-diamino-2-(7-fluoro-1-(2-fluorobenzyl)-1H-indazol-3-yl)pyrimidin-5-yl) carbamate (0.20 g, 0.41 mmol), cyclopropylamine (0.15 g, 2.6 mmol) and triethylamine (0.86 mL, 6.2 mmol) were added into N,N-dimethylformamide (15 mL). The mixture was stirred at 50° C. for 3 hours. The reaction mixture cooled to room temperature and poured into water (50 mL). The resulting mixture was extracted with ethyl acetate (50 mL×2). The combined organic layers were washed with water (50 mL) and saturated brine (50 mL), dried over anhydrous sodium sulfate, and filtered. The filtrate was evaporated to remove the solvent, and the residue was purified by silica gel chromatography eluted with dichloromethane/methanol (v/v=50/1, 0.5% triethylamine) to give a light yellow solid product (0.032 g, 17%).

MS (ESI, pos. ion) m/z: 451.3 (M+1);
$^1$H NMR (400 MHz, DMSO-d$_6$) δ (ppm) 8.56 (d, J=8.0 Hz, 1H), 7.38-7.30 (m, 1H), 7.28-7.09 (m, 4H), 7.02-6.92 (m, 2H), 6.32 (s, 1H), 6.00 (s, 4H), 5.83 (s, 2H), 2.60-2.52 (m, 1H), 0.64-0.55 (m, 2H), 0.50-0.44 (m, 2H).

Example 41

1-(3-((4,6-diamino-2-(7-fluoro-1-(2-fluorobenzyl)-1H-indazol-3-yl)pyrimidin-5-yl)amino)pyrrolidin-1-yl)ethanone

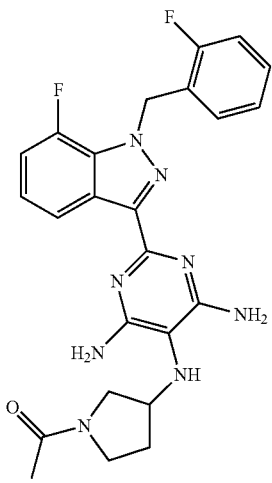 [SMILES: CC(=O)N1CCC(Nc2c(N)nc(-c3nn(Cc4ccccc4F)c4c(F)cccc34)nc2N)C1]

To 20 mL methanol were added 2-(7-fluoro-1-(2-fluorobenzyl)-1H-indazol-3-yl)pyrimidine-4,5,6-triamine (0.20 g, 0.54 mmol), 1-acetylpyrrolidin-3-one (0.10 g, 0.79 mmol) and acetic acid (0.16 mL, 2.8 mmol). The mixture was stirred at room temperature for 1 hour, then to the mixture was added sodium cyanoborohydride (0.17 g, 2.7 mmol). Then the resulting mixture was stirred at rt overnight. The mixture was evaporated to remove the solvent, then to the residue was added ethyl acetate (60 mL), and the resulting mixture was washed with saturated aqueous sodium bicarbonate solution (60 mL), water (60 mL) and saturated brine (60 mL). The aqueous layer was dried over anhydrous sodium sulfate, and filtered. The filtrate was evaporated to remove the solvent, and the residue was purified by silica gel chromatography eluted with dichloromethane/methanol (v/v=100/1, 0.5% triethylamine) to give a light yellow solid product (0.082 g, 31%).

MS (ESI, pos. ion) m/z: 479.2 (M+1);

$^1$H NMR (400 MHz, DMSO-$d_6$) δ (ppm) 8.44 (d, J=8.2 Hz, 1H), 7.27-7.13 (m, 2H), 7.11-7.01 (m, 2H), 6.95 (t, J=7.4 Hz, 1H), 6.81 (t, J=7.3 Hz, 1H), 5.96 (s, 2H), 5.15 (d, J=11.5 Hz, 4H), 4.03-3.36 (m, 6H), 2.17-1.94 (m, 5H).

Example 42

4,6-diamino-2-(7-fluoro-1-(2-fluorobenzyl)-1H-indazol-3-yl)pyrimidine-5-carboxylic acid

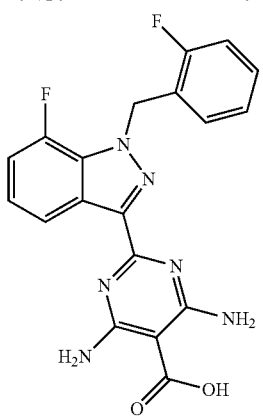 [SMILES: Nc1nc(-c2nn(Cc3ccccc3F)c3c(F)cccc23)nc(N)c1C(=O)O]

Step 1: ethyl 4,6-dihydroxy-2-(7-fluoro-1-(2-fluorobenzyl)-1H-indazol-3-yl)pyrimidine-5-carboxylate 7-Fluoro-1-(2-fluorobenzyl)-1H-indazole-3-carboximidamide (2.00 g, 6.99 mmol) and triethyl methanetricarboxylate (2.43 g, 10.48 mmol) were added into ethanol (30 mL). The mixture was heated to reflux and stirred overnight. The reaction mixture was cooled to room temperature and filtered, and the filter cake was dried in vacuo to give a white solid (2.23 g, 75%).

MS (ESI, pos. ion) m/z: 427.6 (M+1).

Step 2: ethyl 4,6-dichloro-2-(7-fluoro-1-(2-fluorobenzyl)-1H-indazol-3-yl)pyrimidine-5-carboxylate Ethyl 4,6-dihydroxy-2-(7-fluoro-1-(2-fluorobenzyl)-1H-indazol-3-yl)pyrimidine-5-carboxylate (2.00 g, 4.69 mmol) was added into phosphorus oxychloride (10 mL). The mixture was heated to reflux and stirred overnight. The reaction mixture was evaporated to remove the solvent, and to the residue was added dichloromethane (100 mL), and the resulting mixture was washed with saturated aqueous sodium bicarbonate solution (60 mL), water (60 mL) and saturated brine (60 mL), dried over anhydrous sodium sulfate, and filtered. The filtrate was evaporated to remove the solvent, and the residue was purified by silica gel chromatography eluted with dichloromethane/ethyl acetate ((v/v)=100) to give a light yellow solid product (1.37 g, 63%).

Step 3: ethyl 4,6-diamino-2-(7-fluoro-1-(2-fluorobenzyl)-1H-indazol-3-yl)pyrimidine-5-carboxylate Ethyl 4,6-dichloro-2-(7-fluoro-1-(2-fluorobenzyl)-1H-indazol-3-yl)pyrimidine-5-carboxylate (1.00 g, 2.96 mmol) was added into a solution of ammonia in methanol (20 mL, 7 mol/L), then the mixture was stirred for 24 hours at 60° C. in a closed reaction vessel. The mixture was cooled to room temperature and filtered, then the filter cake was washed with water (30 mL) and methanol (30 mL), and dried in vacuo to give a light yellow solid (1.01 g, 81%).

Step 4: 4,6-diamino-2-(7-fluoro-1-(2-fluorobenzyl)-1H-indazol-3-yl)pyrimidine-5-carboxylic acid To a mixed solvent of methanol (15 mL), water (8 mL) and tetrahydrofuran (15 mL) was added ethyl 4,6-diamino-2-(7-fluoro-1-(2-fluorobenzyl)-1H-indazol-3-yl)pyrimidine-5-carboxylate (0.51 g, 1.2 mmol), then to the mixture was added sodium hydroxide solid (0.10 g, 2.5 mmol). The resulting mixture was stirred at room temperature overnight. The solvent was removed, and to the residue was added water (100 mL). The mixture was adjusted with hydrochloric acid (1 mol/L) to pH 5, and filtered. The filter cake was concentrated in vacuo to dry, and then triturated with ethyl acetate (50 mL) to give a light yellow solid (0.32 g, 67%).

MS (ESI, pos. ion) m/z: 397.2 (M+1);

$^1$H NMR (400 MHz, DMSO-$d_6$) δ (ppm) 8.61 (d, J=7.9 Hz, 1H), 7.70 (s, 4H), 7.42-7.33 (m, 1H), 7.32-7.18 (m, 3H), 7.14 (t, J=7.4 Hz, 1H), 6.99 (t, J=7.1 Hz, 1H), 5.86 (s, 2H).

Example 43 methyl (4,6-diamino-2-(7-fluoro-1-((3-fluoropyridin-4-yl)methyl)-1H-indazol-3-yl)pyrimidin-5-yl) carbamate

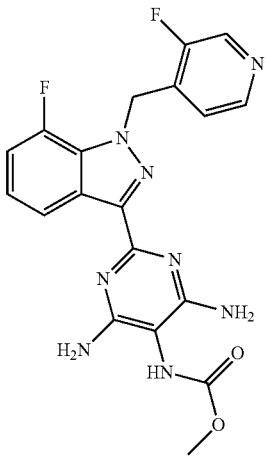 [SMILES: COC(=O)Nc1c(N)nc(-c2nn(Cc3ccncc3F)c3c(F)cccc23)nc1N]

Step 1: 4-(bromomethyl)-3-fluoropyridine hydrobromide (3-Fluoropyridin-4-yl)methanol (500 mg, 3.933 mmol) was dissolved in chloroform (20 mL) at 0° C., then phosphorus tribromide (0.37 mL, 3.9 mmol) was added dropwise. After the addition, the reaction mixture was stirred at room temperature overnight. The mixture was filtered, and the filter cake was washed with chloroform. The filter cake was dried in vacuo to give the crude product as a yellow solid (927 mg, 86.97%), which was used in the next step without further purification.

MS (ESI, pos. ion) m/z: 190.2 (M+1).

Step 2: 7-fluoro-1-((3-fluoropyridin-4-yl)methyl)-3-iodo-1H-indazole

7-Fluoro-3-iodo-1H-indazole (870 mg, 3.32 mmol) was dissolved in N,N-dimethylformamide (60 mL), then 4-(bromomethyl)-3-fluoropyridine hydrobromide (927 mg, 3.421 mmol) and cesium carbonate (2.72 g, 8.35 mmol) were added. The mixture was stirred for 2 hours at room temperature. The reaction mixture was extracted with ethyl acetate (100 mL×2). The combined organic layers were washed with water (50 mL) and saturated brine (50 mL), dried over anhydrous sodium sulfate, and filtered. The filtrate was concentrated in vacuo to give brown oil (940 mg, 76.29%).

MS (ESI, pos. ion) m/z: 371.9 (M+1).

Step 3: 7-fluoro-1-((3-fluoropyridin-4-yl)methyl)-1H-indazole-3-carbonitrile Cuprous cyanide (250 mg, 2.791 mmol) and 7-fluoro-1-((3-fluoropyridin-4-yl)methyl)-3-iodo-1H-indazole (940 mg, 2.533 mmol) was dissolved in dimethylsulfoxide (80 mL) under nitrogen protection. The mixture was stirred at 150° C. for 3.5 hours. The reaction mixture was cooled to room temperature, and quenched with ammonium hydroxide. The reaction mixture was extracted with ethyl ether (100 mL×2). The combined organic layers were washed with water (60 mL) and saturated brine (50 mL), dried over anhydrous sodium sulfate, and filtered. The filtrate with concentrated in vacuo to remove the solvent, and the residue was purified by silica-gel column chromatography (petroleum ether/ethyl acetate (v/v)=4/1) to give a white solid (255 mg, 37.26%).

MS (ESI, pos. ion) m/z: 271.4 (M+1).

Step 4: 7-fluoro-1-((3-fluoropyridin-4-yl)methyl)-1H-indazole-3-carboximidamide To a 250 mL two-neck flask was added sodium methoxide (3.26 g, 60.3 mmol), then to the mixture were added methanol (110 mL) and 7-fluoro-1-((3-fluoropyridin-4-yl)methyl)-1H-indazole-3-carbonitrile (4.08 g, 15.1 mmol), and the mixture was stirred for 2 hours at room temperature. Then to the mixture were added ammonium chloride (1.05 g, 19.6 mmol) and glacial acetic acid (3.5 mL, 61 mmol). The reaction mixture was refluxed overnight. The mixture was cooled to room temperature, and concentrated by rotary evaporation to remove the solvent. To the residue was added water (120 mL). The resulting mixture was adjusted with aqeous sodium hydroxide solution (2 mol/L) to pH 10. The mixture was filtered, and the filter cake was washed with water, dried in vacuo to give an offwhite solid (4.24 g, 97.7%).

MS (ESI, pos. ion) m/z: 288.1 (M+1).

Step 5: 2-(7-fluoro-1-((3-fluoropyridin-4-yl)methyl)-1H-indazol-3-yl)-5-(phenyldiazenyl)pyrimidine-4,6-diamine 7-Fluoro-1-((3-fluoropyridin-4-yl)methyl)-1H-indazole-3-carboximidamide (2.0 g, 7.0 mmol) was dissolved in N,N-dimethylformamide (80 mL), then triethylamine (3.5 mL, 25 mmol) was added into the mixture. The resulting mixture was heated to 85° C. under nitrogen protection, and to the mixture was added benzeneazomalononitrile (2.4 g, 14 mmol). After the addition, the mixture was heated to 100° C. and stirred for 5 hours. The reaction mixture was cooled to room temperature and used directly in the next step without further purification.

MS (ESI, pos. ion) m/z: 458.1 (M+1).

Step 6: 2-(7-fluoro-1-((3-fluoropyridin-4-yl)methyl)-1H-indazol-3-yl)pyrimidine-4,5,6-triamine To the reaction mixture of the previous step was added 10% Pd/C (250 mg). The mixture was stirred at rt overnight in hydrogen atmosphere. The mixture was filtered through a celite pad, and the filter cake was washed with methanol, then the filtrates were collected, and concentrated in vacuo to remove the solvent. The crude product was purified by silica gel chromatography eluted with dichloromethane/methanol (v/v=10/1) to give a brown solid (1.15 g, 46%).

MS (ESI, pos. ion) m/z: 369.5 (M+1).

Step 7: methyl (4,6-diamino-2-(7-fluoro-1-((3-fluoropyridin-4-yl)methyl)-1H-indazol-3-yl)pyrimidin-5-yl)carbamate 2-(7-Fluoro-1-((3-fluoropyridin-4-yl)methyl)-1H-indazol-3-yl)pyrimidine-4,5,6-triamine (400 mg, 1.09 mmol) was dissolved in pyridine (5 mL, 62.1 mmol), then methylchloroformate (0.25 mL, 3.20 mmol) were added dropwise at 0° C. The reaction mixture was continued to stir for 0.5 hour at 0° C., then heated to room temperature and stirred for 3 hours. The resulting mixture was concentrated in vacuo to remove the solvent, and the residue was purified by silica gel chromatograph (methanol/ethyl acetate (v/v)=1/15) to give the title compound as a white solid (150 mg, 32.39%).

MS (ESI, pos. ion) m/z: 427.6 (M+1);

$^1$H NMR (400 MHz, DMSO-d$_6$) δ (ppm) 8.63 (s, 1H), 8.45 (d, J=7.1 Hz, 1H), 8.36 and 8.06 (2 br s, 2H) 7.80 (s, 4H), 7.41 (d, J=11.1 Hz, 2H), 7.09 (s, 1H), 6.03 (s, 2H), 3.66 (s, 3H).

Example 44

4,6-diamino-N-cyclopropyl-2-(7-fluoro-1-(2-fluorobenzyl)-1H-indazol-3-yl) pyrimidine-5-carboxamide

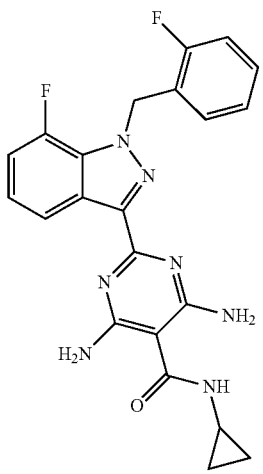 [SMILES: Nc1nc(-c2nn(Cc3ccccc3F)c3c(F)cccc23)nc(N)c1C(=O)NC1CC1]

To N,N-dimethylformamide (8 mL) were added 4,6-diamino-2-(7-fluoro-1-(2-fluorobenzyl)-1H-indazol-3-yl) pyrimidin-5-acetic acid (0.060 g, 0.15 mmol) and cyclopropylamine (0.026 mL, 0.38 mmol). Then O-(7-azabenzotriazol-1-yl)-N,N,N',N'-te-tramethyluronium hexafluorophosphate (0.086 g, 0.23 mmol) and triethylamine (0.063 mL, 0.45 mmol) were added at 0° C. After addition, the mixture was stirred at 50° C. overnight. The reaction mixture was cooled to room temperature, and to the mixture was added water (50 mL), and the resulting mixture was extracted with ethyl acetate (40 mL×2). The combined organic layers were washed with water (50 mL) and saturated brine (50 mL), dried over anhydrous sodium sulfate and filtered. The filtrate was concentrated on a rotary evaporator and the residue was purified by silica gel chromatograph (dichloromethane/methanol (v/v)=100/1) to give a light yellow solid (0.020 g, 30%).

MS (ESI, pos. ion) m/z: 436.1 (M+1);

$^1$H NMR (400 MHz, DMSO-d$_6$) δ (ppm) 8.58 (d, J=8.0 Hz, 1H), 8.08 (d, J=3.4 Hz, 1H), 7.36 (dd, J=13.7, 6.2 Hz, 1H), 7.30-7.09 (m, 4H), 6.98 (t, J=7.3 Hz, 1H), 6.65 (s, 4H), 5.84 (s, 2H), 2.80-2.72 (m, 1H), 0.66-0.58 (m, 4H).

Example 45

4-amino-2-(7-fluoro-1-(2-fluorobenzyl)-1H-indazol-3-yl)-N,N-dimethyl pyrimidine-5-carboxamide

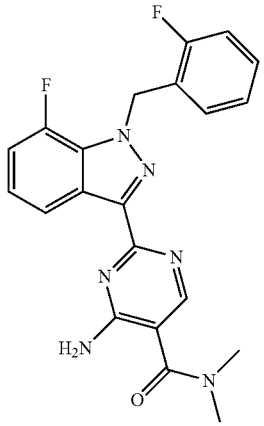 [SMILES: CN(C)C(=O)c1cnc(-c2nn(Cc3ccccc3F)c3c(F)cccc23)nc1N]

To N,N-dimethylformamide (10 mL) were added 4-amino-2-(7-fluoro-1-(2-fluorobenzyl)-1H-indazol-3-yl) pyrimidine-5-carboxylic acid (0.10 g, 0.26 mmol) and a solution of dimethylamine in tetrahydrofuran (0.26 mL, 0.52 mmol, 2 mol/L). Then O-(7-azabenzotriazol-1-yl)-N,N,N',N'-te-tramethyluronium hexafluorophosphate (0.12 g, 0.32 mmol) and triethylamine (0.11 mL, 0.79 mmol) were added at 0° C. After addition, the mixture was stirred at room temperature overnight. To the reaction mixture was added water (50 mL). The resulting mixture was extracted with ethyl acetate (40 mL×2). The combined organic layers were washed with water (50 mL) and saturated brine (50 mL), dried over anhydrous sodium sulfate, and filtered. The filtrate was concentrated on a rotary evaporator and the residue was purified by silica gel chromatography eluted with dichloromethane/methanol (v/v=100/1) to give a white solid product (0.078 g, 73%).

MS (ESI, pos. ion) m/z: 409.2 (M+1);

$^1$H NMR (400 MHz, DMSO-d$_6$) δ (ppm) 8.49 (d, J=7.9 Hz, 1H), 8.28 (s, 1H), 7.41-7.11 (m, 7H), 7.06 (t, J=7.3 Hz, 1H), 5.87 (s, 2H), 2.98 (s, 6H).

Example 46

(4-amino-2-(7-fluoro-1-(2-fluorobenzyl)-1H-indazol-3-yl)pyrimidin-5-yl) (morpholino)methanone

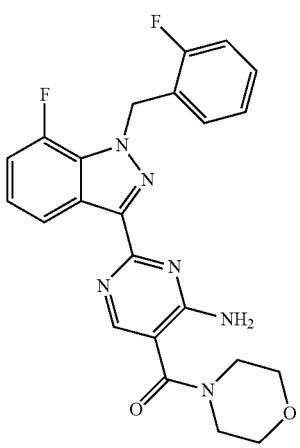 [SMILES: Nc1nc(-c2nn(Cc3ccccc3F)c3c(F)cccc23)ncc1C(=O)N1CCOCC1]

To N,N-dimethylformamide (10 mL) were added 4-amino-2-(7-fluoro-1-(2-fluorobenzyl)-1H-indazol-3-yl)pyrimidine-5-carboxylic acid (0.10 g, 0.26 mmol) and morpholine (0.027 mL, 0.31 mmol). Then O-(7-azabenzotriazol-1-yl)-N,N,N',N'-te-tramethyluronium hexafluorophosphate (0.12 g, 0.32 mmol) and triethylamine (0.11 mL, 0.79 mmol) were added at 0° C. After addition, the mixture was stirred at room temperature overnight. To the reaction mixture was added water (50 mL) to quench the reaction. The resulting mixture was extracted with ethyl acetate (30 mL×2). The combined organic layers were washed with water (50 mL) and saturated brine (50 mL), dried over anhydrous sodium sulfate, and filtered. The filtrate was concentrated on a rotary evaporator and the residue was purified by silica gel chromatography eluted with dichloromethane/methanol (v/v=50/1) to give a white solid (0.11 g, 93%).

MS (ESI, pos. ion) m/z: 451.1 (M+1);

$^1$H NMR (400 MHz, DMSO-d$_6$) δ (ppm) 8.49 (d, J=7.9 Hz, 1H), 8.28 (s, 1H), 7.45-7.18 (m, 6H), 7.14 (t, J=7.4 Hz, 1H), 7.05 (t, J=7.3 Hz, 1H), 5.87 (s, 2H), 3.68-3.58 (m, 4H), 3.56-3.46 (m, 4H).

Example 47

(4-amino-2-(7-fluoro-1-(2-fluorobenzyl)-1H-indazol-3-yl)pyrimidin-5-yl) (pyrrolidin-1-yl)methanone

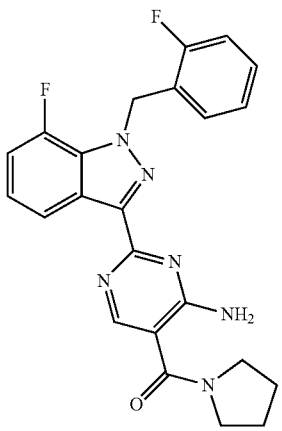 [SMILES: Nc1nc(-c2nn(Cc3ccccc3F)c3c(F)cccc23)ncc1C(=O)N1CCCC1]

To N,N-dimethylformamide (10 mL) were added 4-amino-2-(7-fluoro-1-(2-fluorobenzyl)-1H-indazol-3-yl)pyrimidine-5-carboxylic acid (0.10 g, 0.26 mmol) and pyrrolidine (0.026 mL, 0.32 mmol). Then O-(7-azabenzotriazol-1-yl)-N,N,N',N'-te-tramethyluronium hexafluorophosphate (0.12 g, 0.32 mmol) and triethylamine (0.11 mL, 0.79 mmol) were added at 0° C. After addition, the mixture was stirred at room temperature overnight. To the reaction mixture was added water (50 mL) to quench the reaction. The resulting mixture was extracted with ethyl acetate (30 mL×2). The combined organic layers were washed with water (50 mL) and saturated brine (50 mL), dried over anhydrous sodium sulfate, and filtered. The filtrate was concentrated on a rotary evaporator and the residue was purified by silica gel chromatography eluted with dichloromethane/ethyl acetate ((v/v)=200/1, 0.5% triethylamine) to give a white solid (0.026 g, 23%).

MS (ESI, pos. ion) m/z: 435.3 (M+1);

$^1$H NMR (400 MHz, DMSO-d$_6$) δ (ppm) 8.48 (d, J=7.8 Hz, 1H), 8.40 (s, 1H), 7.45-7.17 (m, 6H), 7.14 (t, J=7.5 Hz, 1H), 7.05 (t, J=7.1 Hz, 1H), 5.86 (s, 2H), 3.50-3.45 (m, 4H), 1.92-1.76 (m, 4H).

Example 48

2-(4-amino-2-(7-fluoro-1-(2-fluorobenzyl)-1H-indazol-3-yl)pyrimidine-5-carboxamido)acetic acid

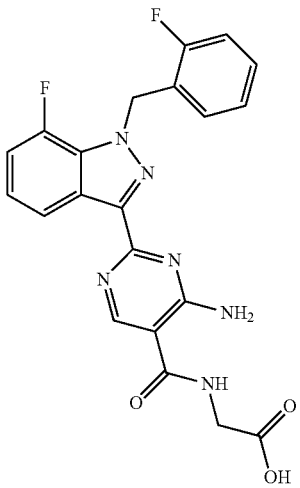 [SMILES: Nc1nc(-c2nn(Cc3ccccc3F)c3c(F)cccc23)ncc1C(=O)NCC(=O)O]

Step 1: benzyl 2-(4-amino-2-(7-fluoro-1-(2-fluorobenzyl)-1H-indazol-3-yl)pyrimidine-5-carboxamido)acetate To N,N-dimethylformamide (10 mL) were added 4-amino-2-(7-fluoro-1-(2-fluorobenzyl)-1H-indazol-3-yl)pyrimidine-5-carboxylic acid (0.050 g, 0.13 mmol) and benzyl glycinate hydrochloride (0.11 g, 0.55 mmol). Then O-(7-azabenzotriazol-1-yl)-N,N,N',N'-te-tramethyluronium hexafluorophosphate (0.075 g, 0.20 mmol) and triethylamine (0.18 mL, 1.3 mmol) were added. After addition, the mixture was stirred at room temperature overnight. The reaction mixture was poured into water. The resulting mixture was extracted with ethyl acetate (20 mL×2). The combined organic layers were washed with water (30 mL) and saturated brine (30 mL), dried over anhydrous sodium sulfate, and filtered. The filtrate was evaporated to remove the solvent, and the residue was purified by silica gel chromatography eluted with dichloromethane/methanol ((v/v)=200/1, 0.5% triethylamine) to give a white solid (0.065 g, 94%).

MS (ESI, pos. ion) m/z: 529.2 (M+1).

Step 2: 2-(4-amino-2-(7-fluoro-1-(2-fluorobenzyl)-1H-indazol-3-yl)pyrimidine-5-carboxamido)acetic acid Benzyl 2-(4-amino-2-(7-fluoro-1-(2-fluorobenzyl)-1H-indazol-3-yl)pyrimidine-5-carboxamido)acetate (0.065 g, 0.12 mmol) and 10% Pd/C (0.050 g) were added into methanol (10 mL), and the mixture was reacted overnight in hydrogen atmosphere. The mixture was filtered. The filtrate was evaporated to remove the solvent, and the residue was purified by silica gel chromatography eluted with dichloromethane/methanol (v/v=10/1, 0.5% triethylamine) to give a white solid (0.035 g, 65%).

MS (ESI, pos. ion) m/z: 439.1 (M+1);
$^1$H NMR (400 MHz, DMSO-$d_6$) δ (ppm) 8.99 (t, J=5.7 Hz, 1H), 8.83 (s, 1H), 8.51 (d, J=7.7 Hz, 1H), 8.02 (s, 2H), 7.40-7.19 (m, 4H), 7.15 (t, J=7.4 Hz, 1H), 7.05 (t, J=7.2 Hz, 1H), 5.88 (s, 2H), 3.92 (d, J=5.6 Hz, 2H).

Example 49

4-amino-2-(7-fluoro-1-(2-fluorobenzyl)-1H-indazol-3-yl)-N-(2-hydroxyethyl)pyrimidine-5-carboxamide

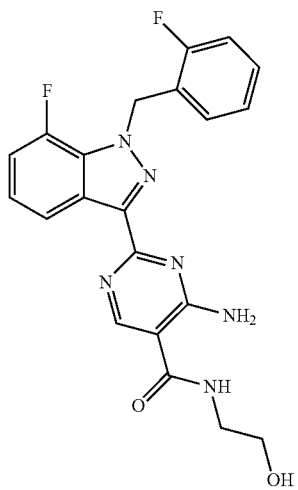 [SMILES: Nc1nc(-c2nn(Cc3ccccc3F)c3c(F)cccc23)ncc1C(=O)NCCO]

Step 1: 4-amino-2-(7-fluoro-1-(2-fluorobenzyl)-1H-indazol-3-yl)pyrimidine-5-carbonyl chloride 4-Amino-2-(7-fluoro-1-(2-fluorobenzyl)-1H-indazol-3-yl)pyrimidine-5-carboxylic acid (0.10 g, 0.26 mmol) and thionyl chloride (2 mL) were added into dichloromethane (10 mL), then the mixture was refluxed overnight. The mixture was evaporated to remove the solvent to give a light yellow solid (0.10 g, 95%).

Step 2: 4-amino-2-(7-fluoro-1-(2-fluorobenzyl)-1H-indazol-3-yl)-N-(2-hydroxyethyl) pyrimidine-5-carboxamide Ethanolamine (0.076 g, 1.2 mmol) and triethylamine (0.10 mL, 0.72 mmol) were added into dichloromethane (10 mL). Then a solution of 4-amino-2-(7-fluoro-1-(2-fluorobenzyl)-1H-indazol-3-yl)pyrimidine-5-carbonyl chloride (0.10 g, 0.25 mmol) in dichloromethane (10 mL) was added under an ice-bath condition. After addition, the mixture was heated to room temperature and stirred for 4 hours. The reaction mixture was poured into water, and the resulting mixture was extracted with dichloromethane (30 mL×2). The combined organic layers were washed with water (50 mL) and saturated brine (50 mL), dried over anhydrous sodium sulfate. The mixture was filtered. The filtrate was evaporated to remove the solvent, and the residue was purified by silica gel chromatography eluted with dichloromethane/methanol ((v/v)=100/1, 0.5% triethylamine) to give a white solid (0.085 g, 80%).

MS (ESI, pos. ion) m/z: 425.1 (M+1);
$^1$H NMR (400 MHz, DMSO-$d_6$) δ (ppm) 8.81 (s, 1H), 8.63 (t, J=5.4 Hz, 1H), 8.50 (d, J=7.8 Hz, 1H), 8.02 (s, 2H), 7.41-7.21 (m, 4H), 7.15 (t, J=7.5 Hz, 1H), 7.04 (t, J=7.3 Hz, 1H), 5.89 (s, 2H), 4.77 (t, J=5.6 Hz, 1H), 3.54 (q, J=6.0 Hz, 2H), 3.38-3.32 (m, 2H).

Example 50

(4-amino-2-(7-fluoro-1-(2-fluorobenzyl)-1H-indazol-3-yl)pyrimidin-5-yl) (piperazin-1-yl)methanone

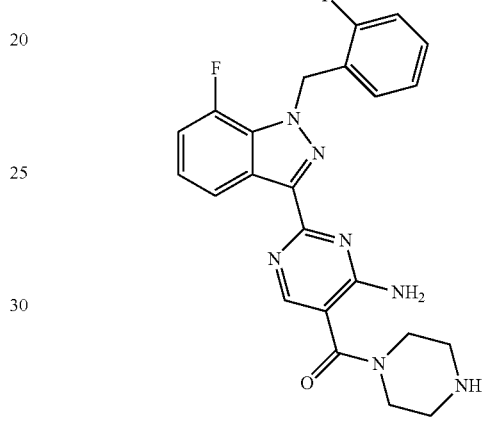

To N,N-dimethylformamide (10 mL) were added 4-amino-2-(7-fluoro-1-(2-fluorobenzyl)-1H-indazol-3-yl) pyrimidine-5-carboxylic acid (0.080 g, 0.21 mmol) and piperazine (0.090 g, 1.0 mmol). Then O-(7-azabenzotriazol-1-yl)-N,N,N',N'-te-tramethyluronium hexafluorophosphate (0.15 g, 0.39 mmol) was added. After addition, the mixture was stirred at room temperature overnight. The reaction mixture was poured into water (50 mL). The resulting mixture was extracted with ethyl acetate (30 mL×2). The combined organic layers were washed with water (50 mL) and saturated brine (50 mL), dried over anhydrous sodium sulfate, and filtered. The filtrate was evaporated to remove the solvent, and the residue was purified by silica gel chromatography eluted with dichloromethane/methanol (v/v=50/1, 0.5% triethylamine) to give a white solid (0.079 g, 84%).

MS (ESI, pos. ion) m/z: 450.1 (M+1);
$^1$H NMR (400 MHz, DMSO-$d_6$) δ (ppm) 8.50 (d, J=7.9 Hz, 1H), 8.25 (s, 1H), 7.44-6.98 (m, 8H), 5.87 (s, 2H), 3.56-3.35 (m, 5H), 2.78-2.64 (m, 4H).

Example 51

(4-amino-2-(7-fluoro-1-(2-fluorobenzyl)-1H-indazol-3-yl)pyrimidin-5-yl) (1,1-dioxidothiomorpholino)methanone

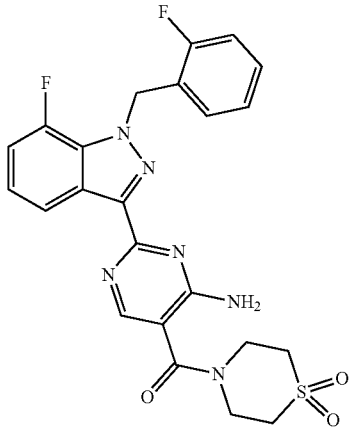 [SMILES: Nc1nc(-c2nn(Cc3ccccc3F)c3c(F)cccc23)ncc1C(=O)N1CCS(=O)(=O)CC1]

To N,N-dimethylformamide (10 mL) were added 4-amino-2-(7-fluoro-1-(2-fluorobenzyl)-1H-indazol-3-yl)pyrimidine-5-carboxylic acid (0.10 g, 0.26 mmol) and thiomorpholine 1,1-dioxide (0.046 g, 0.34 mmol). Then O-(7-azabenzotriazol-1-yl)-N,N,N',N'-te-tramethyluronium hexafluorophosphate (0.12 g, 0.32 mmol) and triethylamine (0.11 mL, 0.79 mmol) were added. After the addition, the mixture was stirred at rt overnight. To the reaction mixture was added ethyl acetate (60 mL), and the mixture was poured into water (60 mL) and saturated brine (60 mL). The organic layer was dried over anhydrous sodium sulfate, and filtered. The filtrate was evaporated to remove the solvent, and the residue was purified by silica gel chromatography eluted with dichloromethane/methanol ((v/v)=100/1, 0.5% triethylamine) to give a white solid (0.096 g, 73%).

MS (ESI, pos. ion) m/z: 499.0 (M+1);
$^1$H NMR (400 MHz, DMSO-d$_6$) δ (ppm) 8.49 (d, J=7.9 Hz, 1H), 8.33 (s, 1H), 7.72-6.97 (m, 8H), 5.87 (s, 2H), 3.89 (s, 4H), 3.29 (s, 4H).

Example 52

(4-amino-2-(7-fluoro-1-(2-fluorobenzyl)-1H-indazol-3-yl)pyrimidin-5-yl) (4,4-difluoropiperidin-1-yl)methanone

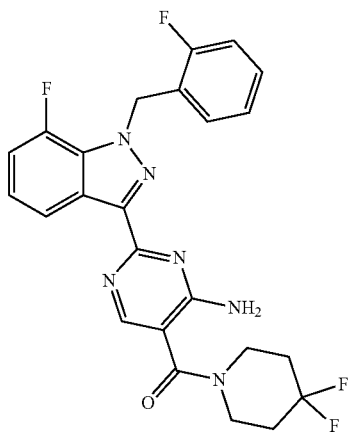 [SMILES: Nc1nc(-c2nn(Cc3ccccc3F)c3c(F)cccc23)ncc1C(=O)N1CCC(F)(F)CC1]

To N,N-dimethylformamide (10 mL) were added 4-amino-2-(7-fluoro-1-(2-fluorobenzyl)-1H-indazol-3-yl)pyrimidine-5-carboxylic acid (0.10 g, 0.26 mmol) and 4,4-difluoropiperidine hydrochloride (0.050 g, 0.32 mmol). Then O-(7-azabenzotriazol-1-yl)-N,N,N',N'-te-tramethyluronium hexafluorophosphate (0.12 g, 0.32 mmol) and triethylamine (0.15 mL, 1.1 mmol) were added under an ice-bath condition. After the addition, the mixture was stirred at room temperature overnight. To the reaction mixture was added ethyl acetate (60 mL), and the mixture was washed with water (60 mL) and saturated brine (60 mL). The organic layer was dried over anhydrous sodium sulfate, and filtered. The filtrate was evaporated to remove the solvent, and the residue was purified by silica gel chromatography eluted with dichloromethane/methanol (v/v=200/1, 0.5% triethylamine) to give a white solid (0.11 g, 87%).

MS (ESI, pos. ion) m/z: 485.3 (M+1);
$^1$H NMR (400 MHz, DMSO-d$_6$) δ (ppm) 8.49 (d, J=7.9 Hz, 1H), 8.30 (s, 1H), 7.46-6.97 (m, 8H), 5.87 (s, 2H), 3.68-3.52 (m, 4H), 2.16-2.00 (m, 4H);
$^{19}$F NMR (376 MHz, DMSO-d$_6$) δ (ppm) −95.93 (s), −118.61 (d, J=7.5 Hz), −133.67 (d, J=7.5 Hz).

Example 53

(4-amino-2-(7-fluoro-1-(2-fluorobenzyl)-1H-indazol-3-yl)pyrimidin-5-yl) (4-methylpiperazin-1-yl)methanone

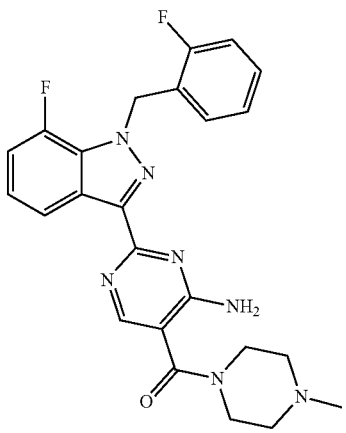 [SMILES: CN1CCN(C(=O)c2cnc(-c3nn(Cc4ccccc4F)c4c(F)cccc34)nc2N)CC1]

To N,N-dimethylformamide (10 mL) were added 4-amino-2-(7-fluoro-1-(2-fluorobenzyl)-1H-indazol-3-yl)pyrimidine-5-carboxylic acid (0.10 g, 0.26 mmol) and 1-methylpiperazine (0.038 mL, 0.34 mmol). Then O-(7-azabenzotriazol-1-yl)-N,N,N',N'-te-tramethyluronium hexafluorophosphate (0.12 g, 0.32 mmol) and triethylamine (0.11 mL, 0.79 mmol) were added under an ice-bath condition. After the addition, the mixture was stirred at room temperature overnight. To the reaction mixture was added ethyl acetate (60 mL), and the mixture was washed with water (60 mL) and saturated brine (60 mL) in turn. The organic layer was dried over anhydrous sodium sulfate, and filtered. The filtrate was evaporated to remove the solvent, and the residue was purified by silica gel chromatography eluted with dichloromethane/methanol (v/v=100/1, 0.5% triethylamine) to give a white solid (0.086 g, 71%).

MS (ESI, pos. ion) m/z: 464.1 (M+1);

¹H NMR (400 MHz, DMSO-d₆) δ (ppm) 8.49 (d, J=8.1 Hz, 1H), 8.25 (s, 1H), 7.60-6.90 (m, 8H), 5.87 (s, 2H), 3.50 (s, 4H), 2.35 (s, 4H), 2.20 (s, 3H).

Example 54

(4-amino-2-(7-fluoro-1-(2-fluorobenzyl)-1H-indazol-3-yl)pyrimidin-5-yl) (3-hydroxyazetidin-1-yl) methanone

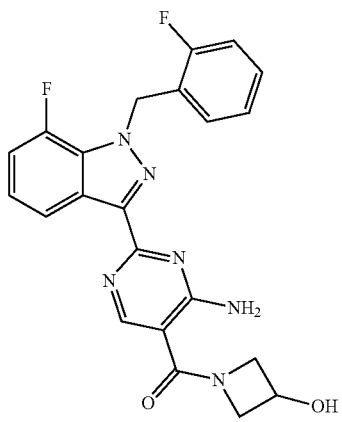 [SMILES: Nc1nc(-c2nn(Cc3ccccc3F)c3c(F)cccc23)ncc1C(=O)N1CC(O)C1]

To N,N-dimethylformamide (6 mL) were added 4-amino-2-(7-fluoro-1-(2-fluorobenzyl)-1H-indazol-3-yl)pyrimidine-5-carboxylic acid (0.050 g, 0.13 mmol) and azetidin-3-ol hydrochloride (0.029 g, 0.26 mmol). Then O-(7-azabenzotriazol-1-yl)-N,N,N',N'-tetramethyluronium hexafluorophosphate (0.075 g, 0.20 mmol) and triethylamine (0.091 mL, 0.65 mmol) were added. The mixture was stirred at rt overnight. The reaction mixture was poured into water. The resulting mixture was extracted with ethyl acetate (30 mL×2). The combined organic layers were washed with water (50 mL) and saturated brine (50 mL), dried over anhydrous sodium sulfate, and filtered. The filtrate was evaporated to remove the solvent, and the residue was purified by silica gel chromatography eluted with dichloromethane/methanol (v/v=30/1) to give a white solid (0.017 g, 30%).

MS (ESI, pos. ion) m/z: 437.3 (M+1);

¹H NMR (400 MHz, DMSO-d₆) δ (ppm) 8.53-8.46 (m, 2H), 7.79 (s, 2H), 7.42-7.20 (m, 4H), 7.15 (t, J=7.5 Hz, 1H), 7.07 (t, J=7.1 Hz, 1H), 5.88 (s, 2H), 5.80 (d, J=5.9 Hz, 1H), 4.61-4.46 (m, 2H), 4.38-4.22 (m, 1H), 4.19-4.00 (m, 1H), 3.92-3.73 (m, 1H).

Example 55

2-(7-fluoro-1-(2-fluorobenzyl)-1H-indazol-3-yl)pyrimidine-5-carboxylic acid

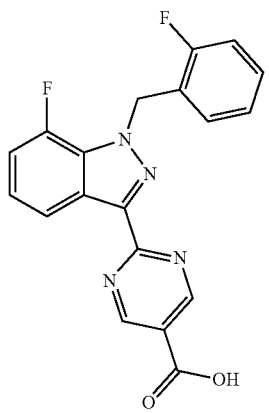 [SMILES: O=C(O)c1cnc(-c2nn(Cc3ccccc3F)c3c(F)cccc23)nc1]

Step 1: ethyl 2-(7-fluoro-1-(2-fluorobenzyl)-1H-indazol-3-yl)pyrimidine-5-carboxylate 7-Fluoro-1-(2-fluorobenzyl)-1H-indazole-3-carboximidamide (1.20 g, 4.19 mmol) and ethyl 2-formyl-3-oxopropanoate (0.73 g, 5.1 mmol) were added into ethanol (30 mL). The mixture was heated to reflux and stirred for 6 hours. The mixture was cooled to rt, and evaporated to remove the solvent, and the residue was purified by silica gel chromatography eluted with petroleum ether/ethyl acetate (v/v=10/1) to give a light yellow solid product (0.65 g, 39%).

MS (ESI, pos. ion) m/z: 395.2 (M+1).

Step 2: 2-(7-fluoro-1-(2-fluorobenzyl)-1H-indazol-3-yl)pyrimidine-5-carboxylic acid To a mixed solvent of water (10 mL), tetrahydrofuran (10 mL) and methanol (10 mL) was added ethyl 2-(7-fluoro-1-(2-fluorobenzyl)-1H-indazol-3-yl)pyrimidine-5-carboxylate (0.71 g, 1.8 mmol), then to the mixture was added sodium hydroxide solid (0.11 g, 2.8 mmol). The resulting mixture was stirred at room temperature for 3 hours. The mixture was evaporated to remove the solvent, and to the residue was added water (100 mL). The mixture was washed with dichloromethane (60 mL), and the aqueous layer was adjusted with hydrochloric acid (1 mol/L) to pH 4, then filtered by suction. The filter cake was washed with water, and the filter cake was dried in vacuo to give a light yellow solid (0.43 g, 65%).

MS (ESI, pos. ion) m/z: 367.2 (M+1);

¹H NMR (400 MHz, DMSO-d₆) δ (ppm) 9.28 (s, 2H), 8.43 (d, J=7.5 Hz, 1H), 7.44-7.28 (m, 3H), 7.29-7.21 (m, 1H), 7.21-7.08 (m, 2H), 5.93 (s, 2H).

Example 56

2-(7-fluoro-1-(2-fluorobenzyl)-1H-indazol-3-yl)-N-methylpyrimidine-5-carboxamide

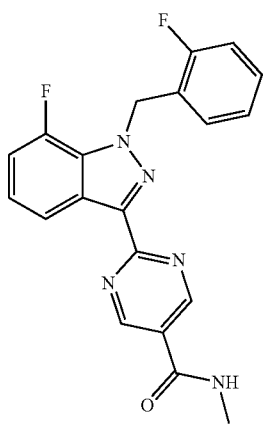 [SMILES: CNC(=O)c1cnc(-c2nn(Cc3ccccc3F)c3c(F)cccc23)nc1]

Step 1: 2-(7-fluoro-1-(2-fluorobenzyl)-1H-indazol-3-yl)pyrimidine-5-carbonyl chloride 2-(7-Fluoro-1-(2-fluorobenzyl)-1H-indazol-3-yl)pyrimidine-5-carboxylic acid (0.10 g, 0.27 mmol) was added into dichloromethane (10 mL), then a drop of N,N-dimethylformamide and oxalyl chloride (0.33 mL) were added at 0° C., then the mixture was stirred at room temperature overnight. The mixture was evaporated to remove the solvent and give a light yellow solid (0.11 g, 100%).

Step 2: 2-(7-fluoro-1-(2-fluorobenzyl)-1H-indazol-3-yl)-N-methylpyrimidine-5-carboxamide A solution of methylamine in tetrahydrofuran (0.34 mL, 0.68 mmol, 2 mol/L) and N,N-diisopropylethylamine (0.17 mL, 1.0 mmol) were added into dichloromethane (10 mL). Then a solution of 2-(7-fluoro-1-(2-fluorobenzyl)-1H-indazol-3-yl)pyrimidine-5-carbonyl chloride (0.13 g, 0.34 mmol) in dichloromethane (10 mL) was added at 0° C. After addition, the mixture was heated to room temperature and stirred overnight. To the mixture was added dichloromethane (100 mL), and the resulting mixture was washed with saturated aqueous sodium bicarbonate solution (80 mL), water (80 mL) and saturated brine (80 mL). The aqueous layer was dried over anhydrous sodium sulfate, and filtered. The filtrate was evaporated to remove the solvent, and the residue was purified by silica gel chromatography eluted with dichloromethane/methanol ((v/v)=200/1, 0.5% triethylamine) to give a light yellow solid product (0.075 g, 59%).

MS (ESI, pos. ion) m/z: 380.1 (M+1);

$^1$H NMR (400 MHz, DMSO-d$_6$) δ (ppm) 9.29 (s, 2H), 8.86 (d, J=4.4 Hz, 1H), 8.41 (d, J=8.1 Hz, 1H), 7.42-7.29 (m, 3H), 7.28-7.21 (m, 1H), 7.19-7.09 (m, 2H), 5.93 (s, 2H), 2.86 (d, J=4.5 Hz, 3H).

Example 57

N-cyclopropyl-2-(7-fluoro-1-(2-fluorobenzyl)-1H-indazol-3-yl)pyrimidine-5-carboxamide

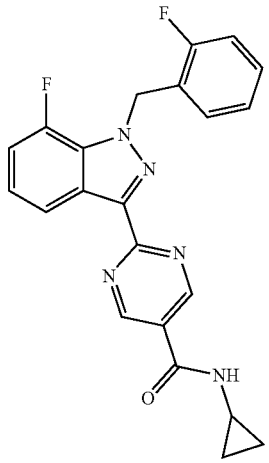 [SMILES: O=C(NC1CC1)c1cnc(-c2nn(Cc3ccccc3F)c3c(F)cccc23)nc1]

Cyclopropylamine (0.040 g, 0.70 mmol) and N,N-diisopropylethylamine (0.14 mL, 0.85 mmol) were added into dichloromethane (10 mL). Then a solution of 2-(7-fluoro-1-(2-fluorobenzyl)-1H-indazol-3-yl)pyrimidine-5-carbonyl chloride (0.11 g, 0.29 mmol) in dichloromethane (10 mL) was added at 0° C. After addition, the mixture was heated to room temperature and stirred overnight. To the reaction mixture was added dichloromethane (100 mL), and the resulting mixture was washed with saturated aqueous sodium bicarbonate (80 mL), water (80 mL) and saturated brine (80 mL), dried over anhydrous sodium sulfate and filtered. The filtrate was concentrated on a rotary evaporator and the residue was purified by silica gel chromatograph (dichloromethane/methanol (v/v)=200/1, 0.5% triethylamine) to give a light yellow solid (0.065 g, 56%).

MS (ESI, pos. ion) m/z: 406.2 (M+1);

$^1$H NMR (400 MHz, DMSO-d$_6$) δ (ppm) 9.26 (s, 2H), 8.86 (d, J=3.9 Hz, 1H), 8.45-8.37 (m, 1H), 7.42-7.29 (m, 3H), 7.29-7.21 (m, 1H), 7.20-7.09 (m, 2H), 5.93 (s, 2H), 2.95-2.86 (m, 1H), 0.80-0.73 (m, 2H), 0.67-0.60 (m, 2H).

Example 58

(2-(7-fluoro-1-(2-fluorobenzyl)-1H-indazol-3-yl)pyrimidin-5-yl)(morpholino) methanone

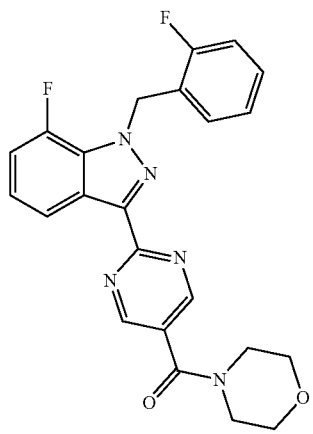 [SMILES: O=C(c1cnc(-c2nn(Cc3ccccc3F)c3c(F)cccc23)nc1)N1CCOCC1]

To N,N-dimethylformamide (10 mL) were added 2-(7-fluoro-1-(2-fluorobenzyl)-1H-indazol-3-yl)pyrimidine-5-carboxylic acid (0.10 g, 0.27 mmol) and morpholine (0.036 g, 0.41 mmol). Then O-(7-azabenzotriazol-1-yl)-N,N,N',N'-te-tramethyluronium hexafluorophosphate (0.16 g, 0.42 mmol) was added. The mixture was stirred at room temperature overnight. The reaction mixture was poured into water (50 mL). The resulting mixture was extracted with ethyl acetate (30 mL×2). The combined organic layers were washed with water (40 mL) and saturated brine (40 mL), dried over anhydrous sodium sulfate mixture and filtered. The filtrate was evaporated to remove the solvent, and the residue was purified by silica gel chromatography eluted with dichloromethane/methanol (v/v=100/1, 0.5% triethylamine) to give a white solid (0.076 g, 64%).

MS (ESI, pos. ion) m/z: 436.2 (M+1);

$^1$H NMR (400 MHz, DMSO-$d_6$) δ (ppm) 9.03 (s, 2H), 8.40 (d, J=7.7 Hz, 1H), 7.42-7.20 (m, 4H), 7.21-7.10 (m, 2H), 5.92 (s, 2H), 3.77-3.42 (m, 8H).

Example 59

3-((5-fluoro-2-(7-fluoro-1-(2-fluorobenzyl)-1H-indazol-3-yl)pyrimidin-4-yl) amino)propan-1-ol

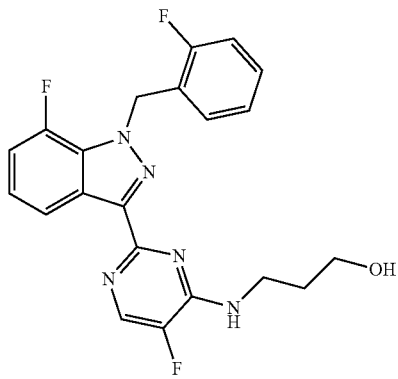 [SMILES: OCCCNc1nc(-c2nn(Cc3ccccc3F)c3c(F)cccc23)ncc1F]

Step 1: 3-(4-chloro-5-fluoropyrimidin-2-yl)-7-fluoro-1-(2-fluorobenzyl)-1H-indazole 5-Fluoro-2-(7-fluoro-1-(2-fluorobenzyl)-1H-indazol-3-yl)pyrimidin-4-ol (1.21 g, 6.99 mmol) was added into phosphorus oxychloride (30 mL). The mixture was heated to reflux and stirred for 3 hours. The reaction mixture was evaporated to remove the solvent, and to the residue was added ice-water (60 mL). The resulting mixture was adjusted with saturated aqueous sodium bicarbonate to pH 7, then extracted with dichloromethane (60 mL×2). The combined organic layers were washed with water (80 mL) and saturated brine (80 mL), dried over anhydrous sodium sulfate. The mixture was filtered. The filtrate was evaporated to remove the solvent, and the residue was purified by silica gel chromatography eluted with dichloromethane to give a white solid (1.03 g, 80.9%).

MS (ESI, pos. ion) m/z: 375.0 (M+1).

Step 2: 3-((5-fluoro-2-(7-fluoro-1-(2-fluorobenzyl)-1H-indazol-3-yl)pyrimidin-4-yl) amino)propan-1-ol 3-(4-Chloro-5-fluoropyrimidin-2-yl)-7-fluoro-1-(2-fluorobenzyl)-1H-indazole (0.20 g, 0.53 mmol), 3-aminopropan-1-ol (0.20 mL, 2.6 mmol) and triethylamine (0.22 mL, 1.6 mmol) were added into N,N-dimethylformamide (10 mL). The mixture was stirred at 100° C. for 2 hours. The reaction mixture was cooled to room temperature, and ethyl acetate (80 mL) was added. The mixture was washed with water (80 mL) and saturated brine (80 mL), dried over anhydrous sodium sulfate and filtered. The filtrate was concentrated on a rotary evaporator and the residue was purified by silica gel chromatograph (dichloromethane/methanol (v/v)=60/1, 0.5% triethylamine) to give a white solid (0.13 g, 59%).

MS (ESI, pos. ion) m/z: 414.2 (M+1);

$^1$H NMR (400 MHz, DMSO-$d_6$) δ (ppm) 8.37 (d, J=7.8 Hz, 1H), 8.25 (d, J=3.7 Hz, 1H), 7.79 (t, J=5.2 Hz, 1H), 7.36 (dd, J=13.6, 5.8 Hz, 1H), 7.32-7.19 (m, 3H), 7.14 (t, J=7.5 Hz, 1H), 7.04 (t, J=7.0 Hz, 1H), 5.86 (s, 2H), 4.60 (t, J=5.2 Hz, 1H), 3.60 (dd, J=13.0, 6.6 Hz, 2H), 3.54 (dd, J=11.5, 6.0 Hz, 2H), 1.88-1.75 (m, 2H).

Example 60

2-((5-fluoro-2-(7-fluoro-1-(2-fluorobenzyl)-1H-indazol-3-yl)pyrimidin-4-yl) amino)ethanol

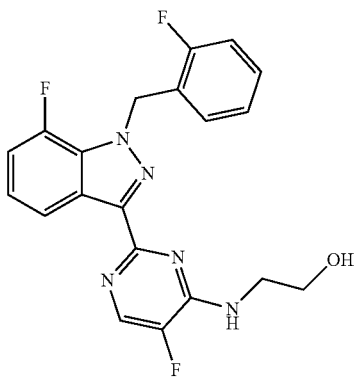 [SMILES: OCCNc1nc(-c2nn(Cc3ccccc3F)c3c(F)cccc23)ncc1F]

3-(4-Chloro-5-fluoropyrimidin-2-yl)-7-fluoro-1-(2-fluorobenzyl)-1H-indazole (0.20 g, 0.53 mmol), 2-aminoethanol (0.089 mL, 1.6 mmol) and triethylamine (0.21 mL, 1.6 mmol) were added into N,N-dimethylformamide (20 mL). The mixture was stirred at 80° C. for 3 hours. The reaction mixture cooled to rt and poured into water (50 mL). The resulting mixture was extracted with ethyl acetate (40 mL×2). The combined organic layers were washed with water (60 mL) and saturated brine (60 mL), dried over anhydrous sodium sulfate, and filtered. The filtrate was evaporated to remove the solvent, and the residue was purified by silica gel chromatography eluted with dichloromethane/methanol (v/v=100/1, 0.5% triethylamine) to give a light yellow solid product (0.11 g, 52%).

MS (ESI, pos. ion) m/z: 400.10 (M+1);

$^1$H NMR (400 MHz, DMSO-$d_6$) δ (ppm) δ 8.33 (d, J=7.7 Hz, 1H), 8.26 (d, J=3.6 Hz, 1H), 7.72 (s, 1H), 7.41-7.19 (m, 4H), 7.14 (t, J=7.5 Hz, 1H), 7.03 (t, J=7.3 Hz, 1H), 5.87 (s, 2H), 4.86 (s, 1H), 3.63 (dd, J=11.0, 6.3 Hz, 4H);

$^{19}$F NMR (376 MHz, DMSO-$d_6$) δ (ppm) −118.65 (d, J=7.8 Hz), −133.75 (d, J=7.9 Hz), −155.49 (s).

Example 61

2-((5-fluoro-2-(7-fluoro-1-(2-fluorobenzyl)-1H-indazol-3-yl)pyrimidin-4-yl)amino)acetic acid

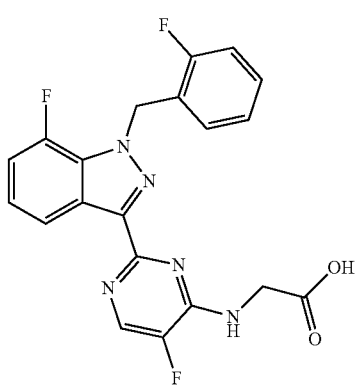 [SMILES: O=C(O)CNc1nc(-c2nn(Cc3ccccc3F)c3c(F)cccc23)ncc1F]

Step 1: benzyl 2-((5-fluoro-2-(7-fluoro-1-(2-fluorobenzyl)-1H-indazol-3-yl)pyrimidin-4-yl) amino)acetate 3-(4-Chloro-5-fluoropyrimidin-2-yl)-7-fluoro-1-(2-fluorobenzyl)-1H-indazole (0.15 g, 0.40 mmol), benzyl 2-aminoacetate hydrochloride (0.12 g, 0.60 mmol) and triethylamine (0.16 mL, 1.2 mmol) were added into N,N-dimethylformamide (10 mL). The mixture was stirred at 60° C. overnight. The reaction mixture cooled to room temperature and poured into water (50 mL). The resulting mixture was extracted with ethyl acetate (40 mL×2). The combined organic layers were washed with water (60 mL) and saturated brine (60 mL), dried over anhydrous sodium sulfate, and filtered. The filtrate was evaporated to remove the solvent, and the residue was purified by silica gel chromatography eluted with dichloromethane/methanol ((v/v)=200/1, 0.5% triethylamine) to give a light yellow solid product (0.12 g, 60%).

MS (ESI, pos. ion) m/z: 504.3 (M+1).

Step 2: 2-((5-fluoro-2-(7-fluoro-1-(2-fluorobenzyl)-1H-indazol-3-yl)pyrimidin-4-yl) amino)acetic acid Benzyl 2-((5-fluoro-2-(7-fluoro-1-(2-fluorobenzyl)-1H-indazol-3-yl)pyrimidin-4-yl) amino)acetate (0.11 g, 0.22 mmol) and 10% Pd/C (0.10 g) were added into methanol (10 mL), and the mixture was reacted overnight in hydrogen atmosphere. The mixture was filtered. The filtrate was evaporated to remove the solvent, and the residue was purified by silica gel chromatography eluted with dichloromethane/methanol (v/v=50/1, 0.5% triethylamine) to give a white solid (0.005 g, 6%).

MS (ESI, pos. ion) m/z: 414.2 (M+1);
$^1$H NMR (400 MHz, DMSO-$d_6$) δ (ppm) 8.32 (d, J=7.6 Hz, 1H), 8.27 (d, J=3.5 Hz, 1H), 7.51 (s, 1H), 7.39-7.31 (m, 1H), 7.30-7.20 (m, 3H), 7.13 (t, J=7.5 Hz, 1H), 7.02 (t, J=7.2 Hz, 1H), 5.86 (s, 2H), 3.96 (s, 2H).

Example 62

2-(4-(5-fluoro-2-(7-fluoro-1-(2-fluorobenzyl)-1H-indazol-3-yl)pyrimidin-4-yl) piperazin-1-yl)ethanol

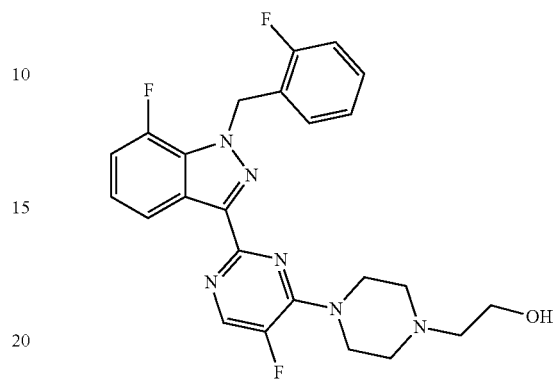

Step 1: 7-fluoro-3-(5-fluoro-4-(piperazin-1-yl)pyrimidin-2-yl)-1-(2-fluorobenzyl)-1H-indazole 3-(4-Chloro-5-fluoropyrimidin-2-yl)-7-fluoro-1-(2-fluorobenzyl)-1H-indazole (0.20 g, 0.53 mmol), piperazine (0.14 g, 1.6 mmol) and triethylamine (0.21 mL, 1.6 mmol) were added into N,N-dimethylformamide (20 mL). The mixture was stirred at 80° C. for 3 hours. The reaction mixture cooled to room temperature and poured into water (50 mL). The resulting mixture was extracted with ethyl acetate (40 mL×2). The combined organic layers were washed with water (60 mL) and saturated brine (60 mL), dried over anhydrous sodium sulfate, and filtered. The filtrate was evaporated to remove the solvent, and the residue was purified by silica gel chromatography eluted with dichloromethane/methanol (v/v=100/1, 0.5% triethylamine) to give a light yellow solid product (0.21 g, 93%).

MS (ESI, pos. ion) m/z: 425.3 (M+1).

Step 2: 2-(4-(5-fluoro-2-(7-fluoro-1-(2-fluorobenzyl)-1H-indazol-3-yl)pyrimidin-4-yl) piperazin-1-yl) ethanol To acetonitrile (10 mL) were added 7-fluoro-3-(5-fluoro-4-(piperazin-1-yl)pyrimidin-2-yl)-1-(2-fluorobenzyl)-1H-indazole (0.25 g, 0.59 mmol), 2-bromoethanol (0.063 mL, 0.89 mmol) and cesium carbonate (0.38 g, 1.2 mmol), then the mixture was refluxed for 8 hours. The reaction mixture cooled to room temperature and water (60 mL) was added. The resulting mixture was extracted with ethyl acetate (50 mL×2). The combined organic layers were washed with water (60 mL) and saturated brine (60 mL), dried over anhydrous sodium sulfate, and filtered. The filtrate was concentrated on a rotary evaporator, and the residue was purified by silica gel chromatography eluted with dichloromethane/methanol ((v/v)=100/1, 0.5% triethylamine) to give a white solid (0.12 g, 43%).

MS (ESI, pos. ion) m/z: 469.1 (M+1);
$^1$H NMR (400 MHz, DMSO-$d_6$) δ (ppm) 8.40 (d, J=6.7 Hz, 1H), 8.25 (d, J=7.3 Hz, 1H), 7.40-7.20 (m, 4H), 7.14 (t, J=7.5 Hz, 1H), 7.02 (t, J=7.6 Hz, 1H), 5.87 (s, 2H), 4.48 (t, 1H), 3.82 (t, 4H), 3.55 (q, J=5.9 Hz, 2H), 2.60 (t, 4H), 2.46 (t, J=6.0 Hz, 2H);

$^{19}$F NMR (376 MHz, DMSO-d$_6$) δ (ppm) −118.62 (d, J=7.5 Hz), −133.58 (d, J=7.5 Hz), −145.32 (s).

Example 63 methyl (4,6-diamino-2-(5-fluoro-1-(2-fluorobenzyl)-1H-indazol-3-yl)pyrimidin-5-yl)carbamate

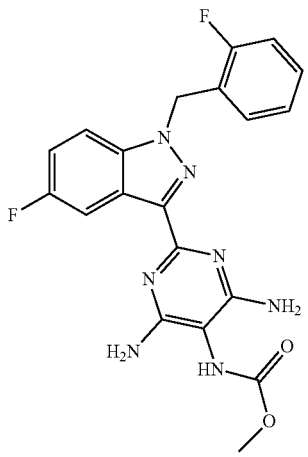 [SMILES: COC(=O)Nc1c(N)nc(-c2nn(Cc3ccccc3F)c3ccc(F)cc23)nc1N]

Step 1: 5-fluoro-3-iodo-1H-indazole

5-Fluoro-1H-indazole (10.00 g, 73.46 mmol) was added into N,N-dimethylformamide (80 mL), then Iodine (28.0 g, 110 mmol) and potassium hydroxide (6.20 g, 110 mmol) were added. After addition, the mixture was reacted for 1 hour at room temperature. The reaction mixture was poured into aqueous sodium thiosulfate solution (300 mL, 5%). The resulting mixture was extracted with ethyl acetate (100 mL×2). The combined organic layers were washed with water (100 mL) and saturated brine (100 mL), dried over anhydrous sodium sulfate, and filtered. The filtrate was concentrated on a rotary evaporator to give a light yellow solid (18.3 g, 95.1%).

Step 2: 5-fluoro-1-(2-fluorobenzyl)-3-iodo-1H-indazole 5-fluoro-3-iodo-1H-indazole (14.8 g, 56.5 mmol) and cesium carbonate (20.2 g, 62.0 mmol) was dissolved in N,N-dimethylformamide (60 mL), then 1-(bromomethyl)-2-fluorobenzene (7.15 mL, 59.3 mmol) was added. After the addition, the mixture was stirred for 1 hour at room temperature. The reaction mixture was poured into water (100 mL). The resulting mixture was extracted with ethyl acetate (100 mL×2). The combined organic layers were washed with water (100 mL) and saturated brine (100 mL), dried over anhydrous sodium sulfate, filtered. The filtrate was evaporated to remove the solvent, and the crude product was recrystallized from isopropanol (10 mL/1 g). The mixture was filtered, and the filter cake was dried in vacuo at 60° C. to give a light yellow solid (13.3 g, 63.6%).

MS (ESI, pos. ion) m/z: 371.1 (M+1).

Step 3: 5-fluoro-1-(2-fluorobenzyl)-1H-indazole-3-carbonitrile

5-Fluoro-1-(2-fluorobenzyl)-3-iodo-1H-indazole (10.29 g, 27.80 mmol) and cuprous cyanide (2.71 g, 30.6 mmol) were added into dimethyl sulfoxide (60 mL). After addition, the mixture was heated to 150° C. and stirred overnight. To the reaction mixture was added ethyl acetate (80 mL), and the mixture was washed with ammonium hydroxide/water (1/1, 100 mL×2) and saturated brine (100 mL), dried over anhydrous sodium sulfate, and filtered. The filtrate was evaporated to remove the solvent and give a light yellow solid (6.18 g, 82.6%).

MS (ESI, pos. ion) m/z: 270.2 (M+1).

Step 4: 5-fluoro-1-(2-fluorobenzyl)-1H-indazole-3-carboximidamide

To methanol (60 mL) were added 5-fluoro-1-(2-fluorobenzyl)-1H-indazole-3-carbonitrile (6.10 g, 22.65 mmol) and a solution of sodium methoxide in methanol (6.80 mL, 33.98 mmol, 5 mol/L). The mixture was stirred at room temperature overnight. To the reaction mixture were added acetic acid (1.94 mL, 33.98 mmol) and ammonium chloride (1.82 g, 33.98 mmol). After addition, the mixture was heated to reflux and reacted for 5 hours. The reaction mixture cooled to room temperature and evaporated to remove the solvent. The residue was triturated with acetone (20 mL), then the mixture was filtered. The filter cake was added into water, and the mixture was adjusted with potassium carbonate to pH 10. The resulting mixture was extracted with ethyl acetate (80 mL×2). The combined organic layers were washed with water (100 mL) and saturated brine (100 mL), dried over anhydrous sodium sulfate, and filtered. The filtrate was evaporated to give a light yellow solid (4.21 g, 65.0%).

Step 5: 2-(5-fluoro-1-(2-fluorobenzyl)-1H-indazol-3-yl)-5-(phenyldiazenyl)pyrimidine-4,6-diamine 5-Fluoro-1-(2-fluorobenzyl)-1H-indazole-3-carboximidamide (3.14 g, 11.0 mmol) and benzeneazomalononitrile (2.24 g, 13.2 mmol) were added into N,N-dimethylformamide (30.00 mL). The mixture was stirred at 100° C. overnight. The mixture was cooled to rt, and the reaction mixture was concentrated on a rotary evaporator to give the crude product which was used in the next step without further purification.

MS (ESI, pos. ion) m/z: 457.1 (M+1).

Step 6: 2-(5-fluoro-1-(2-fluorobenzyl)-1H-indazol-3-yl)pyrimidine-4,5,6-triamine 2-(5-Fluoro-1-(2-fluorobenzyl)-1H-indazol-3-yl)-5-(phenyldiazenyl)pyrimidine-4,6-diamine (5.00 g, 11.0 mmol) was dissolved in N,N-dimethylformamide (30.00 mL), then 10% Pd/C (1.00 g, 9.40 mmol) was added. After addition, the resulting mixture was stirred at 60° C. for 24 hours in hydrogen atmosphere. The reaction mixture was poured into water (100 mL). The resulting mixture was extracted with ethyl acetate (100 mL×2). The combined organic layers were washed with water (100 mL) and saturated brine (100 mL), dried over anhydrous sodium sulfate, and filtered. The filtrate was evaporated to remove the solvent, and the residue was purified by silica gel chromatography eluted with dichloromethane/methanol (v/v=30/1, 0.5% triethylamine) to give a light yellow solid product (1.58 g, 39.3%).

MS (ESI, pos. ion) m/z: 368.3 (M+1).

Step 7: methyl (4,6-diamino-2-(5-fluoro-1-(2-fluorobenzyl)-1H-indazol-3-yl)pyrimidin-5-yl)carbamate 2-(5-Fluoro-1-(2-fluorobenzyl)-1H-indazol-3-yl)pyrimidine-4,5,6-triamine (1.58 g, 4.30 mmol) and pyridine (3.46 mL, 43.0 mmol) was dissolved in dichloromethane (30.00 mL), then methylchloroformate (0.50 mL, 6.5 mmol) were added dropwise at 0° C. After the addition, the reaction mixture was stirred at room temperature for 24 hours. The reaction mixture was filtered, and washed with dichloromethane (20 mL). The filter cake was added into ethyl acetate (80 mL). The mixture was washed with saturated aqueous sodium bicarbonate (80 mL) and saturated brine (80 mL). The organic layer was dried over anhydrous sodium sulfate, and filtered. The filtrate was evaporated to remove the solvent, and the residue was purified by silica gel chromatography eluted with dichloromethane/methanol ((v/v)=30/1, 0.5% triethylamine) to give a light yellow solid product (1.21 g, 66.1%).

MS (ESI, pos. ion) m/z: 426.3 (M+1);

$^1$H NMR (400 MHz, DMSO-$d_6$) δ (ppm) 8.45 (dd, J=9.7, 2.2 Hz, 1H), 8.04 (s, 1H), 7.74 (dd, J=9.1, 4.2 Hz, 1H), 7.40-7.28 (m, 2H), 7.27-7.18 (m, 1H), 7.13 (t, J=7.4 Hz, 1H), 7.06 (t, J=7.2 Hz, 1H), 6.20 (s, 4H), 5.80 (s, 2H), 3.62 (s, 3H).

Bioactivity Detection

Example A

Effects of Compounds of the Invention on a Recombinant Guanylate Cyclase Reporter Cell Line Transfection of Soluble Guanylate Cyclase (sGC) gene into CHO-K1 cells and selection of cells with stably and highly expressed sGC: Rat sGCα1 and Rat sGCβ1 Genes were synthesized, and then pcDNA3.1(+)-rat sGCα1 and pcDNA3.1/Hygro (+)-rat sGCβ1 plasmid were constructed; the plasmid was co-transfected into CHO-K1 cells, and a positive clone cell line stably expressing CHO-K1-Rat sGC was selected using the Cisbio cGMP HTRF assay kit.

The activity of the compound on the CHO-K1-Rat sGC monoclonal cell line was determined: The CHO-K1-Rat sGC monoclonal cell line was cultured, and used for test operation at degree of fusion of about 70% to 90%. The cells were resuspended in complete medium after TrypLE digestion; the cells were inoculated in a 384-well (low volume tissues culture treated) cell culture plate at a seeding density of 7500/well in 25 μL of complete medium and incubated at 37° C. in 5% $CO_2$ atmosphere for 20 hours; the test compounds were dissolved and dilute with DMSO to give 10 concentration gradients (2× working concentration); 384-well cell culture plates were centrifugated (200 g) for 3 seconds by inversion at RT, medium was removed; The test compounds in each different concentration gradient and corresponding reagent were added into each cell well according to the detection process of Cisbio cGMP HTRF assay kit. The data were collected with Envision HTRF detector and the $EC_{50}$ value of each compound in activating soluble guanylate cyclase was calculated.

TABLE 2

Effect of compounds of the invention on a recombinant guanylate cyclase reporter cell line

| Example Number | $EC_{50}$ (μM) |
|---|---|
| Example 2 | 0.22 |
| Example 6 | 0.23 |
| Example 9 | 0.68 |
| Example 10 | 0.37 |
| Example 11 | 0.082 |
| Example 12 | 0.12 |

TABLE 2-continued

Effect of compounds of the invention on a recombinant guanylate cyclase reporter cell line

| Example Number | $EC_{50}$ (μM) |
|---|---|
| Example 13 | 0.036 |
| Example 14 | 0.062 |
| Example 15 | 0.30 |
| Example 16 | 0.69 |
| Example 17 | 0.42 |
| Example 25 | 0.86 |
| Example 26 | 0.10 |
| Example 28 | 0.094 |
| Example 30 | 0.82 |
| Example 31 | 0.035 |
| Example 32 | 0.089 |
| Example 34 | 0.81 |
| Example 42 | 0.76 |
| Example 44 | 0.34 |
| Example 45 | 0.16 |
| Example 46 | 0.20 |
| Example 47 | 0.12 |
| Example 49 | 0.27 |
| Example 51 | 0.42 |
| Example 52 | 0.11 |
| Example 53 | 0.39 |
| Example 54 | 0.14 |
| Example 56 | 0.34 |
| Example 57 | 0.079 |
| Example 59 | 0.058 |
| Example 60 | 0.120 |
| Example 62 | 0.075 |

Conclusion:

As can be seen from the data in table 2, the compounds of the present invention can preferably activate the activity of the sGC expressed by CHO-K1-Rat sGC monoclonal cell line, that is, the compounds of the present invention have an activating effect on the recombinant guanylate cyclase.

Example B

Pharmacokinetic Activity of the Compounds of the Invention

Preparation of test compound solution: The test compound was formulated with 5% dimethylsulfoxide, 5% Solutol HS 15 and 90% physiological saline to give solution, which was used for oral and intravenous administration.

Male SD rats weighing 190-250 g were randomly divided into two groups, each group had three members; one group received test compound at a dose of 1.0 mg/kg by intravenous injection, the other group received test compound at a dose of 2.5 or 5.0 mg/kg by oral. After dosing, blood samples were collected at time points of 0.0833, 0.25, 0.5, 1.0, 2.0, 4.0, 7.0 and 24 h. Standard curve was plotted based on concentrations of the samples in a suitable range, the concentrations of test compounds in plasma samples were determined by using AB SCIEX API4000 LC-MS/MS in MRM mode. Pharmacokinetic parameters were calculated according to drug concentration-time curve using a noncompartmental method by WinNonLin 6.3 software.

TABLE 3

Pharmacokinetic data of the compounds of the invention

| Example Number | Administration route | dosage (mg/kg) | $T_{max}$ (h) | $C_{max}$ (ng/ml) | $AUC_{last}$ (h*ng/ml) | $T_{1/2}$ (h) | Cl (ml/min/kg) | Vss (l/kg) | F (%) |
|---|---|---|---|---|---|---|---|---|---|
| Example 2 | iv | 1 | 0.083 | 680 | 2020 | 3.7 | 6.16 | 1.88 | 138.6 |
| | po | 5 | 2 | 1130 | 14000 | 3.61 | | | |
| Example 5 | iv | 1 | 0.083 | 2820 | 10300 | 4.49 | 1.59 | 0.483 | 93.4 |
| | po | 5 | 3.5 | 2690 | 39700 | 10.9 | | | |
| Example 6 | iv | 1 | 0.083 | 1310 | 2700 | 1.57 | 6.18 | 1.07 | 135.3 |
| | po | 5 | 1.33 | 2480 | 18300 | 2.98 | | | |
| Example 10 | iv | 1 | 0.083 | 1500 | 7520 | 3.54 | 2.21 | 0.63 | 99.6 |
| | po | 5 | 2 | 3070 | 37500 | 4.34 | | | |
| Example 11 | iv | 1 | 0.083 | 834 | 1220 | 1.37 | 13.4 | 1.35 | 107.3 |
| | po | 5 | 1.67 | 1080 | 6580 | 2.45 | | | |
| Example 13 | iv | 1 | 0.083 | 778 | 921 | 0.916 | 90.5 | 6.38 | 109.8 |
| | po | 5 | 1.67 | 1170 | 5010 | 1.57 | | | |
| Example 15 | iv | 1 | 0.083 | 981 | 2060 | 5.56 | 7.91 | 2.03 | 86 |
| | po | 5 | 3 | 768 | 8860 | 3.13 | | | |

Conclusion:

As can be seen from table 3, the compounds of the present invention have better pharmacokinetic properties in vivo, such as good exposure, longer half-life and higher bioavailability, etc.

Example C

Inhibition of hERG Potassium Channel by the Compounds of the Invention

1. Preparation of Compound Solution:

Each compound was weighed and dissolved in DMSO and diluted with DMSO to a serial solution (30, 10, 3.3, 1.1, 0.37 mM). The above serial solutions were diluted to 1000-fold with the extracellular fluid to prepare test solutions (final concentration was 30, 10, 3.3, 1.1, 0.37 μM respectively).

2. Culture and Preparation of HEC293 Cells Expressing hERG K$^+$ Channels:

The HEK293 cells that overexpressed the hERG potassium channel were cultured in a 37° C., 5% $CO_2$ incubator, and the culture medium contained DMEM, 15% fetal bovine serum, and 1% penicillin-streptomycin. When the cell density reached 80% of the culture plate, the cells were digested with trypsin/EDTA and transferred to a centrifuge tube, centrifuged at 1000 rpm for 3 minutes, then supernatant was discarded, and the cell culture medium was added. The cells were mixed uniformly by gently blowing and beating. The cells were then dripped into round coverslip, the cells were adhered and used for experiments. The cell density was less than 50%, and the cells were incubated overnight before use.

3. Record the Membrane Current with Electrophysiological Manual Patch Clamp System The experimental cells after sliding were transferred to a cell bath embedded in an inverted microscope platform, and the extracellular fluid was perfused at a perfusion rate of 2.7 mL/min. The experiment was started after 5 minutes of stabilization of the cell pellet. The PATCHMASTER acquisition system was used to amplify the recording membrane current using a HEKA EPC-10 patch clamp (HEKA Instruments Inc., D-67466 Lambrecht, Pfalz, Germany). All experiments were done at room temperature (22-24° C.). P-97 microelectrode pulling apparatus (Sutter Instrument Company, One Digital Drive, Novato, Calif. 94949) straightening electrode (BF150-110-10) was used in the experiment. The inner diameter of the electrode was 1-1.5 mm, and the water inlet resistance after filling with the inner liquid was 2-4 MΩ.

The electrophysiological stimulation scheme for hERG potassium channel was: firstly, voltage clamp membrane potential was set at −80 mV, cells were given +20 mV voltage stimulation for 2 s, then the hERG potassium channel was activated, and then repolarized to −50 mV for 5 s, then outward tail current was generated, stimulation frequency was once every 15 s. current value was the peak value of tail current.

The whole cell recording mode was used to record the channel current in the experiment. Firstly, the extracellular fluid was perfused (approximately 2 mL per minute) and the data were continuous recorded, and the current was kept steady (the current decay was less than 5% in 5 minutes). The peak value of tail current was the control current value. The extracellular fluid containing the test compound was then perfused and the data were continuous recorded until the compound's inhibitory effect on the hERG current reached a steady state, at this time point the peak value of tail current was the current value after dosing. After the steady state was reached, if the hERG current after flushing with the extracellular fluid was regained or close to the size prior to addition of the compound, perfusion could be continued to test other concentrations or compounds. 30 μM Quinidine was used as a positive control in the experiment to ensure that the cells used were normal.

In this study, the ratio of the maximum current value of the compound treatment group to the maximum current value of the control group was calculated by measuring the maximum current of the control group and the compound treatment group, and the inhibitory effect of the test compound on the hERG potassium channel at the test concentration was evaluated.

TABLE 4

Inhibition of the hERG potassium channel by compounds of the invention

| Example Number | $IC_{50}$ (μM) |
|---|---|
| Example 5 | >30 |
| Example 10 | 19.9 |

Conclusion:

The compound of the present invention has no obvious inhibitory effect on the hERG potassium channel.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, a hydrate, a solvate, or a pharmaceutically acceptable salt thereof,

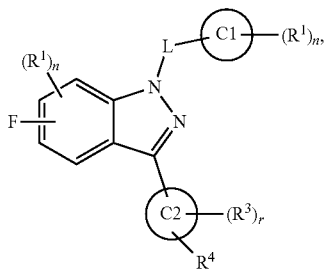

wherein
L is -($CR^aR^b$)$_t$;
t is 1, 2, 3 or 4;
each $R^a$ and $R^b$ is independently H, or D;
C1 is

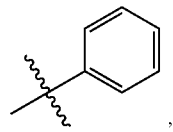

wherein,

is the bond through which C1 is attached to L;

C2 is

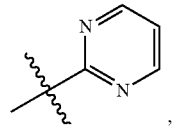

wherein,

is the bond through which C2 is attached to indazole;
each $R^1$ is independently H, D, F, Cl, Br, I, or CN;
each $R^2$ is independently H, D, F, Cl, Br, I, or CN;
each $R^3$ is independently H, D, F, Cl, Br, I, CN, NO$_2$, mercapto, $C_{1-6}$ alkyl, $C_{2-6}$ alkenyl, $C_{2-6}$ alkynyl, halo $C_{1-6}$ alkyl, $(CR^{6a}R^{6b})_j NR^{5a}R^{5b}$, - or —$(CR^{6a}R^{6b})_j OR^9$;
each $R^3$ is unsubstituted or independently substituted with 1, 2, 3 or 4 $R^x$;
$R^4$ is D, F, Cl, Br, I, CN, NO$_2$, mercapto, $C_{1-6}$ alkyl, $C_{2-6}$ alkenyl, $C_{2-6}$ alkynyl, halo $C_{1-6}$ alkyl, —$(CR^{6c}R^{6d})_g$— $C_{3-6}$ cycloalkyl, —$(CR^{6c}R^{6d})_g$—$C_{2-5}$ heterocyclyl, —$(CR^{6c}R^{6d})_g NR^{5c}R^{5d}$, —$(CR^{6c}R^{6d})_g C(=O)$ $(CR^{6c}R^{6d})_h NR^{5c}R^{5d}$, —$(CR^{6c}R^{6d})_g C(=O)$ $(CR^{6c}R^{6d})_h OR^{9a}$, —$(CR^{6c}R^{6d})_g N(R^{5e})(CR^{6c}R^{6d})_i C(=O)(CR^{6c}R^{6d})_h OR^{9a}$, —$(CR^{6c}R^{6d})_g N(R^{5e})C(=O)$ $R^{8a}$, —$(CR^{6c}R^{6d})_g N(R^{5e})C(=O)(CR^{6c} R^{6d})_h NR^{5c}R^{5d}$,- or —$(CR^{6c}R^{6d})_g C(=O)R^{8a}$; $R^4$ is unsubstituted or substituted with 1, 2, 3 or 4 $R^y$;
each $R^{5e}$ is independently H, D, or $C_{1-6}$ alkyl;
each $R^{5a}$ and $R^{5b}$ is independently H, D, $C_{1-6}$ alkyl, hydroxy $C_{1-6}$ alkyl, halo $C_{1-6}$ alkyl, or $C_{1-6}$ alkoxy-$C_{1-6}$-alkyl; or, $R^{5a}$ and $R^{5b}$, together with the N atom to which they are attached, form a 3- to 10-membered heterocyclic ring;
each $R^{5c}$ and $R^{5d}$ is independently H, D, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy-$C_{1-6}$-alkyl, $C_{1-6}$ alkoxycarbonyl, $C_{1-6}$ alkylcarbonyl, $C_{1-6}$ alkylaminocarbonyl, $C_{3-6}$ cycloalkyl, $C_{2-5}$ heterocyclyl, $C_{6-10}$ aryl, $C_{1-5}$ heteroaryl, $C_{3-6}$ cycloalkylcarbonyl, $C_{2-5}$ heterocyclylcarbonyl, $C_{6-10}$ arylcarbonyl, $C_{1-5}$ heteroarylcarbonyl, $C_{3-6}$ cycloalkyl-$C_{1-6}$-alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$-alkyl; or, $R^{5c}$ and $R^{5d}$, together with the N atom to which they are attached, form a 3- to 10-membered heterocyclic ring or 3- to 10-membered heteroaromatic ring;
each $R^{6c}$ and $R^{6d}$ is independently H, D, F, Cl, Br, I, CN, or $C_{1-6}$ alkyl;
each $R^{8a}$ is independently H, D, amino, hydroxy, mercapto, $C_{1-6}$ alkyl, $C_{2-6}$ alkenyl, $C_{2-6}$ alkynyl, halo $C_{1-6}$ alkyl, $C_{1-6}$ alkoxy, halo $C_{1-6}$ alkoxy, $C_{1-6}$ alkylamino, $C_{3-6}$ cycloalkyl, $C_{2-5}$ heterocyclyl, $C_{6-10}$ aryl or $C_{1-5}$ heteroaryl;
each $R^9$ is independently H or D;
each $R^{9a}$ is independently H, D, $C_{1-6}$ alkyl, $C_{2-6}$ alkenyl, $C_{2-6}$ alkynyl, halo $C_{1-6}$ alkyl, $C_{3-6}$ cycloalkyl, $C_{2-5}$ heterocyclyl, $C_{6-10}$ aryl, $C_{1-5}$ heteroaryl, $C_{3-6}$ cycloalkyl-$C_{1-6}$-alkyl, $C_{2-5}$ heterocyclyl-$C_{1-6}$-alkyl, $C_{6-10}$ aryl-$C_{1-6}$-alkyl or $C_{1-5}$ heteroaryl-$C_{1-6}$ alkyl;
each $R^x$ is independently oxo, H, D, F, Cl, Br, I, hydroxy, mercapto, $C_{1-6}$ alkyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy or $C_{1-6}$ alkylamino;

each $R^y$ is independently oxo, H, D, F, Cl, Br, I, CN, amino, hydroxy, mercapto, $C_{1-6}$ alkyl, $C_{2-6}$ alkenyl, $C_{2-6}$ alkynyl, hydroxy $C_{1-6}$ alkyl, amino $C_{1-6}$ alkyl, cyano $C_{1-6}$ alkyl, halo $C_{1-6}$ alkyl, $C_{1-6}$ alkoxy, halo $C_{1-6}$ alkoxy, $C_{1-6}$ alkylamino, acyl, sulfonyl, $C_{1-6}$ alkylcarbonyl, $C_{1-6}$ alkylsulfonyl, $C_{1-6}$ alkylcarbonylamino, $C_{1-6}$ alkylsulfonylamino, $C_{1-6}$ alkoxycarbonylamino, $C_{3-6}$ cycloalkyl, $C_{2-5}$ heterocyclyl, $C_{6-10}$ aryl or $C_{1-5}$ heteroaryl;

each n, and h is independently 0, 1, 2, 3 or 4;

each j, g and i is independently 0, m is 0, 1, 2 or 3;

r is 0, 1 or 2.

2. The compound according to claim 1 having Formula (IV), Formula (IVa), Formula (IVb) or Formula (IVc), or a stereoisomer, a geometric isomer, a tautomer, an N-oxide, a hydrate, a solvate, or a pharmaceutically acceptable salt thereof,

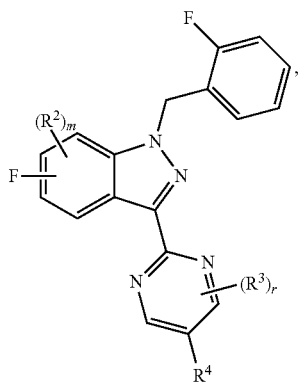

(IV)

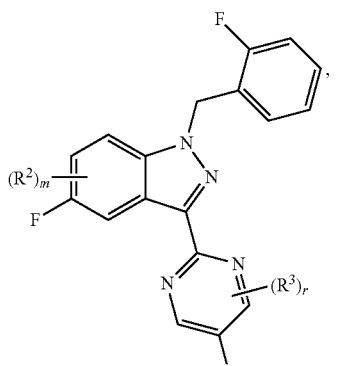

(IVa)

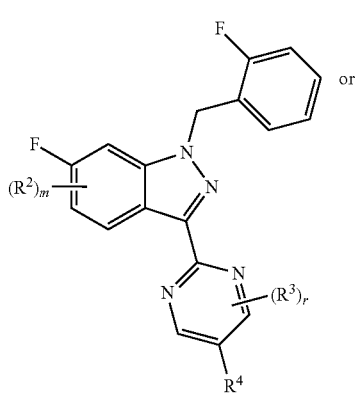

(IVb) or

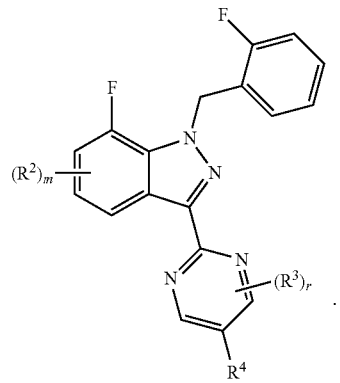

(IVc)

3. The compound according to claim 1, wherein $R^4$ is D, F, Cl, Br, I, CN, $NO_2$, mercapto, $C_{1-4}$ alkyl, $C_{2-4}$ alkenyl, $C_{2-4}$ alkynyl, halo $C_{1-4}$ alkyl, $C_{3-6}$ cycloalkyl, $C_{2-5}$ heterocyclyl, —$NR^{5c}R^{5d}$, —C(=O)$NR^{5c}R^{5d}$, —$N(R^{5e})C(=O)$ $(CR^{6c}R^{6d})_hOR^{9a}$, —$N(R^{5e})C(=O)R^{8a}$, —$N(R^{5e})C(=O)$ $NR^{5c}R^{5d}$, or —$C(=O)R^{8a}$; $R^4$ is unsubstituted or substituted with 1, 2, 3 or 4 $R^y$.

4. The compound according to claim 1, wherein $R^4$ is D, F, Cl, Br, I, CN, $NO_2$, mercapto, methyl, ethyl, propyl, butyl, vinyl, propenyl, allyl, ethynyl, propynyl, trifluoromethyl, difluoromethyl, 2,2-difluoroethyl, chloroethyl, 2,2,2-trifluoroethyl, 2-chloro-1-methylethyl, cyclopropyl, cyclobutyl, cyclopentyl, cyclohexyl, tetrahydrofuranyl, morpholinyl, piperidinyl, piperazinyl, pyrrolidinyl, pyrazolidinyl, oxomorpholinyl, thiomorpholinyl, 4,4-dioxothiomorpholinyl, oxazolidinyl, thiazolidinyl, 1,1-dioxoisothiazolidinyl, oxo-1,3-oxazinylalkyl, —$NR^{5c}R^{5d}$, —$C(=O)NR^{5c}R^{5d}$, —$N(R^{5e})C(=O)(CR^{6c}R^{6d})_hOR^{9a}$, —$N(R^{5e})C(=O)R^{8a}$, —$N(R^{5e})C(=O)NR^{5c}R^{5d}$, or —$C(=O)R^{8a}$; $R^4$ is unsubstituted or substituted with 1, 2, 3 or 4 $R^y$.

5. The compound according to claim 1, wherein
each $R^3$ is independently H, D, F, Cl, Br, I, CN, $NO_2$, mercapto, $C_{1-4}$ alkyl, $C_{2-4}$ alkenyl, $C_{2-4}$ alkynyl, halo $C_{1-4}$ alkyl, $NR^{5a}R^{5b}$, or —$OR^9$; each $R^3$ is unsubstituted or substituted with 1, 2, 3 or 4 $R^x$.

6. The compound of claim 1, wherein
each $R^3$ is independently H, D, F, Cl, Br, I, CN, $NO_2$, mercapto, methyl, ethyl, propyl, butyl, trifluoromethyl, 2,2-difluoroethyl, —$NR^{5a}R^{5b}$, or —$OR^9$; each $R^3$ is unsubstituted or independently substituted with 1, 2, 3 or 4 $R^x$.

7. The compound according to claim 1, wherein each $R^{5a}$ and $R^{5b}$ is independently H, D, $C_{1-4}$ alkyl, hydroxy $C_{1-4}$ alkyl, halo $C_{1-4}$ alkyl, or $C_{1-4}$ alkoxy-$C_{1-4}$-alkyl; or, $R^{5a}$ and $R^{5b}$, together with the N atom to which they are attached, form a 3- to 6-membered heterocyclic ring;

each $R^{5c}$ and $R^{5d}$ is independently H, D, $C_{1-4}$ alkyl, $C_{2-4}$ alkenyl, $C_{2-4}$ alkynyl, hydroxy $C_{1-4}$ alkyl, amino $C_{1-4}$ alkyl, cyano $C_{1-4}$ alkyl, halo $C_{1-4}$ alkyl, $C_{1-4}$ alkoxy-$C_{1-4}$-alkyl, $C_{1-4}$ alkoxycarbonyl, $C_{1-4}$ alkylcarbonyl, $C_{1-4}$ alkylaminocarbonyl, $C_{3-6}$ cycloalkyl, $C_{2-5}$ heterocyclyl, $C_{6-10}$ aryl, $C_{1-5}$ heteroaryl, $C_{3-6}$ cycloalkylcarbonyl, $C_{2-5}$ heterocyclylcarbonyl, $C_{6-10}$ arylcarbonyl, $C_{1-5}$ heteroarylcarbonyl, $C_{3-6}$ cycloalkyl-$C_{1-3}$-alkyl, $C_{2-5}$ heterocyclyl-$C_{1-3}$-alkyl, $C_{6-10}$ aryl-$C_{1-3}$-alkyl or $C_{1-5}$ heteroaryl-$C_{1-3}$-alkyl; or, $R^{5c}$ and $R^{5d}$, together with the N atom to which they are attached, form a 3- to 6-membered heterocyclic ring or 3- to 6-membered heteroaromatic ring;

each $R^{9a}$ is independently H, D, $C_{1-4}$ alkyl, $C_{2-4}$ alkenyl, $C_{2-4}$ alkynyl, halo $C_{1-4}$ alkyl, $C_{3-6}$ cycloalkyl, $C_{2-5}$ heterocyclyl, $C_{6-10}$ aryl, $C_{1-5}$ heteroaryl, $C_{3-6}$ cycloalkyl-$C_{1-3}$-alkyl, $C_{2-5}$ heterocyclyl-$C_{1-3}$-alkyl, $C_{6-10}$ aryl-$C_{1-3}$-alkyl or $C_{1-5}$ heteroaryl-$C_{1-3}$-alkyl.

8. The compound according to claim 1, wherein each $R^{5a}$ and $R^{5b}$ is independently H, D, methyl, ethyl, propyl, butyl, hydroxymethyl, hydroxyethyl, hydroxypropyl, hydroxybutyl, trifluoromethyl, chloroethyl, 2,2,2-trifluoroethyl, 2,2-difluoroethyl, 2-chloro-1-methylethyl, methoxymethyl, or methoxyethyl; or, $R^{5a}$ and $R^{5b}$, together with the N atom to which they are attached, form an azetidine, pyrrolidine, oxazolidine, thiazolidine, isothiazolidine, piperidine, morpholine, piperazine, thiomorpholine, or 1,3-oxazinane;

each $R^{5c}$ and $R^{5d}$ is independently H, D, methyl, ethyl, propyl, butyl, hydroxymethyl, hydroxyethyl, hydroxypropyl, hydroxybutyl, amino $C_{1-4}$ alkyl, cyano $C_{1-4}$ alkyl, trifluoromethoxy, chloroethyl, 2,2,2-trifluoroethyl, 2,2-difluoroethyl, 2-chloro-1-methylethyl, methoxymethyl, methoxyethyl, methoxycarbonyl, ethoxycarbonyl, propoxycarbonyl, methylcarbonyl, ethylcarbonyl, methylaminocarbonyl, ethylaminocarbonyl, cyclopropyl, cyclobutyl, cyclopentyl, cyclohexyl, azetidinyl, pyrrolidyl, tetrahydrofuranyl, tetrahydropyranyl, morpholinyl, piperidinyl, piperazinyl, phenyl, pyridinyl, pyrimidinyl, cyclopropylcarbonyl, cyclopentylcarbonyl, cyclohexylcarbonyl, cyclopropyloxycarbonyl, tetrahydrofurylcarbonyl, tetrahydropyranylcarbonyl, piperidylcarbonyl, piperazinylcarbonyl, morpholinylcarbonyl, tetrahydrothiophenylcarbonyl, pyrrolidinylcarbonyl, phenylcarbonyl, pyridylcarbonyl, pyrimidinylcarbonyl, pyrrolylcarbonyl, imidazolylcarbonyl, pyrazolylcarbonyl, thienylcarbonyl, furylcarbonyl, cyclopropylmethyl, cyclobutylmethyl, tetrahydropyranylmethyl, tetrapyranylethyl, tetrahydrofuranylmethyl, tetrahydrofuranylethyl, phenylmethyl, phenylethyl, pyridylmethyl, pyrazolylmethyl, pyrazolylethyl, pyridylethyl or $C_{2-5}$ heterocyclyl-$C_{1-3}$-alkyl; or, $R^{5c}$ and $R^{5d}$, together with the N atom to which they are attached, form an azetidine, pyrrolidine, oxazolidine, thiazolidine, isothiazolidine, piperidine, morpholine, piperazine, thiomorpholine, 1,3-oxazinane, pyrrole, pyrazole, imidazole or triazolyl.

9. The compound according to claim 1, wherein each $R^{9a}$ is independently H, D, methyl, ethyl, propyl, butyl, $C_{2-4}$ alkenyl, $C_{2-4}$ alkynyl, trifluoromethyl, chloroethyl, 2,2,2-trifluoroethyl, 2,2-difluoroethyl, 2-chloro-1-methylethyl, cyclopropyl, cyclobutyl, cyclopentyl, cyclohexyl, pyrrolidinyl, tetrahydrofuranyl, morpholinyl, piperidinyl, piperazinyl, phenyl, pyridyl, pyrimidinyl, cyclopropylmethyl, cyclobutylmethyl, phenylmethyl, phenylethyl, pyridylmethyl, pyridylethyl or $C_{2-5}$ heterocyclyl-$C_{1-3}$-alkyl.

10. The compound according to claim 1, wherein each $R^{8a}$ is independently H, D, amino, hydroxy, mercapto, methyl, ethyl, propyl, butyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, cyclopropyl, cyclobutyl, cyclopentyl, cyclohexyl, azetidinyl, tetrahydropyranyl, pyrrolidinyl, tetrahydrofuranyl, tetrahydrothienyl, morpholinyl, piperidinyl, piperazinyl, thiomorpholinyl, 1,1-dioxothiomorpholinyl, phenyl, pyrrolyl, thienyl, furyl, pyridyl or pyrimidinyl;

each $R^{5e}$ is independently H, D, methyl, ethyl, propyl, or butyl;

each $R^{6c}$ and $R^{6d}$ is independently H, D, F, Cl, Br, I, CN, methyl, ethyl, propyl, or butyl.

11. The compound according to claim 1, wherein each $R^x$ is independently oxo, H, D, F, Cl, Br, I, hydroxy, mercapto, methyl, ethyl, propyl, butyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, or dimethylamino;

each $R^y$ is independently oxo, H, D, F, Cl, Br, I, CN, amino, hydroxy, mercapto, methyl, ethyl, propyl, butyl, $C_{2-4}$ alkenyl, $C_{2-4}$ alkynyl, hydroxymethyl, hydroxyethyl, amino $C_{1-4}$ alkyl, cyano $C_{1-4}$ alkyl, trifluoromethyl, chloroethyl, 2,2,2-trifluoroethyl, 2,2-difluoroethyl, 2-chloro-1-methylethyl, methoxy, ethoxy, propoxy, trifluoromethoxy, methylamino, dimethylamino, $C_{1-3}$ alkylcarbonyl, $C_{1-3}$ alkylsulfonyl, $C_{1-3}$ alkylcarbonylamino, $C_{1-3}$ alkylsulfonamino, methoxyformylamino, $C_{2-3}$ alkoxycarbonylamino, cyclopropyl, cyclobutyl, cyclopentyl, cyclohexyl, $C_{2-5}$ heterocyclyl, phenyl or $C_{1-5}$ heteroaryl.

12. The compound according to claim 1 having one of the following structures or a stereoisomer, a geometric isomer, a tautomer, an N-oxide, a hydrate, a solvate, or a pharmaceutically acceptable salt thereof,

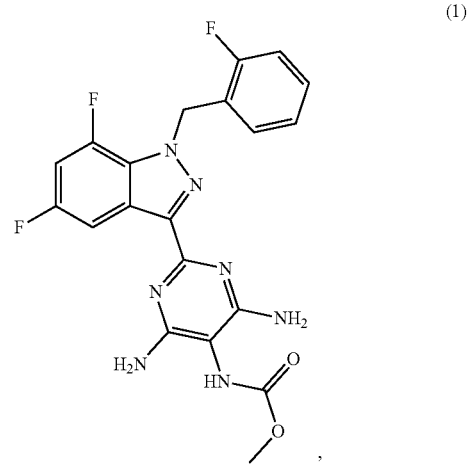

(1)

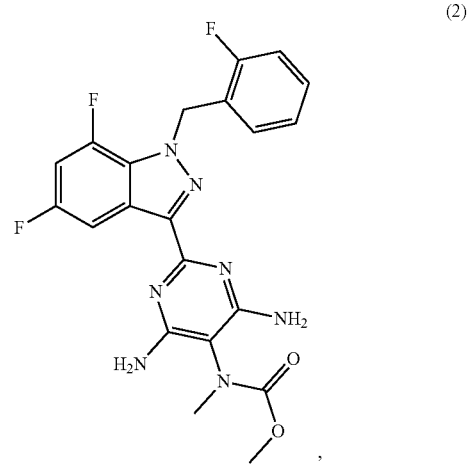

(2)

175
-continued
(5)
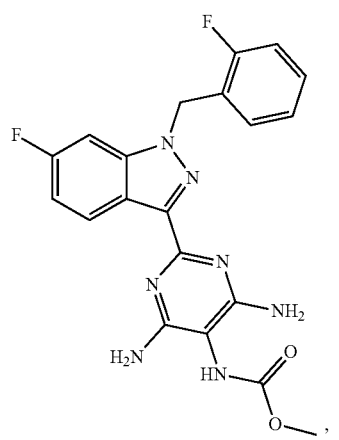
(6)
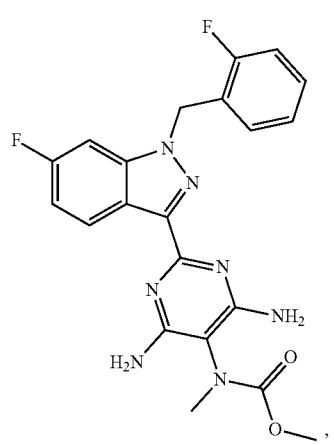
(9)
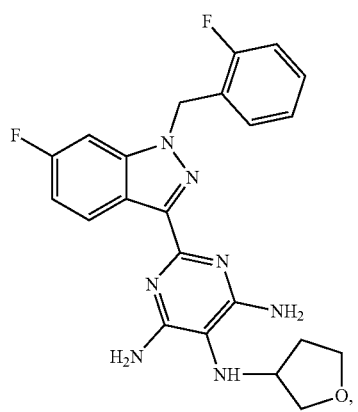
176
-continued
(10)
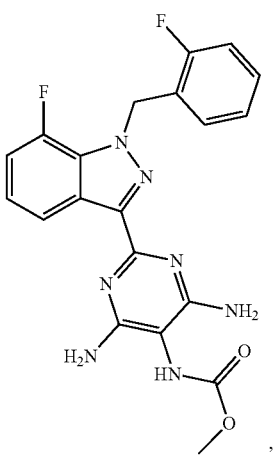
(11)
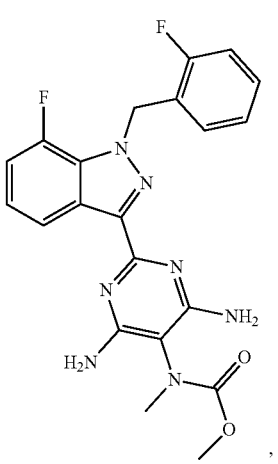
(12)
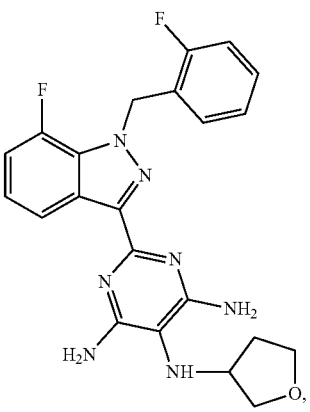

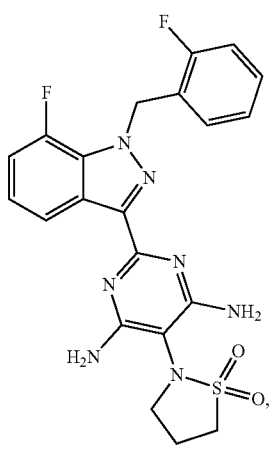
(13)
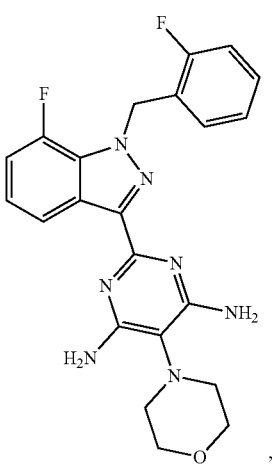
(14)
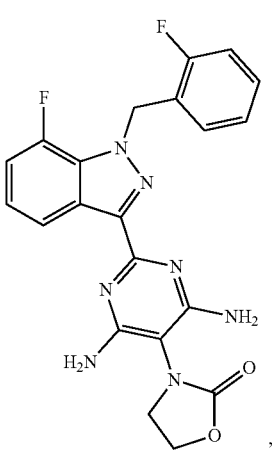
(15)
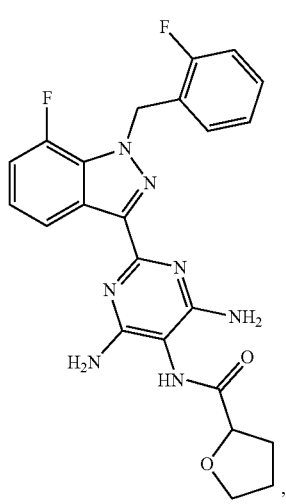
(16)
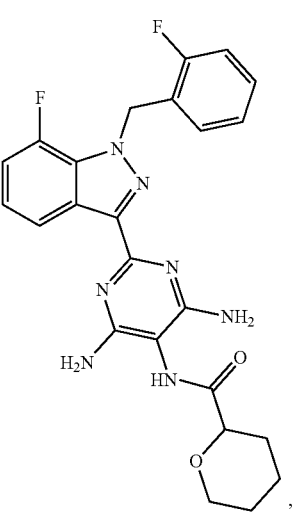
(17)
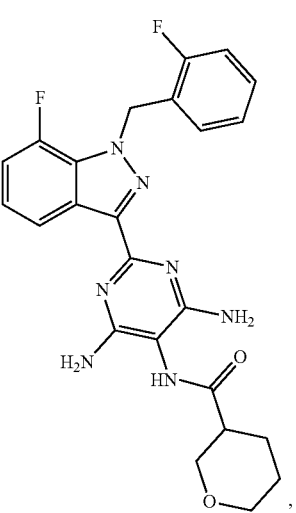
(18)

(25)
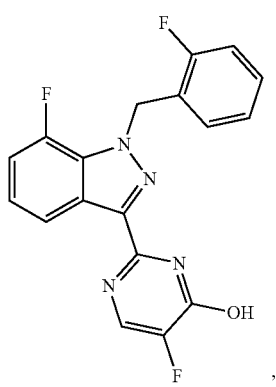
(26)
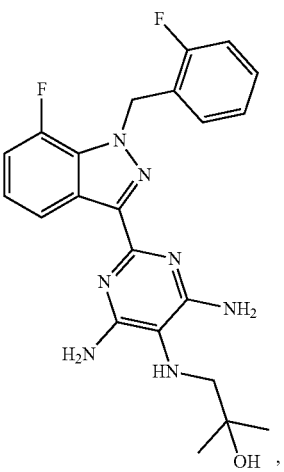
(27)
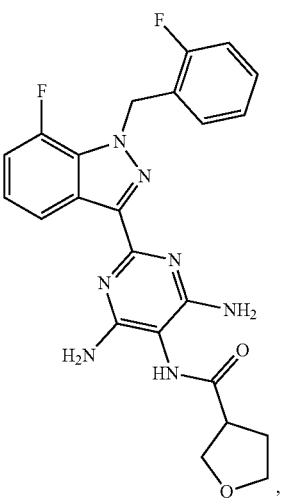
(28)
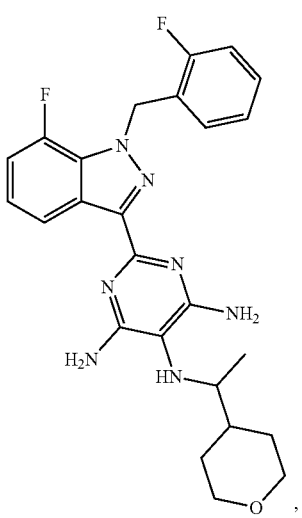
(29)
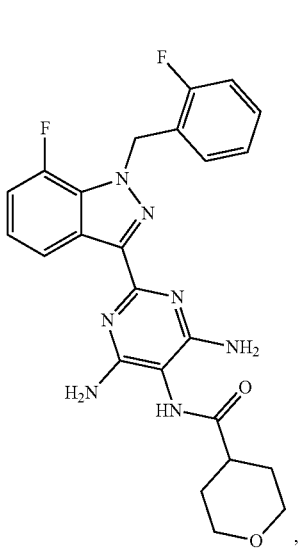
(30)
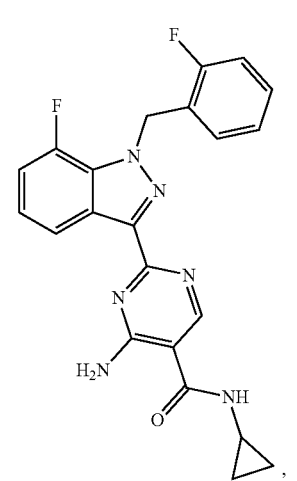

-continued
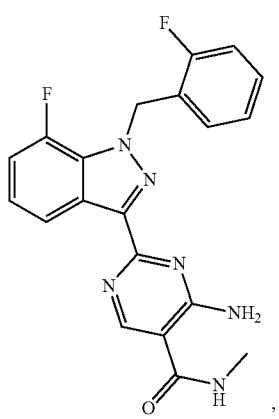
(31)
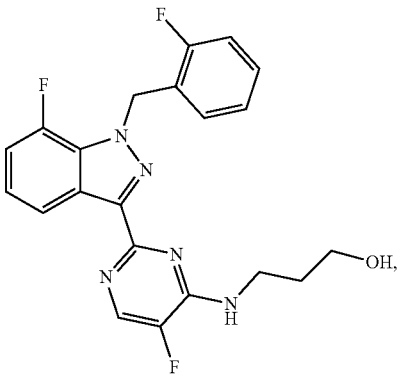
(38)
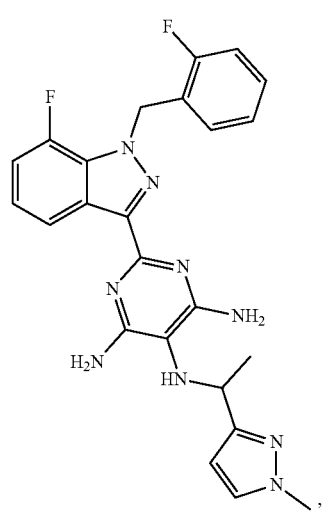
(32)
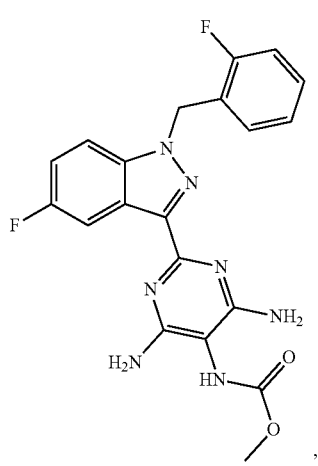
(39)
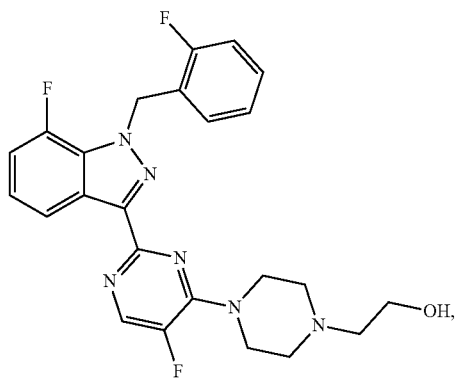
(37)
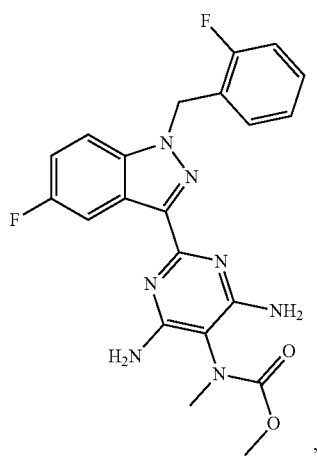
(40)

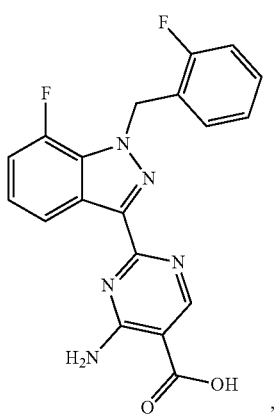
(41)
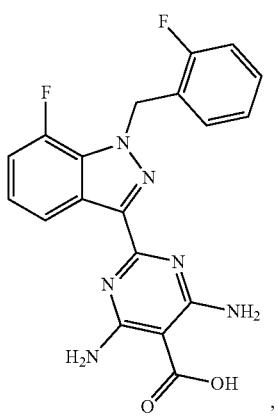
(42)
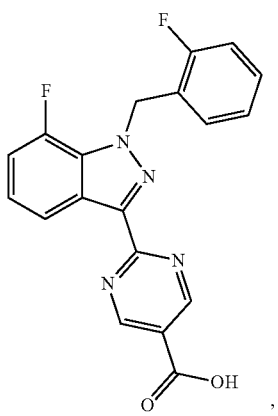
(43)
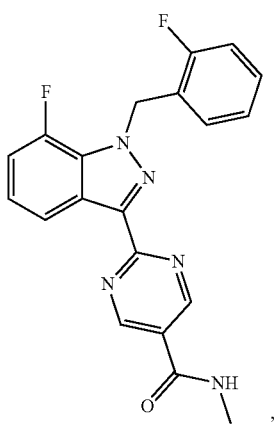
(44)
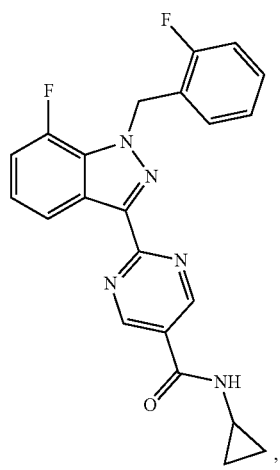
(45)
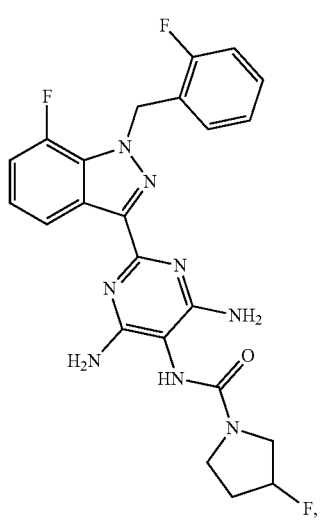
(46)
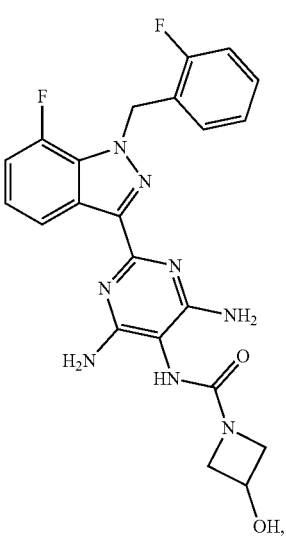
(47)

-continued
(48)
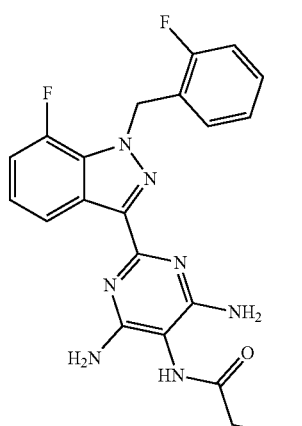
(49)
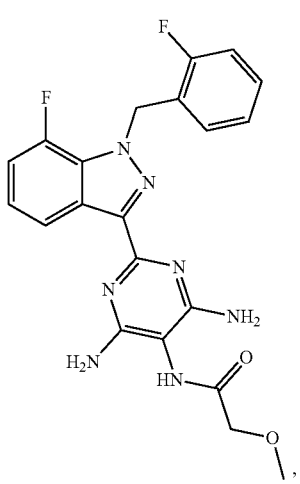
(50)
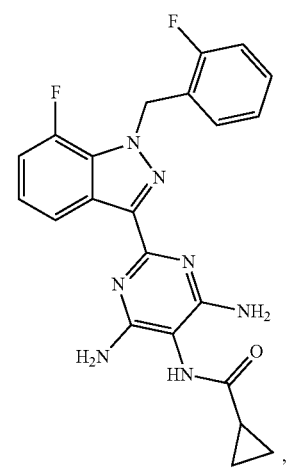
-continued
(51)
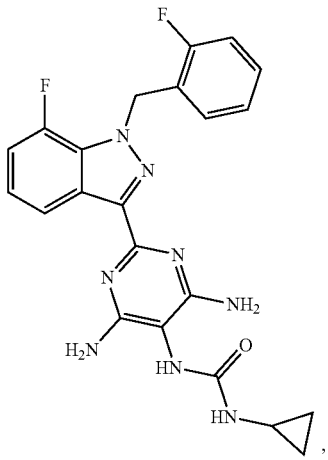
(52)
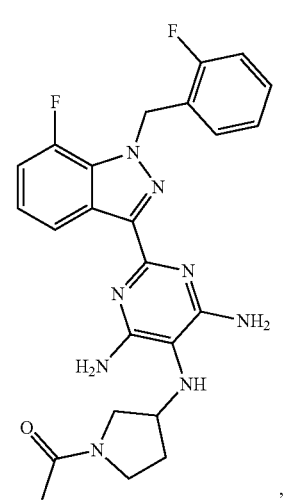
(53)
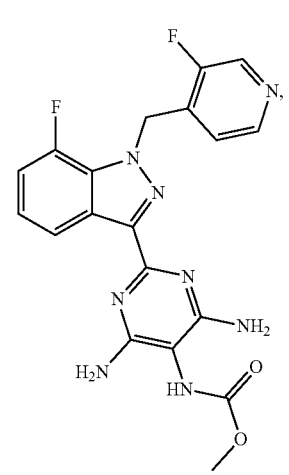

-continued
(54)
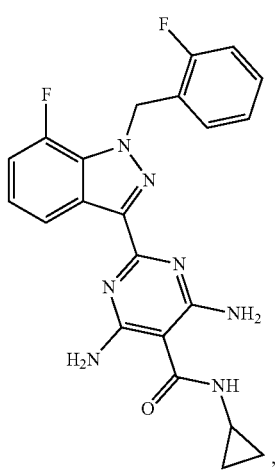
(55)
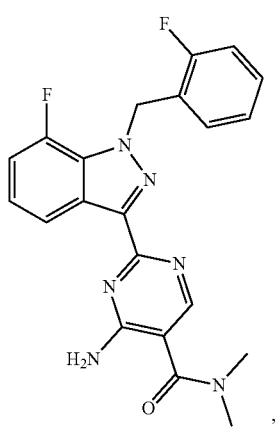
(56)
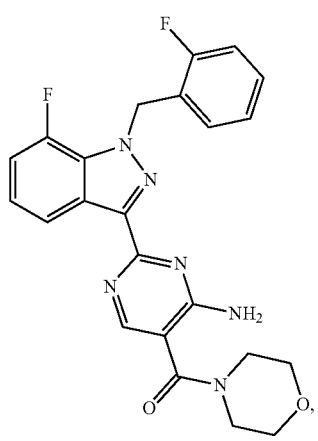
-continued
(57)
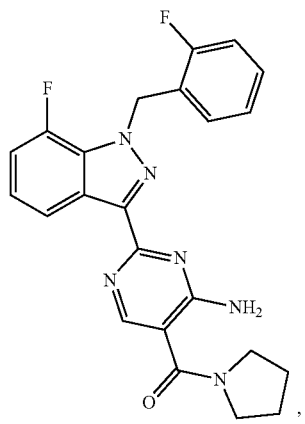
(58)
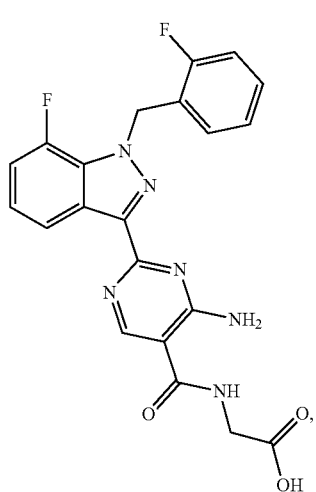
(59)

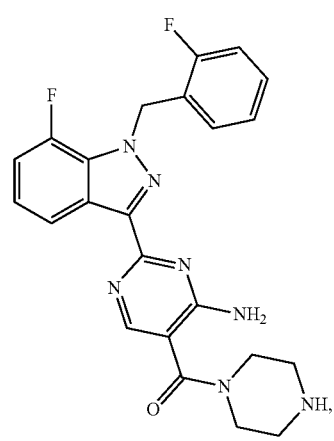
(60)
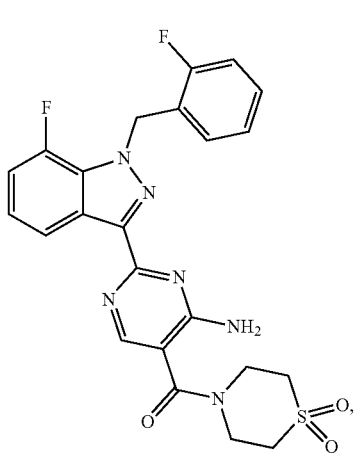
(61)
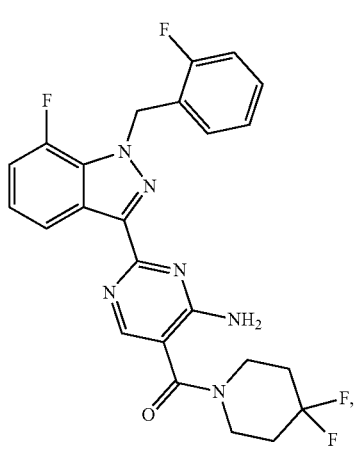
(62)
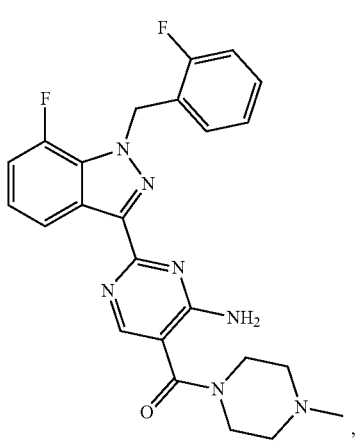
(63)
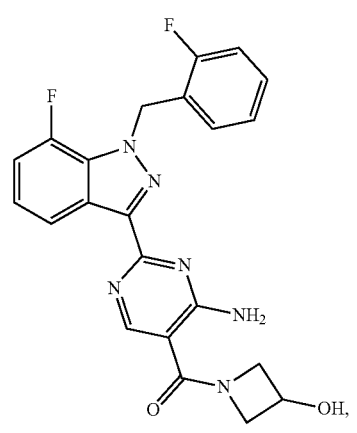
(64)
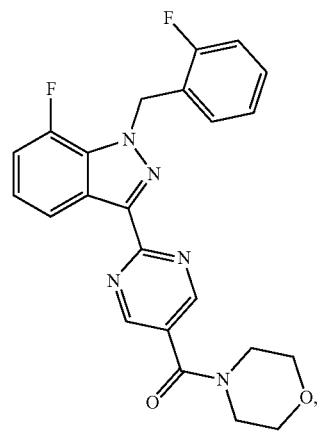
(65)
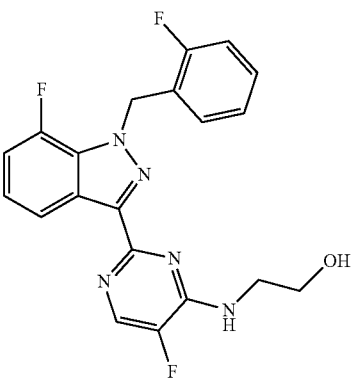
(66)
or (67)

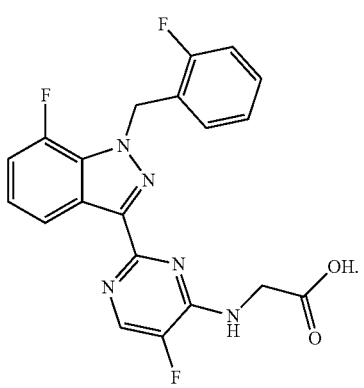

13. A pharmaceutical composition comprising the compound of claim 1; and further comprising at least one of pharmaceutically acceptable carrier, excipient, diluent, adjuvant and vehicle.

14. The compound according to claim 1 having Formula (II), Formula (IIa), Formula (IIb) or Formula (IIc), or a stereoisomer, a geometric isomer, a tautomer, an N-oxide, a hydrate, a solvate, or a pharmaceutically acceptable salt thereof, (II)

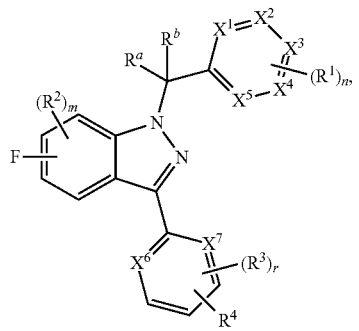

(IIa)

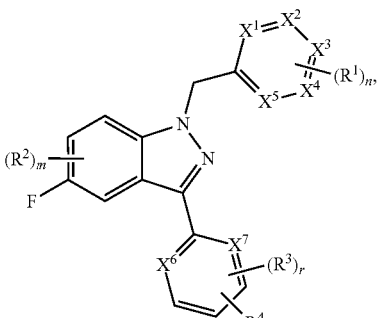

(IIb)

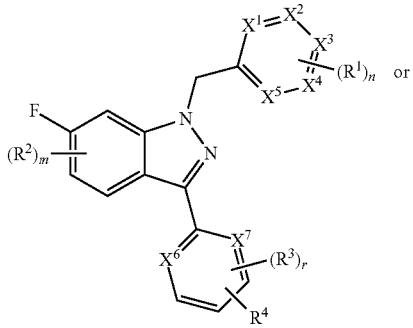

(IIc)

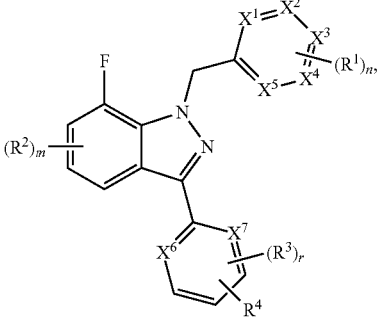

wherein each $X^1$, $X^2$, $X^3$, $X^4$ and $X^5$ is independently CH; $X^6$ is N and $X^7$ is N.

* * * * *